(12) United States Patent
Ruben et al.

(10) Patent No.: US 6,903,072 B2
(45) Date of Patent: Jun. 7, 2005

(54) KERATINOCYTE GROWTH FACTOR-2

(75) Inventors: Steven M. Ruben, Olney, MD (US);
Pablo Jimenez, Ellicott City, MD (US);
D. Roxanne Duan, Bethesda, MD (US); Mark A. Rampy, Gaithersburg, MD (US); Donna Mendrick, Mt. Airy, MD (US); Jun Zhang, Bethesda, MD (US); Jian Ni, Rockville, MD (US); Paul A. Moore, Germantown, MD (US); Timothy A. Coleman, Gaithersburg, MD (US); Joachim R. Gruber, Chestnut Hill, MA (US); Patrick J. Dillon, Carlsbad, CA (US); Reiner L. Gentz, Rockville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/345,373

(22) Filed: Jul. 1, 1999

(65) Prior Publication Data
US 2003/0077695 A1 Apr. 24, 2003

Related U.S. Application Data

(63) Continuation of application No. 09/023,082, filed on Feb. 13, 1998, now Pat. No. 6,077,692, which is a continuation-in-part of application No. 08/910,875, filed on Aug. 13, 1997, now abandoned, and a continuation-in-part of application No. 08/862,432, filed on May 23, 1997, now abandoned, which is a division of application No. 08/461,195, which is a continuation-in-part of application No. PCT/US95/01790, filed on Feb. 14, 1995, now abandoned.

(60) Provisional application No. 60/055,561, filed on Aug. 13, 1997, provisional application No. 60/639,045, filed on Feb. 28, 1997, and provisional application No. 60/023,852, filed on Aug. 13, 1996.

(51) Int. Cl.$^7$ ............... A61K 38/18; C07K 14/50; C12N 15/18; C12N 1/21

(52) U.S. Cl. ............... 514/12; 514/2; 530/399; 530/402; 435/69.4; 435/69.7; 435/243

(58) Field of Search ................... 530/350, 399; 514/12

(56) References Cited

U.S. PATENT DOCUMENTS

| | | |
|---|---|---|
| 5,194,596 A | 3/1993 | Tischer et al. |
| 5,350,836 A | 9/1994 | Kopchick et al. |
| 5,580,856 A | 12/1996 | Prestrelski et al. |
| 5,677,278 A | 10/1997 | Gospodarowicz et al. |
| 5,703,047 A | 12/1997 | Wilson |
| 5,731,170 A | 3/1998 | Rubin et al. |
| 5,773,252 A | 6/1998 | Greene et al. |
| 5,773,586 A | 6/1998 | Gospodarowicz et al. |
| 5,814,605 A | 9/1998 | Pierce et al. |
| 5,824,643 A | 10/1998 | Pierce et al. |
| 5,843,883 A | 12/1998 | Gospodarowicz et al. |
| 5,863,767 A | 1/1999 | Gospodarowicz et al. |
| 6,077,692 A * | 6/2000 | Ruben et al. ............ 435/69.4 |
| 6,238,888 B1 | 5/2001 | Gentz et al. |
| 2002/0016295 A1 | 2/2002 | Gentz et al. |

FOREIGN PATENT DOCUMENTS

| | | |
|---|---|---|
| EP | 0 619 370 A1 | 10/1994 |
| GB | 2 321 852 A | 8/1998 |
| JP | 7-345689 | 12/1995 |
| JP | 8-103240 | 3/1996 |
| JP | 8-214378 | 7/1996 |
| JP | 10-330283 | 12/1998 |
| JP | 10-330284 | 12/1998 |
| JP | 10-330285 | 12/1998 |
| WO | WO 90/08771 | 8/1990 |
| WO | WO 92/14480 | 9/1992 |
| WO | WO 92/22304 | 12/1992 |
| WO | WO 93/21908 | 11/1993 |
| WO | WO 94/22427 | 10/1994 |
| WO | WO 94/23032 | 10/1994 |
| WO | WO 95/01434 | 1/1995 |
| WO | WO 95/03831 | 2/1995 |
| WO | WO 95/24928 | 9/1995 |
| WO | WO 95/24928 A3 | 10/1995 |
| WO | WO 96/11949 | 4/1996 |
| WO | WO 96/11950 | 4/1996 |
| WO | WO 96/11951 | 4/1996 |
| WO | WO 96/11952 | 4/1996 |
| WO | WO 96/22369 | 7/1996 |
| WO | WO 96/25422 | 8/1996 |
| WO | WO 97/20929 | 12/1997 |
| WO | WO 98/06844 | 2/1998 |
| WO | WO 98/16243 | 4/1998 |
| WO | WO 98/16642 | 4/1998 |
| WO | WO 99/32135 | 7/1999 |
| WO | WO 99/41282 | 8/1999 |
| WO | WO 00/72872 | 12/2000 |
| WO | WO 01/02433 | 1/2001 |

OTHER PUBLICATIONS

Bowie et al. Science 247: 1306–1310, 1990.*
Wells. Biochemistry 29: 8509–8517, 1990.*
Ngo et al. The Protein Folding Problem and Tertiary Structure, pp. 14–16, 1994.*
Robson et al. Introduction to Proteins and Protein Engineering, p. 41, 1986.*

(Continued)

Primary Examiner—Christine J. Saoud
(74) Attorney, Agent, or Firm—Human Genome Science, Inc.

(57) ABSTRACT

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a Keratinocyte Growth Factor, sometimes hereinafter referred to as "KGF-2" also formerly known as Fibroblast Growth Factor 12 (FGF-12). This invention further relates to the therapeutic use of KGF-2 to promote or accelerate wound healing. This invention also relates to novel mutant forms of KGF-2 that show enhanced activity, increased stability, higher yield or better solubility.

12 Claims, 64 Drawing Sheets

OTHER PUBLICATIONS

Jimenez, P.A., and Rampy, M.A., "Keratinocyte Growth Factor–2 Accelerates Wound Healing in Incisional Wounds," *J. Surg. Res. 81*:238–242, Academic Press, Inc. (Feb. 1999).

NCBI Entrez, GenBank Report, Accession No. U67918, Jimenez, P.A. et al., National Center for Biotechnology Information (Jul. 1997).

Finch, P. W. et al., "Human KGF Is FGF–Related with Properties of a Paracrine Effector of Epithelial Cell Growth," *Science 245*:752–755 (1989).

Hartung, H. et al., "Murine FGF–12 and FGF–13: expression in embryonic nervous sytem, connective tissue and heart," *Mech. Develop. 64*:31–39 (Jun. 1997).

Hartung, H. et al., "Assignment' of Fgf12 to mouse chromosome bands 1681→B3 in situ hybridization," *Cytogenet. Cell Genet. 76*:185–186 (Apr. 1997).

Jimenez, P. et al., "Effect of Topical Keratinocyte Growth Factor–2 on Wound Healing In A Glucocorticoid–Impaired Model," *J. Cutan Pathol. 24*:105 (Feb. 1997).

Jimenez, P.A. et al., "Effect of Keratinocyte Growth Factor–2 on Cell Proliferation In Vivo," *FASEB J. 11*:AS23, Abstract No. 3025 (Apr. 1997).

Kelley, M. J. et al., "Emergence of the keratinocyte growth factor multigene family during the great ape radiation," *Proc. Natl. Acad. USA 89*:9287–9291 (1992).

Mason, I. J. et al., "FGF–7 (keratinocyte growth factor) expression during mouse development suggests roles in myogenesis, forebrain regionalisation and epithelial–mesenchymal interactions," *Mech. Dev. 45*:15–30 (Jan. 1994).

Miyamoto, M. et al., "Molecular Cloning of a Novel Cytokine cDNA Encoding the Ninth Member of the Fibroblast Growth Factor Family, Which Has a Unique Secretion Property," *Mol. Cell. Biol. 13*(7):4251–4259 (1993).

Ron, D. et al., "Expression of Biologically Active Recombinant Keratinocyte Growth Factor," *J. Biol. Chem. 268*(4):2984–2988 (1993).

Yamasaki, M. et al., "Structure and Expression of the Rat mRNA Encoding a Novel Member of the Fibrolast Growth Factor Family," *J. Biol. Chem. 271*:15918–15921 (Jul. 1996).

Yan, G. et al., "Sequence of Rat Keratinocyte Growth Factor (Heparin–Binding Growth Factor Type 7)," *In Vitro Cell. Dev. Biol. 27A*:437–438 (1991).

NCBI Entrez, GenBank Report with Revision History, Accession No. M79878, McCombie, W.R. et al. (1992).

NCBI Entrez, GenBank Report with Revision History, Accession No. T52063, Hillier, L. et al. (Feb. 1995).

NCBI Entrez, GenBank Report with Revision History, Accession No. D46201, Sasaki T. et al. (Aug. 1995).

NCBI Entrez, GenBank Report with Revision History, Accession No. D46420, Sasaki, T. et al. (Aug. 1995).

NCBI Entrez, GenBank Report with Revision History, Accession No. D54216, Fujiwara, T. et al. (Sep. 1995).

NCBI Entrez, GenBank Report with Revision History, Accession No. D68729, Kohara, Y. et al. (Dec. 1995).

NCBI Entrez, GenBank Report with Revision History, Accession No. D69248, Kohara, Y. et al. (Dec. 1995).

NCBI Entrez, GenBank Report with Revision History, Accession No. D65627, Kohara, Y. et al. (Dec. 1995).

NCBI Entrez, GenBank Report with Revision History, Accession No. D66221, Kohara, Y. et al. (Dec. 1995).

NCBI Entrez, GenBank Report with Revision History, Accession No. C02000, Okubo, K. (Jul. 1996).

NCBI Entrez, GenBank Report with Revision History, Accession No. W29377, Marra, M. et al. (Sep. 1996).

NCBI Entrez, GenBank Report with Revision History, Accession No. W32720, Hillier, L. et al. (Oct. 1996).

NCBI Entrez, GenBank Report with Revision History, Accession No. W60824, Hillier, L. et al. (Oct. 1996).

NCBI Entrez, GenBank Report with Revision History, Accession No. T70682, Shen, B. et al. (Oct. 1996).

NCBI Entrez, GenBank Report with Revision History, Accession No. AA094753, Liew, C.C. (Oct. 1996).

NCBI Entrez, GenBank Report with Revision History, Accession No. AA133331, Hillier, L. et al. (Nov. 1996).

NCBI Entrez, GenBank Report with Revision History, Accession No. AA190058, Marra, M. et al. (Jan. 1997).

NCBI Entrez, GenBank Report with Revision History, Accession No. AA018953, Hillier, L. et al. (Jan. 1997).

NCBI Entrez, GenBank Report with Revision History, Accession No. AA240978, Marra, M. et al. (Mar. 1997).

NCBI Entrez, GenBank Report with Revision History, Accession No. AA289560, Marra, M. et al. (Apr. 1997).

NCBI Entrez, GenBank Report with Revision History, Accession No. AA296993, Adams, et al. (Apr. 1997).

NCBI Entrez, GenBank Report with Revision History, Accession No. AA298937, Adams, M.D. et al. (Apr. 1997).

NCBI Entrez, GenBank Report with Revision History, Accession No. AA312184, Adams, M.D. et al. (Apr. 1997).

NCBI Entrez, GenBank Report with Revision History, Accession No. AA312483, Adams, M.D. et al. (Apr. 1997).

NCBI Entrez, GenBank Report with Revision History, Accession No. AA356781, Adams, M.D. et al. (Apr. 1997).

NCBI Entrez, GenBank Report with Revision History, Accession No. AA412789, Marra, M. et al. (May 1997).

NCBI Entrez, GenBank Report with Revision History, Accession No. Marra, M. et al. (Jun. 1997).

NCBI Entrez, GenBank Report with Revision History, Accession No. C38464, Kohara, Y. et al. (Sep. 1997).

NCBI Entrez, GenBank Report with Revision History, Accession No. C56505, Kohara, Y. et al. (Sep. 1997).

NCBI Entrez, GenBank Report with Revision History, Accession No. C57074, Kohara, Y. et al. (Sep. 1997).

NCBI Entrez, GenBank Report with Revision History, Accession No. C58558, Kohara, Y. et al. (Sep. 1997).

NCBI Entrez, GenBank Report with Revision History, Accession No. C58846, Kohara, Y. et al. (Sep. 1997).

NCBI Entrez, GenBank Report with Revision History, Accession No. C59317, Kohara, Y. et al. (Sep. 1997).

NCBI Entrez, GenBank Report with Revision History, Accession No. C59311, Kohara, Y. et al. (Sep. 1997).

NCBI Entrez, GenBank Report with Revision History, Accession No. AA605609, Clark, M. et al. (Sep. 1997).

NCBI Entrez, GenBank Report with Revision History, Accession No. AA621871, NCI–CGAP (Oct. 1997).

NCBI Entrez, GenBank Report with Revision History, Accession No. AA621888, NCI–CGAP (Oct. 1997).

NCBI Entrez, GenBank Report with Revision History, Accession No. AA675470, Marra, M. et al. (Nov. 1997).

NCBI Entrez, GenBank Report with Revision History, Accession No. AA675519, Marra, M. et al. (Nov. 1997).

NCBI Entrez, GenBank Report with Revision History, Accession No. AA838994, Marra, M. et al. (Feb. 1997).

NCBI Entrez, GenBank Report with Revision History, Accession No. H35048, Lee, N.H. et al. (Apr. 1997).

NCBI Entrez, GenBank Report with Revision History, Accession No. AA906051, NCI–CGAP (May 1998).

NCBI Entrez, GenBank Report with Revision History, Accession No. C78836, Ko, M.S.H. et al. (Jun. 1998).

English language translation of JP 7–345689 (Document AP2).

English language translation of JP 8–103240 (Document AL3).

English language translation of JP 8–214378 (Document AL4).

English language translation of WO 97/20929 (Document AO4).

English language translation of JP 10–330283 (Document AO5).

English language translation of JP 10–330284 (Document AP5).

English language translation of JP 10–330285 (Document AL6).

International Search Report for International Application No. PCT/US95/01790, filed Jun. 7, 1995.

* cited by examiner

```
    ATGTGGAAATGGATACTGACACATTGTGCCTCAGCCTTTCCCCACCTGCCCGGCTGCTGC
1   ---------+---------+---------+---------+---------+---------+   60
    TACACCTTTACCTATGACTGTGTAACACGGAGTCGGAAAGGGGTGGACGGGCCGACGACG

M  W  K  W  I  L  T  H  C  A  S  A  F  P  H  L  P  G  C  C

TGCTGCTGCTTTTTGTTGCTGTTCTTGGTGTCTTCCGTCCCTGTCACCTGCCAAGCCCTT
61  ---------+---------+---------+---------+---------+---------+   120
    ACGACGACGAAAAACAACGACAAGAACCACAGAAGGCAGGGACAGTGGACGGTTCGGGAA

C  C  C  F  L  L  L  F  L  V  S  S  V  P  V  T  C  Q  A  L

GGTCAGGACATGGTGTCACCAGAGGCCACCAACTCTTCTTCCTCCTCCTTCTCCTCTCCT
121 ---------+---------+---------+---------+---------+---------+   180
    CCAGTCCTGTACCACAGTGGTCTCCGGTGGTTGAGAAGAAGGAGGAGGAAGAGGAGAGGA

G  Q  D  M  V  S  P  E  A  T  N  S  S  S  S  F  S  S  P

TCCAGCGCGGGAAGGCATGTgCGGAGCTACAATCACCTTCAAGGAGATGTCCGCTGGAGA
181 ---------+---------+---------+---------+---------+---------+   240
    AGGTCGCGCCCTTCCGTACAcGCCTCGATGTTAGTGGAAGTTCCTCTACAGGCGACCTCT

S  S  A  G  R  H  V  R  S  Y  N  H  L  Q  G  D  V  R  W  R
MATCH WITH FIG. 1B
```

FIG.1A

MATCH WITH FIG. 1A

```
      AAGCTATTCTCTTTCACCAAGTACTTTCTCAAGATTGAGAAGAACGGGAAGGTCAGCGGG
241   ---------+---------+---------+---------+---------+---------+   300
      TTCGATAAGAGAAAGTGGTTCATGAAAGAGTTCTAACTCTTCTTGCCCTTCCAGTCGCCC

K  L  F  S  F  T  K  Y  F  L  K  I  E  K  N  G  K  V  S  G

ACCAAGAAGGAGAACTGCCCGTACAGCATCCTGGAGATAACATCAGTAGAAATCGGAGTT
301   ---------+---------+---------+---------+---------+---------+   360
      TGGTTCTTCCTCTTGACGGGCATGTCGTAGGACCTCTATTGTAGTCATCTTTAGCCTCAA

T  K  K  E  N  C  P  Y  S  I  L  E  I  T  S  V  E  I  G  V

GTTGCCGTCAAAGCCATTAACAGCAACTATTACTTAGCCATGAACAAGAAGGGGAAACTC
361   ---------+---------+---------+---------+---------+---------+   420
      CAACGGCAGTTTCGGTAATTGTCGTTGATAATGAATCGGTACTTGTTCTTCCCCTTTGAG

V  A  V  K  A  I  N  S  N  Y  Y  L  A  M  N  K  K  G  K  L

TATGGCTCAAAAGAATTTAACAATGACTGTAAGCTGAAGGAGAGGATAGAGGAAAATGGA
421   ---------+---------+---------+---------+---------+---------+   480
      ATACCGAGTTTTCTTAAATTGTTACTGACATTCGACTTCCTCTCCTATCTCCTTTTACCT

Y  G  S  K  E  F  N  N  D  C  K  L  K  E  R  I  E  E  N  G
```

MATCH WITH FIG. 1C

FIG.1B

MATCH WITH FIG. 1B

```
     TACAATACCTATGCATCATTTAACTGGCAGCATAATGGGAGGCAAATGTATGTGGCATTG
481  ------+---------+---------+---------+---------+---------+  540
     ATGTTATGGATACGTAGTAAATTGACCGTCGTATTACCCTCCGTTTACATACACCGTAAC

Y  N  T  Y  A  S  F  N  W  Q  H  N  G  R  Q  M  Y  V  A  L

AATGGAAAAGGAGCTCCAAGGAGAGGACAGAAAACACGAAGGAAAAACACCTCTGCTCAC
541  ------+---------+---------+---------+---------+---------+  600
     TTACCTTTTCCTCGAGGTTCCTCTCCTGTCTTTTGTGCTTCCTTTTTGTGGAGACGAGTG

N  G  K  G  A  P  R  R  G  Q  K  T  R  R  K  N  T  S  A  H

TTTCTTCCAATGGTGGTACACTCATAG
601  ------+---------+-------     627
     AAAGAAGGTTACCACCATGTGAGTATC

```
        1                                                                   50
FGF4    MS.GPGTAAV  ALLPAVLLAL  LA........  .PWAGRGGAA  APTAPNGTLE
FGF6    MSRGAGRLQG  TLWALVFLGI  LV........  .GMVVPSPAG  TR.ANNTLLD
FGF5    .......MSL  SFLLLLFFSH  LILSAWAHGE  KRLAPKGQPG  PAATDRNPIG
FGF1    ..........  ..........  ..........  ..........  ..........
FGF2    ..........  ..........  ..........  ..........  ..........
FGF9    ..........  ..........  ..........  ..MAPLGEVG  NYFGVQDAVP
FGF7    ..........  ......MHKW  ILTWILPTLL  .....YRSCF  HIICLVGTIS
KGF2    ..........  ......MWKW  ILTHCASAFP  HLPGCCCCCF  LLLFLVSSVP
FGF3    ..........  ..........  ..........  .......MGL  IWLLLLSLLE
FGF8    MGSPRSALSC  LLLHLLVLCL  QAQVRSAAQK  RGPGAGNPAD  TLGQGHEDRP 51                                                                  100
FGF4    AELERRWESL  VALSLARLPV  AA..QPKEAA  VQSGAGDY..  ...LLGIKRL
FGF6    S...RGWGTL  LSRSRAGLAG  EI......AG  VNWESG.Y..  ...LVGIKRQ
FGF5    SSSRQSSSSA  MSSSSASSSP  AASLGSQGSG  LEQSSFQW..  ...SPSGRRT
FGF1    ......MAEG  EITTFTALTE  KFN...LPPG  .......N..  ...YK...KP
FGF2    ......MAAG  SITTLPALPE  DGGSGAFPPG  .......H..  ...FK...DP
FGF9    FGNVPVLPVD  SPVLLSDHLG  QSEAGGLPRG  PAVTDLDH..  ...LKGILRR
FGF7    LACNDMTPEQ  M...ATNVNC  ......SSPE  RHTRSYDY..  ...MEGGDIR
KGF2    VTCQALGQDM  VSPEATNSSS  SSFSSPSSAG  RHVRSYNH..  ...LQ.GDVR
FGF3    PGWPAAGPGA  ..........  ...RLRRDAG  GRGGVYEH..  ...L.GGAPR
FGF8    FGQRSRAGKN  FTNPAPNYPE  EGSKEQRDSV  LPKVTQRHVR  EQSLVTDQLS
```

MATCH WITH FIG. 2B

FIG. 2A

MATCH WITH FIG. 2A

```
       101                                                                    150
FGF4   RRL.....YC NVGIGFHLQA LPDGRIGGAH ADT.RDSLLE LSPVERGV.V
FGF6   RRL.....YC NVGIGFHLQV LPDGRISGTH EEN.PYSLLE ISTVERGV.V
FGF5   GSL.....YC RVGIGFHLQI YPDGKVNGSH EAN.MLSVLE IFAVSQGI.V
FGF1   KLL.....YC SNG.GHFLRI LPDGTVDGTR DRSDQHIQLQ LSAESVGE.V
FGF2   KRL.....YC KNG.GFFLRI HPDGRVDGVR EKSDPHIKLQ LQAEERGV.V
FGF9   RQL.....YC R.T.GFHLEI FPNGTIQGTR KDHSRFGILE FISIAVGL.V
FGF7   VRR.....LF CRT.QWYLRI DKRGKVKGTQ EMKNNYNIME IRTVAVGI.V
KGF2   WRK.....LF SFT.KYFLKI EKNGKVSGTK KENCPYSILE ITSVEIGV.V
FGF3   RRK.....LY CAT.KYHLQL HPSGRVNGSL .ENSAYSILE ITAVEVGI.V
FGF8   RRLIRTYQLY SRTSGKHVQV LANKRINAMA EDGDPFAKLI VETDTFGSRV 151                                                                    200
FGF4   SIFGVASRFF VAMSSKGKLY G.SPFFTDEC TFKEILLPNN YNAYESYKYP
FGF6   SLFGVRSALF VAMNSKGRLY A.TPSFQEEC KFRETLLPNN YNAYESDLYQ
FGF5   GIRGVFSNKF LAMSKKGKLH A.SAKFTDDC KFRERFQENS YNTYASAIHR
FGF1   YIKSTETGQY LAMDTDGLLY G.SQTPNEEC LFLERLEENH YNTYISKKH.
FGF2   SIKGVCANRY LAMKEDGRLL A.SKCVTDEC FFFERLESNN YNTYRSRKY.
FGF9   SIRGVDSGLY LGMNEKGELY G.SEKLTQEC VFREQFEENW YNTYSSNLYK
FGF7   AIKGVESEFY LAMNKEGKLY A.KKECNEDC NFKELILENH YNTYAS....
KGF2   AVKAINSNYY LAMNKKGKLY G.SKEFNNDC KLKERIEENG YNTYAS....
FGF3   AIRGLFSGRY LAMNKRGRLY A.SEHYSAEC EFVERIHELG YNTYASRLYR
FGF8   RVRGAETGLY ICMNKKGKLI AKSNGKGKDC VFTEIVLENN YTALQNAKY.
```

MATCH WITH FIG. 2C

FIG. 2B

MATCH WITH FIG. 2B

```
          201                                                              250
FGF4      ..........  GM......FI  ALSKNGKTKK  G..NRVSPTM  KVTHFLPRL.
FGF6      ..........  GT......YI  ALSKYGRVKR  G..SKVSPIM  TVTHFLPRI.
FGF5      ..........  TEKTGREWYV  ALNKRGKAKR  GCSPRVKPQH  ISTHFLPRFK
FGF1      ..........  ...AEKNWFV  GLKKNGSCKR  G..PRTHYGQ  KAILFLPLPV
FGF2      ..........  ...T..SWYV  ALKRTGQYKL  G..SKTGPGQ  KAILFLPMSA
FGF9      HV........  ..DTGRRYYV  ALNKDGTPRE  G..TRTKRHQ  KFTHFLPRPV
FGF7      .......AKW  THNGGEM.FV  ALNQKGIPVR  G..KKTKKEQ  KTAHFLPMAI
KGF2      .......FNW  QHNGRQM.YV  ALNGKGAPRR  G..QKTRRKN  TSAHFLPMVV
FGF3      TVSSTPGARR  QPSAERLWYV  SVNGKGRPRR  G..FKTRRTQ  KSSLFLPRVL
FGF8      ..........  .....EGWYM  AFTRKGRPRK  G..SKTRQHQ  REVHFMKRLP 251                                                              300
FGF4      ..........  ..........  ..........  ..........  ..........
FGF6      ..........  ..........  ..........  ..........  ..........
FGF5      QSEQPELSFT  VTVPEKKNPP  SPIKSKIPLS  APRKNTNSVK  YRLKFRFG..
FGF1      SSD.......  ..........  ..........  ..........  ..........
FGF2      KS........  ..........  ..........  ..........  ..........
FGF9      DPDKVPELYK  DILSQS....  ..........  ..........  ..........
FGF7      T.........  ..........  ..........  ..........  ..........
KGF2      HS........  ..........  ..........  ..........  ..........
FGF3      DHRDHEMVRQ  LQSGLPRPPG  KGVQPRRRRQ  KQSPDNLEPS  HVQASRLGSQ
FGF8      RGHHTTEQSL  RFEFLNYPPF  TRSLRGSQRT  WAPEPR....  ..........
```

MATCH WITH FIG. 2D

FIG. 2C

MATCH WITH FIG. 2C

301
FGF4    . . . . . .
FGF6    . . . . . .
FGF5    . . . . . .
FGF1    . . . . . .
FGF2    . . . . . .
FGF9    . . . . . .
FGF7    . . . . . .
KGF2    . . . . . .
FGF3    LEASAH
FGF8    . . . . . .

FIG.2D

```
GGAATTCCGG GAAGAGAGGG AAGAAAACAA CGGCGACTGG GCAGCTGCCT CCACTTCTGA      60
CAACTCCAAA GGGATATACT TGTAGAAGTG GCTCGCAGGC TGGGGCTCCG CAGAGAGAGA    120
CCAGAAGGTG CCAACCGCAG AGGGGTGCAG ATATCTCCCC CTATTCCCCA CCCCACCTCC    180
CTTGGGTTTT GTTCACCGTG CTGTCATCTG TTTTTCAGAC CTTTTTGGCA TCTAACATGG    240
TGAAGAAAGG AGTAAAGAAG AGAACAAAGT AACTCCTGGG GGAGCGAAGA GCGCTGGTGA    300
CCAACACCAC CAACGCCACC ACCAGCTCCT GCTGCTGCGG CCACCCACGT CCACCATTTA    360
CCGGGAGGCT CCAGAGGCGT AGGCAGCGGA TCCGAGAAAG GAGCGAGGGG AGTCAGCCGG    420
CTTTTCCGAG GAGTTATGGA TGTTGGTGCA TTCACTTCTG GCCAGATCCG CGCCCAGAGG    480
GAGCTAACCA GCAGCCACCA CCTCGAGCTC TCTCCTTGCC TTGCATCGGG TCTTACCCTT    540
CCAGTATGTT CCTTCTGATG AGACAATTTC CAGTGCCGAG AGTTTCAGTA CA ATG        595
                                                         Met
```

```
TGG AAA TGG ATA CTG ACA CAT TGT GCC TCA GCC TTT CCC CAC CTG CCC     643
Trp Lys Trp Ile Leu Thr His Cys Ala Ser Ala Phe Pro His Leu Pro

GGC TGC TGC TGC TGC TGC TTT TTG TTG CTG TTC TTG GTG TCT TCC GTC     691
Gly Cys Cys Cys Cys Cys Phe Leu Leu Leu Phe Leu Val Ser Ser Val

CCT GTC ACC TGC CAA GCC CTT GGT CAG GAC ATG GTG TCA CCA GAG GCC     739
Pro Val Thr Cys Gln Ala Leu Gly Gln Asp Met Val Ser Pro Glu Ala

ACC AAC TCT TCT TCC TCC TCC TTC TCC TCT CCT TCC AGC GCG GGA AGG     787
Thr Asn Ser Ser Ser Ser Ser Phe Ser Ser Pro Ser Ser Ala Gly Arg

CAT GTG CGG AGC TAC AAT CAC CTT CAA GGA GAT GTC CGC TGG AGA AAG     835
His Val Arg Ser Tyr Asn His Leu Gln Gly Asp Val Arg Trp Arg Lys

CTA TTC TCT TTC ACC AAG TAC TTT CTC AAG ATT GAG AAG AAC GGG AAG     883
Leu Phe Ser Phe Thr Lys Tyr Phe Leu Lys Ile Glu Lys Asn Gly Lys

GTC AGC GGG ACC AAG AAG GAG AAC TGC CCG TAC AGC ATC CTG GAG ATA     931
Val Ser Gly Thr Lys Lys Glu Asn Cys Pro Tyr Ser Ile Leu Glu Ile

ACA TCA GTA GAA ATC GGA GTT GTT GCC GTC AAA GCC ATT AAC AGC AAC     979
Thr Ser Val Glu Ile Gly Val Val Ala Val Lys Ala Ile Asn Ser Asn

TAT TAC TTA GCC ATG AAC AAG AAG GGG AAA CTC TAT GGC TCA AAA GAA    1027
Tyr Tyr Leu Ala Met Asn Lys Lys Gly Lys Leu Tyr Gly Ser Lys Glu

TTT AAC AAT GAC TGT AAG CTG AAG GAG AGG ATA GAG GAA AAT GGA TAC    1075
Phe Asn Asn Asp Cys Lys Leu Lys Glu Arg Ile Glu Glu Asn Gly Tyr
```

FIG.3A

| | |
|---|---|
| AAT ACC TAT GCA TCA TTT AAC TGG CAG CAT AAT GGG AGG CAA ATG TAT<br>Asn Thr Tyr Ala Ser Phe Asn Trp Gln His Asn Gly Arg Gln Met Tyr | 1123 |
| GTG GCA TTG AAT GGA AAA GGA GCT CCA AGG AGA GGA CAG AAA ACA CGA<br>Val Ala Leu Asn Gly Lys Gly Ala Pro Arg Arg Gly Gln Lys Thr Arg | 1171 |
| AGG AAA AAC ACC TCT GCT CAC TTT CTT CCA ATG GTG GTA CAC TCA<br>Arg Lys Asn Thr Ser Ala His Phe Leu Pro Met Val Val His Ser | 1216 |
| TAGAGGAAGG CAACGTTTGT GGATGCAGTA AAACCAATGG CTCTTTTGCC AAGAATAGTG | 1276 |
| GATATTCTTC ATGAAGACAG TAGATTGAAA GGCAAAGACA CGTTGCAGAT GTCTGCTTGC | 1336 |
| TTAAAAGAAA GCCAGCCTTT GAAGGTTTTT GTATTCACTG CTGACATATG ATGTTCTTTT | 1396 |
| AATTAGTTCT GTGTCATGTC TTATAATCAA GATATAGGCA GATCGAATGG GATAGAAGTT | 1456 |
| ATTCCCAAGT GAAAAACATT GTGGCTGGGT TTTTTGTTGT TGTTGTCAAG TTTTTGTTTT | 1516 |
| TAAACCTCTG AGATAGAACT TAAAGGACAT AGAACAATCT GTTGAAAGAA CGATCTTCGG | 1576 |
| GAAAGTTATT TATGGAATAC GAACTCATAT CAAAGACTTC ATTGCTCATT CAAGCCTAAT | 1636 |
| GAATCAATGA ACAGTAATAC GTGCAAGCAT TTACTGGAAA GCACTTGGGT CATATCATAT | 1696 |
| GCACAACCAA AGGAGTTCTG GATGTGGTCT CATGGAATAA TTGAATAGAA TTTAAAAATA | 1756 |
| TAAACATGTT AGTGTGAAAC TGTTCTAACA ATACAAATAG TATGGTATGC TTGTGCATTC | 1816 |
| TGCCTTCATC CCTTTCTATT TCTTTCTAAG TTATTTATTT AATAGGATGT TAAATATCTT | 1876 |
| TTGGGGTTTT AAAGAGTATC TCAGCAGCTG TCTTCTGATT TATCTTTTCT TTTTATTCAG | 1936 |
| CACACCACAT GCATGTTCAC GACAAAGTGT TTTTAAAACT TGGCGAACAC TTCAAAAATA | 1996 |
| GGAGTTGGGA TTAGGGAAGC AGTATGAGTG CCCGTGTGCT ATCAGTTGAC TTAATTTGCA | 2056 |
| CTTCTGCAGT AATAACCATC AACAATAAAT ATGGCAATGC TGTGCCATGG CTTGAGTGAG | 2116 |
| AGATGTCTGC TATCATTTGA AAACATATAT TACTCTCGAG GCTTCCTGTC TCAAGAAATA | 2176 |
| GACCAGAAGG CCAAATTCTT CTCTTTCAAT ACATCAGTTT GCCTCCAAGA ATATACTAAA | 2236 |
| AAAAGGAAAA TTAATTGCTA AATACATTTA AATAGCCTAG CCTCATTATT TACTCATGAT | 2296 |
| TTCTTGCCAA ATGTCATGGC GGTAAAGAGG CTGTCCACAT CTCTAAAAAC CCTCTGTAAA | 2356 |
| TTCCACATAA TGCATCTTTC CCAAAGGAAC TATAAAGAAT TTGGTATGAA GCGCAACTCT | 2416 |

FIG.3B

```
CCCAGGGGCT TAAACTGAGC AAATCAAATA TATACTGGTA TATGTGTAAC CATATACAAA    2476
AACCTGTTCT AGCTGTATGA TCTAGTCTTT ACAAAACCAA ATAAAACTTG TTTTCTGTAA    2536
ATTTAAAGAG CTTTACAAGG TTCCATAATG TAACCATATC AAAATTCATT TTGTTAGAGC    2596
ACGTATAGAA AAGAGTACAT AAGAGTTTAC CAATCATCAT CACATTGTAT TCCACTAAAT    2656
AAATACATAA GCCTTATTTG CAGTGTCTGT AGTGATTTTA AAAATGTAGA AAAATACTAT    2716
TTGTTCTAAA TACTTTTAAG CAATAACTAT AATAGTATAT TGATGCTGCA GTTTTATCTT    2776
CATATTTCTT GTTTTGAAAA AGCATTTTAT TGTTTGGACA CAGTATTTTG GTACAAAAAA    2836
AAAGACTCAC TAAATGTGTC TTACTAAAGT TTAACCTTTG GAAATGCTGG CGTTCTGTGA    2896
TTCTCCAACA AACTTATTTG TGTCAATACT TAACCAGCAC TTCCAGTTAA TCTGTTATTT    2956
TTAAAAATTG CTTTATTAAG AAATTTTTTG TATAATCCCA TAAAAGGTCA TATTTTTCCC    3016
ATTCTTCAAA AAAACTGTAT TTCAGAAGAA ACACATTTGA GGCACTGTCT TTTGGCTTAT    3076
AGTTTAAATT GCATTTCATC ATACTTTGCT TCCAACTTGC TTTTTGGCAA ATGAGATTAT    3136
AAAAATGTTT AATTTTTGTG GTTGGAATCT GGATGTTAAA ATTTAATTGG TAACTCAGTC    3196
TGTGAGCTAT AATGTAATGC ATTCCTATCC AAACTAGGTA TCTTTTTTTC CTTTATGTTG    3256
AAATAATAAT GGCACCTGAC ACATAGACAT AGACCACCCA CAACCTAAAT TAAATGTTTG    3316
GTAAGACAAA TACACATTGG ATGACCACAG TAACAGCAAA CAGGGCACAA ACTGGATTCT    3376
TATTTCACAT AGACATTTAG ATTACTAAAG AGGGCTATGT GTAAACAGTC ATCATTATAG    3436
TACTCAAGAC ACTAAAACAG CTTCTAGCCA AATATATTAA AGCTTGCAGA GGCCAAAAAT    3496
AGAAAACATC TCCCCTGTCT CTCCCACATT TCCCTCACAG AAAGACAAAA AACCTGCCTG    3556
GTGCAGTAGC TCACACCTGT AATCCCAGCA GTTTGGGAGA CTGTGGGAAG ATGGCTTGAG    3616
TCCAGGAGTT CTAGACAGGC CTGAGAAACC TAGTGAGACA TCCTTCTCTT AAACAAAACA    3676
AAACAAAACA AATGTAGCCA TGCGTGGTGG CATATACCTG TGGTCCCAAC TACTCAGGAG    3736
GCTGAAACGG AAGGATCTCT TGGGCCCCAG GAGTTTGAGG CTGCAGTGAG CTATAATCTT    3796
GCCATTGCAC TCCAGCCTGG GTGAAAAAGA GCCAGAAAGA AAGGAAAGAG AGAAAAGAGA    3856
AAAGAAAGAG AGAAAAGACA GAAAGACAGG AAGGAAGGAA GGAAGGAAGG AAGGAAGGAA    3916
GGAAGCAAGG AAAGAAGGAA GGAAGGAAAG AAGGGAGGGA AGGAAGGAGA GAGAAAGAAA    3976
GATTGTTTGG TAAGGAGTAA TGACATTCTC TTGCATTTAA AAGTGGCATA TTTGCTTGAA    4036
```

FIG.3C

```
ATGGAAATAG AATTCTGGTC CCTTTTGCAA CTACTGAAGA AAAAAAAAAG CAGTTTCAGC    4096
CCTGAATGTT GTAGATTTGA AAAAAAAAAA AAAAAAACTC GAGGGGGGGC CCGTACCCAA    4156
TTCGCCCTAT AGTGAGTCGT A                                              4177
```

FIG.3D

ATGAGAGGATCGCATCACCATCACCATCACGGATCCTGCCAGGCTCTGGGTC
AGGACATGGTTTCTCCGGAAGCTACCAACTCTTCCTCTTCCTCTTTCTCTTCCC
CGTCTTCCGCTGGTCGTCACGTTCGTTCTTACAACCACCTGCAGGGTGACGTTC
GTTGGCGTAAACTGTTCTCTTTCACCAAATACTTCCTGAAAATCGAAAAA
AACGGTAAAGTTTCTGGGACCAAGAAGGAGAACTGCCCGTACAGCATCCTG
GAGATAACATCAGTAGAAATCGGAGTTGTTGCCGTCAAAGCCATTAACAG
CAACTATTACTTAGCCATGAACAAGAAGGGGAAACTCTATGGCTCAAAAG
AATTTAACAATGACTGTAAGCTGAAGGAGAGGATAGAGGAAAATGGAT
ACAATACCTATGCATCATTTAACTGGCAGCATAATGGGAGGCAAATGTAT
GTGGCATTGAaTGGAAAAGGAGCTCCAaGGAGAGGACAGAAAACACGAAG
GAAAAACACCTCTGCTCACTTTCTTCCAATGGTGGTACACTCATAG

MRGSHHHHHHGSCQALGQDMVSPEATNSSSSSFSSPSSAGRHVRSYNHLQGD
VRWRKLFSFTKYFLKIEKNGKVSGTKKENCPYSILEITSVEIGVVAVKAINSN
YYLAMNKKGKLYGSKEFNNDCKLKERIEENGYNTYASFNWQHNGRQMYVA
LNGKGAPRRGQKTRRKNTSAHFLPMVVHS kgf-2 synthetic cys37 Bam HI
AAAGGATCCTGCCAGGCTCTGGGTCAGGACATG

FIG.15

```
ATGTGGAAATGGATACTGACCCACTGCGCTTCTGCTTTCCCGCACCTGCCGGGTTGCTGC  60
Met Trp Lys Trp Ile Leu Thr His Cys Ala Ser Ala Phe Pro His Leu Pro Gly Cys Cys

TGCTGCTGCTTCCTGCTGCTGTTCCTGGTTTCTTCTGTTCCGGTTACCTGCCAGGCTCTG 120
Cys Cys Cys Phe Leu Leu Leu Phe Leu Val Ser Ser Val Pro Val Thr Cys Gln Ala Leu

GGTCAGGACATGGTTTCTCCGGAAGCTACCAACTCTTCCTCTTCCTCTTTCTCTTCCCCG 180
Gly Gln Asp Met Val Ser Pro Glu Ala Thr Asn Ser Ser Ser Ser Ser Phe Ser Ser Pro

ACTTCCGCTGGTCGTCACGTTCGTTCTTACAACCACCTGCAGGGTGACGTTCGTTGGCGT 240
Thr Ser Ala Gly Arg His Val Arg Ser Tyr Asn His Leu Gln Gly Asp Val Arg Trp Arg

AAACTGTTCTCTTTCACCAAATACTTCCTGAAAATCGAAAAAAACGGTAAAGTTTCTGGG 300
Lys Leu Phe Ser Phe Thr Lys Tyr Phe Leu Lys Ile Glu Lys Asn Gly Lys Val Ser Gly

ACCAAGAAGGAGAACTGCCCGTACAGCATCCTGGAGATAACATCAGTAGAAATCGGAGTT 360
Thr Lys Lys Glu Asn Cys Pro Tyr Ser Ile Leu Glu Ile Thr Ser Val Glu Ile Gly Val

GTTGCCGTCAAAGCCATTAACAGCAACTATTACTTAGCCATGAACAAGAAGGGGAAACTC 420
Val Ala Val Lys Ala Ile Asn Ser Asn Tyr Tyr Leu Ala Met Asn Lys Lys Gly Lys Leu

TATGGCTCAAAAGAATTTAACAATGACTGTAAGCTGAAGGAGAGGATAGAGGAAAATGGA 480
Tyr Gly Ser Lys Glu Phe Asn Asn Asp Cys Lys Leu Lys Glu Arg Ile Glu Glu Asn Gly

TACAATACCTATGCATCATTTAACTGGCAGCATAATGGGAGGCAAATGTATGTGGCATTG 540
Tyr Asn Thr Tyr Ala Ser Phe Asn Trp Gln His Asn Gly Arg Gln Met Tyr Val Ala Leu

AATGGAAAAGGAGCTCCAAGGAGAGGACAGAAAACACGAAGGAAAAACACCTCTGCTCAC 600
Asn Gly Lys Gly Ala Pro Arg Arg Gly Gln Lys Thr Arg Arg Lys Asn Thr Ser Ala His

TTTCTTCCAATGGTGGTACACTCATAG 627
Phe Leu Pro Met Val Val His Ser *
```

FIG.23

```
ATGACCTGCCAGGCTCTGGGTCAGGACATGGTTTCTCCGGAAGCTACCAACTCTTCCTCT    60
MetThrCysGlnAlaLeuGlyGlnAspMetValSerProGluAlaThrAsnSerSerSer

TCCTCTTTCTCTTCCCCGTCTTCCGCTGGTCGTCACGTTCGTTCTTACAACCACCTGCAG   120
SerSerPheSerSerProSerSerAlaGlyArgHisValArgSerTyrAsnHisLeuGln

GGTGACGTTCGTTGGCGTAAACTGTTCTCTTTCACCAAATACTTCCTGAAAATCGAAAAA   180
GlyAspValArgTrpArgLysLeuPheSerPheThrLysTyrPheLeuLysIleGluLys

AACGGTAAAGTTTCTGGGACCAAGAAGGAGAACTGCCCGTACAGCATCCTGGAGATAACA   240
AsnGlyLysValSerGlyThrLysLysGluAsnCysProTyrSerIleLeuGluIleThr

TCAGTAGAAATCGGAGTTGTTGCCGTCAAAGCCATTAACAGCAACTATTACTTAGCCATG   300
SerValGluIleGlyValValAlaValLysAlaIleAsnSerAsnTyrTyrLeuAlaMet

AACAAGAAGGGGAAACTCTATGGCTCAAAAGAATTTAACAATGACTGTAAGCTGAAGGAG   360
AsnLysLysGlyLysLeuTyrGlySerLysGluPheAsnAsnAspCysLysLeuLysGlu

AGGATAGAGGAAAATGGATACAATACCTATGCATCATTTAACTGGCAGCATAATGGGAGG   420
ArgIleGluGluAsnGlyTyrAsnThrTyrAlaSerPheAsnTrpGlnHisAsnGlyArg

CAAATGTATGTGGCATTGAATGGAAAAGGAGCTCCAAGGAGAGGACAGAAAACACGAAGG   480
GlnMetTyrValAlaLeuAsnGlyLysGlyAlaProArgArgGlyGlnLysThrArgArg

AAAAACACCTCTGCTCACTTTCTTCCAATGGTGGTACACTCATAG   525
LysAsnThrSerAlaHisPheLeuProMetValValHisSer *
```

FIG.24A

```
ATGACTTGCCAGGCACTGGGTCAAGACATGGTTTCCCCGGAAGCTACCAACAGCTCCAGCTCTAGCTTCA
|++++|++++|++++|++++|++++|++++|++++|++++|++++|++++|++++|++++|++++|++++|- 70
TACTGAACGGTCCGTGACCCAGTTCTGTACCAAAGGGGCCTTCGATGGTTGTCGAGGTCGAGATCGAAGT
  M  T  C  Q  A  L  G  Q  D  M  V  S  P  E  A  T  N  S  S  S  S  F

GCAGCCCATCTAGCGCAGGTCGTCACGTTCGCTCTTACAACCACTTACAGGGTGATGTTCGTTGGCGCAA
|++++|++++|++++|++++|++++|++++|++++|++++|++++|++++|++++|++++|++++|++++|- 140
CGTCGGGTAGATCGCGTCCAGCAGTGCAAGCGAGAATGTTGGTGAATGTCCCACTACAAGCAACCGCGTT
  S  S  P  S  S  A  G  R  H  V  R  S  Y  N  H  L  Q  G  D  V  R  W  R  K

ACTGTTCAGCTTTACCAAGTACTTCCTGAAAATCGAAAAAAACGGTAAAGTTTCTGGGACCAAGAAGGAG
|++++|++++|++++|++++|++++|++++|++++|++++|++++|++++|++++|++++|++++|++++|- 210
TGACAAGTCGAAATGGTTCATGAAGGACTTTTAGCTTTTTTTGCCATTTCAAAGACCCTGGTTCTTCCTC
   L  F  S  F  T  K  Y  F  L  K  I  E  K  N  G  K  V  S  G  T  K  K  E

AACTGCCCGTACAGCATCCTGGAGATAACATCAGTAGAAATCGGAGTTGTTGCCGTCAAAGCCATTAACA
|++++|++++|++++|++++|++++|++++|++++|++++|++++|++++|++++|++++|++++|++++|- 280
TTGACGGGCATGTCGTAGGACCTCTATTGTAGTCATCTTTAGCCTCAACAACGGCAGTTTCGGTAATTGT
   N  C  P  Y  S  I  L  E  I  T  S  V  E  I  G  V  V  A  V  K  A  I  N

GCAACTATTACTTAGCCATGAACAAGAAGGGGAAACTCTATGGCTCAAAAGAATTTAACAATGACTGTAA
|++++|++++|++++|++++|++++|++++|++++|++++|++++|++++|++++|++++|++++|++++|- 350
CGTTGATAATGAATCGGTACTTGTTCTTCCCCTTTGAGATACCGAGTTTTCTTAAATTGTTACTGACATT
   S  N  Y  Y  L  A  M  N  K  K  G  K  L  Y  G  S  K  E  F  N  N  D  C  K

GCTGAAGGAGAGGATAGAGGAAAATGGATACAATACCTATGCATCATTTAACTGGCAGCATAATGGGAGG
|++++|++++|++++|++++|++++|++++|++++|++++|++++|++++|++++|++++|++++|++++|- 420
CGACTTCCTCTCCTATCTCCTTTTACCTATGTTATGGATACGTAGTAAATTGACCGTCGTATTACCCTCC
   L  K  E  R  I  E  E  N  G  Y  N  T  Y  A  S  F  N  W  Q  H  N  G  R

CAAATGTATGTGGCATTGAATGGAAAAGGAGCTCCAAGGAGAGGACAGAAAAACACGAAGGAAAAACACCT
|++++|++++|++++|++++|++++|++++|++++|++++|++++|++++|++++|++++|++++|++++|- 490
GTTTACATACACCGTAACTTACCTTTTCCTCGAGGTTCCTCTCCTGTCTTTTGTGCTTCCTTTTTGTGGA
   Q  M  Y  V  A  L  N  G  K  G  A  P  R  R  G  Q  K  T  R  R  K  N  T

CTGCTCACTTTCTTCCAATGGTGGTACACTCATAG
|++++|++++|++++|++++|++++|++++|++++▶ 525
GACGAGTGAAAGAAGGTTACCACCATGTGAGTATC
   S  A  H  F  L  P  M  V  V  H  S
                                   ▶
```

FIG.24B

ATGACCTGCCAGGCTCTGGGTCAGGACATGGTTTCTCCGGAAGCTACCAACTCTTCC
TCTTCCTCTTTCTCTTCCCCGTCTTCCGCTGGTCGTCACGTTCGTTCTTACAACCAC
CTGCAGGGTGACGTTCGTTGGCGTAAACTGTTCTCTTTCACCAAATACTTCCTGAAA
ATCGAAAAAAACGGTAAAGTTTCTGGGACCAAGAAGGAGAACTGCCCGTACAGCATC
CTGGAGATAACATCAGTAGAAATCGGAGTTGTTGCCGTCAAAGCCATTAACAGCAAC
TATTACTTAGCCATGAACAAGAAGGGGAAACTCTATGGCTCAAAAGAATTTAACAAT
GACTGTAAGCTGAAGGAGAGGATAGAGGAAAATGGATACAATACCTATGCATCATTT
AACTGGCAGCATAATGGGAGGCAAATGTATGTGGCATTGAATGGAAAAGGAGCTCCA
AGGAGAGGACAGAAAACACGAAGGAAAAACACCTCTGCTCACTTTCTTCCAATGGTG
GTACACTCATAG

MTCQALGQDMVSPEATNSSSSSFSSPSSAGRHVRSYNHLQGDVRWRKLFSFTKYFLKIE
KNGKVSGTKKENCPYSILEITSVEIGVVAVKAINSNYYLAMNKKGKLYGSKEFNNDCKL
KERIEENGYNTYASFNWQHNGRQMYVALNGKGAPRRGQKTRRKNTSAHFLPMVVHS.

FIG.25

ATGGCTGGTCGTCACGTTCGTTCTTACAACCACCTGCAGGGTGACGTTCGTTGGCGT
AAACTGTTCTCTTTCACCAAATACTTCCTGAAAATCGAAAAAAACGGTAAAGTTTCT
GGGACCAAGAAGGAGAACTGCCCGTACAGCATCCTGGAGATAACATCAGTAGAAATC
GGAGTTGTTGCCGTCAAAGCCATTAACAGCAACTATTACTTAGCCATGAACAAGAAG
GGGAAACTCTATGGCTCAAAAGAATTTAACAATGACTGTAAGCTGAAGGAGAGGATA
GAGGAAAATGGATACAATACCTATGCATCATTTAACTGGCAGCATAATGGGAGGCAA
ATGTATGTGGCATTGAATGGAAAAGGAGCTCCAAGGAGAGGACAGAAAACACGAAGG
AAAAACACCTCTGCTCACTTTCTTCCAATGGTGGTACACTCATAG

MAGRHVRSYNHLQGDVRWRKLFSFTKYFLKIEKNGKVSGTKKENCPYSILEITSVEIGV
VAVKAINSNYYLAMNKKGKLYGSKEFNNDCKLKERIEENGYNTYASFNWQHNGRQMYVA
LNGKGAPRRGQKTRRKNTSAHFLPMVVHS.

FIG.26

ATGGTTCGTTGGCGTAAACTGTTCTCTTTCACCAAATACTTCCTGAAAATCGAAAAA
AACGGTAAAGTTTCTGGGACCAAGAAGGAGAACTGCCCGTACAGCATCCTGGAGATA
ACATCAGTAGAAATCGGAGTTGTTGCCGTCAAAGCCATTAACAGCAACTATTACTTA
GCCATGAACAAGAAGGGGAAACTCTATGGCTCAAAAGAATTTAACAATGACTGTAAG
CTGAAGGAGAGGATAGAGGAAAATGGATACAATACCTATGCATCATTTAACTGGCAG
CATAATGGGAGGCAAATGTATGTGGCATTGAATGGAAAAGGAGCTCCAAGGAGAGGA
CAGAAAACACGAAGGAAAAACACCTCTGCTCACTTTCTTCCAATGGTGGTACACTCA
TAG

MVRWRKLFSFTKYFLKIEKNGKVSGTKKENCPYSILEITSVEIGVVAVKAINSNYYLAM
NKKGKLYGSKEFNNDCKLKERIEENGYNTYASFNWQHNGRQMYVALNGKGAPRRGQKTR
RKNTSAHFLPMVVHS.

FIG.27

ATGGAAAAAAACGGTAAAGTTTCTGGGACCAAGAAGGAGAACTGCCCGTACAGCAT
CCTGGAGATAACATCAGTAGAAATCGGAGTTGTTGCCGTCAAAGCCATTAACAGCA
ACTATTACTTAGCCATGAACAAGAAGGGGAAACTCTATGGCTCAAAAGAATTTAAC
AATGACTGTAAGCTGAAGGAGAGGATAGAGGAAAATGGATACAATACCTATGCATC
ATTTAACTGGCAGCATAATGGGAGGCAAATGTATGTGGCATTGAATGGAAAAGGAG
CTCCAAGGAGAGGACAGAAAACACGAAGGAAAAACACCTCTGCTCACTTTCTTCCA
ATGGTGGTACACTCATAG

MEKNGKVSGTKKENCPYSILEITSVEIGVVAVKAINSNYYLAMNKKGKLYGSKEFNNDC
KLKERIEENGYNTYASFNWQHNGRQMYVALNGKGAPRRGQKTRRKNTSAHFLPMVVH
S.

FIG.28

ATGGAGAACTGCCCGTACAGCATCCTGGAGATAACATCAGTAGAAATCGGAGTTGT
TGCCGTCAAAGCCATTAACAGCAACTATTACTTAGCCATGAACAAGAAGGGGAAAC
TCTATGGCTCAAAAGAATTTAACAATGACTGTAAGCTGAAGGAGAGGATAGAGGAA
AATGGATACAATACCTATGCATCATTTAACTGGCAGCATAATGGGAGGCAAATGTA
TGTGGCATTGAATGGAAAAGGAGCTCCAAGGAGAGGACAGAAAACACGAAGGAAAA
ACACCTCTGCTCACTTTCTTCCAATGGTGGTACACTCATAG

MENCPYSILEITSVEIGVVAVKAINSNYYLAMNKKGKLYGSKEFNNDCKLKERIEENGY
NTYASFNWQHNGRQMYVALNGKGAPRRGQKTRRKNTSAHFLPMVVHS.

FIG.29

ATGGTCAAAGCCATTAACAGCAACTATTACTTAGCCATGAACAAGAAGGGGAAACT
CTATGGCTCAAAAGAATTTAACAATGACTGTAAGCTGAAGGAGAGGATAGAGGAAA
ATGGATACAATACCTATGCATCATTTAACTGGCAGCATAATGGGAGGCAAATGTAT
GTGGCATTGAATGGAAAAGGAGCTCCAAGGAGAGGACAGAAAACACGAAGGAAAAA
CACCTCTGCTCACTTTCTTCCAATGGTGGTACACTCATAG

MVKAINSNYYLAMNKKGKLYGSKEFNNDCKLKERIEENGYNTYASFNWQHNGRQMY
VALNGKGAPRRGQKTRRKNTSAHFLPMVVHS.

FIG.30

ATGGGGAAACTCTATGGCTCAAAAGAATTTAACAATGACTGTAAGCTGAAGGAGAG
GATAGAGGAAAATGGATACAATACCTATGCATCATTTAACTGGCAGCATAATGGGA
GGCAAATGTATGTGGCATTGAATGGAAAAGGAGCTCCAAGGAGAGGACAGAAAACA
CGAAGGAAAAACACCTCTGCTCACTTTCTTCCAATGGTGGTACACTCATAG

MGKLYGSKEFNNDCKLKERIEENGYNTYASFNWQHNGRQMYVALNGKGAPRRGQKT
RRKNTSAHFLPMVVHS.

FIG.31

ATGACCTGCCAGGCTCTGGGTCAGGACATGGTTTCTCCGGAAGCTACCAACTCTTCC
TCTTCCTCTTTCTCTTCCCCGTCTTCCGCTGGTCGTCACGTTCGTTCTTACAACCAC
CTGCAGGGTGACGTTCGTTGGCGTAAACTGTTCTCTTTCACCAAATACTTCCTGAAA
ATCGAAAAAAACGGTAAAGTTTCTGGGACCAAGAAGGAGAACTGCCCGTACAGCATC
CTGGAGATAACATCAGTAGAAATCGGAGTTGTTGCCGTCAAAGCCATTAACAGCAAC
TATTACTTAGCCATGAACAAGAAGGGGAAACTCTATGGCTCAAAAGAATTTAACAAT
GACTGTAAGCTGAAG

MTCQALGQDMVSPEATNSSSSSFSSPSSAGRHVRSYNHLQGDVRWRKLFSFTKYFLKIE
KNGKVSGTKKENCPYSILEITSVEIGVVAVKAINSNYYLAMNKKGKLYGSKEFNNDCKL
K

FIG.32

ATGGCTGGTCGTCACGTTCGTTCTTACAACCACCTGCAGGGTGACGTTCGTTGGCGT
AAACTGTTCTCTTTCACCAAATACTTCCTGAAAATCGAAAAAAACGGTAAAGTTTCT
GGGACCAAGAAGGAGAACTGCCCGTACAGCATCCTGGAGATAACATCAGTAGAAATC
GGAGTTGTTGCCGTCAAAGCCATTAACAGCAACTATTACTTAGCCATGAACAAGAAG
GGGAAACTCTATGGCTCAAAAGAATTTAACAATGACTGTAAGCTGAAG

MAGRHVRSYNHLQGDVRWRKLFSFTKYFLKIEKNGKVSGTKKENCPYSILEITSVEIGV
VAVKAINSNYYLAMNKKGKLYGSKEFNNDCKLK

FIG.33

C-37 To Ser

ATGACCTCTCAGGCTCTGGGTCAGGACATGGTTTCTCCGGAAGCTACCAACTCTTCC
TCTTCCTCTTTCTCTTCCCCGTCTTCCGCTGGTCGTCACGTTCGTTCTTACAACCAC
CTGCAGGGTGACGTTCGTTGGCGTAAACTGTTCTCTTTCACCAAATACTTCCTGAAA
ATCGAAAAAACGGTAAAGTTTCTGGGACCAAGAAGGAGAACTGCCCGTACAGCATC
CTGGAGATAACATCAGTAGAAATCGGAGTTGTTGCCGTCAAAGCCATTAACAGCAAC
TATTACTTAGCCATGAACAAGAAGGGGAAACTCTATGGCTCAAAAGAATTTAACAAT
GACTGTAAGCTGAAGGAGAGGATAGAGGAAAATGGATACAATACCTATGCATCATTT
AACTGGCAGCATAATGGGAGGCAAATGTATGTGGCATTGAATGGAAAAGGAGCTCCA
AGGAGAGGACAGAAAACACGAAGGAAAAACACCTCTGCTCACTTTCTTCCAATGGTG
GTACACTCATAG

FIG. 34

C-106 To Ser

ATGACCTGCCAGGCTCTGGGTCAGGACATGGTTTCTCCGGAAGCTACCAACTCTTCC
TCTTCCTCTTTCTCTTCCCCGTCTTCCGCTGGTCGTCACGTTCGTTCTTACAACCAC
CTGCAGGGTGACGTTCGTTGGCGTAAACTGTTCTCTTTCACCAAATACTTCCTGAAA
ATCGAAAAAACGGTAAAGTTTCTGGGACCAAGAAGGAGAACTCTCCGTACAGCATC
CTGGAGATAACATCAGTAGAAATCGGAGTTGTTGCCGTCAAAGCCATTAACAGCAAC
TATTACTTAGCCATGAACAAGAAGGGGAAACTCTATGGCTCAAAAGAATTTAACAAT
GACTGTAAGCTGAAGGAGAGGATAGAGGAAAATGGATACAATACCTATGCATCATTT
AACTGGCAGCATAATGGGAGGCAAATGTATGTGGCATTGAATGGAAAAGGAGCTCCA
AGGAGAGGACAGAAAACACGAAGGAAAAACACCTCTGCTCACTTTCTTCCAATGGTG
GTACACTCATAG

FIG. 35

EFFECT OF KGF-2 Δ33 ON NORMAL WOUND HEALING RAT MODEL

| TREATMENT GROUPS | WOUND SIZE (mm) | % WOUND CLOSURE | HISTOLOGICAL SCORE | RE-EPITH. (μm) | BrdU SCORE |
|---|---|---|---|---|---|
| NO TREATMENT | 25.9±2.5 | 58.8±3.7 | 6.8±0.2 | 1142±141 | 3.8±0.4 |
| BUFFER | 25.1±1.7 | 60.2±2.6 | 6.4±0.2 | 923±61 | 5.0±0.4 |
| KGF-2/Δ33 (0.1μg) | 22.0±0.9 | 65±1.4 | 6.8±0.2 | 1275±148 | 4.6±0.7 |
| KGF-2/Δ33 (0.4μg) | 21.1±1.4 | 68.4±2.4 | 8.0±0.5* p=0.0445 | 1310±182 | 4.2±0.7 |
| KGF-2/Δ33 (1.0μg) | 19.9±1.5 | 66.2±2.1 | 8.4±0.4 p=0.0159* p=0.0053† | 1389±115 p=0.0074† | 3.3±0.25 p=0.0217† |
| KGF-2/Δ33 (4.0μg) | 18.1±1.6 p=0.0398* p=0.0200† | 71.2±2.6 p=0.0367* p=0.0217† | 8.5±0.3 p=0.0047* p=0.0445† | 1220±89 p=0.0254† | 5.3±0.9 |

FIG.37

```
                                    -35         Operator 1
1   AAGCTTAAAAAACTGCAAAAAATAGT TTGACT TGTGAGCGGATAACAAT -10               Operator 2
50   TAAGAT GTACCCA ATTGTGAGCGGATAACAAT TCACACATTAA

S/D
94   A GAGGAG AAATTA CATATG
```

FIG. 51

KERATINOCYTE GROWTH FACTOR-2

The present application is a continuation of Ser. No. 09/023,082, filed Feb. 13, 1998 now U.S. Pat No. 6,077,692; said Ser. No. 09/023,082 claims benefit of the filing dates of provisional applications 60/055,561, filed Aug. 13, 1997 and 60/039,045, filed Feb. 28, 1997; said Ser. No. 09/023,082 is a continuation-in-part of Ser. No. 08/910,875, filed Aug. 13, 1997, now abandoned; said Ser. No. 08/910,875 claims benefit of the filing date of provisional application No. 60/023,852, filed Aug. 13, 1996; said Ser. No. 09/023,082 is also a continuation-in-part of Ser. No. 08/862,432, filed May 23, 1997, now abandoned; said Ser. No. 08/862,432 is a divisional of Ser. No. 08/461,195, filed Jun. 5, 1995, now abandoned; said Ser. No. 08/461,195 is a continuation-in-part of PCT/US95/01790, filed Feb. 14, 1995; the disclosures of all of which are herein incorporated by reference.

FIELD OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a Keratinocyte Growth Factor, sometimes hereinafter referred to as "KGF-2" also formerly known as Fibroblast Growth Factor 12 (FGF-12). This invention further relates to the therapeutic use of KGF-2 to promote or accelerate wound healing. This invention also relates to novel mutant forms of KGF-2 that show enhanced activity, increased stability, higher yield or better solubility. In addition, this invention relates to a method of purifying the KGF-2 polypeptide.

BACKGROUND OF THE INVENTION

The fibroblast growth factor family has emerged as a large family of growth factors involved in soft-tissue growth and regeneratior. It presently includes several members that share a varying degree of homology it the protein level, and that, with one exception, appear to have a similar broad mitogenic spectrum, i.e., they promote the proliferation of a variety of cells of mesodermal and neuroectodermal origin and/or promote angiogenesis.

The pattern of expression of the different members of the family is very different, ranging from extremely restricted expressions of some stages of development, to rather ubiquitous expression in a variety of tissues and organs. All the members appear to bind heparin and heparin sulfate proteoglycans and glycosaminoglycans and strongly concentrate in the extracellular matrix. KGF was originally identified as a member of the FGF family by sequence homology or factor purification and cloning. Keratinocyte growth factor (KGF) was isolated as a mitogen for a cultured murine keratinocyte line (Rubin, J. S. et al., *Proc. Natl. Acad. Sci. USA* 86:802–806 (1989)). Unlike the other members of the FGF family, it has little activity on mesenchyme-derived cells but stimulates the growth of epithelial cells. The Keratinocyte growth factor gene encodes a 194-amino acid polypeptide (Finch, P. W. et al., *Science* 245:752–755 (1989)). The N-terminal 64 amino acids are unique, but the remainder of the protein has about 30% homology to bFGF. KGF is the most divergent member of the FGF family. The molecule has a hydrophobic signal sequence and is efficiently secreted. Post-translational modifications include cleavage of the signal sequence and N-linked glycosylation at one site, resulting in a protein of 28 kDa. Keratinocyte growth factor is produced by fibroblast derived from skin and fetal lung (Rubin et al. (1989)). The Keratinocyte growth factor mRNA was found to be expressed in adult kidney, colon and ilium, but not in brain or lung (Finch, P. W. et al. *Science* 245:752–755 (1989)). KGF displays the conserved regions within the FGF protein family. KGF binds to the FGF-2 receptor with high affinity.

Impaired wound healing is a significant source of morbidity and may result in such complications as dehiscence, anastomotic breakdown and, non-healing wounds. In the normal individual, wound healing, is achieved uncomplicated. In contrast, impaired healing is associated with several conditions such as diabetes, infection, immunosuppression, obesity and malnutrition (Cruse, P. J. and Foord, R., *Arch. Surg.* 107:206 (1973); Schrock, T. R. et al., *Ann. Surg.* 177:513 (1973); Poole, G. U., Jr., *Surgery* 97:631 (1985); Irvin, G. L. et al., *Am. Surg.* 51:418 (1985)).

Wound repair is the result of complex interactions and biologic processes. Three phases have been described in normal wound healing: acute inflammatory phase, extracellular matrix and collagen synthesis, and remodeling (Peacock, E. E., Jr., *Wound Repair*, 2nd edition, W B Saunders, Philadelphia (1984)). The process involves the interaction of keratinocytes, fibroblasts arid inflammatory cells at the wound site.

Tissue regeneration appears to be controlled by specific peptide factors which regulate the migration and proliferation of cells involved in the repair process (Barrett, T. B. et al., *Proc. Natl. Acad. Sci. USA* 81:6772–6774 (1985); Collins, T. et al., *Nature* 316:748–750 (1985)). Thus, growth factors may be promising therapeutics in the treatment of wounds, burns and other skin disorders (Rifkin, D. B. and Moscatelli, *J. Cell. Biol.* 109:1–6 (1989); Spori, M. B. et al., *J. Cell. Biol.* 105:1039–1045 (1987); Pierce, G. F. et al., *J. Cell. Biochem.* 45;319–326 (1991)). The sequence of the healing process is initiated during an acute inflammatory phase with the deposition of provisional tissue. This is followed by re-epithelialization, collagen synthesis and deposition, fibroblast proliferation, and neovascularization, all of which ultimately define the remodeling phase (Clark, R. A. F., *J. Am. Acad. Dermatol.* 13:701 (1985)). These events are influenced by growth factors and cytokines secreted by inflammatory cells or by the cells localized at the edges of the wound (Assoian, R. K. et al., *Nature (Lond.)* 309:804 (1984); Nemeth, G. G. et al., "Growth Factors and Their Role in Wound and Fracture Healing," *Growth Factors and Other Aspects of Wound Healing in Biological and Clinical Implications*, New York (1988), pp. 1–17.

Several polypeptide growth factors have been identified as being involved in wound healing, including keratinocyte growth factor (KGF) (Antioniades, H. et al., *Proc. Natl. Acad. Sci. USA* 88:565 (1991)), platelet derived growth factor (PDGF)(Antioniades, H. et al., *Proc. Natl. Acad Sci. USA* 88:565 (1991); Staiano-Coico, L. et al., *Jour. Exp. Med.* 178:865–878 (1993)), basic fibroblast growth factor (bFGF) (Golden, M. A. et al., *J. Clin. Invest.* 87:406 (1991)), acidic fibroblast growth factor (aFGF) (Mellin, T. N. et al., *J. Invest. Dermatol.* 104:850–855 (1995)), epidermal growth factor (EGF) (Whitby, D. J. and Ferguson, W. J., *Dev. Biol.* 147:207 (1991)), transforming growth factor-α (TGF-α) (Gartner, M. H. et al., *Surg. Forum* 42:643 (1991); Todd, R. et al., *Am. J. Pathol.* 138;1307 (1991)), transforming growth factor-β (TGF-β) (Wong, D. T. W. et al., *Am. J. Pathol.* 143:622 (1987)), neu differentiation factor (rNDF) (Danilenko, D. M. et al., *J. Clin. Invest.* 95;842–851 (1995)), insulin-like growth factor I (IGF-1), and insulin-like growth factor II (IGF-II) (Cromack, D. T. et al, *J. Surg. Res.* 42:622 (1987)).

It has been reported that rKGF-1 in the skin stimulates epidermal keratinocytes, keratinocytes within hair follicles and sebaceous; glands (Pierce, G. F. et al., *J. Exp. Med.* 179:831–840 (1994)).

SUMMARY OF THE INVENTION

The present invention provides isolated nucleic acid molecules comprising a polynucleotide encoding the keratinocyte growth factor (KGF-2) having the amino acid sequence is shown in FIG. 1 [SEQ ID NO:2] or the amino acid sequence encoded by the cDNA clone deposited as ATCC Deposit Number 75977 on Dec. 16, 1994. The nucleotide sequence determined by sequencing the deposited KGF-2 clone, which is shown in FIG. 1 [SEQ ID NO:1], contains an open reading frame encoding a polypeptide of 208 amino acid residues, including an initiation codon at positions 1–3, with a predicted leader sequence of about 35 or 36 amino acid residues, and a deduced molecular weight of about 23.4 kDa. The amino acid sequence of the mature KGF-2 is shown in FIG. 1, amino acid residues about 36 or 37 to 208 [SEQ ID NO:2].

The polypeptide of the present invention has been putatively identified as a member of the FGF family, more particularly the polypeptide has been putatively identified as KGF-2 as a result of amino acid sequence homology with other members of the FGF family.

In accordance with one aspect of the present invention, there are provided novel mature polypeptides which are KGF-2 as well as biologically active and diagnostically or therapeutically useful fragments, analogs and derivatives thereof. The polypeptides of the present invention are of human origin.

In accordance with another aspect of the present invention, there are provided isolated nucleic acid molecules encoding human KGF-2, including mRNAs, DNAs, cDNAs, genomic DNA, as well as antisense analogs thereof, and biologically active and diagnostically or therapeutically useful fragments thereof.

In accordance with another aspect of the present invention, there is provided a process for producing such polypeptide by recombinant techniques through the use of recombinant vectors, such as cloning and expression plasmids useful as reagents in the recombinant production of KGF-2 proteins, as well as recombinant prokaryotic and/or eukaryotic host cells comprising a human KGF-2 nucleic acid sequence.

In accordance with yet a further aspect of the present invention, there is provided a process for utilizing such polypeptide, or polynucleotide encoding such polypeptide for therapeutic purposes, for example, to stimulate epithelial cell proliferation and basal keratinocytes for the purpose of wound healing, and to stimulate hair follicle production and healing of dermal wounds. KGF-2 may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associted with systemic treatment with steroids, radiation therapy and antineoplastic drugs and antimetabolites. KGF-2 can be used to promote dermal reestablishment subsequent to dermal loss KGF-2 can be used to increase the adherence of skin grafts to a wound bed and to stimulate re-epithelialization from the wound bed. The following are types of grafts that KGF-2 could be used to increase adherence to a wound bed: autografts, artificial skin, allografts, autodermic graft, autoepdermic grafts, avacular grafts, Blair-Brown grafts, bone graft, brephoplastic grafts, cutis graft, delayed graft, dermic graft, epidermic graft, fascia graft, full thickness graift, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. KGF-2 can be used to promote skin strength and to improve the appearance of aged skin.

It is believed that KGF-2 will also produce changes in hepatocyte proliferation, and epithelial cell proliferation in the lung, breast, pancreas, stomach, small intesting, and large intestine. KGF-2 can promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. KGF-2 can promote proliferation of endothelial cells, keratinocytes, and basal keratinocytes.

KGF-2 can also be used to reduce the side effects of gut toxicity that result from radiation, chemotherapy treatments or viral infections. KGF-2 may have a cytoprotective effect on the small intestine mucosa. KGF-2 may also stimulate healing of mucositis (mouth ulcers) that result from chemotherapy and viral infections.

KGF-2 can further be used in full regeneration of skin in full and partial thickness skin defects, including burns, (i.e., repopulation of hair follicles, sweat glands, and sebaceous glands), treatment of other skin defects such as psoriasis. KGF-2 can be used to treat epidermolysis bullosa, a defect in adherence of the epidermis to the underlying dermis which results in frequent, open and painful blisters by accelerating reepithelialization of these lesions. KGF-2 can also be used to treat gastric and doudenal ulcers and help heal by scar formation of the mucosal lining and regeneration of glandular mucosa and duodenal mucosal lining more rapidly. Inflamamatory bowel diseases, such as Crohn's disease and ulcerative colitis, are diseases which result in destruction of the mucosal surface of the small or large intestine, respectively. Thus, KGF-2 could be used to promote the resurfacing of the mucosal surface to aid more rapid healing and to prevent progression of inflammatory bowel disease. KGF-2 treatment is expected to have a significant effect on the production of mucus throughout the gastrointestinal tract and could be used to protect the intestinal mucosa from injurious substances that are ingested or following surgery. KGF-2 can be used to treat diseases associate with the under expression of KGF-2.

Moreover, KGF-2 can be used to prevent and heal damage to the lungs due to various pathological states. A growth factor such as KGF-2 which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and burns, that cause necrosis of the bronchiolar epithelium and alveoli could be effectively treated KGF-2. Also, KGF-2 could be used to stimulate the proliferation of and differentiation of type II pneumocytes, which may help treat or prevent disease such as hyaline membrane diseases, such as infant respiratory distress syndrome and bronchopulmonary displasia, in premature infants.

KGF-2 could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, KGF-2 could be used treat or prevent the onset of diabetes mellitus. In patients with newly diagnosed Types I and II diabetes, where some islet cell function remains, KGF-2 could be used to maintain the islet function so as to alleviate, delay or prevent permenant manifestation of the disease. Also, KGF-2 could be used as an auxiliary in islet cell transplantation to improve or promote islet cell function.

In accordance with yet a further aspect of the present invention, there are provided antibodies against such polypeptides.

In accordance with another aspect of the present invention, there are provided nucleic acid probes comprising nucleic acid molecules of sufficient length to specifically hybridize to human KGF-2 sequences.

In accordance with a further aspect of the present invention, there are provided mimetic peptides of KGF-2 which can be used as therapeutic peptides. Mimetic KGF-2 peptides are short peptides which mimic the biological activity of the KGF-2 protein by binding to and activating the cognate receptors of KGF-2. Mimetic KGF-2 peptides can also bind to and inhibit the cognate receptors of KGF-2.

In accordance with yet another aspect of the present invention, there are provided antagonists to such polypeptides, which may be used lo inhibit the action of such polypeptides, for example, to reduce scarring during the wound healing process and to prevent and/or treat tumor proliferation, diabetic retinopathy, rheumatoid arthritis, oesteoarthritis and tumor growth. KGF-2 antagonists can also be used to treat diseases associate with the over expression of KGF-2.

In accordance with yet another aspect of the present invention, there are provided diagnostic assays for detecting diseases or susceptibility to diseases related to mutations in KGF-2 nucleic acid sequences or over-expression of the polypeptides encoded by such sequences.

In accordance with another aspect of the present invention, there is provided a process for utilizing such polypeptides, or polynucleotides encoding such polypeptides, for in vitro purposes related to scientific research, synthesis of DNA and manufacture of DNA vectors.

Thus, one aspect of the invention provides an isolated nucleic acid molecule comprising a polynucleotide having a nucleotide sequence selected from the group consisting of: (a) a nucleotide sequence encoding the KGF-2 polypeptide having the complete amino acid sequence in FIG. 1 [SEQ ID NO:2]; (b) a nucleotide sequence encoding the mature KGF-2 polypeptide having the amino acid sequence at positions 36 or 37 to 208 in FIG. 1 [SEQ ID NO:2]; (c) a nucleotide sequence encoding the KGF-2 polypeptide having the complete amino acid sequence encoded by the cDNA clone contained in ATCC Deposit No. 75977; (d) a nucleotide sequence encoding the mature KGF-2 polypeptide having the amino acid sequence encoded by the cDNA clone contained in ATCC Deposit No.75977; and (e) a nucleotide sequence complementary to any of the nucleotide sequences in (a), (b), (c) or (d) above.

Further embodiments of the invention include isolated nucleic acid molecules that comprise a polynucleotide having a nucleotide sequence at least 90% identical, and more preferably at least 95%, 97%, 98% or 99% identical, to any of the nucleotide sequences in (a), (b), (c), (d) or (e), above, or a polynucleotide which hybridizes under stringent hybridization conditions to a polynucleotide in (a), (b), (c), (d) or (e), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a KGF-2 having an amino acid sequence in (a), (b), (c) or (d), above.

The invention further provides an isolated KGF-2 polypeptide having amino acid sequence selected from the group consisting of: (a) the amino acid sequence of the KGF-2 polypeptide having the complete 208 amino acid sequence, including the leader sequence shown in FIG. 1 [SEQ ID NO:2]; (b) the amino acid sequence of the mature KGF-2 polypeptide (without the leader) having the amino acid sequence at positions 36 or 37 to 208 in FIG. 1 [SEQ ID NO:2]; (c) the amino acid sequence of the KGF-2 polypeptide having the complete amino acid sequence, including the leader, encoded by the cDNA clone contained in ATCC Deposit No.75977; and (d) the amino acid sequence of the mature KGF-2 polypeptide having the amino acid sequence encoded by the cDNA clone contained in ATCC Deposit No. 75977. The polypeptides of the present invention also include polypeptides having an amino acid sequence with at least 90% similarity, and more preferably at least 95% similarity to those described in (a), (b), (c) or (d) above, as well as polypeptides having an amino acid sequence at least 80% identical, more preferably at least 90% identical, and still more preferably 95%, 97%, 98% or 99% identical to those above.

An additional aspect of the invention relates to a peptide or polypeptide which has the amino acid sequence of an epitope-bearing portion of a KGF-2 polypeptide having an amino acid sequence described in (a), (b), (c) or (d), above. Peptides or polypeptides having the amino acid sequence of an epitope-bearing portion of a KGF-2 polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention. In another embodiment, the invention provides an isolated antibody that binds specifically to a KGF-2 polypeptide having an amino acid sequence described in (a), (b), (c) or (d) above.

In accordance with another aspect of the present invention, novel variants of KGF-2 are described. These can be produced by deleting or substituting one or more amino acids of KGF-2. Natural mutations are called allelic variations. Allelic variations can be silent (no change in the encoded polypeptide) or may have altered amino acid sequence. In order to attempt to improve or alter the characteristics of native KGF-2, protein engineering may be employed. Recombinant DNA technology known in the art can be used to create novel polypeptides. Muteins and deletion mutations can show, e.g., enhanced activity or increased stability. In addition, they could be purified in higher yield and show better solubility at least under certain purification and storage conditions.

These and other aspects of the present invention should be apparent to those skilled in the art from the teachings herein.

BRIEF DESCRIPTION OF THE FIGURES

The following drawings are illustrative of embodiments of the invention and are not meant to limit the scope of the invention as encompassed by the claims.

FIGS. 2A–2D are an illustration of a comparison of the amino acid sequence of the polypeptide of the present invention and other fibroblast growth factors. [SEQ ID NOS:13–22]

FIGS. 3A–3D show the full length mRNA and amino acid sequence for the KGF-2 gene. [SEQ ID NOS:23 and 24]

FIG. 15 shows the DNA sequence and the protein expressed from the pQE60-Cyst37 construct [SEQ ID NOS: 29 and 30]. The expressed KGF-2 protein contains the sequence from Cysteine at position 37 to Serine at position 208 with a 6X(His) tag attached to the N-terminus of the protein.

FIG. 23 shows the DNA and protein sequence [SEQ ID NOS: 38 and 39] for the *E.coli* optimized full length KGF-2.

FIGS. 24A and B show the DNA and protein sequences [SEQ ID NOS:42, 43, 54, and 55] for the *E.coli* optimized mature KGF-2.

FIG. 25 shows the DNA and the encoded protein sequence [SEQ ID NOS:65 and 66] for the KGF-2 deletion construct comprising amino acids 36 to 208 of KGF-2.

FIG. 26 shows the DNA and the encoded protein sequence [SEQ ID NOS:67 and 68] for the KGF-2 deletion construct comprising amino acids 63 to 208 of KGF-2.

FIG. 27 shows the DNA and the encoded protein sequence [SEQ ID NOS:69 and 70] for the KGF-2 deletion construct comprising amino acids 77 to 208 of KGF-2.

FIG. 28 shows the DNA and the encoded protein sequence [SEQ ID NOS:71 and 72] for the KGF-2 deletion construct comprising amino acids 93 to 208 of KGF-2.

FIG. 29 shows the DNA and the encoded protein sequence [SEQ ID NOS:73 and 74] for the KGF-2 deletion construct comprising amino acids 104 to 208 of KGF-2.

FIG. 30 shows the DNA and the encoded protein sequence [SEQ ID NOS:75 and 76] for the KGF-2 deletion construct comprising am:no acids 123 to 208 of KGF-2.

FIG. 31 shows the DNA and the encoded protein sequence [SEQ ID NOS:77 and 78] for the KGF-2 deletion construct comprising am no acids 138 to 208 of KGF-2.

FIG. 32 shows the DNA and the encoded protein sequence [SEQ ID NOS:79 and 80] for the KGF-2 deletion construct comprising amino acids 36 to 153 of KGF-2.

FIG. 33 shows the DNA and the encoded protein sequence [SEQ ID NOS:81 and 82] for the KGF-2 deletion construct comprising amino acids 63 to 153 of KGF-2.

FIG. 34 shows the DNA sequence for the KGF-2 Cysteine-37 to Serine mutant construct [SEQ ID NO:83].

FIG. 35 shows the DNA sequence for the KGF-2 Cysteine-37/Cysteine-106 to Serine mutant construct [SEQ ID NO:84].

FIG. 37 shows the effect of KGF-2Δ33 on wound healing in normal rats. Male, SD, 250–300 g, rats (n=5) were given 6 mm full-thickness dorsal wounds. Wounds were measured with a caliper and treated with various concentrations of KGF-2Δ33 and buffer for four days commencing, on the day of surgery. On the final day, wounds were harvested. Statistical analysis was performed using an unpaired t-test. *Value is compared to No Treatment Control. †Value is compared to Buffer Control.

FIG. 51 shows the nucleotide sequence of the regulatory elements of the pHE promoter (SEQ ID NO:148). The two lac operator sequences, the Shine-Delgarno sequence (S/D), and the terminal HindIII and NdeI restriction sites (italicized) are indicated.

DETAILED DESCRIPTION

Figure 22A:
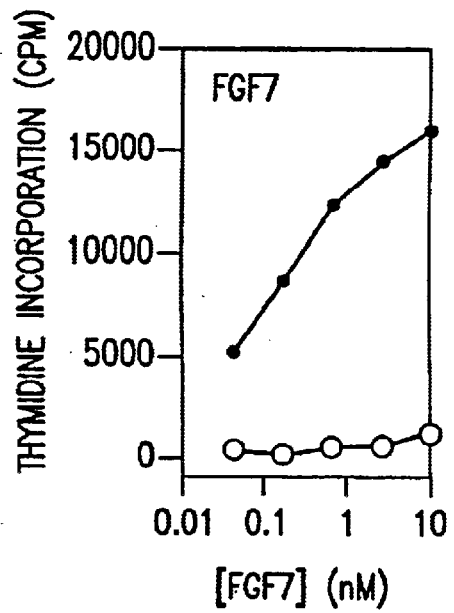
FIG. 22 (A) shows the stimulation of thymidine incorporation by KGF-2 and FGF7 in Baf3 cells transfected with FGFR1 and FGFR2. The effects of KGF-2 (right panel) and FGF7 (left panel) on the proliferation of Baf3 cells transfected with FGFR1iiib (open circle) or FGFR2iiib/KGFR (solid Circle were examined. Y-axis represents the amount of [3H]thymidine incoroporation (cpm) into DNA of Baf3 cells. X-axis represents the final concentration of KGF-2 or FGF7 added to the tissue culture media. (B) shows the stimulation of thymidine incorporation by KGF-2Δ33 in Baf3 cells transfected with FGFR2iiib (C) shows the stimulation of thymidine incorporation by KGF-2 (white bar), KGF-2Δ33 (black bar) and KGF-2Δ28 (grey bar) in Baf3 cells transfected with FGFR2iiib.
Figures 1, 22A:
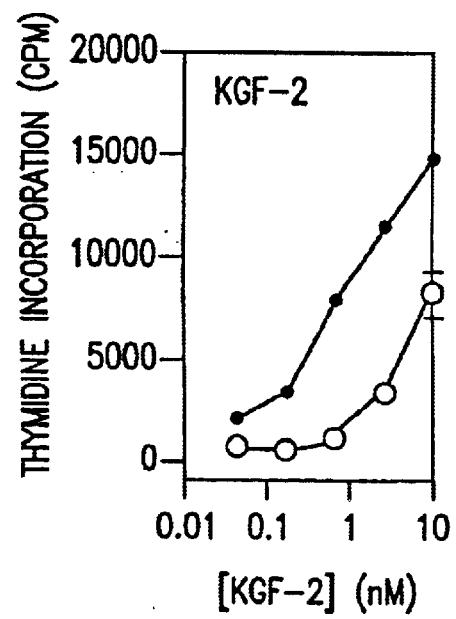
FIGS. 1A–1C illustrate the cDNA and corresponding deduced amino acid sequence of the polypeptide of the present invention. The initial 35 or 36 amino acid residues represent the putative leader sequence (underlined). The standard one letter abbreviations for amino acids are used. Sequencing inaccuracies are a common problem when attempting to determine polynucleotide sequences. Sequencing was performed using a 373 Automated DNA sequencer (Applied Biosystems, Inc.). Sequencing accuracy is predicted to be greater than 97% accurate. [SEQ ID NO:1]

In accordance with an aspect of the present invention, there is provided an isolated nucleic acid (polynucleotide) which encodes for the polypeptide having the deduced amino acid sequence of FIG. 1 (SEQ ID NO:2) or for the polypeptide encoded by the cDNA of the clone deposited as ATCC Deposit No. 75977 on Dec. 16, 1994 at the American Type Culture Collection, Patent Depository 10801, University Boulevard, Manassas, Va. 20110-2209.

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonuclectide sequence is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxyribonucleotide A, G or C of SEQ ID NO:1 has been replaced by the corresponding ribonucleotide A, G or C, and each deoxyribonucleotide T has been replaced by a ribonucleotide U.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with an initiation codon at positions 1–3 of the nucleotide sequence shown in FIG. 1 (SEQ ID NO:1); DNA molecules comprising the coding sequence for the mature KGF-2 protein shown in FIG. 1 (last 172 or 173 amino acids) (SEQ ID NO:2); and DNA molecules which comprise a sequence substantially different from those described above but which, due to the degeneracy of the genetic code, still encode the KJF-2 protein. Of course, the genetic code is well known in the art. Thus, it would be routine for one skilled in the art to generate the degenerate variants described above.

A polynucleotide encoding a polypeptide of the present invention may be obtained from a human prostate and fetal lung. A fragment of the cDNA encoding the polypeptide was initially isolated from a library derived from a human normal prostate. The open reading frame encoding the full length protein was subsequently isolated from a randomly primed human fetal lung cDNA library. It is structurally related to the FGF family. It contains an open reading frame encoding a protein of 208 amino acid residues of which approximately the first 35 or 36 amino acid residues are the putative leader sequence such that the mature protein comprises 173 or 172 amino acids. The protein exhibits the highest degree of homology to human keratinocyte growth factor with 45% identity and 82% similarity over a 206 amino acid stretch. It is also important that sequences that are conserved through the FGF family are found to be conserved in the protein of the present invention.

In addition, results from nested PCR of KGF-2 cDNA from libraries showed that there were potential alternative spliced forms of KGF-2. Specifically, using primers flanking the N-terminus of the open reading frame of KGF-2, PCR products of 0.2 kb and 0.4 kb were obtained from vatrious cDNA libraries. A 0.2 kb size was the expected product for KGF-2 while the 0.4 kb size may result from an alternatively spliced form of KGF-2. The 0.4 kb product was observed in libraries from stomach cancer, adult testis, duodenum and pancreas.

The polynucleotide of the present invention may be in the form of RNA or in the form of DNA, which DNA includes cDNA, genomic DNA, and synthetic DNA. The DNA may be doublestranded or single-stranded, and if single stranded may be the coding strand or non-coding (anti-sense) strand.

The coding sequence which encodes the mature polypeptide may be identical to the coding sequence shown in FIG. 1 (SEQ ID NO:1) or that of the deposited clone or may be a different coding sequence which coding sequence, as a result of the redundancy or degeneracy of the genetic code, encodes the same mature polypeptide as the DNA of FIG. 1 (SEQ ID NO:1) or the deposited cDNA.

The polynucleotide which encodes for the predicted mature polypeptide of FIG. 1 (SEQ ID NO.2) or for the predicted mature polypeptide encoded by the deposited cDNA may include: only the coding sequence for the mature polypeptide; the coding sequence for the mature polypeptide and additional coding sequence such as a leader or secretary sequence or a proprotein sequence; the coding sequence for the mature polypeptide (and optionally additional coding sequence) and non-coding sequence, such as intron or non-coding sequence 5' and/or 3' of the coding sequence for the predicted mature polypeptide. In addition, a full length mRNA has been obtained which contains 5' and 3' untranslated regions of the gene (FIG. 3 (SEQ ID NO:23)).

As one of ordinary skill would appreciate, due to the possibilities of sequencing errors discussed above, as well as the variability of cleavage sites for leaders in different known proteins, the actual KGF-2 polypeptide encoded by the deposited cDNA comprises about 208 amino acids, but may be anywhere in the range of 200–220 amino acids; and the actual leader sequence of this protein is about 35 or 36 amino acids, but may be anywhere in the range of about 30 to about 40 amino acids.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO.2) or the polypeptide encoded by the cDNA of the deposited clone. The variant of the polynucleotide may be a naturally occurring allelic variant of the polynucleotide or a nonnaturally occurring variant of the polynucleotide.

Thus, the present invention includes polynucleotides encoding the same predicted mature polypeptide as shown in FIG. 1 (SEQ ID NO:2) or the same predicted mature polypeptide encoded by the cDNA of the deposited clone as well as variants of such polynucleotides which variants encode for a fragment, derivative or analog of the polypeptide of FIG. 1 (SEQ ID NO:2) or the polypeptide encoded by the cDNA of the deposited clone. Such nucleotide variants include deletion variants, substitution variants and addition or insertion variants.

The present invention includes polynucleotides encoding mimetic peptides of KGF-2 which can be used as therapeutic peptides. Mimetic KGF-2 peptides are short peptides which mimic the biological activity of the KGF-2 protein by binding to and activating the cognate receptors of KGF-2. Mimetic KGF-2 peptides can also bind to and inhibit the cognate receptors of KGF-2. KGF-2 receptors include, but are not limited to, FGFR2iiib and FGFR1iiib. Such mimetic peptides are obtained from methods such as, but not limited to, phage display or combinatorial chemistry. For example the method disclosed by Wrighton et al. Science 273:458–463 (1996) to generate mimetic KGF-2 peptides.

As hereinabove indicated, the polynucleotide may have a coding sequence which is a naturally occurring allelic variant of the coding sequence shown in FIG. 1 (SEQ ID NO:1)

or of the coding sequence of the deposited clone. As known in the art, an allelic variant is an alternate form of a polynucleotide sequence which may have a substitution, deletion or addition of one or more nucleotides, which does not substantially alter the function of the encode polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both prosequence and a presequence (leader sequence).

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilsoni, I. et al. *Cell* 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAS which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or cDNA to determine which members of the library the probe hybridizes to.

Further embodiments of the invention include isolated nucleic acid molecules comprising a polynucleotide having a nucleotide sequence at least 90% identical, and more preferably at least 95%, 96%, 97%, 98% or 99% identical to (a) a nucleotide sequence encoding the full-length KGF-2 polypeptide having the complete amino acid sequence in FIG. 1 (SEQ ID NO:2), including the predicted leader sequence; (b) a nucleotide sequence encoding the mature KGF-2 polypeptide (full-length polypeptide with the leader removed) having the amino acid sequence at positions about 36 or 37 to 208 in FIG. 1 (SEQ ID NO:2); (c) a nucleotide sequence encoding the full-length KGF-2 polypeptide having the complete amino acid sequence including the leader encoded by the cDNA clone contained in ATCC Deposit No. 75977; (d) a nucleotide sequence encoding the mature KGF-2 polypeptide having the amino acid sequence encoded by the cDNA clone contained in ATCC Deposit No. 75977; (e) a nucleotide sequence encoding any of the KGF-2 analogs or deletion mutants described below; or (f) a nucleotide sequence complementary to any of the nucleotide sequences in (a), (b), (c),(d), or (e).

By a polynucleotide having a nucleotide sequence at least, for example, 95% "identical" to a reference nucleotide sequence encoding a KGF-2 polypeptide is intended that the nucleotide sequence of the polynucleotide is identical to the reference sequence except that the polynucleotide sequence may include up to five point mutations per each 100 nucleotides of the reference nucleotide sequence encoding the KGF-2 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIG. 1 (SEQ ID NO:1) or to the nucleotides sequence of the deposited cDNA clone can be determined conventionally using known computer programs such as the Bestfit program (Wisconsin Sequence Analysis Package, Version 8 for Unix, Genetics Computer Group, University Reseaich Park, 575 Science Drive, Madison, Wis. 53711. Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to the nucleic acid sequence shown in FIG. 1 [SEQ ID NO:1] or to the nucleic acid sequence of the deposited cDNA, irrespective of whether they encode a polypeptide having KGF-2 activity. This is because even where a particular nucleic acid molecule does not encode a polypeptide having KGF-2 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having KGF-2 activity include, inter alia, (1) isolating the KGF-2 gene or allelic variants thereof in a cDNA library; (2) in situ hybridization (e.g., "FISH") to metaphase chromosomal spreads to provide precise chromosomal location of the KGF-2 gene, as described in Verma et al., *Human Chromosomes: A Manual of Basic Techniques*, Pergamon Press, New York (1988); and Northern Blot analysis for detecting KGF-2 mRNA expression in specific tissues.

Preferred, however, are nucleic acid molecules having sequences at least 90%, 95%, 96%, 97%, 98% or 99% identical to the nucleic acid sequence shown in FIG. 1 [SEQ ID NO:1] or to the nucleic acid sequence of the deposited cDNA which do, in fact, encode a polypeptide having KGF-2 protein activity. By "a polypeptide having KGF-2 activity" is intended polypeptides exhibiting activity similar, but not necessarily identical, to an activity of the wild-type KGF-2 protein of the invention or an activity that is enhanced over that of the wild-type KGF-2 protein (either the full-length protein or, preferably, the mature protein), as measured in a particular biological assay.

Assays of KGF-2 activity are disclosed, for example, in Examples 10 and 11 below. These assays can be used to measure KGF-2 activity of partially purified or purified native or recombinant protein.

KGF-2 stimulates the proliferation of epidermal keratinocyes but not mesenchymal cells such as fibroblasts. Thus, "a polypeptide having KGF-2 protein activity" includes polypeptides that exhibit the KGF-2 activity, in the keratinocyte proliferation assay set forth in Example 10 and will bind to the FGF receptor isoforms 1-iiib and 2-iiib (Example 11). Although the degree of activity need not be identical to that of the KGF-2 protein, preferably, "a polypeptide having KGF-2 protein activity" will exhibit substantially similar activity as compared to the KGF-2 protein (i.e., the candidate polypeptide will exhibit greater activity or not more than about tenfold less and, preferably, not more than about twofold less activity relative to the reference KGF-2 protein).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIG. 1 [SEQ ID NO:1] will encode a polypeptide "having KGF-2 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having KGF-2 protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein.

The present invention further relates to polynucleotides which hybridize to the hereinabove-described sequences if there is at least 70%, preferably at least 90%, and more preferably at least 95% and still more preferably 96%, 97%, 98%, 99% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 1 (SEQ ID NO:1) or the deposited cDNA(s).

An example of "stringent hybridization conditions" includes overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC al about 65° C.

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Of course, polynucleotides hybridizing to a larger portion of the reference polynucleotide (e.g., the deposited cDNA clone), for instance, a portion 50–750 nt in length, or even to the entire length of the reference polynucleotide, are also useful as probes according to the present invention, as are polynucleotides corresponding to most, if not all, of the nucleotide sequence of the deposited cDNA or the nucleotide sequence as shown in FIG. 1 [SEQ ID NO:1]. By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIG. 1 [SEQ ID NO:1]). As indicated, such portions are useful diagnostically either as a probe according to conventional DNA hybridization techniques or as primers for amplification of a target sequence by the polymerase chain reaction (PCR), as described, for instance, in *Molecular Cloning, A Laboratory Manual*, 2nd. edition, edited by Sambrook, J., Fritsch, E. F. and Maniatis, T., (1989), Cold Spring Harbor Laboratory Press, the entire disclosure of which is hereby incorporated herein by reference.

Since a KGF-2 cDNA clone has been deposited and its determined nucleotide sequence is provided in FIG. 1 [SEQ ID NO:1], generating polynucleotides which hybridize to a portion of the KGF-2 cDNA molecule would be routine to the skilled artisan. For example, restriction endonuclease cleavage or shearing by sonication of the KGF-2 cDNA clone could easily be used to generate DNA portions of various sizes which are polynucleotides that hybridize to a portion of the KGF-2 cDNA molecule. Alternatively, the hybridizing polynucleotides of the present invention could be generated synthetically according to known techniques. Of course, a polynucleotide which hybridizes only to a poly A sequence (such as the 3' terminal poly(A) tract of the KGF-2 cDNA shown in FIG. 1 [SEQ ID NO:1]), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

The invention further provides isolated nucleic acid molecules comprising a polynucleotide encoding an epitope-bearing portion of the KGF-2 protein. In particular, isolated nucleic acid molecules are provided encoding polypeptides comprising the following amino acid residues in FIG. 1 (SEQ ID NO:2), which the present inventors have determined are antigenic regions of the KGF-2 protein:

1. Gly41-Asn71:
GQDMVSPEATNSSSSSFSSPSSAGRHVRSYN;    [SEQ ID NO:25]

2. Lys91-Ser109:
KIEKNGKVSGTKKENCPYS;    [SEQ ID NO:26]

3. Asn135-Tyr164:
NKKGKLYGSKEFNNDCKLKERIEENGYNTY; and [SEQ ID NO 27]

4. Asn181-Ala199:
NGKGAPRRGQKTRRKNTSA.    [SEQ ID NO:28]

Also, there are two additonal shorter predicted antigenic areas, Gln74-Arg78 of FIG. 1 (SEQ ID NO:2) and Gln170-Gln175 of FIG. 1 (SEQ ID NO:2). Methods for gererating such epitope-bearing portions of KGF-2 are described in detail below.

The deposit(s) referred to herein will be maintained under the terms of the Budapest Treaty on the International Recognition of the Deposit of Micro-organisms for purposes of Patent Procedure. These deposits are provided merely as a convenience to those of skill in the art and are not an admission that a deposit is required under 35 U.S.C. § 112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

KGF-2 Polypeptides and Fragments

The present invention further relates to a polypeptide which has the deduced amino acid sequence of FIG. 1 (SEQ ID NO:2) or which has the amino acid sequence encoded by the deposited cDNA, as well as fragments, analogs and derivatives of such polypeptide.

As one of ordinary skill would appreciate, due to the possibilities of sequencing errors discussed above, as well as the variability of cleavage sites for leaders in different known proteins, the actual KGF-2 polypeptide encoded by the deposited cDNA comprises about 208 amino acids, but may be anywhere in the range of 200–220 amino acids; and the actual leader sequence of this protein is about 35 or 36 amino acids, but may be anywhere in the range of about 30 to about 40 amino acids.

The terms "fragment," "derivative" and "analog" when referring to the polypeptide, of FIG. 1 (SEQ ID NO:2) or that encoded by the deposited cDNA, means a polypeptide which retains essentially the same biological function or activity as such polypeptide. Thus, an analog includes a proprotein which can be activated by cleavage of the pro-protein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretary sequence or a sequence which is employed for purification of the mature polypeptide or a proprotein sequence. Such fragments, derivatives and analogs are deemed to be within the scope of those skilled in the art from the teachings herein.

The terms "peptide" and "oligopeptide" are considered synonymous (as is commonly recognized) and each term can be used interchangeably as the context requires to indicate a chain of at least to amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

It will be recognized in the art that some amino acid sequences of the KGF-2 polypeptide can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the KGF-2 polypeptide which show substantial KGF-2 polypeptide activity or which include regions of KGF-2 protein such as the protein portions discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As indicated in detail above, further guidance concerning which amino acid changes are likely to be phenotypically silent (i.e., are not likely to have a significant deleterious effect on a function) can be found in Bowie, J. U., et al., "Deciphering the Message in Protein Sequences: Tolerance to Amino Acid Substitutions," *Science* 247:1306–1310 (1990).

The present invention includes mimetic peptides of KGF-2 which can be used as therapeutic peptides. Mimetic KGF-2 peptides are short peptides which mimic the biological activity of the KGF-2 protein by binding to and activating the cognate receptors of KGF-2. Mimetic KGF-2 peptides can also bind to and inhibit the cognate receptors of KGF-2. KGF-2 receptors include, but are not limited to, FGFR2iiib and FGFR1iiib. Such mimetic peptides are obtained from methods such as, but not limited to, phage display or combinatorial chemistry. For example, the method disclosed by Wrighton et al. *Science*, 273:458–463 (1996) can be used to generate mimetic KGF-2 peptides.

The polypeptides and polynucleotides of the present invention are preferably provided in an isolated form, and preferably are purified to homogeneity.

The polypeptides of the present invention are preferably in an isolated form. By "isolated polypeptide" is intended a polypeptide removed from its native environment. Thus, a polypeptide produced and/or contaned within a recombinant host cell is considered isolated for purposes of the present invention. Also intended are polypeptides that have been purified, partially or substantially, from a recombinant host cell or a native source.

The polypeptides of the present invention include the polypeptide of SEQ ID NO:2 (in Particular the mature polypeptide) as well as polypeptides which have at least 90%, 95%, 96%, 97%, 98%, 99% similarity (more preferably at least 90%, 95%, 96%, 97%, 98%, 99% identity) to the polypeptide of SEQ ID NO:2 and also include portions of such polypeptides with such portion of the polypeptide (such as the deletion mutants described below) generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (*Advances in Applied Mathematics* 2: 482–489, 1981) to find the best segment of similarity between two sequences.

By a polypeptide having an amino acid sequence at least, for example, 95% "identical" to a reference amino acid sequence of a KGF-2 polypeptide is intended that the amino acid sequence of the polypeptide is identical to the reference sequence except that the polypeptide sequence may include up to five amino acid alterations per each 100 amino acids of the reference amino acid of the KGF-2 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIG. 1 [SEQ ID NO:2] or to the amino acid sequence encoded by deposited cDNA clone can be determined conventionally using known computer programs such the Bestfit program (Wisconsin Sequence Analysis Package, Version 8 for Unix, Genetics Computer Group, University Reseaich Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

As described in detail below, the polypeptides of the present invention can be used to raise polyclonal and monoclonal antibodies, which are useful in diagnostic assays for detecting KGF-2 protein expression as described below or as agonists and antagonists capable of enhancing or inhibiting KGF-2 protein function. Further, such polypeptides can be used in the yeast two-hybrid system to "capture" KGF-2 protein binding proteins which are also candidate agonist and antagonist according to the present invention. The yeast two hybrid system is described in Fields and Song, *Nature* 340:245–246 (1989).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al, *Proc. Natl. Acad Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. *Science* 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, soluble peptides, especially those containing proline residues, usually are effective. Sutcliffe et al., supra, at 661. For instance, 18 of 20 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes post translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson et al., *Cell* 37:767–778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30, 40, 50, 60, 70, 80, 90, 100, or 150 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

Non-limiting examples of antigenic polypeptides or peptides that can be used to generate KGF-2-specific antibodies include the following:

1. Gly41-Asn71:
GQDMVSPEATNSSSSSFSSPSSAGRHVRSYN;          [SEQ ID NO:25]

2. Lys91-Ser109:
KIEKNGKVSGTKKENCPYS;                      [SEQ ID NO:26]

3. Asn135-Tyr164:
NKKGKLYGSKEFNNDCKLKERIEENGYNTY; and       [SEQ ID NO:27]

4. Asn181-Ala199:
NGKGAPRRGQKTRRKNTSA.                      [SEQ ID NO:28]

Also, there are two additonal shorter predicted antigenic areas, Gln74-Arg78 of FIG. 1 (SEQ ID NO:2) and Gln170-Gln175 of FIG. 1 (SEQ ID NO:2).

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies.

Epitope-bearing peptides also may be synthesized using known methods of chemical synthesis. For instance, Houghten has described a simple, method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. Houghten, R. A. (1985) General method for the rapid solid-phase synthesis of large numbers of peptides: specificity of antigen-antibody interaction at the level of individual amino acids. *Proc. Natl. Acad. Sci. USA* 82:5131–5135. This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. Houghten et al., supra, at 5134.

Epitope-bearing peptides and polypeptides of the invention are used to induce antibodies according to methods well known in the art. See for instance, Sutcliffe et al., supra; Wilson et al., supra; Chow, M. et al., *Proc. Natl. Acad. Sci. USA* 82:910–914; and Bittle, F. J. et al., *J. Gen. Virol.* 66:2347–2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 μg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$–$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

As one of skill in the art will appreciate, KGF-2 polypeptides of the present invention and the epitope-bearing fragments thereof described above can be combined with parts of the constant domain of immunoglobulins (IgG), resulting in chimeric polypeptides. These fusion proteins facilitate, purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84–86 (1988)). Fusion proteins that have a disulfide-linked dimeric structure due to the IgG part can also be more efficient in binding and neutralizing other molecules than the monomeric KGF-2 protein or protein fragment alone (Fountoulakis et al, *J Biochem* 270:3958–3964 (1995)).

In accordance with the present invention, novel variants of KGF-2 are also described. These can be produced by deleting or substituting one or more amino acids of KGF-2. Natural mutations are called allelic variations. Allelic variations can be silent (no change in the encoded polypeptide) or may have altered amino acid sequence.

In order to attempt to improve or alter the characteristics of native KGF-2, protein engineering may be employed. Recombinant DNA technology known to those skilled in the art can be used to create novel polypeptides. Muteins and deletions can show, e.g., enhanced activity or increased stability. In addition, they could be purified in higher yield and show better solubility at least under certain purification and storage conditions. Set forth below are examples of mutations that can be constructed.

Amino Terminal and Carboxy Terminal Deletions

Various members of the FGF family have been modified using recombinant DNA technology. Positively charged molecules have been substituted or deleted in both aFGF and bFGF that are important for heparin binding. The modified molecules resulted in reduced heparin binding activity. Accordingly, it is known that the amount of modified molecule sequestered by heparin in a patient would be reduced, increasing the potency as more FGF would reach the appropriate receptor. (EP 0 298 723).

Native KGF-2 is relatively unstable in the aqueous state and it undergoes chemical and physical degradation resulting in loss of biological activity during processing and storage. Native KGF-2 is also prone to aggregation in aqueous solution, at elevated temperatures and it becomes inactivated under acidic conditions.

In order to improve or alter one or more characteristics of native KGF-2, protein engineering may be employed. Ron et al., *J. Biol. Chem.*, 268(4): 2984–2988 (1993) reported modified KGF proteins that had heparin binding activity even if the 3, 8, or 27 amino terminal amino acid residues were missing. The deletion of 3 and 8 amino acids had full activity. More deletions of KGF have been described in PCT/IB95/00971. The deletion of carboxyterminal amino acids can enhance the activity of proteins. One example is interferon gamma that shows up to ten times higher activity by deleting ten amino acid residues from the carboxy terminus of the protein (Döbeli et al., *J. of Biotechnology* 7:199–216 (1988)). Thus, one aspect of the invention is to provide polypeptide analogs of KGF-2 and nucleotide sequences encoding such analogs that exhibit enhanced stability (e.g., when exposed to typical pH, thermal conditions or other storage conditions) relative to the native KGF-2 polypeptide.

Particularly preferred KGF-2 polypeptides are shown below (numbering starts with the first amino acid in the protein (Met) (FIG. 1 (SEQ ID NO:2)):

Thr (residue 36) -- Ser (residue 208)
Cys (37) -- Ser (208)
Gln (38) -- Ser (208)
Ala (39) -- Ser (208)
Leu (40) -- Ser (208)
Gly (41) -- Ser (208)
Gln (42) -- Ser (208)
Asp (43) -- Ser (208)
Met (44) -- Ser (208)
Val (45) -- Ser (208)
Ser (46) -- Ser (208)
Pro (47) -- Ser (208)
Gln (48) -- Ser (208)
Ala (49) -- (Ser (208)
Thr (50) -- Ser (208)
Asn (51) -- Ser (208)
Ser (52) -- Ser (208)
Ser (53) -- Ser (208)
Ser (54) -- Ser (208)
Ser (55) -- Ser (208)
Ser (56) -- Ser (208)
Phe (57) -- Ser (208)
Ser (59) -- Ser (208)
Ser (62) -- Ser (208)
Ala (63) -- Ser (208)
Gly (64) -- Ser (208)
Arg (65) -- Ser (208)
Val (67) -- Ser (208)
Ser (69) -- Ser (208)
Val (77) -- Ser (208)
Arg (80) -- Ser (208)
Met(1), Thr (36), or Cys (37) -- His (207)
Met (1), Thr (36), or Cys (37) -- Val (206)
Met (1), Thr (36), or Cys (37) -- Val (205)
Met(1), Thr (36), or Cys (37) -- Met (204)
Met(1), Thr (36), or Cys (37) -- Pro (203)
Met(1), Thr (36), or Cys(37) -- Leu (202)
Met(1), Thr (36), or Cys (37) -- Phe (201)
Met(1), Thr (36), or Cys (37) -- His (200)
Met(1), Thr (36), or Cys (37) -- Ala (199)
Met(1), Thr (36), or Cys (37) -- Ser (198)
Met (1), Thr (36), or Cys (37) -- Thr (197)
Met(1), Thr (36), or Cys (37) -- Asn (196)
Met(1), Thr (36), or Cys (37) -- Lys (195)
Met (1), Thr (36), or Cys (37) -- Arg (194)

-continued

| Met(1), Thr (36), or Cys (37) -- Arg (193) |
| Met(1), Thr (36), or Cys (37) -- Thr (192) |
| Met(1), Thr (36), or Cys (37) -- Lys (191) |
| Met(1), Thr (36), or Cys (37) -- Arg (188) |
| Met(1), Thr (36), or Cys (37) -- Arg (187) |
| Met(1), Thr (36), or Cys (37) -- Lys (183) |

Preferred embodiments include the N-terminal deletions Ala (63)-Ser (208) (KGF-2Δ28) (SEQ ID NO:68) and Ser (69)-Ser (208) (KGF-2Δ33) (SEQ ID NO:96). Other preferred N-terminal and C-terminal deletion mutants are described in Examples 13 and 16 (c) of the specification and include: Ala (39)-Ser (208) (SEQ ID NO:116); Pro (47)-Ser (208) of FIG. 1 (SEQ ID NO:2); Val (77)-Ser (208) (SEQ ID NO:70); Glu (93)-Ser (208) (SEQ ID NO:72); Glu (104)-Ser (208) (SEQ ID NO:74); Val (123)-Ser (208) (SEQ ID NO:76); and Gly (138)-Ser (208) (SEQ ID NO:78). Other preferred C-terminal deletion mutants include: Met (1), Thr (36), or Cys (37)-Lys (153) of FIG. 1 (SEQ ID NO:2).

Also included by the present invention are deletion mutants having amino acids deleted from both the N-terminus and the C-terminus. Such mutants include all combinations of the N-terminal deletion mutants and C-terminal deletion mutants described above, e.g., Ala (39)-His (200) of FIG. 1 (SEQ ID NO:2), Met (44)-Arg (193) of FIG. 1 (SEQ ID NO:2), Ala (63)-Lys (153) of FIG. 1 (SEQ ID NO:2), Ser (69)-Lys (153) of FIG. 1 (SEQ ID NO:2), etc. etc. etc. . . . Those combinations can be made using recombinant techniques known to those skilled in the art.

Thus, in one aspect, N-terminal deletion mutants are provided by the present invention. Such mutants include those comprising the amino acid sequence shown in FIG. 1 (SEQ ID NO:2) except for a deletion of at least the first 38 N-terminal amino acid residues (i.e., a deletion of at least Met (1)-Gln (38)) but not more than the first 147 N-terminal amino acid residues of FIG. 1 (SEQ ID NO:2). Alternatively, the deletion will include at least the first 38 N-terminal amino acid residues (i.e., a deletion of at least Met (1)-Gln (38)) but not more than the first 137 N-terminal amino acid residues of FIG. 1 (SEQ ID NO:2). Alternatively, the deletion will include at least the first 46 N-terminal amino acid residues but not more than the first 137 N-terminal amino acid residues of FIG. 1 (SEQ ID NO:2). Alternatively, the deletion will include at least the first 62 N-terminal amino acid residues but not more than the first 137 N-terminal amino acid residues of FIG. 1 (SEQ ID NO:2). Alternatively, the deletion will include at least the first 68 N-terminal amino acid residues but not more than the first 137 N-terminal amino acid residues of FIG. 1 (SEQ ID NO:2). Alternatively, the deletion will include at least the first 76 N-terminal amino acid residues but not more than the first 137 N-terminal amino acid residues of FIG. 1 (SEQ ID NO:2). Alternatively, the deletion will include at least the first 92 N-terminal amino acid residues but not more than the first 137 N-terminal amino acid residues of FIG. 1 (SEQ ID NO:2). Alternatively, the deletion will include at least the first 103 N-terminal amino acid residues but not more than the first 137 N-terminal amino acid residues of FIG. 1 (SEQ ID NO:2). Alternatively, the deletion will include at least the first 122 N-terminal amino acid residues but not more than the first 137 N-terminal amino acid residues of FIG. 1 (SEQ ID NO:2).

In addition to the ranges of N-terminal deletion mutants described above, the present invention is also directed to all combinations of the above described ranges, e.g., deletions of at least the first 62 N-terminal amino acid residues but not more than the first 68 N-terminal amino acid residues of FIG. 1 (SEQ ID NO:2); deletions of at least the first 62 N-terminal amino acid residues but not more than the first 76 N-terminal amino acid residues of FIG.1 (SEQ ID NO:2); deletions of at least the first 62 N-terminal amino acid residues but not more than the first 92 N-terminal amino acid residues of FIG. 1 (SEQ ID NO:2); deletions of at least the first 62 N-terminal amino acid residues but not more than the first 103 N-terminal amino acid residues of FIG. 1 (SEQ ID NO:2); deletions of at least the first 68 N-terminal amino acid residues but not more than the first 76 N-terminal amino acid residues of FIG. 1 (SEQ ID NO:2); deletions of at least the first 68 N-terminal amino acid residues but not more than the first 92 N-terminal amino acid residues of FIG. 1 (SEQ ID NO:2); deletions of at least the first 68 N-terminal amino acid residues but not more than the first 103 N-terminal amino acid residues of FIG. 1 (SEQ ID NO:2); deletions of at least the first 46 N-terminal amino acid :residues but not more than the first 62 N-terminal amino acid residues of FIG. 1 (SEQ ID NO:2); deletions of at least the first 46 N-terminal amino acid residues but not more than the first 68 N-terminal amino acid residues of FIG. 1 (SEQ ID NO:2); deletions of at least the first 46 N-terminal amino acid residues but not more than the first 76 N-terminal amino acid residues of FIG. 1 (SEQ ID NO:2); etc. etc. etc. . . .

In another aspect, C-terminal deletion mutants are provided by the present invention. Preferably, the N-terminal amino acid residue of said C-terminal deletion mutants is amino acid residue 1 (Met), 36 (Thr), or 37 (Cys) of FIG. 1 (SEQ ID NO:2). Such mutants include those comprising the amino acid sequence shown in FIG. 1 (SEQ ID NO:2) except for a deletion of at least the last C-terminal amino acid residue (Ser (208)) but not more than the last 55 C-terminal amino acid residues (i.e., a deletion of amino acid residues Glu (154)-Ser (208)) of FIG. 1 (SEQ ID NO:2). Alternatively, the deletion will include at least the last C-terminal amino acid residue but not more than the last 65 C-terminal amino acid residues of FIG. 1 (SEQ ID NO:2). Alternatively, the deletion will include at least the last 10 C-terminal amino acid residues but not more than the last 55 C-terminal amino acid residues of FIG. 1 (SEQ ID NO:2). Alternatively, the deletion will include at least the last 20 C-terminal amino acid residues but not more than the last 55 C-terminal amino acid residues of FIG. 1 (SEQ ID NO:2). Alternatively, the deletion will include at least the last 30 C-terminal amino acid residues but not more than the last 55 C-terminal amino acid residues of FIG. 1 (SEQ ID NO:2). Alternatively, the deletion sill include at least the last 40 C-terminal amino acid residues but not more than the last 55 C-terminal amino acid residues of FIG. 1 (SEQ ID NO:2). Alternatively, the deletion will include at least the last 50 C-terminal amino acid residues but not more than the last 55 C-terminal amino acid residues of FIG. 1 (SEQ ID NO:2).

In addition to the ranges of C-terminal deletion mutants described above, the present invention is also directed to all combinations of the above described ranges, e.g., deletions of at least the last C-terminal amino acid residue but not more than the last 10 C-terminal amino acid residues of FIG. 1 (SEQ ID NO:2); deletions of at least the last C-terminal amino acid residue but not more than the last 20 C-terminal amino acid residues of FIG. 1 (SEQ ID NO:2); deletions of at least the last C-terminal amino acid residue but not more than the last 30 C-terminal amino acid residues of FIG. 1 (SEQ ID NO:2); deletions of at least the last C-terminal amino acid residue but not more than the last 40 C-terminal amino acid residues of FIG. 1 (SEQ ID NO:2); deletions of at least tile last 10 C-terminal amino acid residues but not more than the last 20 C-terminal amino acid residues of FIG. 1 (SEQ ID NO:2); deletions of at least the last 10 C-terminal amino acid residues but not more than the last 30 C-terminal amino acid residues of FIG. 1 (SEQ ID NO:2); deletions of at least the last 10 C-terminal amino acid residues but not more than the last 40 C-terminal amino acid residues of FIG. 1 (SEQ ID NO:2); deletions of at least the last 20 C-terminal amino acid residues but not more than the last 30 C-terminal amino acid residues of FIG. 1 (SEQ ID NO:2); etc. etc. etc. . . .

In yet another aspect, also included by the present invention are deletion mutants having amino acids deleted from both the N-terminal and C-terminal residues. Such mutants include all combinations of the N-terminal deletion mutants and C-terminal deletion mutants described above. Such mutants include those comprising the amino acid sequence shown in FIG. 1 (SEQ ID NO:2) except for a deletion of at least the first 46 N-terminal amino acid residues but not more than the first 137 N-terminal amino acid residues of FIG. 1 (SEQ ID NO:2) and a deletion of at least the last C-terminal amino acid residue but not more than the last 55 C-terminal amino acid residues of FIG. 1 (SEQ ID NO:2). Alternatively, a deletion can include at least the first 62, 68, 76, 92, 103, or 122 N-terminal amino acids but not more than the first 137 N-terminal amino acid residues of FIG. 1 (SEQ ID NO:2) and a deletion of at least the last 10, 20, 30, 40, or 50 C-terminal amino acid residues but not more than the last 55 C-terminal amino acid residues of FIG. 1 (SEQ ID NO:2). Further included are all combinations of the above described ranges.

Substitution of Amino Acids

A further aspect of the present invention also includes the substitution of amino acids. Native mature KGF-2 contains 44 charged residues, 32 of which carry a positive charge. Depending on the location of such residues in the protein's three dimensional structure, substitution of one or more of these clustered residues with amino acids carrying a negative charge or a neutral charge may alter the electrostatic interactions of adjacent residues and may be useful to achieve increased stability and reduced aggregation of the protein. Aggregation of proteins cannot only result in a loss of activity but be problematic when preparing pharmaceutical formulations, because they can be immunogenic (Pinckard et al., Clin. Exp. Immunol. 2:331–340 (1967), Robbins et al., Diabetes 36: 838–845 (1987), Cleland et al., Crit. Rev. Therapeutic Drug Carrier Systems 10: 307–377 (1993)). Any modification should give consideration to minimizing charge repulsion in the tertiary structure of the protein molecule. Thus, of special interest are substitutions of charged amino acid with another charge and with neutral or negatively charged amino acids. The latter results in proteins with a reduced positive charge to improve the characteristics of KGF-2. Such improvements include increased stability and reduced aggregation of the analog as compared to the native KGF-2 protein.

The replacement of amino acids can also change the selectivity of binding to cell surface receptors. Ostade et al., Nature 361: 266–268 (1993), described certain TNF alpha mutations resulting in selective binding of TNF alpha to only one of the two known TNF receptors.

KGF-2 molecules may include one or more amino acid substitutions, deletions or additions, either from natural mutation or human manipulation. Examples of some preferred mutations are: Ala (49) Gln, Asn (51) Ala, Ser (54) Val, Ala (63) Pro, Gly (64) Glu, Val (67) Thr, Trp (79) Val, Arg (80) Lys, Lys (87) Arg, Tyr (88) Trp, Phe (89) Tyr, Lys (91) Arg, Ser (99) Lys, Lys (102) Gin, Lys 103(Glu), Glu (104) Met, Asn (105) Lys, Pro (107) Asn, Ser (109) Asn, Leu (111) Met, Thr (114) Arg, Glu(117) Ala, Val (120) Ile, Val (123) Ile, Ala (125) Gly, Ile (126) Val, Asn (127) Glu, Asn (127) Gln, Tyr (130) Phe, Met (134) Thr, Lys (136) Glu, Lys (137) Glu, Gly (142) Ala, Ser (143) Lys, Phe (146) Ser, Asn (148) Glu, Lys (151) Asn, Leu (152) Phe, Glu (154) Gly, Glu (154) Asp, Arg (155) Leu, Glu (157) Leu, Gly (160) His, Phe (167) Ala, Asn (168) Lys, Gln (170) Thr, Arg (174) Gly, Tyr (177) Phe, Gly (182) Gln, Ala (185) Val, Ala (185) Leu, Ala (185) Ile, Arg (187) Gln (190) Lys, Lys (195) Glu, Thr (197) Lys, Ser (198) Thr, Arg (194) Glu, Arg (194) Gln, Lys (191) Glu, Lys (191) Gln, Arg (188) Glu, Arg (188) Gln, Lys (183) Glu.

By the designation, for example, Ala (49) Gln is intended that the Ala at position 49 of FIG. 1 (SEQ ID NO:2) is replaced by Gln.

Changes are preferably of minor nature, such as conservative amino acid substitutions that do not significantly affect the folding or activity of the protein. Examples of conservative amino acid substitutions known to those skilled in the art are set forth below:

| | |
|---|---|
| Aromatic: | phenylalanine |
| | tryptophan |
| | tyrosine |
| Hydrophobic: | leucine |
| | isoleucine |
| | valine |
| Polar: | glutamine |
| | asparagine |
| Basic: | arginine |
| | lysine |
| | histidine |
| Acidic: | aspartic acid |
| | glutamic acid |
| Small: | alanine |
| | serine |
| | threonine |
| | methionine |
| | glycine |

Of course, the number of amino acid substitutions a skilled artisan would make depends on many factors, including those described above. Generally speaking, the number of substitutions for any given KGF-2 polypeptide will not be more than 50, 40, 30, 20, 10, 5, or 3, depending on the objective. For example, a number of substitutions that can be made in the C-terminus of KGF-2 to improve stability are described above and in Example 22.

Amino acids in KGF-2 that are essential for function can be identified by methods well known in the art, such as site-directed mutagenesis or alanine-scanning mutagenesis (Cunningham and Wells, Science 244 :1081–1085 (1989). The latter procedure introduces single alanine mutations at every residue in the molecule. The resulting mutant molecules are then tested for biological activity such as receptor binding or in vitro and in vivo proliferative activity. (See, e.g., Examples 10 and 11). Sites that are critical for ligand-receptor binding can also be determined by structural analyzis such as crystalization, nuclear magnetic resonance or photoaffinity labelling. (See for example: Smith et al., J. Mol. Biol., 224: 899–904 (1992); and de Vos et al. Science, 255: 306–312 (1992).)

Another aspect of the present invention substitutions of serine for cysteine at amino acid positions 37 and 106 and 150. An uneven number of cysteins means that at least one cysteine residue is available for intermolecular crosslinks or bonds that can cause the protein to adopt an undesirable tertiary structure. Novel KGF-2 proteins that have one or more cysteine replaced by serine or e.g. alanine are generally purified at a higher yield of soluble, correctly folded protein. Although not proven, it is believed that the cysteine residue at position 106 is important for function. This cysteine residue is highly conserved among all other FGF family members.

A further aspect of the present invention are fusions of KGF2 with other proteins or fragments thereof such as fusions or hybrids with other FGF proteins, e.g. KGF (FGF-7), bFGF, aFGF, FGF-5, FGF-6, etc. Such a hybrid has been reported for KGF (FGF-7). In the published PCT application no. 90/08771 a chimeric protein has been produced consisting of the first 40 amino acid residues of KGF and the C-terminal portion of AFGF. The chimera has been reported to target keratinocytes like KGF, but lacked suceptibility to heparin, a characteristic of aFGF but not KGF. Fusions with parts of the constant domain of immunoglobulins (IgG) show often an increased halflife time in vivo. This has been shown, e.g., for chimeric proteins consisting of the first two domains of the human CD4-polypeptide with various domains of the constant regions of the heavy or light chains of mammalian immunoglobulins (European Patent application, Publication No. 394 827, Traunecker et al., Nature, 331, 84–86 (1988). Fusion proteins that have a disulfide-linked dimeric structure can also be more efficient in binding monomeric molecules alone (Fountoulakis et al., *J. of Biochemistry*, 270: 3958–3964, (1995)).

Antigenic/hydrophilic Parts of KGF-2

As demonstrated in FIG. 4A–4E, there are 4 major highly hydrophilic regions in the KGF-2 protein. Amino acid residues Gly41-Asn71, Lys91-Ser 109, Asn135-Tyr 164 and Asn 181-Ala 199 [SEQ ID NOS: 25–28]. There are two additional shorter predicted antigenic areas, Gln 74-Arg 78 of FIG. 1 (SEQ ID NO:2) and Gln 170-Gln 175 of FIG. 1 (SEQ ID NO:2). Hydrophilic parts are known to be mainly at the outside (surface) of proteins and, therefore, available for antibodies recognizing these regions. Those regions are also likely to be involved in the binding of KGF-2 to its receptor(s). Synthetic peptides derived from these areas can interfere with the binding of KGF-2 to its receptor(s) and, therefore, block the function of the protein. Synthetic peptides from hydrophilic parts of the protein may also be agonistic, i.e. mimic the function of KGF-2.

Thus, the present invention is further directed to isolated polypeptides comprising a hydrophilic region of KGF-2 wherein said polypeptide is not more than 150 amino acids in length, preferably not more than 100, 75, or 50 amino acids in length, which comprise one or more of the above described KGF-2 hydrophilic regions.

Chemical Modifications

The KGF wild type and analogs may be further modified to contain additional chemical moieties not normally part of the protein. Those derivatized moieties may improve the solubility, the biological half life or absorption of the protein. The moieties may also reduce or eliminate any desirable side effects of the proteins and the like. an overview for those moieties can be found in REMINGTON'S PHARMACEUTICAL SCIENCES, 18th ed., Mack Publishing Co., Easton, Pa. (1990). Polyethylene glycol (PEG) is one such chemical moiety which has been used for the preparation of therapeutic proteins. The attachment of PEG to proteins has been shown to protect against proteolysis, Sada et al., *J. Fermentation Bioengineering* 71: 137–139 (1991). Various methods are available for the attachment of certain PEG moieties. For review, see: Abuchowski et al., in Enzymes as Drugs. (Holcerberg and Roberts, eds.) pp. 367–383 (1981). Many published patents describe derivatives of PEG and processes how to prepare them, e.g., Ono et al. U.S. Pat. No. 5,342,940; Nitecki et al. U.S. Pat. No. 5,089,261; Delgado et al. U.S. Pat. No. 5,349,052. Generally, PEG molecules are connected to the protein via a reactive group found on the protein. Amino groups, e.g. on lysines or the amino terminus of the protein are convenient for this attachment among others.

The entire disclosure of each document cited in this section on "Polypeptides and Peptides" is hereby incorporated herein by reference.

Vectors and Host Cells

The present invention also relates to vectors which include the isolated DNA molecules of the present invention, host cells which are genetically engineered with the recombinant vectors, and the production of KGF-2 polypeptides or fragments thereof by recombinant techniques.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention. The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the KGF-2 genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequences) (promoter) to direct cDNA synthesis. As representative examples of such promoters, there may be mentioned: LTR or SV40 promoter, the *E. coli*. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Streptomyces, Salmonella typhimirium*; fungal cells, such as yeast; insect cells such as *Drosophila* S2 and *Spodoptera* Sf9; animal cells such as CHO, COS or Bowes melanoma; adenoviruses; plant cells, etc. The selection of an appropriate host is deemed to be within the scope of those skilled in the art from the teachings herein.

In addition to the use of expression vectors in the practice of the present invention, the present invention further includes novel expression vectors comprising operator and promoter elements operatively linked to nucleotide sequences encoding a protein of interest. One example of such a vector is pHE4–5 which is described in detail below.

Figure 50:
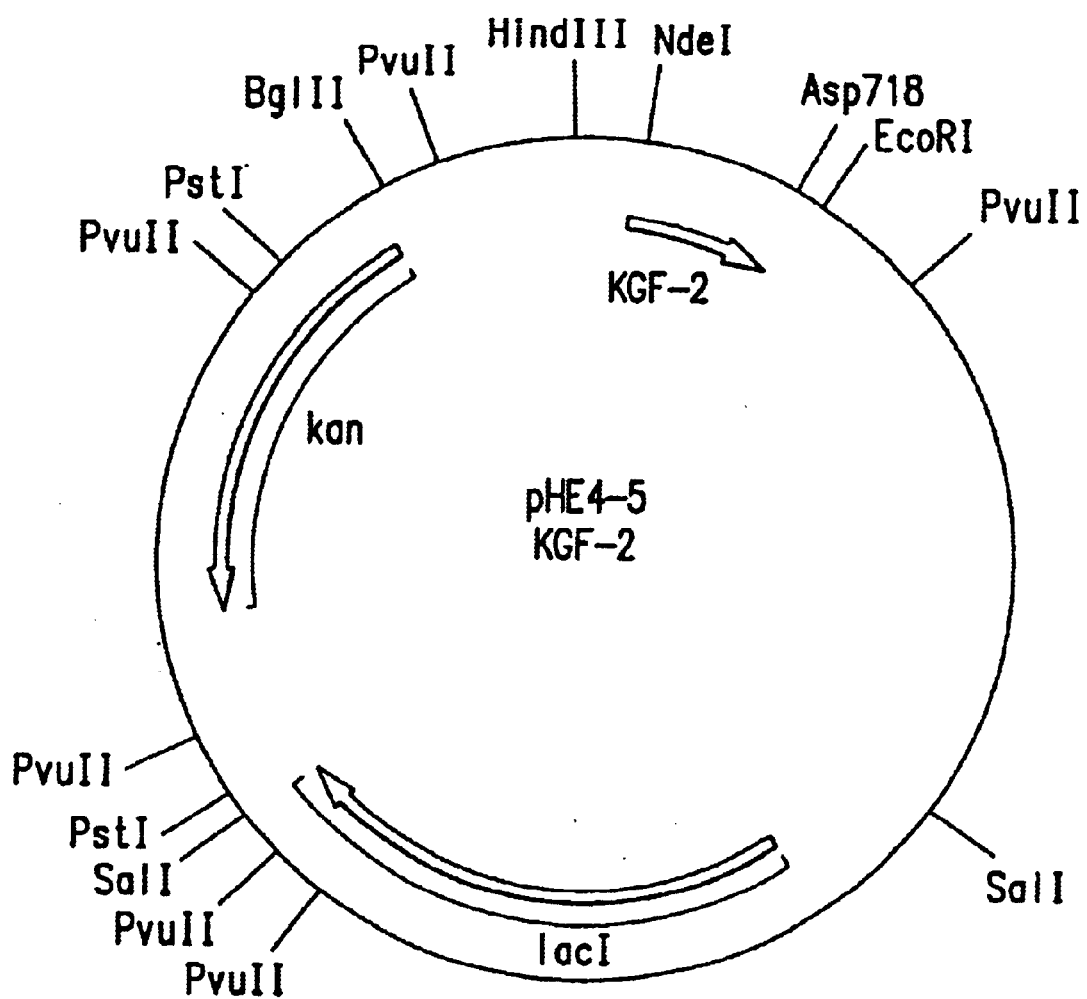
FIG. 50 shows a schematic representation of the pHE4–5 expression vector (SEQ ID NO:147) and the subcloned KGF-2 cDNA coding sequence. The locations of the kanamycin resistance marker gene, the KGF-2 coding sequence, the oriC sequence, and the lacIq coding sequence are indicated.

As summarized in FIGS. 50 and 51, components of the pHE4–5 vector (SEQ ID NO:147) include: 1) a neomycin-phosphotransferase gene as a selection marker, 2) an *E. coli* origin of replication, 3) a T5 phage promoter sequence, 4) two lac operator sequences, 5) a Shine-Delgarno sequence, 6) the lactose operon repressor gene (lacIq). The origin of replication (oriC) is derived from pUC19 (LTI, Gaithersburg, Md.). The promoter sequence and operator sequences were made synthetically. Synthetic production of nucleic acid sequences is well known in the art. CLONTECH 95/96 Catalog, pages 215–216, CLONTECH, 1020 East Meadow Circle, Palo Alto, Calif. 94303. A nucleotide sequence encoding KGF-2 (SEQ ID NO:1), is operatively linked to the promoter and operator by inserting the nucleotide sequence between the NdeI and Asp718 sites of the pHE4–5 vector.

As noted above, the pHE4–5 vector contains a lacIq gene. LacIq is an allele of the lacI gene which confers tight regulation of the lac operator. Amann, E. et al., *Gene* 69:301–315 (1988); Stark, M., *Gene* 51:255–267 (1987). The lacIq gene encodes a repressor protein which binds to lac operator sequences and blocks transcription of down-stream (i.e., 3') sequences. However, the lacIq gene product dissociates from the lac operator in the presence of either lactose or certain lactose analogs, e.g., isopropyl B-D-thiogalactopyranoside (IPTG). KGF-2 thus is not produced in appreciable quantities in uninduced host cells containing the pHE4–5 vector. Induction of these host cells by the addition of an agent such as IPTG, however, results in the expression of the KGF-2 coding sequence.

The promoter/operator sequences of the pHE4–5 vector (SEQ ID NO:148) comprise a T5 phage promoter and two lac operator sequences. One operator is located 5' to the transcriptional start site and the other is located 3' to the same site. These operators, when present in combination with the lacIq gene product, confer tight repression of down-stream sequences in the absence of a lac operon inducer, e.g., IPTG. Expression of operatively linked sequences located down-stream from the lac operators may be induced by the addition of a lac operon inducer, such as IPTG. Binding of a lac inducer to the lacIq proteins results in their release from the lac operator sequences and the initiation of transcription of operatively linked sequences. Lac operon regulation of gene expression is reviewed in Devlin, T., Textbook of Biochemistry with Clinical Correlations, 4th Edition (1997), pages 802–807.

The pHE4 series of vectors contain all of the components of the pHE4–5 vector except for the KGF-2 coding sequence. Features of the pHE$^4$ vectors include optimized synthetic T5 phage promoter, lac operator, and Shine-Delagamo sequences. Further, these sequences are also optimally spaced so that expression of an inserted gene may be tightly regulated and high level of expression occurs upon induction.

Among known bacterial promoters suitable for use in the production of proteins of the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metillothionein-I promoter.

The pHE4–5 vector also contains a Shine-Delgarno sequence 5' to the AUG initiation codon. Shine-Delgarno sequences are short sequences generally located about 10 nucleotides up-stream (Le., 5') from the AUG initiation codon. These sequences essentially direct prokaryotic ribosomes to the AUG initiation codon.

Thus, the present invention is also directed to expression vector useful for the production of the proteins of the present invention. This aspect of the invention is exemplified by the pHE4–5 vector (SEQ ID NO:147). The pHE4–5 vector containing a cDNA insert encoding KGF-2Δ33 was deposited at the ATCC on Jan. 9, 1998 as ATCC No. 209575.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 ((Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene, using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfetion, or electroporation (Davis, L. et al., *Basic Methods in Molecular Biology* (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual*, Second Edition, Cold Spring Harbor, N.Y. (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovimis early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize receptors. For example, EP-A-O 464 533 (Canadian counterpart 2045869) discloses fusion proteins comprising various portions of constant region of immunoglobin molecules together with another human protein or part thereof. In many cases, the Fc part in fusion protein is thoroughly advantageous for use in therapy and diagnosis and thus results, for example, in improved pharmacokinetic properties (EP-A 0232 262). On the other hand, for some uses it would be desirable to be able to delete the Fc pat after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, shIL5- has been fused with Fc portions for the purpose of high-throughput screening assays to identify antagonists of hIL-5. See, D. Bennett et al., *Journal of Molecular Recognition*, Vol. 8 52–58 (1995) and K. Johanson et al., *The Journal of Biological Chemistry*, Vol. 270, No. 16, pp 9459–9471 (1995).

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, *Streptomyces*, and *Staphylococcus*, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 Pharmacia Fine Chemicals, Uppsala, Sweden) and GEM1 (Promega Biotec, Madison, Wis., USA) These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzmar, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The KGF-2 polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

Diagnostic and Therapeutic Applications of KGF-2

As used in the section below, "KGF-2" is intended to refer to the full-length and mature forms of KGF-2 described herein and to the KGF-2 analogs, derivatives and mutants described herein. This invention is also related to the use of the KGF-2 gene as part of a diagnostic assay for detecting diseases or susceptibility to diseases related to the presence of mutations in the KGF-2 nucleic acid sequences.

Individuals carrying mutations in the KGF-2 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature 324:163–166 (1986)) prior to analysis. RNA or cDNA may also be used for the same purpose. As an example, PCR primers complementary to the nucleic acid encoding KGF-2 can be used to identify and analyze KGF-2 mutations. For example, deletions and insertions can be detected by a change in size of the amplified product in comparison to the normal genotype. Point mutations can be identified by hybridizing amplified DNA to radiolabeled KGF-2 RNA or alternatively, radiolabeled KGF-2 antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel ectrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA In addition to more conventional gel-electrophoresis and DNA sequencing, mutations can also be detected by in situ analysis.

The present invention also relates to a diagnostic assay for detecting altered levels of KGF-2 protein in various tissues since an over-expression of the proteins compared to normal control tissue samples may detect the presence of a disease or susceptibility to a disease, for example, a tumor. Assays used to detect levels of KGF-2 protein in a sample derived from a host are well-known to those of skill in the art and include radioimmunoassays, competitive-binding assays, Western Blot analysis, ELISA assays and "sandwich" assay. An ELISA assay (Coligan, et al., Current Protocols in Immunology, 1(2), Chapter 6, (1991)) initially comprises preparing an antibody specific to the KGF-2 antigen, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a non-specific protein like bovine serum albumen. Next, the monoclonal antibodies attach to any KGF-2 proteins attached to the polytyrene dish. All unbound monoclonal antibody is washed out with buffer. The reporter antibody linked to horseradish peroxidase is now placed in the dish resulting in binding of the reporter antibody to any monoclonal antibody bound to KGF-2. Unattached reporter antibody is then washed out. Peroxidase substrates are then added to the dish and the amount of color developed in a given time period is a measurement of the amount of KGF-2 protein present in a given volume of patient sample when compared against a standard curve.

A competition assay may be employed wherein antibodies specific to KGF-2 are attached to a solid support and labeled KGF-2 and a sample derived from the host are passed over the solid support and the amount of label detected, for example by liquid scintillation chromatography, can be correlated to a quantity Of KGF-2 in the sample.

A "sandwich" assay is similar to an ELISA assay. In a "sandwich" assay KGF-2 is passed over a solid support and binds to antibody attached to a solid support. A second antibody is then bound to the KGF-2. A third antibody which is labeled and specific to the second antibody is then passed over the solid support and binds to the second antibody and an amount can then be quantified.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single, chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler & Milstein, *Nature*, 256:495–497 (1975)), the trioma technique, the human B-cell hybridoma technique (Kozbor, et al., *Immunology Today* 4:72 (1983)), and the EBV-hybridoma technique to produce human monoclonal antibodies (Cole, et al., *Monoclonal Antibodies and Cancer Therapy*, Alan R. Liss, Inc., pp. 77–96 (1985)).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The polypeptides of the present invention may be employed to stimulate new blood vessel growth or angiogenesis. Particularly, the polypeptides of the present invention may stimulate keratinocyte cell growth and proliferation. Accordingly the present invention provides a process for utilizing such polypeptide, or polynucleotide encoding such polypeptide for therapeutic purposes, for example, to stimulate epithelial cell proliferation and basal keratinocytes for the purpose of wound healing, and to stimulate hair follicle production and healing of dermal wounds.

As noted above, the polypeptides of the present invention may be employed to heal dermal wounds by stimulating epithelial cell proliferation. These wounds may be of superficial nature or may be deep and involve damage of the dermis and the epidermis of skin. Thus, the present invention provides a method for the promotion of wound healing that involves the administration of an effective amount of KGF-2 to an individual.

The individual to which KGF-2 is administered may heal wounds at a normal rate or may be healing impaired. When administered to an individual who is not healing impaired, KGF-2 is administered to accelerate the normal healing process. When administered to an individual who is healing impaired, KGF-2 is administered to facilitate the healing of wounds which would otherwise heal slowly or not at all. As noted below, a number of afflictions and conditions can result in healing impairment. These afflictions and conditions include diabetes (e.g., Type II diabetes mellitus), treatment with both steroids and other pharmacological agents, and ischemic blockage or injury. Steroids which have been shown to impair wound healing include cortisone, hydrocortisone, dexamethasone, and methylprednisolone.

Non-steroid compounds, e.g., octreotide acetate, have also been shown to impair wound healing. Waddell, B. et al., *Am. Surg.* 63:446–449 (1997). The present invention is believed to promote wound healing in individuals undergoing treatment with such non-steroid agents.

A number of growth factors have been shown to promote wound healing in healing impaired individuals. See, e.g., Steed, D. et al., *J. Am. Coll. Surg.* 183:61–64 (1996); Richard, J. et al., *Diabetes Care* 18: 64–69 (199,5); Steed, D., *J. Vasc. Surg.* 21:71–78 (1995); Kelley, S. et al., *Proc. Soc. Exp. Biol.* 194:320–326 (1990). These growth factors include growth hormone-releasing factor, platelet-derived growth factor, and basic fibroblast growth factor. Thus, the present invention also encompasses the administration of KGF-2 in conjunction with one or more additional growth factors or other agent which promotes wound healing.

The present invention also provides a method for promoting the healing of anastomotic and other wounds caused by surgical procedures in individuals which both heal wounds at a normal rate and are healing impaired. This method involves the administration of an effective amount of KGF-2 to an individual before, after, and/or during anastomotic or other surgery. Anastomosis is the connecting of two tubular structures, as which happens, for example, when a midsection of intestine is removed and the remaining portions are linked together to reconstitute the intestinal tract. Unlike with cutaneous healing, the healing process of anastomotic wounds is generally obscured from view. Further, wound healing, at least in the gastrointestinal tract, occurs rapidly in the absence of complications; however, complications often require correction by additional surgery. Thornton, F. and Barbul, A., *Surg. Clin. North Am.* 77:549–573 (1997). As shown in Examples 21 and 28, treatment with KGF-2 causes a significant decrease in peritoneal leakage and anastomotic constriction following colonic anastomosis. KGF-2 is believed to cause these results by accelerating the healing process thus decreasing the probability of complications arising following such procedures.

Thus, the present invention also provides a method for accelerating healing after anastomoses or other surgical procedures in an individual, which heals wounds at a normal rate or is healing impaired, compromising the administration of an effective amount of KGF-2.

The polypeptides of the present invention may also be employed to stimulate differentiation of cells, for example muscle cells, cells which make up nervous tissue, prostate cells, and lung cells.

KGF-2 may be clinically useful in stimulating wound healing of wounds including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, and burns resulting from heat exposure or chemicals, in normal individuals and those subject to conditions which induce abnormal wound healing such as uremia, malnutrition, vitamin deficiencies, obesity, infection, immunosuppression and complications associated with systemic treatment with steroids, radiation therapy, and antineoplastic drugs and antimetabolites. KGF-2 is also useful for promoting the healing of wounds associated with ischemia and ischemic injury, e.g., chronic venous leg ulcers caused by an impairment of venous circulatory system return and/or insufficiency.

KGF-2 can also be used to promote dermal reestablishment subsequent to dermal loss. In addition, KGF-2 can be used to increase the tensile strength of epidermis and epidermal thickness.

KGF-2 can be used to increase the adherence of skin grafts to a wound bed and to stimulate re-epithelialization from the wound bed. The following are types of grafts that KGF-2 could be used to increase adherence to a wound bed: autografts, artificial skin, allografts, autodermic graft, autoepidermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft.

KGF-2 can be used to promote skin strength and to improve the appearance of aged skin.

It is believed that KGF-2 will also produce changes in hepatocyte proliferation, and epithelial cell proliferation in the lung, breast, pancreas, stomach, small intestine, and large intestine. KGF-2 can promote proliferation of epithelial cells such as sebocytes, hair follicles, hepatocytes, type II pneumocytes, mucin-producing goblet cells, and other epithelial cells and their progenitors contained within the skin, lung, liver, kidney and gastrointestinal tract. As shown in Example 31, KGF-2 stimulates the proliferation of hepatocytes. Thus, KGF-2 can also be used prophylactically or therapeutically to prevent or attenuate acute or chronic viral hepatitis as well as fulminant or subfulminant liver failure caused by diseases such as acute viral hepatitis, cirrhosis, drug- and toxin-induced hepatitis (e.g, acetaminophen, carbon tetrachloride, methotrexate, organic arsenicals, and other hepatotoxins known in the art), autoimmune chronic active hepatitis, liver transplantation, and partial hepatectomy (Cotran et al. *Pathologic basis of disease.* (51 ed). Philadelphia, W. B. Saunders Company, 1994). KGF-2 can also be used to stimulate or promote liver regeneration and in patients with alcoholic liver disease.

Approximately 80% of acute pancreatitis cases are associated with biliary tract disease and alcoholism (Rattner D. W., *Scand J Gastroenterol* 31:6–9 (1996); Cotran et al. *Pathologic basis of disease.* ($5^{th}$ ed). Philadelphia, W. B. Saunders Company, 1994). Acute pancreatitis is an important clinical problem with significant morbidity and mortality (Banerjee et al., *British Journal of Surgery* 81:1096–1103 (1994)). The pathogenesis of this disease is still somewhat unresolved but it is widely recognized that pancreatic enzymes are released within the pancreas leading to proteolysis, interstitial inflammation, fat necrosis, and hemorrhage. Acute pancreatitis can lead to disseminated intravascular coagulation, adult respiratory distress syndrom, shock, and acute renal tubular necrosis (Cotran et al. *Pathologic basis of disease.* ($5^{th}$ ed). Philadelphia, W. B. Saunders Company, 1994). Despite palliative measures, about 5% of these patients die of shock during the first week of the clinical course. In surviving patients, sequelae may include pancreatic abscess, pseudocyst, and duodenal obstruction (Cotran et al. *Pathologic basis of disease.* ($5^{th}$ ed). Philadelphia, W. B. Saunders Company, 1994). Chronic pancreatitis is often a progressive destruction of the pancreas caused by repeated flare-ups of acute pancreatitis. Chronic pancreatitis appears to incur a modestly increased risk of pancreatic carcinoma (Cotran et al. *Pathologic basis of disease.* ($5^{th}$ ed). Philadelphia, W. B. Saunders Company, 1994).

As indicated above and in Example 31, KGF-2 also promotes proliferation of pancreatic cells. Thus, in a further aspect, KGF-2 can be used prophylactically or therapeutically to prevent or attenuate acute or chronic pancreatitis.

KGF-2 can also be used to reduce the side effects of gut toxicity that result from the treatment of viral infections, radiation therapy, chemotherapy or other treatments. KGF-2 may have a cytoprotective effect on the small intestine mucosa. KGF-2 may also be used prophylactically or therapeutically to prevent or attenuate mucositis and to stimulate healing of mucositis (e.g., oral, esophageal, intestinal, colonic, rectal, and anal ulcers) that result from chemotherapy, other agents and viral infections. Thus the present invention also provides a method for preventing or treating diseases or pathological events of the mucosa, including ulcerative colitis, Crohn's disease, and other diseases where the mucosa is damaged, comprising the administration of an effective amount of KGF-2. The present invention similarly provides a method for preventing or treating oral (including odynophagia associated with mucosal injury in the pharynx and hypopharynx), esophageal, gastric, intestinal, colonic and rectal mucositis irrespective of the agent or modality causing this damage.

KGF-2 can promote proliferation of endothelial cells, keratinocytes, and basal keratinocytes. Thus, the present invention also provides a method for stimulating the proliferation of such cell types which involves contacting cells with an effective amount of KGF-2. KGF-2 may be administered to an individual in an effective amount to stimulate cell proliferation in vivo or KGF-2 may be contacted with such cells in vitro.

The present invention further provides a method for promoting urothelial healing comprising administering an effective amount of KGF-2 to an individual. Thus, the present invention provides a method for accelerating the healing or treatment of a variety of pathologies involving urothelial cells (i.e., cells which line the urinary tract). Tissue layers comprising such cells may be damaged by numerous mechanisms including catheterization, surgery, or bacterial infection (e.g., infection by an agent which causes a sexually transmitted disease, such as gonorrhea).

The present invention also encompasses methods for the promotion of tissue healing in the female genital tract comprising the administration of an effective amount of KGF-2. Tissue damage in the female genital tract may be caused by a wide variety of conditions including *Candida* infections trichomoniasis, *Gardnerella*, gonorrhea, chlamydia, mycoplasma infections and other sexually transmitted diseases.

As shown in Examples 10, 18, and 19 KGF-2 stimulates the proliferation of epidermal keratinocytes and increases epidermal thickening. Thus, KGF-2 can be used in full regeneration of skin; in full and partial thickness skin defects, including burns (i.e., repopulation of hair follicles, sweat glands, and sebaceous glands); and the treatment of other skin defects such as psoriasis.

KGF-2 can be used to treat epidermolysis bullosa, a defect in adherence of the epidermis to the underlying dermis which results in frequent, open and painful blisters by accelerating reepithelialization of these lesions. KGF-2 can also be used to treat gastric and duodenal ulcers and help heal the mucosal lining and regeneration of glandular mucosa and duodenal mucosal lining more rapidly. Inflammatory bowel diseases, such as Crohn's disease and ulcerative, colitis, are diseases which result in destruction of the mucosal surface of the small or large intestine, respectively. Thus, KGF-2 could be used to promote the resurfacing of the mucosal surface to aid more rapid healing and to prevent or attenuate progression of inflammatory bowel disease. KGF-2 treatment is expected to have a significant effect on the production of mucus throughout the gastrointestinal tract and could be used to protect the intestinal mucosa from injurious substances that are ingested or following surgery. As noted above, KGF-2 can also be used to promote healing of intestinal or colonic anastomosis. KGF-2 can further be used to treat diseases associate with the under expression of KGF-2.

As shown in Example 32 below, KGF-2 stimulates proliferation of lung epithelial cells. Thus, KGF-2 can be administered prophylactically to reduce or prevent damage to the lungs caused by various pathological states. KGF-2 can also be administered during or after a damaging event occurs to prontote healing. For example, KGF-2 can stimulate proliferation and differentiation and promote the repair of alveoli and bronchiolar epithelium to prevent, attenuate, or treat acute or chronic lung damage. Emphysema, which results in the progressive loss of alveoli, and inhalation injuries, i.e., resulting from smoke inhalation and burns, that cause necrosis of the bronchiolar epithelium and alveoli could be effectively treated using KGF-2 as could damage attributable to chemotherapy, radiation treatment, lung cancer, asthma, black lung and other lung damaging conditions. Also, KGF-2 could be used to stimulate the proliferation of and differentiation of type II pneumocytes, which may help treat or prevent disease such as hyaline membrane diseases, such as infant respiratory distress syndrome and bronchopulmonary dysplasia, in premature infants.

The three causes of acute renal failure are prerenal (e.g., heart failure), intrinsic (e.g., nephrotoxicity induced by chemotherapeutic agents) and postrenal (e.g., urinary tract obstruction) which lead to renal tubular cell death, obstruction of the tubular lumens, and back flow of filtrate into the glomeruli (reviewed by Thadhani et al. *N. Engl. J. Med.* 334:1448–1460 (1996)). Growth factors such as insulin-like growth factor I, osteogenic protein-1, hepatocyte growth factor, and epidermal growth factor have shown potential for ameliorating renal disease in animal models. Taub et al. *Cytokine* 5:175–179 (1993); Vukicevic et al. *J. Am. Soc. Nephrol.* 7:1867 (1996). As shown in Example 31 below, KGF-2 stimulates proliferation of renal epithelial cells and, thus, is useful for alleviating or treating renal diseases and pathologies such as acute and chronic renal failure and end stage renal disease.

KGF-2 could stimulate the proliferation and differentiation of breast tissue and therefor could be used to promote healing of breast tissue injury due to surgery, trauma, or cancer.

In addition, KGF-2 could be used treat or prevent the onset of diabetes mellitus. In patients with newly diagnosed Types I and II diabetes, where some islet cell function remains, KGF-2 could be used to maintain the islet function so as to alleviate, delay or prevent permanent manifestation of the disease. Also, KGF-2 could be used as an auxiliary in islet cell transplantation to improve or promote islet cell function.

Further, the anti-inflammatory property of KGF-2, could be beneficial for treating acute and chronic conditions in which inflammation is a key pathogenesis of the diseases including, but not limiting to, psoriasis, eczema, dermatitis and/or arthritis. Thus, the present invention provides a method for preventing or attenuating inflammation, and diseases involving inflammation, in an individual comprising the administration of an effective amount of KGF-2.

KGF-2 can be used to promote healing and alleviate damage of brain tissue due to injury from trauma, surgery or chemicals.

In addition, since KGF-2 increases the thickness of the epidermis, the protein could be used for improving aged skin, reducing wrinkles in skin, reducing scarring after surgery. Scarring of wound tissues often involves hyperproliferation of dermal fibroblasts. As noted in Example 10, fibroblast proliferation is not stimulated by KGF-2. Therefore, KGF-2 appears to be a mitogen specific for epidermal keratinocytes and induces wound healing with minimal scarring. Thus, the present invention provides a method for promoting the healing of wounds with minimal scarring involving the administration of an effective amount of KGF-2 to an individual. KGF-2 may be administered prior to, during, and/or after the process which produces the wound (e.g. cosmetic surgery, accidental or deliberate tissue trauma caused by a sharp object).

As noted above, KGF-2 also stimulates the proliferation of keratinocytes and hair follicles and therefore can be used to promote hair growth from balding scalp, and in hair transplant patients. Thus, the present invention further provides a method for promoting hair growth comprising the administration of an amount KGF-2 sufficient to stimulate the production of hair follicles.

The present invention also provides a method for protecting an individual from the effects of ionizing radiation, chemotherapy, or treatment with anti-viral agents comprising the administration of an effective amount of KGF-2. The present invention further provides a method for treating tissue damage which results from exposure to ionizing radiation, chemotherapeutic agents, or anti-viral agents comprising the administration of an effective amount of KGF-2. An individual may be exposed to ionizing radiation for a number of reasons, including for therapeutic purposes (e.g., for the treatment of hyperproliferative disorders), as the result of an accidental release of a radioactive isotope into the environment, or during non-invasive medical diagnostic procedures (e.g., X-rays). Further, a substantial number of individuals are exposed to radioactive radon in their work places and homes. Long-term continuous environmental exposure has been used to calculate estimates of lost life expectancy. Johnson, W. and Kearfott, K., *Health Phys.* 73:312–319 (1997). As shown in Example 23, the proteins of the present invention enhance the survival of animals exposed to radiation. Thus, KGF-2 can be used to increase survival rate of individuals suffering radiation-induced injuries, to protect individuals from sub-lethal doses of radiation, and to increase the therapeutic ratio of irradiation in the treatment of afflictions such as hyperproliferative disorders.

KGF-2 may also be used to protect individuals against dosages of radiation, chemotherapeutic drugs or antiviral agents which normally would not be tolerated. When used in this manner, or as otherwise described herein, KGF-2 may be administered prior to, after, and/or during radiation therapy/exposure, chemotherapy or treatment with anti-viral agents. High dosages of radiation and chemotherapeutic agents may be especially useful when treating an individual having an advanced stage of an afflication such as a hyperprolifereative disorder.

In another aspect, the present invention provides a method for preventing or treating conditions such as radiation-induced oral and gastro-intestinal injury, mucositis, intestinal fibrosis, proctitis, radiation-induced pulmonary fibrosis, radiation-induced pneumonitis, radiation-induced pleural retraction, radiation-induced hemopoietic syndrome, radiation-induced myelotoxicity, comprising administering an effective amount of KGF-2 to an individual.

KGF-2 may be used alone or in conjunction with one or more additional agents which confer protection against radiation or other agents. A number of cytokines (e.g., IL-1, TNF, IL-6, IL-12) have been shown to confer such protective. See, e.g., Neta, R. et at., *J. Exp. Med.* 173:1177(1991). Additionally, IL-11 has been shown to protect small intestinal mucosal cells after combined irradiation and chemotherapy, Du, X. X. et al., *Blood* 83:33 (1994), and radiation-induced thoracic injury. Redlich, C. A. et al, *J. Immun.* 157:1705–1710 (1996). Several growth factors have also been shown to confer protection to radiation exposure, e.g., fibroblast growth factor and transforming growth factor beta-3. Ding, I. et al., *Acta Oncol.* 36:337–340 (1997); Potten, C. et al., *Br. J. Cancer* 75:1454–1459 (1997).

Hemorrhagic cystitis is a syndrome associated with certain disease states as well as exposure to drugs, viruses, and toxins. It manifests as difuse bleeding of the endothelial lining of the bladder. Known treatments include intravesical, systemic, and nonpharmacologic therapies (West, N.J., Pharmacotherapy 17:696–706 (1997). Some cytotoxic agents used clinically have side effects resulting in the inhibition of the proliferation of the normal epithelial in the bladder, leading to potentially life-threatening ulceration and breakdown in the epithelial lining. For example, cyclophosphamide is a cytotoxic agent which is biotransformed principally in the liver to active alkylating metabolites by a mixed function microsomal oxidase system. These metabolites interfere with the growth of susceptible rapidly proliferating malignant cells. The mechanism of action is believed to involve cross-linking of tumor cell DNA (Physicians' Desk reference, 1997).

Cyclophosphamide is one example of a cytotoxic agent which causes hemorrhagic cystitis in some patients, a complication which can be severe and in some cases fatal. Fibrosis of the urinary bladder may also develop with or without cystitis. This injury is thought to be caused by cyclophosphamide metabolites excreted in the urine. Hematuria caused by cyclophosphamide usually is present for several days, but may persist. In severe cases medical or surgical treatment is required. Instances of severe hemorrhagic cystitis result in discontinued cyclophosphamide therapy. In addition, urinary bladder malignancies generally occur within two years of cyclophosphamide treatment nd occurs in patients who previously had hemorrhagic cystitis (CYTOXAN (cyclophosphamide) package insert). Cyclophosphamide has toxic effects on the prostate and male reproductive systems. Cyclophosphamide treatment can result in the development of sterility, and result in some degree of testicular atrophy.

Figure 52:
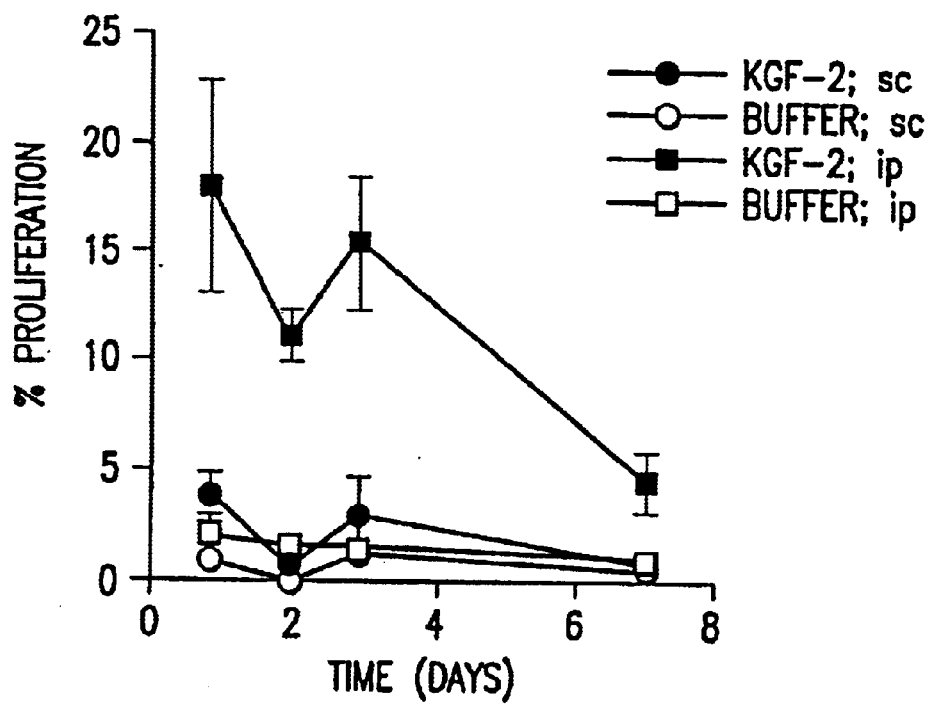
FIG. 52 shows the proliferation of bladder epithelium following ip or sc administration of KGF-2Δ33.
Figure 53:
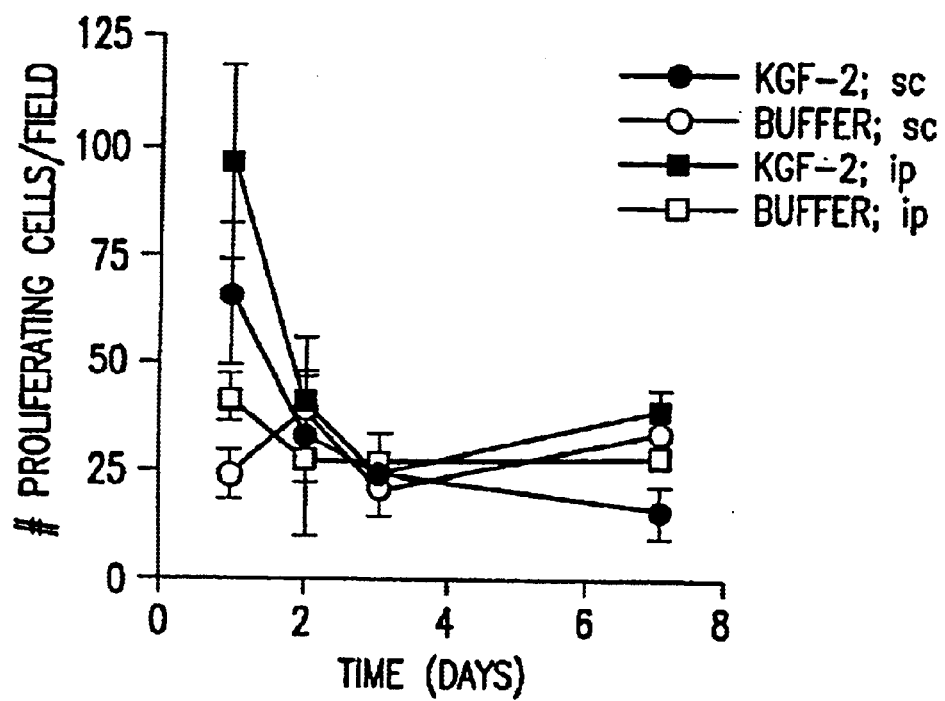
FIG. 53 shows the proliferation of prostatic epithelial cells after systemic administration of KGF-2Δ33.

As shown in FIGS. 52 and 53, systemic administration of KGF-2 to an individual stimulates proliferation of bladder and prostatic epithelial cells. Thus, in one aspect, the present invention provides a method of stimulating proliferation of bladder epithelium and prostatic epithelial cells by administering to an individual an effective amount of a KGF-2 polypeptide. More importantly, as FIGS. 54 and 55 demonstrate, KGF-2 can be used to reduce damage caused by cytotoxic agents having side effects resulting in the inhibition of bladder and prostate epithelial cell proliferation. To reduce such damage, KGF-2 can be administered either before, after, or during treatment with or exposure to the cytotoxic agent. Accordingly, in a further aspect, there is provided a method of reducing damage caused by an inhibition of the normal proliferation of epithelial cells of the bladder or prostate by administering to an individual an effective amount of KGF-2. As indicated, inhibitors of normal proliferation of bladder or prostate epithelium include radiation therapy (causing acute or chronic radiation damage) and cytotoxic agents such as chemotherapeutic or antineoplastic drugs including, but not limited to, cyclophosphamide, busulfan, and ifosfamide. In a further aspect, KGF-2 is administered to reduce or prevent fibrosis and ulceration of the urinary bladder. Preferably, KGF-2 is administered to reduce or prevent hemorrhagic cystitis. Suitable doses, formulations, and administration routes are described below.

As used herein, by "individual" is intended an animal, preferably a mammal (such as apes, cows, horses, pigs, boars, sheep, rodents, goats, dogs, cats, chickens, monkeys, rabbits, ferrets, whales, and dolphins), and more preferably a human.

The signal sequence of KGF-2 encoding amino acids 1 through 35 or 36 may be employed to identify secreted proteins in general by hybridization and/or computational search algorithms.

The nucleotide sequence of KGF-2 could be employed to isolate 5' sequences by hybridization. Plasmids comprising the KGF-2 gene under the control of its native promoter/enhancer sequences could then be used in in vitro studies aimed at the identification of endogenous cellular and viral transactivators of KGF-2 gene expression.

The KGF-2 protein may also be employed as a positive control in experiments designed to identify peptidomimetics acting upon the KGF-2 receptor.

In accordance with yet a further aspect of the present invention, there is provided a process for utilizing such polypeptides, or polynucleotides encoding such polypeptides, for in vitro purposes related to scientific research, synthesis of DNA, manufacture of DNA vectors and for the purpose of providing diagnostics and therapeutics for the treatment of human disease.

Fragments of the full length KGF-2 gene may be used as a hybridization probe for a cDNA library to isolate the full length KGF-2 genes and to isolate other genes which have a high sequence similarity to these genes or similar biological activity. Probes of this type generally have at least 20 bases. Preferably, however, the probes have at least 30 bases and generally do not exceed 50 bases, although they may have a greater number of bases. The probe may also be used to identify a cDNA clone corresponding to a full length transcript and a genomic clone or clones that contain the complete KGF-2 gene including regulatory and promotor regions, exons, and introns. An example of a screen comprises isolating the coding region of the KGF-2 gene by using the known DNA sequence to synthesize an oligonucleotide probe. Labeled oligonucleotides having a sequence complementary to that of the gene of the present invention are used to screen a library of human cDNA, genomic DNA or cDNA to determine which members of the library the probe hybridizes to.

This invention provides a method for identification of the receptors for the KGF-2 polypeptide. The gene encoding the receptor can be identified by numerous methods known to those of skill in the art, for example, ligand panning and FACS sorting (Coligan et al., Current Protocols in Immun., 1(2), Chapter 5 (1991)). Preferably, expression cloning is employed wherein polyadenylated RNA is prepared from a cell responsive to the polypeptides, and a cDNA library created from this RNA is divided into pools and used to transfect COS cells or other cells that are not responsive to the polypeptides. Transfected cells which are grown on glass slides are exposed to the labeled polypeptides. The polypeptides can be labeled by a variety of means including iodination or inclusion of a recognition site for a site-specific protein kinase. Following fixation and incubation, the slides are subjected to autoradiogaphic analysis. Positive pools are identified and sub-pools are prepared and re-transfected using an iterative sub-pooling and rescreening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to x-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

This invention provides a method of screening compounds to identify those which agonize the action of KGF-2 or block the function of KGF-2. An example of such an assay comprises combining a mammalian Keratinocyte cell, the compound to be screened and $^3$[H] thymidine under cell culture conditions where the keratinocyte cell would normally proliferate. A control assay may be performed in the absence of the compound to be screened and compared to the amount of keratinocyte proliferation in the presence of the compound to determine if the compound stimulates proliferation of Keratinocytes.

To screen for antagonists, the same assay may be prepared in the presence of KGF-2 and the ability of the compound to prevent Keratinocyte proliferation is measured and a determination of antagonist ability is made. The amount of Keratinocyte cell proliferation is measured by liquid scintillation chromatography which measures the incorporation of $^3$[H] thymidine.

In another method, a mammalian cell or membrane preparation expressing the KGF-2 receptor would be incubated with labeled KGF-2 in the presence of the compound. The ability of the compound to enhance or block this interaction could then be measured. Alternatively, the response of a known second messenger system following interaction of KGF-2 and receptor would be measured and compared in the presence or absence of the compound. Such second messenger systems include but are not limited to, cAMP guanylate cyclase, ion channels or phosphoinositide hydrolysis.

Examples of potential KGF-2 antagonists include an antibody, or in some cases, an oligonucleotide, which binds to the polypeptide. Alternatively, a potential KGF-2 antagonist may be a mutant form of KGF-2 which binds to KGF-2 receptors, however, no second messenger response is elicited and therefore the action of KGF-2 is effectively blocked.

Another potential KGF-2 antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.* 6:3073 (1979); Cooney et al., *Science* 241:456 (1988); and Dervan et al., *Science* 251:1360 (1991)), thereby preventing transcription and the production of KGF-2. The antisense RNA oligonucleotide hybridizes to the cDNA in vivo and blocks translation of the cDNA molecule into KGF-2 polypeptide (Antisense-Okano, J., *Neurochem.* 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of KGF-2.

Potential KGF-2 antagonists include small molecules which bind to and occupy the binding site of the KGF-2 receptor thereby making the receptor inaccessible to KGF-2 such that normal biological activity is prevented. Examples of small molecules include but are not limited to small peptides or peptide-like molecules.

The KGF-2 antagonists may be employed to prevent the induction of new blood vessel growth or angiogenesis in tumors. Angiogenesis stimulated by KGF-2 also contributes to several pathologies which may also be treated by the antagonists of the present invention, including diabetic retinopathy, and inhibition of the growth of pathological tissues, such as in rheumatoid arthritis.

KGF-2 antagonists may also be employed to treat glomerulonephritis, which is characterized by the marked proliferation of glomerular epithelial cells which form a cellular mass filling Bowman's space.

The antagonists may also be employed to inhibit the over-production of scar tissue seen in keloid formation after surgery, fibrosis after myocardial infarction or fibrotic lesions associated with pulmonary fibrosis and restenosis. KGF-2 antagonists may also be employed to treat other proliferative diseases which are stimulated by KGF-2, including cancer and Kaposi's sarcoma.

KGF-2 antagonists may also be employed to treat keratitus which is a chronic infiltration of the deep layers of the cornea with uveal inflammation characterized by epithelial cell proliferation.

The antagonists may be employed in a composition with a pharmaceutically acceptable carrier, e.g., as hereinafter described.

The polypeptides, agonists and antagonists of the present invention may be employed in combination with a suitable pharmaceutical carrier to comprise a pharmaceutical composition. Such compositions comprise a therapeutically effective amount of the polypeptide, agonist or antagonist and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such containers can be a notice in the form prescribed by a governmental agency regulating the manufacture, use or sale of pharmaceuticals or biological products, which notice reflects approval by the agency of manufacture, use or sale for human administration. In addition, the polypeptides, agonists and antagonists of the present invention may be employed in conjunction with other therapeutic compounds.

The polypeptide having KGF-2 activity may be administered in pharmaceutical compositions in combination with one or more pharmaceutically acceptable excipients. It will be understood that, when administered to a human patient, the total daily usage of the pharmaceutical compositions of the present invention will be decided by the attending physician within the scope of sound medical judgment. The specific therapeutically effective dose level for any particular patient will depend upon a variety of factors including the type and degree of the response to be achieved; the specific composition an other agent, if any, employed; the age, body weight, general health, sex and diet if the patient; the time of administration, route of administration, and rate of excretion of the composition; the duration of the treatment; drugs (such as a chemotherapeutic agent) used in combination or coincidental with the specific composition; and like factors well known in the medical arts. Suitable formulations, known in the art, can be found in *Remington's Pharmaceutical Sciences* (latest edition), Mack Publishing Company, Easton, Pa.

The KGF-2 composition to be used in the therapy will be formulated and dosed in a fashion consistent with good medical practice, taking into account the clinical condition of the individual patient (especially the side effects of treatment with KGF-2 alone), the site of delivery of the KGF-2 composition, the method of administration, the scheduling of administration, and other factors known to practitioners. The "effective amount" of KGF-2 for purposes herein is thus determined by such considerations.

The pharmaceutical compositions may be administered in a convenient manner such as by the oral, topical, intravenous, intraperitoneal, intramuscular, intraarticular, subcutaneous, intranasal, intratracheal or intradermal routes. The pharmaceutical compositions are administered in an amount which is effective for treating and/or prophylaxis of the specific indication. In most cases, the dosage is from about 1 $\mu$g/kg to about 30 mg/kg body weight daily, taking into account the routes of administration, symptoms, etc. However, the dosage can be as low as 0.001 $\mu$g/kg. For example, in the specific case of topical administration dosages are preferably administered from about 0.01 $\mu$g to 9 mg per cm$^2$.

As a general proposition, the total pharmaceutically effective amount of the KGF-2 administered parenterally per more preferably dose will be in the range of about 1 $\mu$g/kg/day to 100 mg/kg/day of patient body weight, although, as noted above, this will be subject to therapeutic discretion. If given continuously, the KGF-2 is typically administered at a dose rate of about 1 $\mu$g/kg/hour to about 50 $\mu$g/kg/hour, either by 1–4 injections per day or by continuous subcutaneous infusions, for example, using a mini-pump. An intravenous bag solution or bottle solution may also be employed.

A course of KGF-2 treatment to affect the fibrinolytic system appears to be optimal if continued longer than a certain minimum number of days, 7 days in the case of the mice. The length of treatment needed to observer changes and the interval following treatment for responses to occur appears to vary depending on the desired effect. Such treatment lengths are indicated in the Examples below.

The KGF-2 polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (U. Sidman et al, *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech* 12:98–105 (1982)), ethylene vinyl acetate (R. Langer et al., Id.) or poly-D-(-)-3-hydroxybutyric acid (EP 133,988). Sustained-release KGF-2 compositions also include liposomally entrapped KGF-2. Liposomes containing KGF-2 are prepared by methods known per se: DE 3,218,121; Epstein, et al., *Proc. Natl. Acad. Sci. USA* 82:3688–3692 (1985); Hwang et al., *Proc. Natl. Acad. Sci. USA* 77:4030–4034 (1980); EP 52,322; EP 36,676; EP 88,046; EP 143,949; EP 142,641; Japanese Pat. Appl 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal KGF-2 therapy.

For parenteral administration, in one embodiment, the, KGF-2 is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the KGF-2 uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes. Suitable formulations, known in the art, can be found in *Remington's Pharmaceutical Sciences* (latest edition), Mack Publishing Company, Easton, Pa.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

KGF-2 is typically formulated in such vehicles at a concentration of about 0.01 $\mu$g/ml to 100 mg/ml, preferably 0.01 $\mu$g/ml to 10 mg/ml, at a pH of about 3 to 8. It will be understood that the use of certain of the foregoing excipients, carriers, or stabilizers will result in the formation of KGF-2 salts.

KGF-2 to be used for therapeutic administration must be sterile. Sterility is readily accomplished by filtration through sterile filtration membranes (e.g., 0.2 micron membranes). Therapeutic KGF-2 compositions generally are placed into a container having a sterile access port, for example, an intravenous solution bag or vial having a stopper pierceable by a hypodermic injection needle.

KGF-2 ordinarily will be stored in unit or multi-dose containers, for example, sealed ampules or vials, as an aqueous solution or as a lyophilized formulation for reconstitution. As an example of a lyophilized formulation, 10-ml vials are filled with 5 ml of sterile-filtered 1% (w/v) aqueous KGF-2 solution, and the resulting mixture is lyophilized. The infusion solution is prepared by reconstituting the lyophilized KGF-2 using bacteriostatic Water-for-Injection.

Dosaging may also be arranged in a patient specific manner to provide a predetermined concentration of an KGF-2 activity in the blood, as determined by an RIA technique, for instance. Thus patient dosaging may be adjusted to achieve regular on-going trough blood levels, as measured by RIA, on the order of from 50 to 1000 ng/ml, preferably 150 to 500 ng/ml.

Pharmaceutical compositions of the invention may be administered orally, rectally, parenterally, intracisternally, intradermally, intravaginally, intraperitoneally, topically (as by powders, ointments, gels, creams, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraaticular injection and infusion.

Preferred KGF-2 formulations are described in U.S. Provisional Appln. No. 60/068493, filed Dec. 22, 1997, which is herein incorporated by reference.

The KGF-2 polypeptides, agonists and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle. Examples of other delivery vehicles include an HSV-based vector system, adeno-associated virus vectors, and inert vehicles, for example, dextran coated ferrite particles.

Retroviruses from which the retroviral plasmid vectors hereinabove mentioned may be derived include, but are not limited to, Moloney Murine Leukemia virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoria Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller et al, *Biotechniques* Vol. 7, No. 9:980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cell lines which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy* 1:5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epitheliel cells.

Chromosome Assays

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al, *Human Chromosomes: a Manual of Basic Techniques*, Pergamon Press, New York (1988).

Once a sequence has been mapped to a precise chromosomal location, the physical position of the sequence on the chromosome can be correlated with genetic map data. Such data are found, for example, in V. McKusilk, *Mendelian Inheritance in Man* (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D., et al., *Nucleic Acids Res.*, 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a frangment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

A cell has been "transformed" by exogenous DNA when such exogenous DNA has been introduced inside the cell membrane. Exogenous DNA may or may not be integrated (covalently linked) inter-chromosomal DNA making the genome of the cell. Prokaryote and yeast, for example, the exogenous DNA may be maintained on an episomal element, such a plasmid. With respect to eukaryotic cells, a stably transformed or transfected cell is one in which the exogenous DNA has become integrated into the chromosome so that it is inherited by daughter cells through chromosome replication. This ability is demonstrated by the ability of the eukaryotic cell to establish cell lines or clones comprised of a population of daughter cell containing the exogenouis DNA. An example of transformation is exhibited in Graham, F. & Van der Eb, A., *Virology*, 52:456–457 (1973).

"Transduction" or "transduced" refers to a process by which cells take up foreign DNA and integrate that foreign DNA into their chromosome. Transduction can be accomplished, for example, by transfection, which refers to various techniques by which cells take up DNA, or infection, by which viruses are used to transfer DNA into cells.

EXAMPLE 1

Bacterial Expression and Purification of KGF-2

The DNA sequence encoding KGF-2, ATCC # 75977, is initially amplified using PCR oligonucleotide primers corresponding to the 5' and 3' end sequences of the processed KGF-2 cDNA (including the signal peptide sequence). The 5' oligonucleotide primer has the sequence 5' CCCCACAT-GTGGAAATGGATACTGACACATTGTGCC 3' (SEQ ID No. 3) contains an Afl III restriction enzyme site including and followed by 30 nucleotides of KGF-2 coding sequence starting from the presumed initiation codon. The 3' sequence 5' CCCAAGCTTCCACAAACGTTGCCTTC-CTCTATGAG 3' (SEQ ID No. 4) contains complementary sequences to Hind III site and is followed by 26 nucleotides of KGF-2. The restriction enzyme sites are compatible with the restriction enzyme sites on the bacterial expression vector pQE-60 (Qiagen, Inc. Chatsworth, Calif.). pQE-60 encodes antibiotic resistance ($Amp^1$), a bacterial origin of replication (ori), an IPTG-regulatable promoter operator (P/O), a ribosome binding site (RBS), a 6-His tag and restriction enzyme sites. pQE-60 is then digested with NcoI and HindIII. The amplified sequences are ligated into pQE-60 and are inserted in frame. The ligation mixture is then used to transform *E. coli* strain M15/rep 4 (Qiagen, Inc.) by the procedure described in Sambrook, J., et al., *Molecular Cloning: A Laboratory Manual*, Cold Spring Laboratory Press, (1989). M15/rep4 contains multiple copies of the plasmid pREP4, which expresses the lacI repressor and also confers kanamycin resistance ($Kan^1$). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 ($O.D.^{600}$) of between 0.4 and 0.6. IPTG ("Isopropyl-B-D-thiogalacto pyranoside") is then added to a final concentration of 1 mM. IPTG interacts with the lacI repressor to cause it to dissociate from the operator, forcing the promoter to direct transcription. Cells are grown an extra 3 to 4 hours. Cells are then harvested by centrifugation. The cell pellet is solubilized in the chaotropic agent 6 Molar Guanidnine HCl. After clarification, solubilized KGF-2 is purified from this solution by chromatography on a Heparin affinity column under conditions that allow for tight binding of the proteins (Hochuli, E., et al., *J. Chromatography* 411:177–184 (1984)). KGF-2 (75% pure) is eluted from the column by high salt buffer.

EXAMPLE 2

Bacterial Expression and Purification of a Truncated Version of KGF-2

The DNA sequence encoding KGF-2, ATCC # 75977, is initially amplified using PCR oligonucleotide primers corresponding to the 5' and 3' sequences of the truncated version of the KGF-2 polypeptide. The truncated version comprises the polypeptide minus the 36 amino acid signal sequence, with a methionine and alanine residue being added just before the cysteine residue which comprises amino acid 37 of the fill-length protein. The 5' oligonucleotide primer has the sequence 5' CATGCCATGGCGTGC-CAAGCCCTTGGTCAGGACATG 3' (SEQ ID No. 5) contains an NcoI restriction enzyme site including and followed by 24 nucleotides of KGF-2 coding sequence. The 3' sequence 5' CCCAAGCTTCCACAAACGTTGCCTTC-CTC TATGAG 3' (SE,Q ID No. 6) contains complementary sequences to Hind III site and is followed by 26 nucleotides of the KGF-2 gene. The restriction enzyme sites are compatible with the restriction enzyme sites on the bacterial expression vector pQE-60 (Qiagen, Inc. Chatsworth, Calif.). pQE-60 encodes antibiotic resistance (Amp[r]), a bacterial origin of replication (ori), an IPTG-regulatable promoter operator (P/0), a ribosome binding site (RBS), a 6-His tag and restriction enzyme sites. pQE-60 is then digested with NcoI and HindIII. The amplified sequences are ligated into pQE-60 and are inserted in frame. The ligation mixture is then used to transform *E. coli* strain M15/rep 4 (Qiagen, Inc.) by the procedure described in Sambrook, J., et al., *Molecular Cloning: A Laboratory Manual*, Cold Spring Laboratory Press, (1989). M15/rep4 contains multiple copies of the plasmid pREP4, which expresses the lacI repressor and also confers kanamycin resistance (Kang[r]). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.[600]) of between 0.4 and 0.6. IPTG ("Isopropyl-B-D-thiogalacto pyranoside") is then added to a final concentration of 1 mM. IPTS induces by inactivating the laci repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized KGF-2 is purified from this solution by chromatography on a Heparin affinity column under conditions that allow for tight binding the proteins (Hochuli, E. et al., *J. Chromatography* 411:177–184 (1984)). KGF-2 protein is eluted from the column by high salt buffer.

EXAMPLE 3

Cloning and Expression of KGF-2 Using the Baculovirus Expression System

The DNA sequence encoding the full length KGF-2 protein, ATCC # 75977, is amplified using PCR oligonucleotide primers corresponding to the 5' and 3' sequences of the gene:

The 5' primer has the sequence 5' GCGGGATCCGCCAT-CATGTGGAAATGGATACTCAC 3' (SEQ ID No. 7) and contains a BamHI restriction enzyme site (in bold) followed by 6 nucleotides resembling an efficient signal for the initiation of translation in eukaryotic cells (Kozak, M., *J. Mol. Biol.*, 196:947–950 (1987)) and just behind the first 17 nucleotides of the KGF-2 gene (the initiation codon or translation "ATG" is underlined).

The 3' primer has the sequence 5' GCGCGGTACCA-CAAACGTTGCCTTCCT 3' (SEQ ID No. 8) and contains the cleavage site for the restriction endonuclease Asp718 and 19 nucleotides complementary to the 3' non-translated sequence of the KGF-2 gene. The amplified sequences are isolated from a 1% agarose gel using a commercially available kit from Qiagen, Inc., Chatsworth, Calif. The fragment is then digested with the endonucleases BamHI and Asp718 and then purified again on a 1% agarose gel. This fragment is designated F2.

The vector pA2 (modification of pVL941 vector, discussed below) is used for the expression of the KGF-2 protein using the baculovirus expression system (for review see: Summers, M. D. & Smith, G. E., *A manual or methods for baculovirus vectors and insect cell culture procedures*, Texas Agricultural Experimental Station Bulletin No. 1555 (1987)). This expression vector contains the strong polyhedrin promoter of the Autographa californica nuclear polyhidrosis virus (AcMNPV) followed by the recognition sites for the restriction endonucleases BamHI and Asp718. The polyadenylation site of the simian virus (SV) 40 is used for efficient polyadenylation. For an easy selection of recombinant viruses the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used such as pAc373, pVL941 and pAcIM1 (Luckow, V. A. & Summers, M. D., *Virology*, 170:31–39).

The plasmid is digested with the restriction enzymes BamHI and Asp718. The DNA is then isolated from a 1% agarose gel using the commercially available kit (Qiagen, Inc., Chatsworth, Calif.). This vector DNA is designated V2.

Fragment F2 and the plasmid V2 are ligated with T4 DNA ligase. *E. coli* HB101 cells are then transformed and bacteria identified that contained the plasmid (pBacKGF-2) with the KGF-2 gene using PCR with both cloning oligonucleotides. The sequence of the cloned fragment is confirmed by DNA sequencing.

5 μg of the plasmid pBacKGF-2 is co-transfected with 1.0 μg of a commercially available linearized baculovirus ("BaculoGold™ baculovirus DNA", Pharmingen, San Diego, Calif.) using the lipofection method (Felgner, et al., *Proc. Natl. Acad Sci. USA*, 84:7413–7417 (1987)).

1 μg of BaculoGold™ virus DNA and 5 μg of the plasmid pBacKGF-2 are mixed in a sterile well of a microtiter plate containing 50 μl of serum free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added drop-wise to the Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses are added to the cells and blue stained plaques are picked with the tip of an Eppendorf pipette. The agar containing the recombinant viruses is then resuspended in an Eppendorf tube containing 200 µl of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant bzculovirus V-KGF-2 at a multiplicity of infection (MOI) of 2. Six hours later the medium is removed and replaced with SF900 II medium minus methionine and cysteine (Life Technologies Inc., Gaithersburg). 42 hours later 5 µCi of $^{35}$S methionine and 5 µCi $^{35}$S cysteine (Amersham) are added. The cells are further incubated for 16 hours before they are harvested by centrifugation and the labelled proteins visualized by SDS-PAGE and autoradiography.

EXAMPLE 4

Most of the vectors used for the transient expression of the KGF-2 protein gene sequence in mammalian cells should carry the SV40 origin of replication. This allows the replication of the vector to high copy numbers in cells (e.g., COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the immediate early promoter of the cytomegalovirus (CMV). However, cellular signals can also be used (e.g., human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 283, H9 and Jurkart cells, mouse NIH3T3 and C127 cells, Cos 1, Cos 7 and CV1, African green monkey cells, quail QC1–3 cells, 293T cells, mouse L cells and Chinese hamster ovary cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Another useful selection marker is the enzyme glutamine synthase (GS) (Murphy et al., *Biochem J*. 227:277–279 (1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., *Molecular and Cellular Biology*, 438–447 (March, 1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

A. Expression of Recombinant KGF-2 in COS Cells

The expression of plasmid, KGF-2 HA was derived from a vector pcDNAI/Amp (Invitrogen) containing: 1) SV40 origin of replication, 2) ampicillin resistance gene, 3) *E. coli* replication origin, 4) CMV promoter followed by a polylinker region, a SV40 intron and polyadenylation site. The HA tag correspond to an epitope derived from the influenza hemagglutinin protein as previously described (Wilson, I., et al., *Cell* 37:767, (1984)). The infusion of HA tag to the target protein allows easy detection of the recombinant protein with an antibody that recognizes the HA epitope. A DNA fragment encoding the entire KGF-2 precursor HA tag fused in frame with the HA tag, therefore, the recombinant protein expression is directed under the CMV promoter.

The plasmid construction strategy is described as follows:

The DNA sequence encoding KGF-2, ATCC #75977, is constructed by PCR using two primers: the 5' primer 5' TAACGAGGATCCGCCATCATGTG-GAAATGGATACTGACACAC 3' (SEQ ID No. 9) contains a BamHI site followed by 22 nucleotides of KGF-2 coding sequence starting from the initiation codon; the 3' sequence 5' TAAGCACTCGAGTGAGTGTACCACCAT-TGGAAGAAATG 3' (SEQ ID No. 10) contains complementary sequences to an XhoI site, HA tag and the last 26 nucleotides of the KGF-2 coding sequence (not including the stop codon). Therefore, the PCR product contains a BamHI site, KGF-2 coding sequence followed by an XhoI site, an HA tag fused in frame, and a translation termination stop codon next to the HA tag. The PCR amplified DNA fragment and the vector, pcDNA-3HA, are digested with BamHI and XhoI restriction enzyme and ligated resulting in pcDNA-3'HA-KGF-2. The ligation mixture is transformed into *E. coli* strain XL1 Blue (Stratagene Cloning Systems, La Jolla, Calif.) the transformed culture is plated on ampicillin media plates and resistant colonies are selected. Plasmid DNA was isolated from transformants and examined by PCR and restriction analysis for the presence of the correct fragment. For expression of the recombinant KGF-2, COS cells were transfected with the expression vector by DEAE- DEXTRAN method (Sambrook, J., et al, *Molecular Cloning: A Laboratory Manual*, Cold Spring Laboratory Press, (1989)). The expression of the KGF-2 HA protein was detected by radiolabelling and immunoprecipitation method (Harlow, E. & Lane, D., *Antibodies: A Laboratory Manual*, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 5 OmM Tris, pH 7.5) (Wilson, I., et al., Id. 37:767 (1984)). Both cell lysate and culture media were precipitated with a HA specific monoclonal antibody. Proteins precipitated were analyzed on 15% SDS-PAGE gels.

B: Expression and Purification of Human KGF-2 Protein Using the CHO Expression System The vector pC1 is used for the expression of KFG-2 protein. Plasmid pC1 is a derivative of the plasmid pSV2-dhfr [ATCC Accession No. 37146]. Both plasmids contain the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, J. Biol. Chem. 253:1357–1370, Hamlin, J. L. and Ma, C. 1990, Biochem. et Biophys. Acta, 1097:107–143, Page, M. J. and Sydenham, M. A. 1991, Biotechnology Vol. 9:64–68). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC1 contains for the expression of the gene of interest a strong promoter of the long terminal repeat (LTR) of the Rouse Sarcoma Virus (Cullen, et al., Molecular and Cellular Biology, March 1985:438–4470) plus a fragment isolated from the enhancer of the immediate early gene of human cytomegalovirus (CMV) (Boshart et al., *Cell* 41:521–530, 1985). Downstream of the promoter are the following single restriction enzyme cleavage sites that allow the integration of the genes: BamHI, Pvull, and Nrul. Behind these cloning sites the plasmid contains translational stop codons in all three reading frames followed by the 3' intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC1 is digested with the restriction enzyme BamHI and then dephosphorylated using calf intestinal phosphates by procedures known in the art. The vector is then isolated from a 1% agarose gel.

The DNA sequence encoding KFG-2, ATCC No. 75977, is amplified using PCR oligonucleotide primers corresponding to the 5' and 3' sequences of the gene:

The 5' primer has the sequence 5' TAACGA <u>GGATCC</u>GCCATCATGTGGAAATGGATACTGACAC 3' (SEQ ID No. 9) containing the underlined BamHI restriction enzyme site followed by 21 bases of the sequence of KGF-2 of FIG. 1 (SEQ ID NO:1). Inserted into an expression vector, as described below, the 5' end of the amplified fragment encoding human KGF-2 provides an efficient signal peptide. An efficient signal for initiation of translation in eukaryotic cells, as described by Kozak M., J. Mol. Biol. 196:947–950 (1987) is appropriately located in the vector portion of the construct.

The 3' primer has the sequence 5' TAAGCAGGATCCT-GAGTGTACCACCATTGGAAGAAATG 3' (SEQ ID NO. 10) containing the BamHI restriction followed by nucleotides complementary to the last 26 nucleotides of the KGF-2 coding sequence set out in FIG. 1 (SEQ ID NO:1), not including the stop codon.

The amplified fragments are isolated from a 1% agarose gel as described above and then digested with the endonuclease BamHI and then purified again on a 1% agarose gel.

The isolated fragment and the dephosphorylated vector are then ligated with T4 DNA ligase. *E. coli* HB101 cells are then transformed and bacteria identified that contained the plasmid pC1. The sequence and orientation of the inserted gene is confirmed by DNA sequencing.

Transfection of CHO-DHFR-cells

Chinese hamster ovary cells lacking an active DHFR enzyme are used for transfection. 5 μg of the expression plasmid C1 are cotransfected pith 0.5 μg of the plasmid pSVneo using the lipofecting method (Felgner et al., supra). The plasmid pSV2-neo contains a dominant selectable marker, the gene neo from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) and cultivated for 10–14 days. After this period, single clones are trypsinized and then seeded in 6-well petri dishes using different concentrations of methotrexate (25 nM, 50 nM, 100 nM, 200 nM, 400 nM). Clones growing at the highest concentrations of methotrexate are then transferred to new 6-well plates containing even higher concentrations of methotrexate (500 nM, 1 μM, 2 μM, 5 μM). The same procedure is repeated until clones grow at a concentration of 100 μM.

The expression of the desired gene product is analyzed by Western blot analysis and SDS-PAGE.

EXAMPLE 5

Transcription and Translation of Recombinant KGF-2 in vitro

A PCR product is derived from the cloned cDNA in the pA2 vector used for insect cell expression of KGF-2. The primers used for this PCR were: 5' ATTAACCCTCAC-TAAAGGGAGGCCATGTGGAAATGGATACTGACA CATTGTGCC 3' (SEQ ID No. 11) and 5'CCCAAGCTTC-CACAAACGTTGCCTTCCTCTATGAG 3'(SEQ ID No. 12).

The first primer contains the sequence of a T3 promoter 5' to the ATG initiation codon. The second primer is complimentary to the 3' end of the KGF-2 open reading frame, and encodes the reverse complement of a stop codon.

The resulting PCR product is purified using a commercially available kit from Qiagen. 0.5 μg of this DNA is used as a template for an in vitro transcription-translation reaction. The reaction is performed with a kit commercially available from Promega under the name of TNT. The assay is performed as described in the instructions for the kit, using radioactively labeled methionine as a substrate, with the exception that only ½ of the indicated volumes of reagents are used and that the reaction is allowed to proceed at 33° C. for 1.5 hours.

Five μl of the reaction is electrophoretically separated on a denaturing 10 to 15% polyacrylamide gel. The gel is fixed for 30 minutes in a mixture of water:Methanol:Acetic acid at 6:3:1 volumes respectively. The gel is then dried under heat and vacuum and subsequently exposed to an X-ray film for 16 hours. The film is developed showing the presence of a radioactive protein band corresponding in size to the conceptually translated KGF-2, strongly suggesting that the cloned cDNA for KGF-2 contains an open reading frame that codes for a protein of the expected size.

EXAMPLE 6

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added.) This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, *DNA*, 7:219–25 (1988)) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and is quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

EXAMPLE 7

KGF-2 Stimulated Wound Healing in the Diabetic Mouse Model

To demonstrate that keratinocyte growth factor-2 (KGF-2) would accelerate the healing process, the genetically diabetic mouse model of wound healing was used. The full thickness wound healing model in the db+/db+ mouse is a well characterized, clinically relevant and reproducible model of impaired wound healing. Healing of the diabetic wound is dependent on formation of granulation tissue and re-epithelialization rather than contraction (Gartner, M. H. et al., *J.Surg. Res*. 52:389 (1992); Greenhalgh, D. G. et al., *Am. J. Pathol*. 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al. *Proc. Natl. Acad. Sci. USA* 77:283–293 (1982)). Animals show polyphagia, polydipsia and polyuria. Mutant diabetic mice (db+/db+) have elevated blood glucose, increased or normal insulin levels, and suppressed cell-mediated immunity (Mandel et al., *J. Immunol*. 120:1375 (1978); Debray-Sachs, M. et al., *Clin. Exp. Immunol*. 51(1): 1–7 (1983); Leiter et al., *Am. J. of Pathol*. 114:46–55 (1985)). Peripheral neuropathy, myocardial complications, and microvascular lesions, basement membrane thickening and glomeruldar filtration abnormalities have been described in these animals (Norido, F. et al., *Exp. Neurol*. 83(2): 221–232 (1984); Robertson et al., Diabetes 29(1):60–67 (1980); Giacomelli et al., *Lab Invest*. 40(4):460–473 (1979); Coleman, D. L., *Diabetes* 31 (*Suppl*) :1–6 (1982)). These homozygous diabetic mice develop hyperglycemia that is resistant to insulin analogous to human type II diabetes (Mandel et al., *J. Immunol*. 120:1375–1377 (1978)).

The characteristics observed in these animals suggests that healing in this model may be similar to the healing observed in human diabetes (Greenhalgh, et al., *Am. J. of Pathol*. 136:1235–1246 (1990)). The results of this study demonstrated that KGF-2 has a potent stimulatory effect on the healing of full thickness wounds in diabetic and non-diabetic heterozygous littermates. Marked effects on re-epithelialization and an increase in collagen fibrils, granulation tissue within the dermis were observed in KGF-2 treated animals. The exogenous application of growth factors may accelerate granulation tissue formation by drawing inflammatory cells into the wound.

Animals

Genetically diabetic female C57BL/KsJ (db+/db+) mice and their non-diabetic (db+/+m) heterozygous littermates were used in this study (Jackson Laboratories). The animals were purchased at 6 weeks of age and were 8 weeks old at the beginning of the study. Animals were individually housed and received food and water ad libitum. All manipulations were performed using aseptic techniques. The experiments were conducted according to tie rules and guidelines of Human Genome Sciences, Inc. Institutional Animal Care and Use Committee and the Guidelines for the Care and Use of Laboratory Animals.

KGF-2

The recombinant human KGF-2 used for the wound healing studies was over-expressed, and purified from pQE60–Cys37, an E. coli expression vector system (pQE-9, Qiagen). The protein expressed from this construct is the KGF-2 from Cystein at position 37 to Serine at position 208 with a 6X(His) tag attached to the N-terminus of the protein (SEQ ID NOS: 29–30) (FIG. 15). Fractions containing greater than 95% pure recombinant materials were used for the experiment. Keratinocyte growth factor-2 was formulated in a vehicle containing 100 mM Tris, 8.0 and 600 mM NaCl. The final concentrations were 80 µg/mL and 8 µg/mL of stock solution. Dilutions were made from stock solution using the same vehicle.

Surgical Wounding

Wounding protocol was performed according to previously reported methods (Tsuboi, R. and Rifkin, D. B., J. Exp. Med. 172:245–251 (1990)). Briefly, on the day of wounding, animals were anesthetized with an intraperitoneal injection of Avertin (0.01 mg/mL), 2,2,2-tribromoethanol and 2-methyl-2-butanol dissolved in deionized water. The dorsal region of the animal was shaved and the skin washed with 70% ethanol solution and iodine. The surgical area was dried with sterile gauze prior to wounding. An 8 mm full-thickness wound was then created using a Keyes tissue punch. Immediately following wounding, the surrounding skin was gently stretched to eliminate wound expansion. The wounds were left open for the duration of the experiment. Application of the treatment was given topically for 5 consecutive days commencing on the day of wounding. Prior to treatment, wounds were gently cleansed with sterile saline and gauze sponges.

Wounds were visually examined and photographed at a fixed distance at the day of surgery and at two day intervals thereafter. Wound closure was determined by daily measurement on days 1–5 and on day 8. Wounds were measured horizontally and vertically using a calibrated Jameson caliper. Wounds were considered healed if granulation tissue was no longer visible and the wound was covered by a continuous epithelium.

KGF-2 was administered using two different doses of KGF-2, one at 4 µg per wound per day for 8 days and the second at 40 µg per wound per day for 8 days in 50 µL of vehicle. Vehicle control groups received 50 µL of vehicle solution.

Animals were euthanized on day 8 with an intraperitoneal injection of sodium pentobarbital (300 mg/kg). The wounds and surrounding skin were then harvested for histology and immunohistochemistry. Tissue specimens were placed in 10% neutral buffered formalin in tissue cassettes between biopsy sponges for further processing.

Experimental Design

Three groups of 10 animals each (5 diabetic and 5 non-diabietic controls) were evaluated: 1) Vehicle placebo control, 2) KGF-2 4 µg/day and 3) KGF-2 40 µg/day. This study was designed as follows:

| N | Group | Treatment |
|---|---|---|
| N = 5 db+/db+ | vehicle | 50 µL |
| N = 5 db+/+m | vehicle | 50 µL |
| N = 5 db+/db+ | KGF-2 | 4 µg/50 µL |

-continued

| N | Group | Treatment |
|---|---|---|
| N = 5 db+/+m | KGF-2 | 4 µg/50 µL |
| N = 5 db+/db+ | KGF-2 | 40 µg/50 µL |
| N = 5 db+/+m | KGF-2 | 40 µg/50 µL |

Measurement of Wound Area and Closure

Wound closure was analyzed by measuring the area in the vertical and horizontal axis and obtaining the total square area of the wound. Contraction was then estimated by establishing the differences between the initial wound area (day 0) and that of post treatment (day 8). The wound area on day 1 was; 64 mm$^2$, the corresponding size of the dermal punch. Calculations were made using the following formula:

[Open area on day 8]–[Open area on day 1]/[Open area on day 1]

Histology

Specimens were fixed in 10% buffered formalin and paraffin embedded blocks were sectioned perpendicular to the wound surface (5 µm) and cut using a Reichert-Jung microtome. Routine hematoxylin-eosin (H&E) staining was performed on cross-sections of bisected wounds. Histologic examination of the wounds were used to assess whether the healing process and the morphologic appearance of the repaired skin was altered by treatment with KGF-2. This assessment included verification of the presence of cell accumulation, inflammatory cells, capillaries, fibroblasts, re-epithelialization and epidermal maturity (Greenhalgh, D. G. et al., Am. J. Pathol. 136:1235 (1990)) (Table 1). A calibrated lens micrometer was used by a blinded observer.

Immunohistochemistry

Re-epithelialization

Tissue sections were stained immunohistochemically with a polyclonal rabbit anti-human keratin antibody using ABC Elite detection system. Human skin was used as a positive tissue control while non-immune IgG was used as a negative control. Keratinocyte growth was determined by evaluating the extent of reepithelialization of the wound using a calibrated lens micrometer.

Cell Proliferation Marker

Proliferating cell nuclear antigen/cyclin (PCNA) in skin specimens was demonstrated by using anti-PCNA antibody (1:50) with an ABC Elite detection system. Human colon cancer served as a positive tissue control and human brain tissue was used as a negative tissue control. Each specimen included a section with omission of the primary antibody and substitution with non-immune mouse IgG. Ranking of these sections was based on the extent of proliferation on a scale of 0–8, the lower side of the scale reflecting slight proliferation to th e higher side reflecting intense proliferation.

Statistical Analysis

Experimental data were analyzed using an unpaired t test. A p value of<0.05 was considered significant. The data were expressed as the mean±SEM.

Results

Effect of KGF-2 on Wound Closure

Figure 4A:
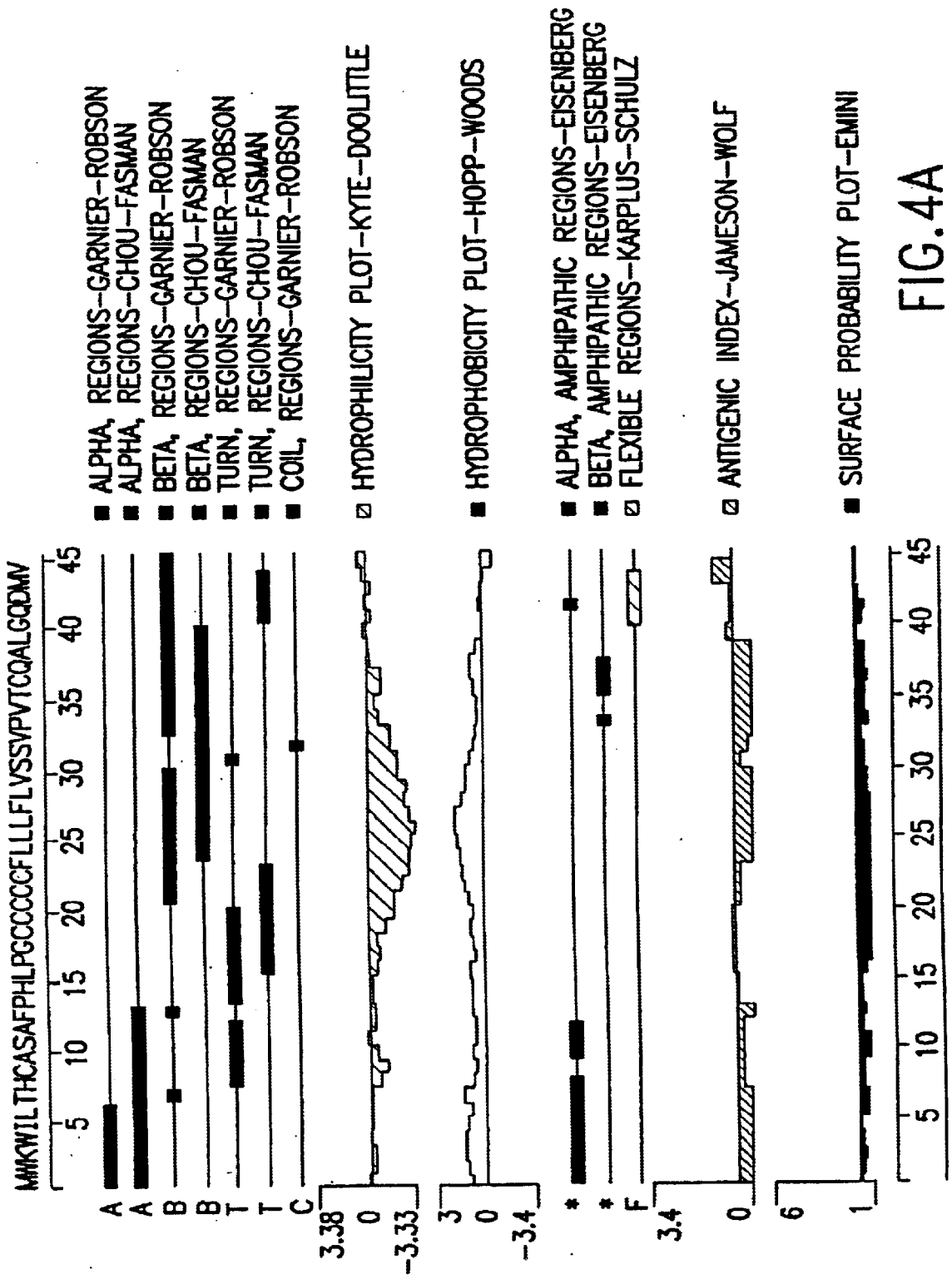
FIGS. 4A–4E show an analysis of the KGF-2 amino acid sequence. Alpha, beta, turn and coil regions; hydrophilicity and hydrophobicity; amphipathic regions; flexible regions; antigenic index and surface probability are shown. In the "Antigenic Index-Jameson-Wolf" graph, amino acid residues amino acid residues 41–109 in FIG. 1 [SEQ ID NO:2] correspond to the shown highly antigenic regions of the KGF-2 protein. Hydrophobic regions (Hopp-Woods Plot) fall below the median line (negative values) while hydrophilic regions (Kyte-Doolittle Plot) are found above the median line (positive values, e.g. amino acid residues 41–109). The plot is over the entire 208 amino acid ORF.
Figure 4B:
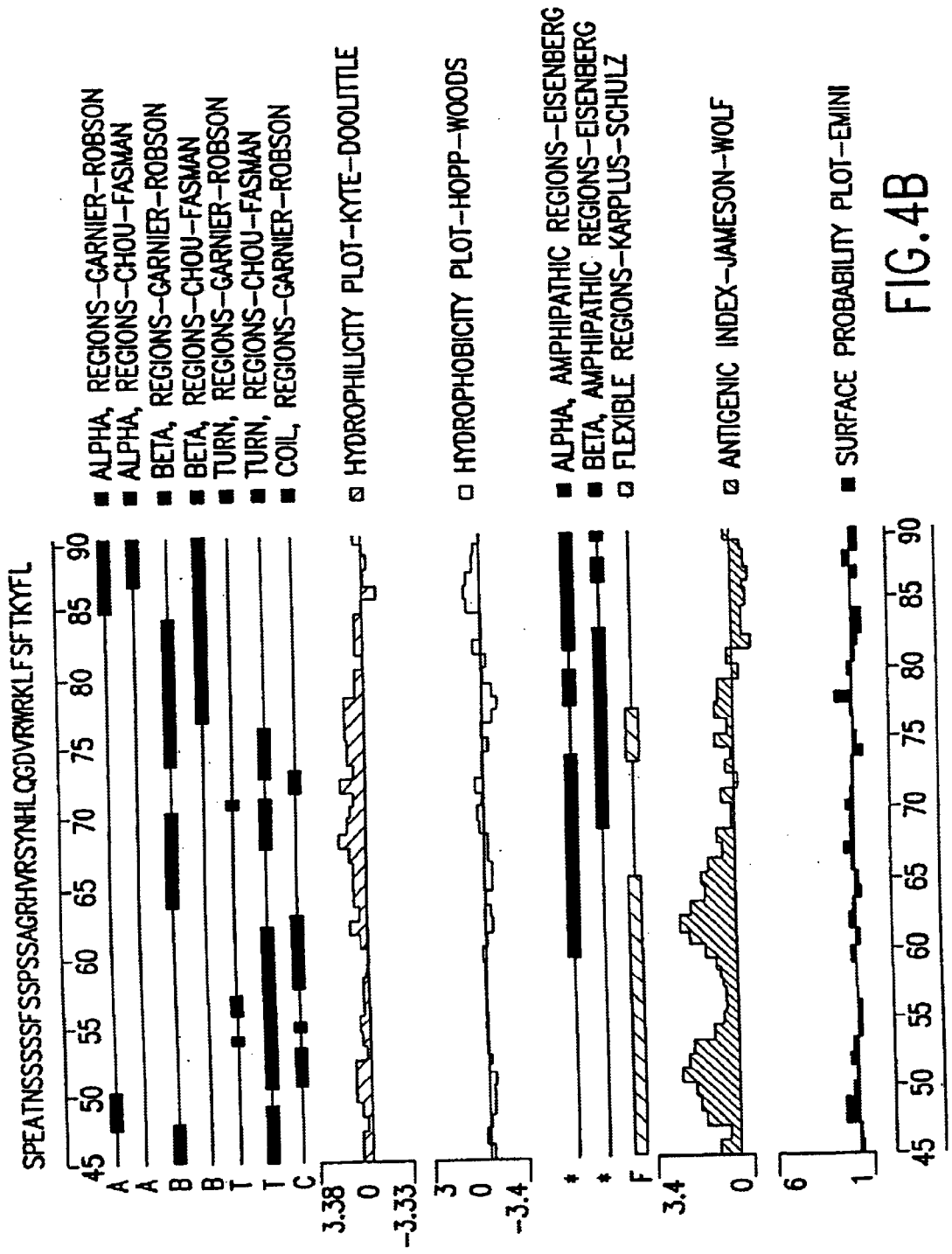
Figure 4C:
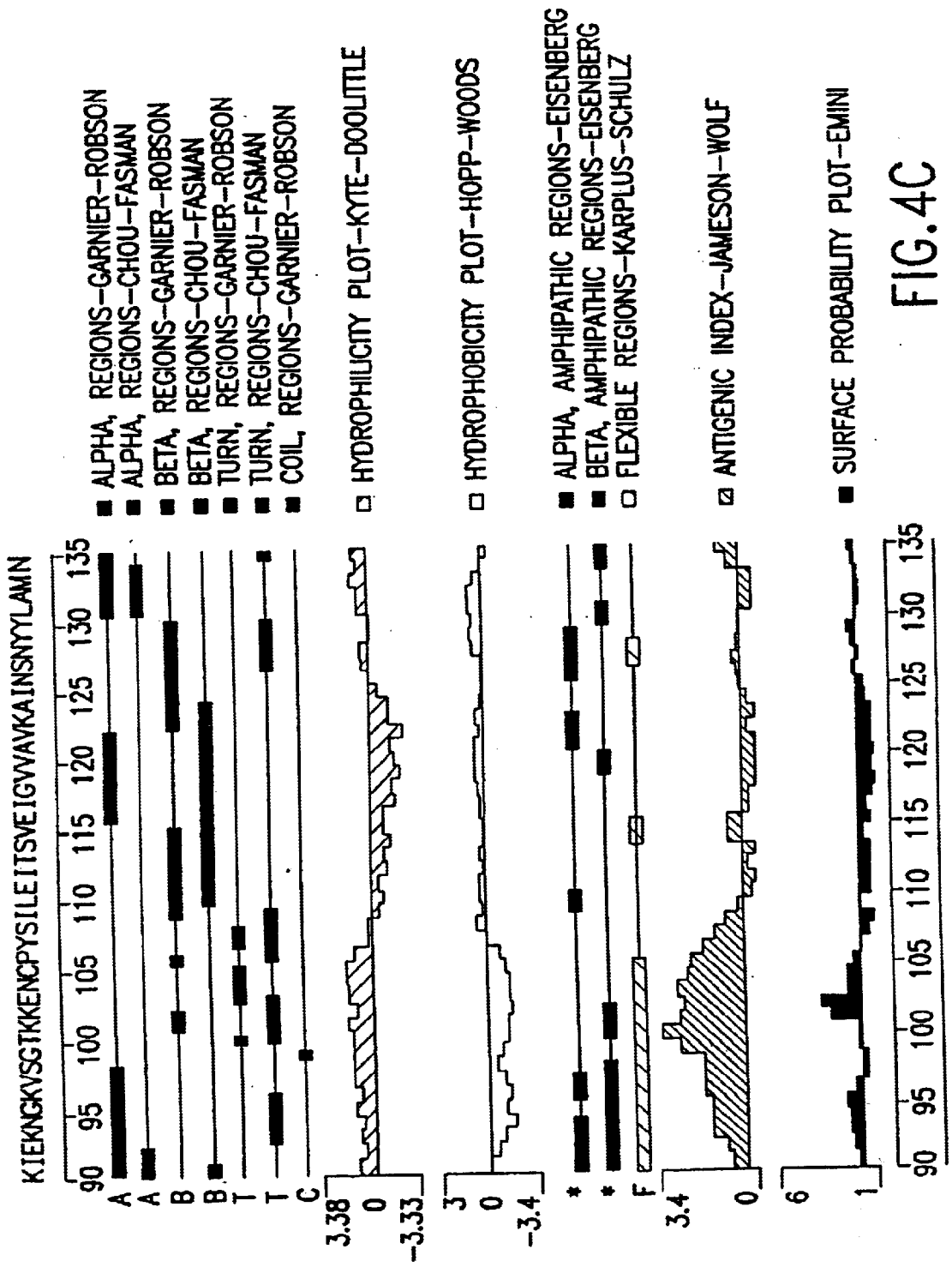
Figure 4D:
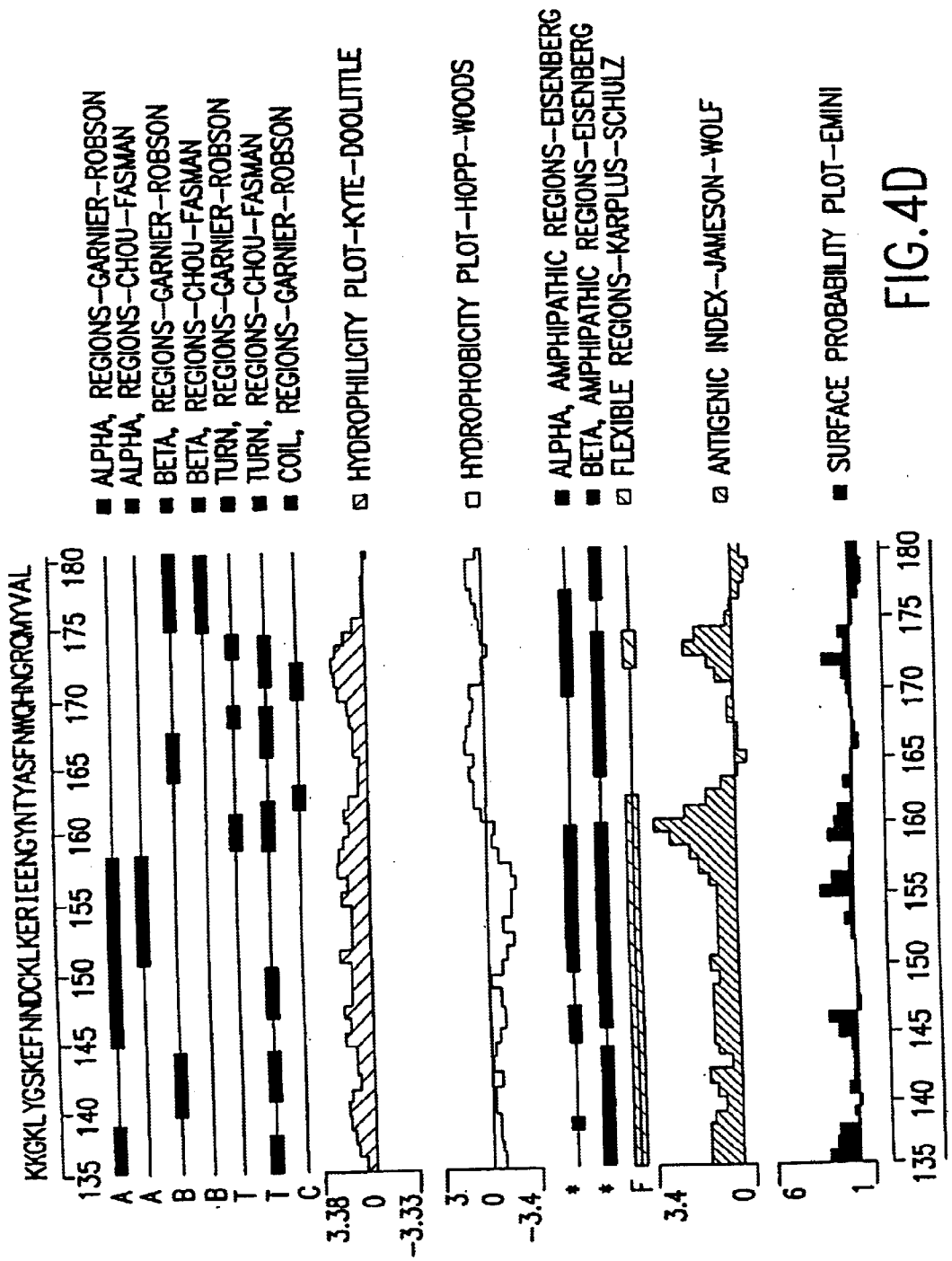
Figure 4E:
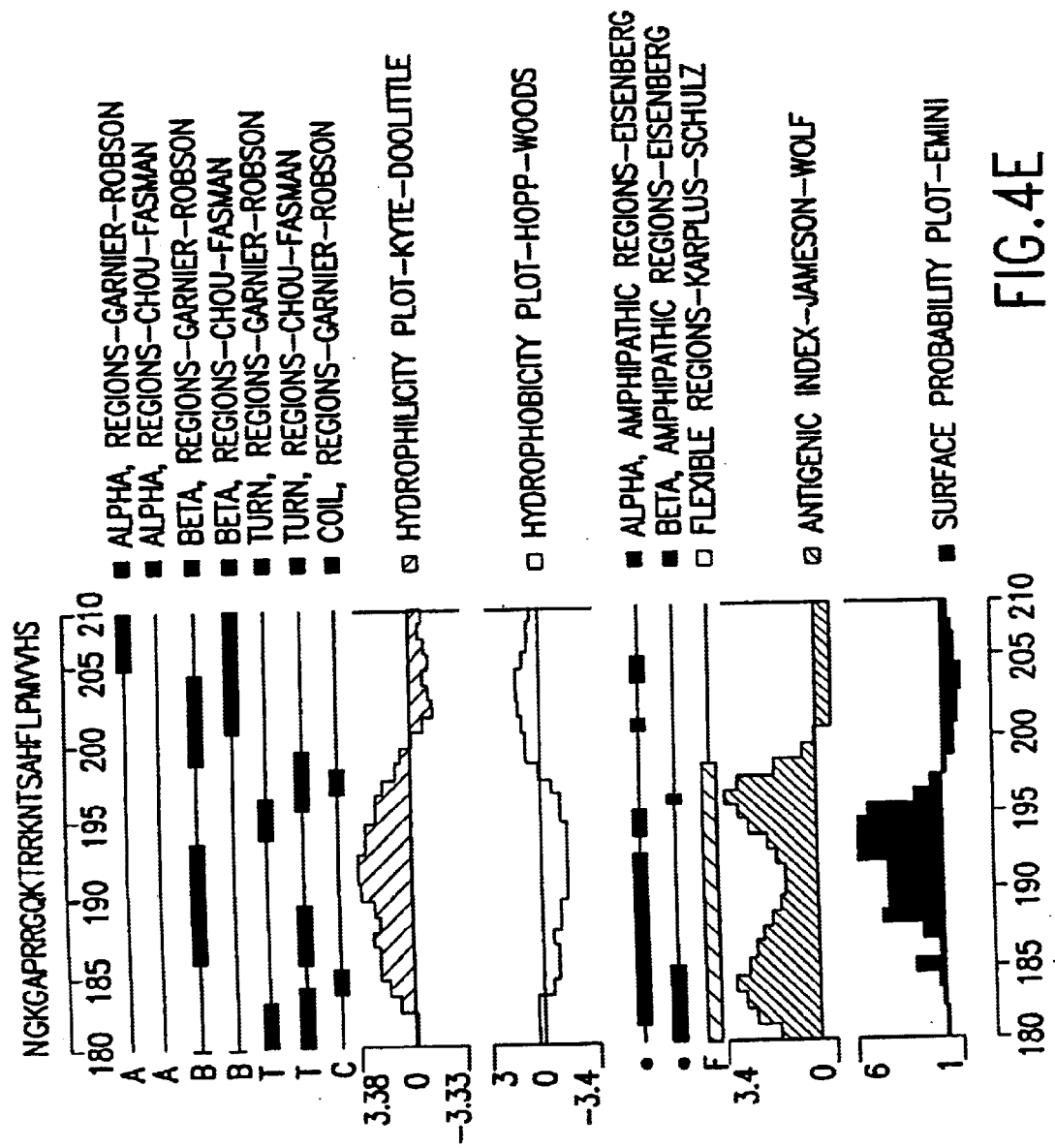
Figure 5:
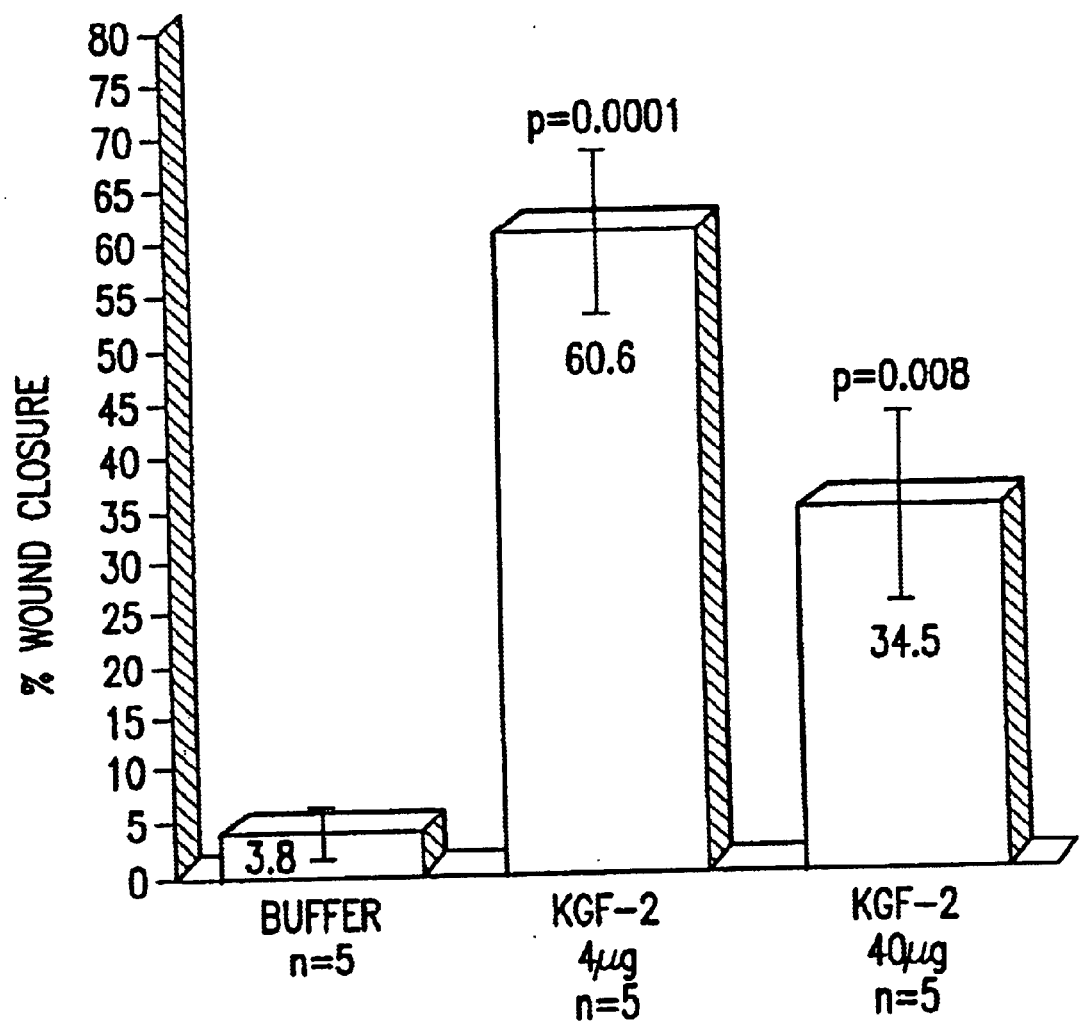
FIG. 5 shows the evaluation of KGF-2 on wound closure in the diabetic mice. Wounds were measured immediately after wounding and every day for 5 consecutive days and on day 8. Percent wound closure was calculated using the following formula: [Area on day 1]–[Area on day 8]/[Area on day 1]. Statisical analysis performed using an unpaired t test (mean+/–SEM, n=5).
Figure 6:
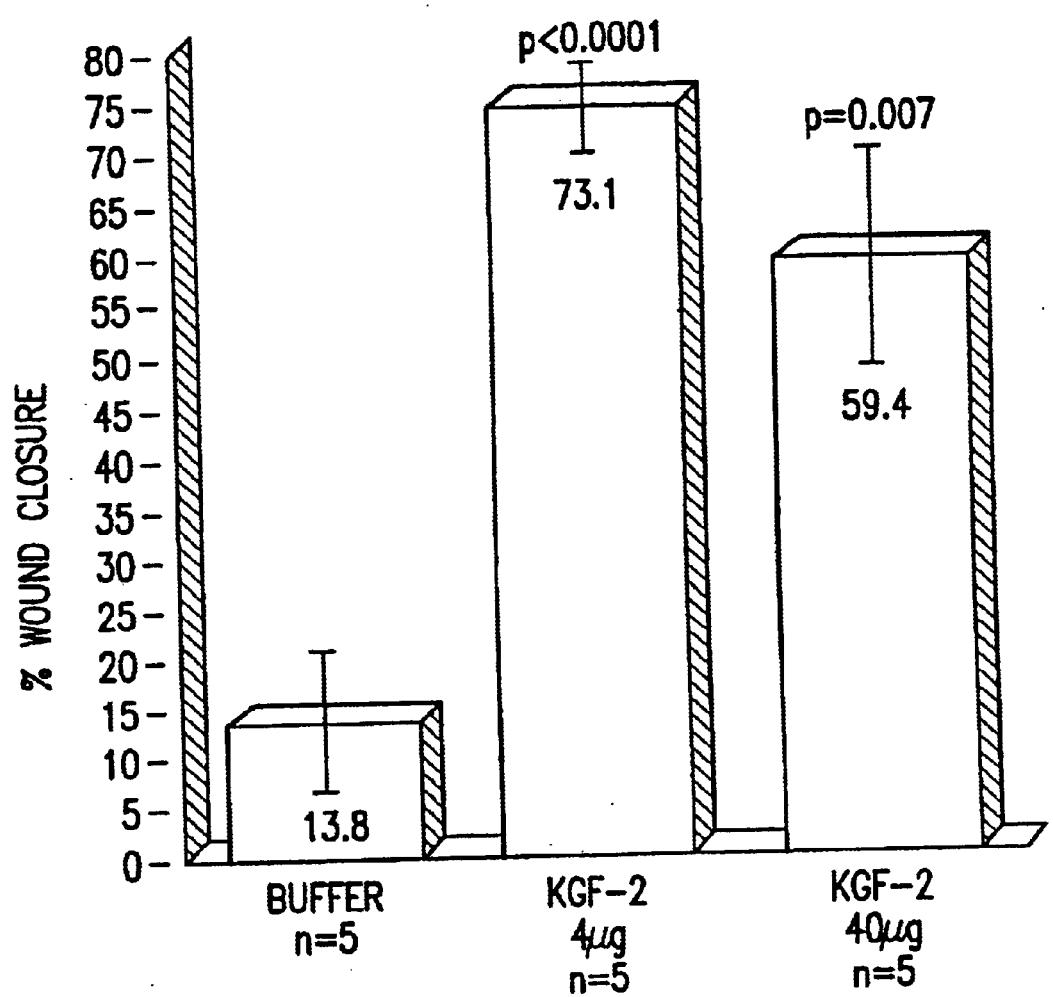
FIG. 6 shows the evaluation of KGF-2 on wound closure in the non-diabetic mice. Wounds were measured immediately after wounding and every day for 5 consecutive days and on day 8. Percent wound closure was calculated using the following formula: [Area on day 1]–[Area on day 8]/[Area on day 1]. Statisical analysis performed using an unpaired t test (mean+/–SEM, n=5).

Diabetic mice showed impaired healing compared to heterozygous normal mice. The dose of 4 µg of KGF-2 per site appeared to produce maximum response in diabetic and non-diabetic animals (FIG. 5, 6). These results were statistically significant (p=0.002 and p<0.0001) when compared with the buffer control groups. Treatment with KGF-2 resulted in a final average closure of 60.6% in the group receiving 4 µg/day and 34.5% in the 40 µg/day group.

Figure 7:
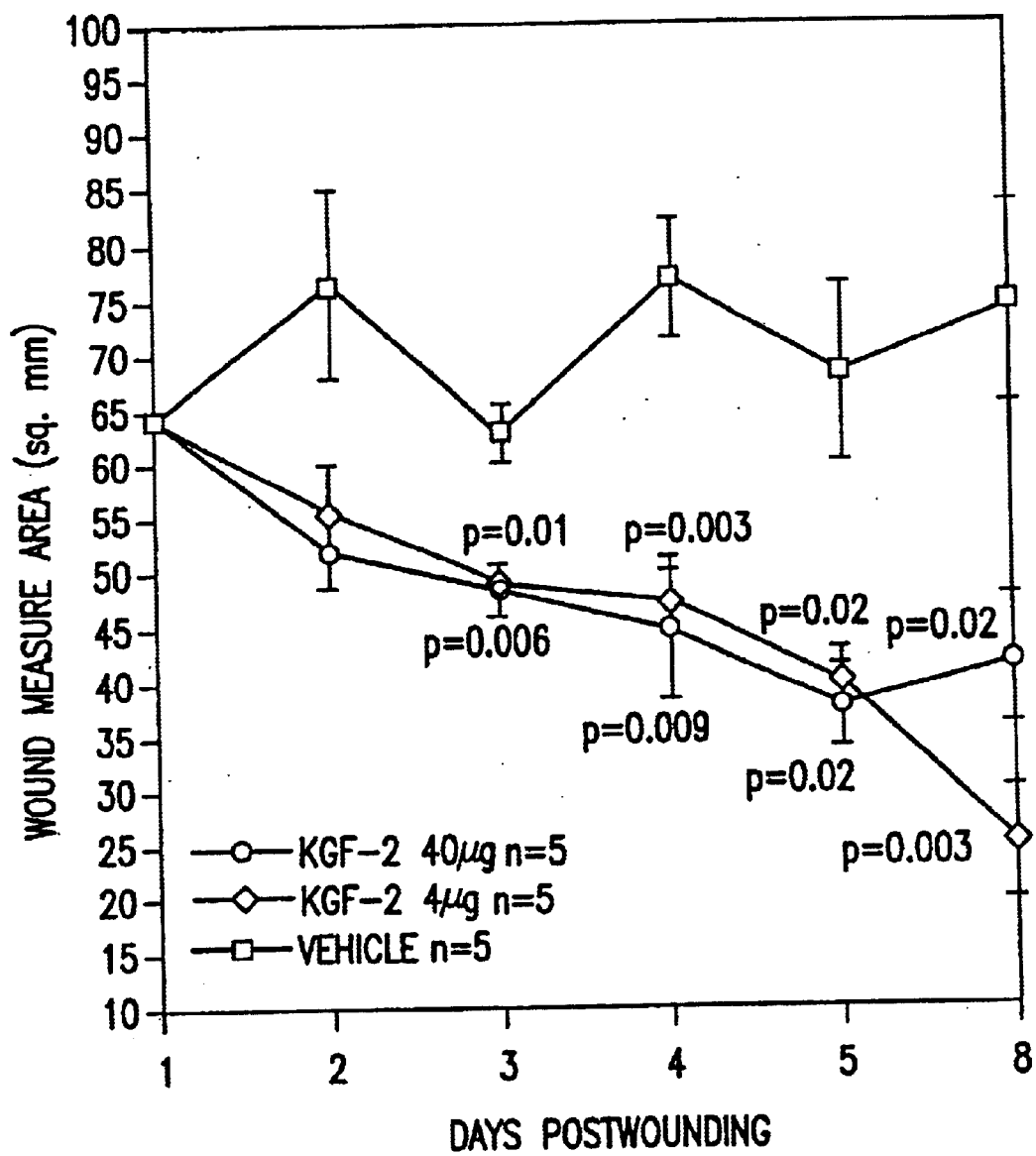
FIG. 7 shows a time course of wound closure in diabetic mice. Wound areas were measured immediately after wounding and every day for 5 consecutive days and on day 8. Values are presented as total area (sq. mm). Statistical analysis performed using an unpaired t test (mean+/–SEM, n=5).
Figure 8:
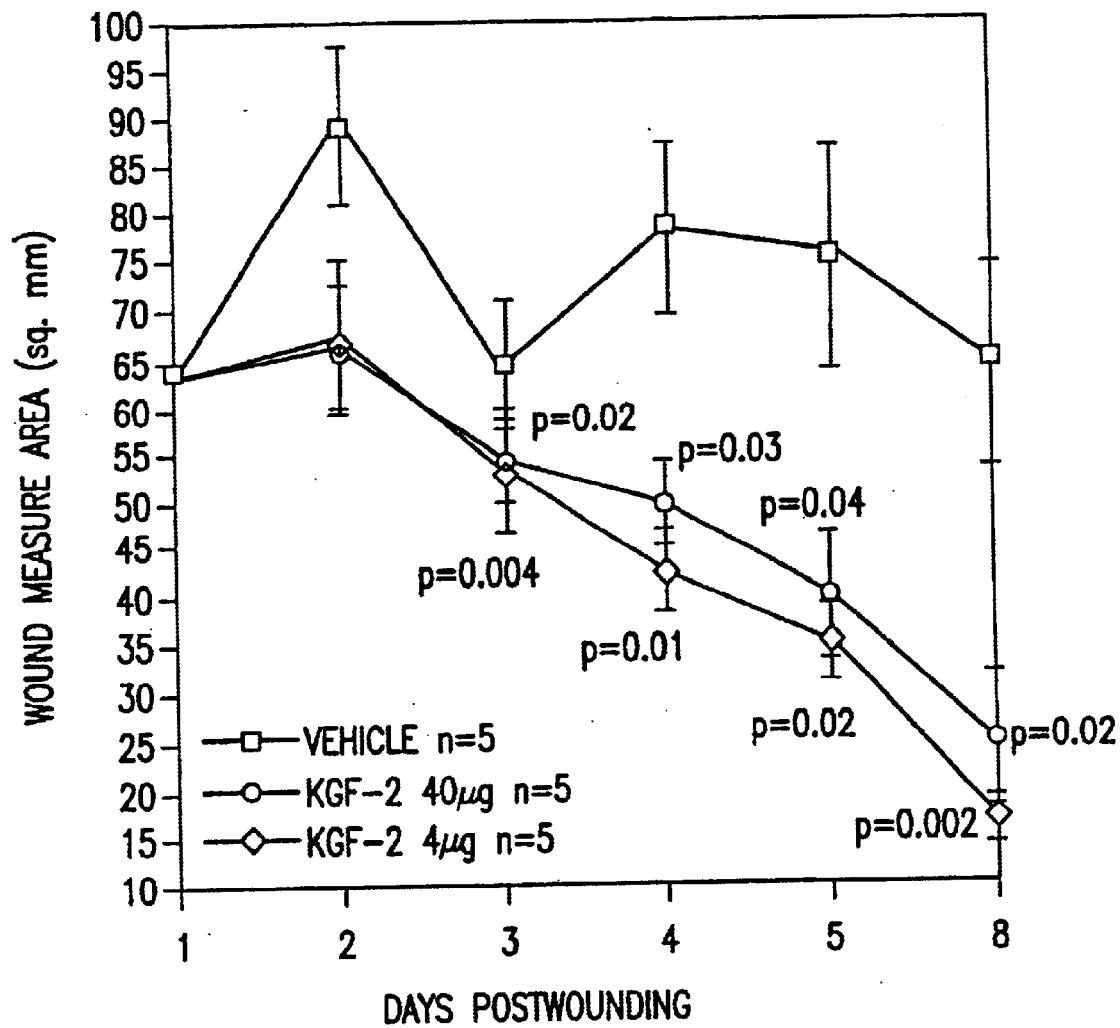
FIG. 8 shows a time course of wound closure in non-diabetic mice. Wound areas were measured immediately after wounding and every day for 5 consecutive days and on day 8. Values are presented as total area (sq. mm). Statistical analysis performed using an unpaired t test (mean+/–SEM, n=5).

Wounds in the buffer control group had only 3.8% closure by day 8. Repeated measurements of wounds on days 2–5 post-wounding and on day 8 taken from the db+/db+ mice treated with KGF-2 demonstrated a significant improvement in the total wound area (sq. mm) by day 3 post-wounding when compared to the buffer control group. This improvement continued and by the end of the experiment, statistically significant results were observed (FIG. 7). Animals in the db/+m groups receiving KGF-2 also showed a greater reduction in the wound area compared to the buffer control groups in repetitive measurements (FIG. 8). These results confirmed a greater rate of wound closure in the KGF-2 treated animals.

Effect of KGF-2 on Histologic Score

Figure 9:
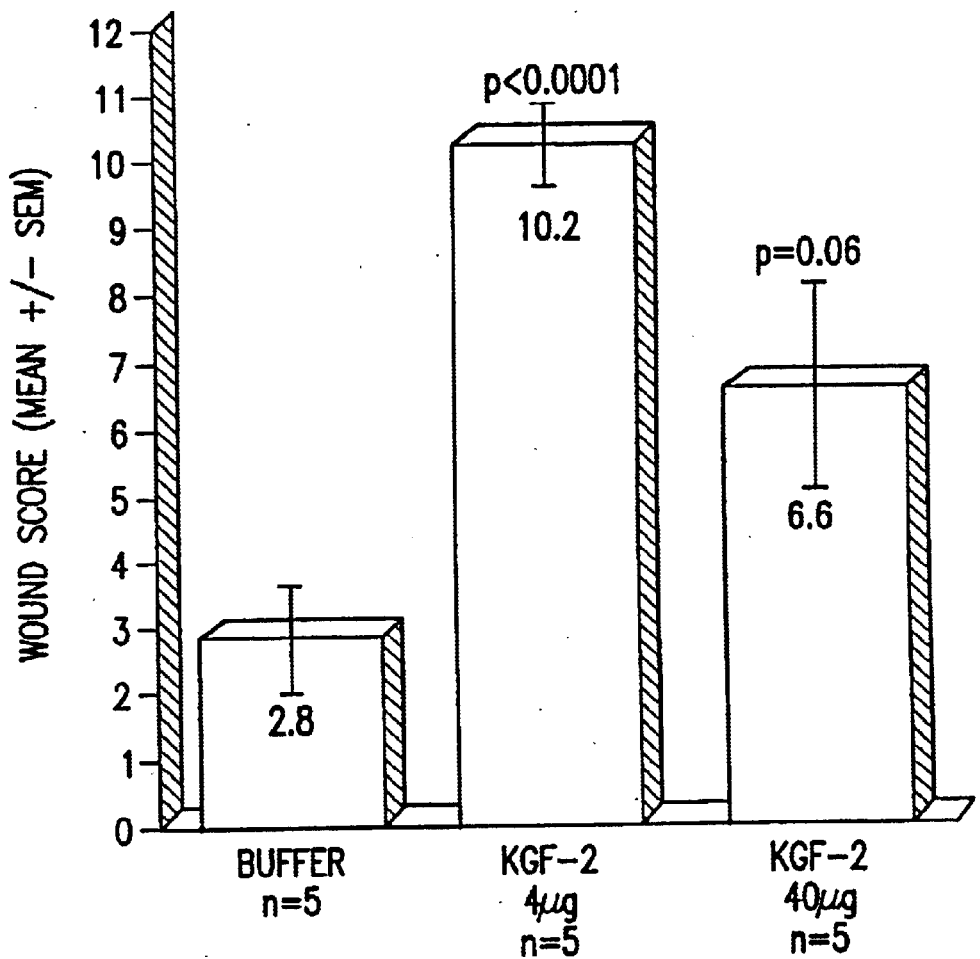
FIG. 9 shows a histopathologic evaluation on KGF-2 on the diabetic mice. Scores were given by a blind observer. Statisical analysis performed using an unpaired t test (mean+/–SEM, n=5).

Histopathologic evaluation of KGF-2 in the diabetic (db+/db+) model on day 8 demonstrated a statistically significant improvement ($p<0.00001$) in the wound score when compared with the buffer control. The pharmacologic effects observed with both the 4 $\mu$g and the 40 $\mu$g doses of KGF-2 were not significantly different from each other. The buffer control group showed minimal cell accumulation with no granulation tissue or epithelial travel while the 4 $\mu$g and 40 $\mu$g doses of KGF-2 ($p<0.0001$ & $p=0.06$ respectively) displayed epithelium covering the wound, neovascularization, granulation tissue formation and fibroblast and collagen deposition (FIG. 9).

Histopathologic assessment of skin wounds was performed on hematoxylin-eosin stained samples. Scoring criteria included a scale of 1–12, a score of one representing minimal cell accumulation with little to no granulation and a score of 12 representing the abundant presence of fibroblasts, collagen deposition and new epithelium covering the wound (Table 1).

TABLE 1

Scoring of Histology Sections

| Score | Criteria |
|---|---|
| 1–3 | None to minimal cell accumulation. No granulation tissue or epithelial travel. |
| 4–6 | Thin, immature granulation that is dominated by inflammatory cells but has few fibroblasts, capillaries or collagen deposition. Minimal epithelial migration. |
| 7–9 | Moderately thick granulation tissue, can range from being dominated by inflammatory cells to more fibroblasts and collagen deposition. Extensive neovascularization. Epithelium can range from minimal to moderate migration. |
| 10–12 | Thick, vascular granulation tissue dominated by fibroblasts and extensive collagen deposition. Epithelium partially to completely covering the wound. |

Figure 10:
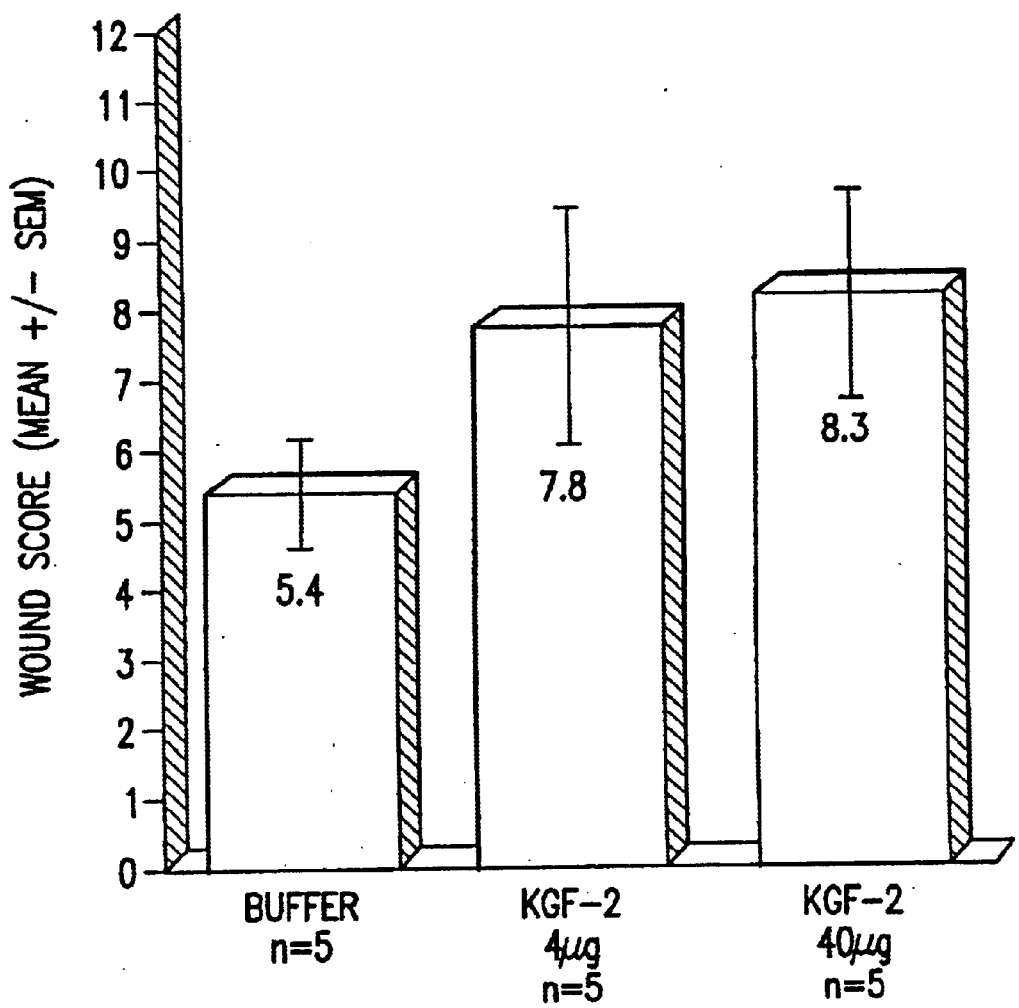
FIG. 10 shows a histopathologic evaluation on KGF-2, on the non-diabetic mice. Scores were given by a blind observer. Statistical analysis performed using an unpaired t test (mean+/–SEM, n=5).

Evaluation of the non diabetic littermates, after both doses of KGF-2, showed no significant activity in comparison with the buffer control group for all measurements evaluated (FIG. 10). The buffer control group showed immature granulation tissue, inflammatory cells, and capillaries. The mean score was higher than the diabetic group indicating impaired healing in the diabetic (db+/db+) mice.

Effect of KGF-2 on Re-epithelialization

Figure 11:
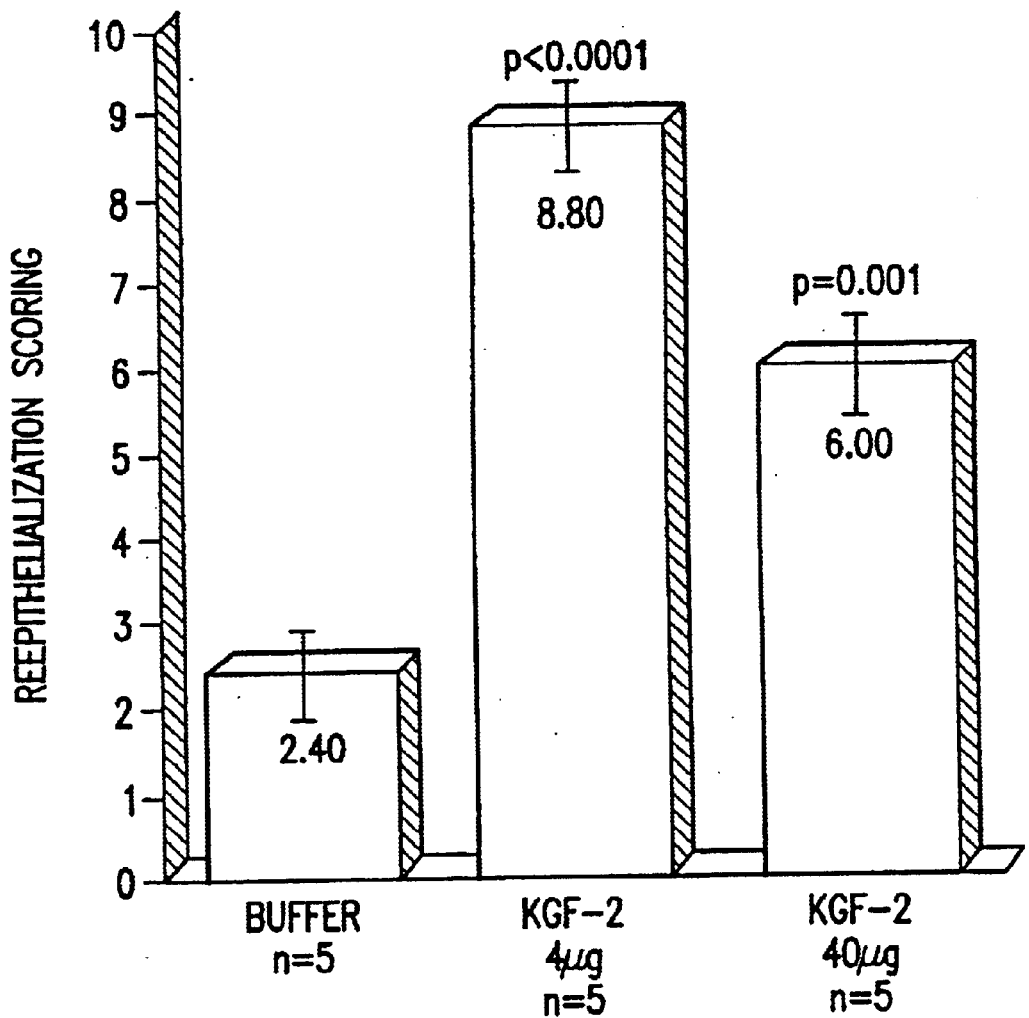
FIG. 11 shows the effect of keratinocyte growth in the diabetic mice. Scores were given by a blind observer. Statisical analysis performed using an unpaired t test (mean+/–SEM, n=5).
Figure 12:
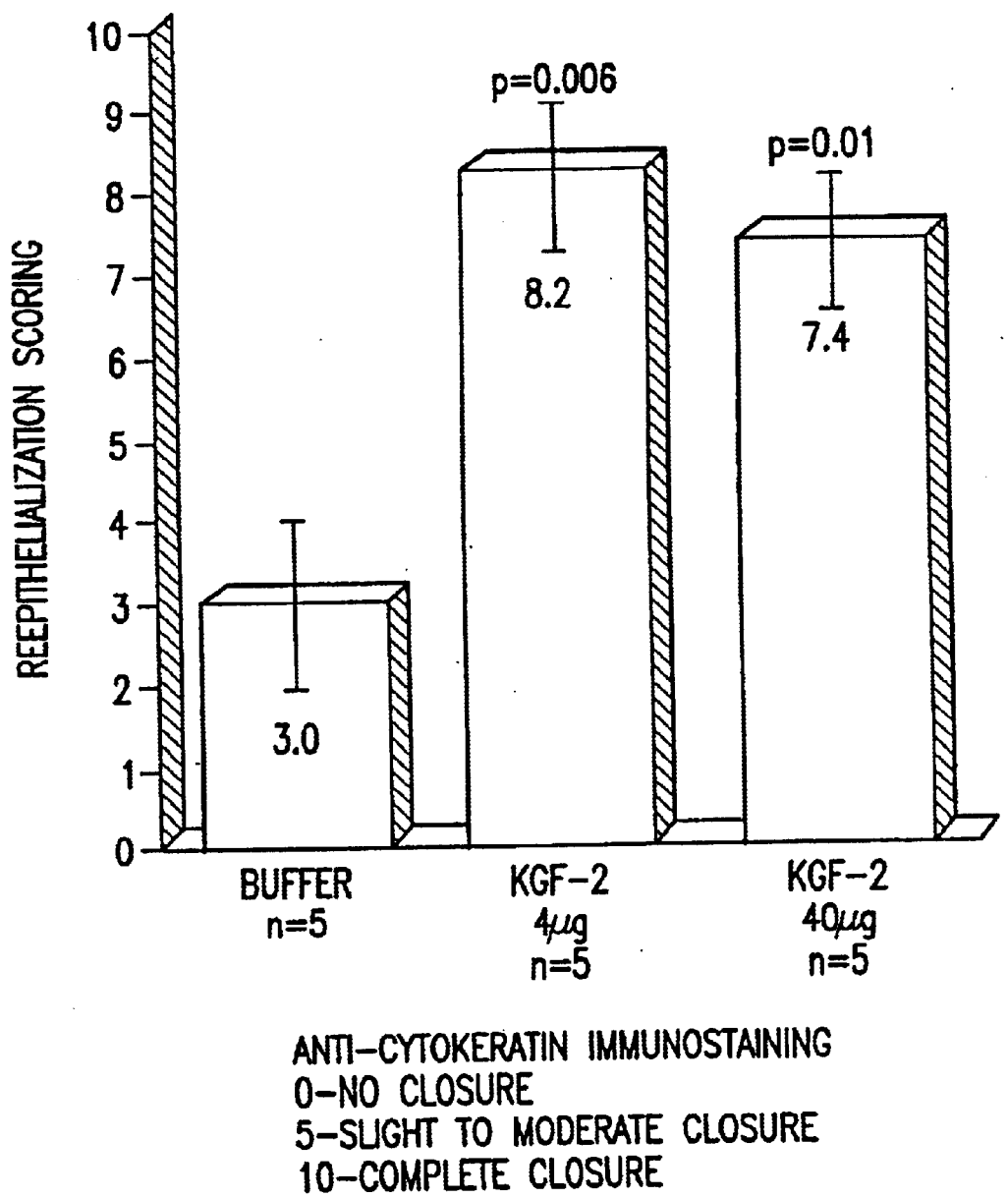
FIG. 12 shows the effect of keratinocyte growth in the non-diabetic mice. Scores were given by a blind observer based. Statisical analysis performed using an unpaired t test (mean+/–SEM, n=5).

Cytokeratine Immunostaining was used to determine the extent of re-epithelialization. Scores were given based on degree of closure on a scale of 0 (no closure) to 8 (complete closure). In the groups receiving 4 $\mu$g/day, there was a statistically significant improvement on the re-epithelialization a score when compared to the buffer control group $p<0.001$ (FIG. 11). In this group, keratinocytes were observed localized in the newly formed epidermis covering the wound. Both doses of KGF-2 also exhibited mitotic figures in various stages. Assessment of the non-diabetic groups at both doses of KGF-2 also significantly improved reepithelialization ranking ($p=0.006$ and 0.01 respectively,) (FIG. 12).

Effect of KGF-2 on Cell Proliferation

Figure 13:
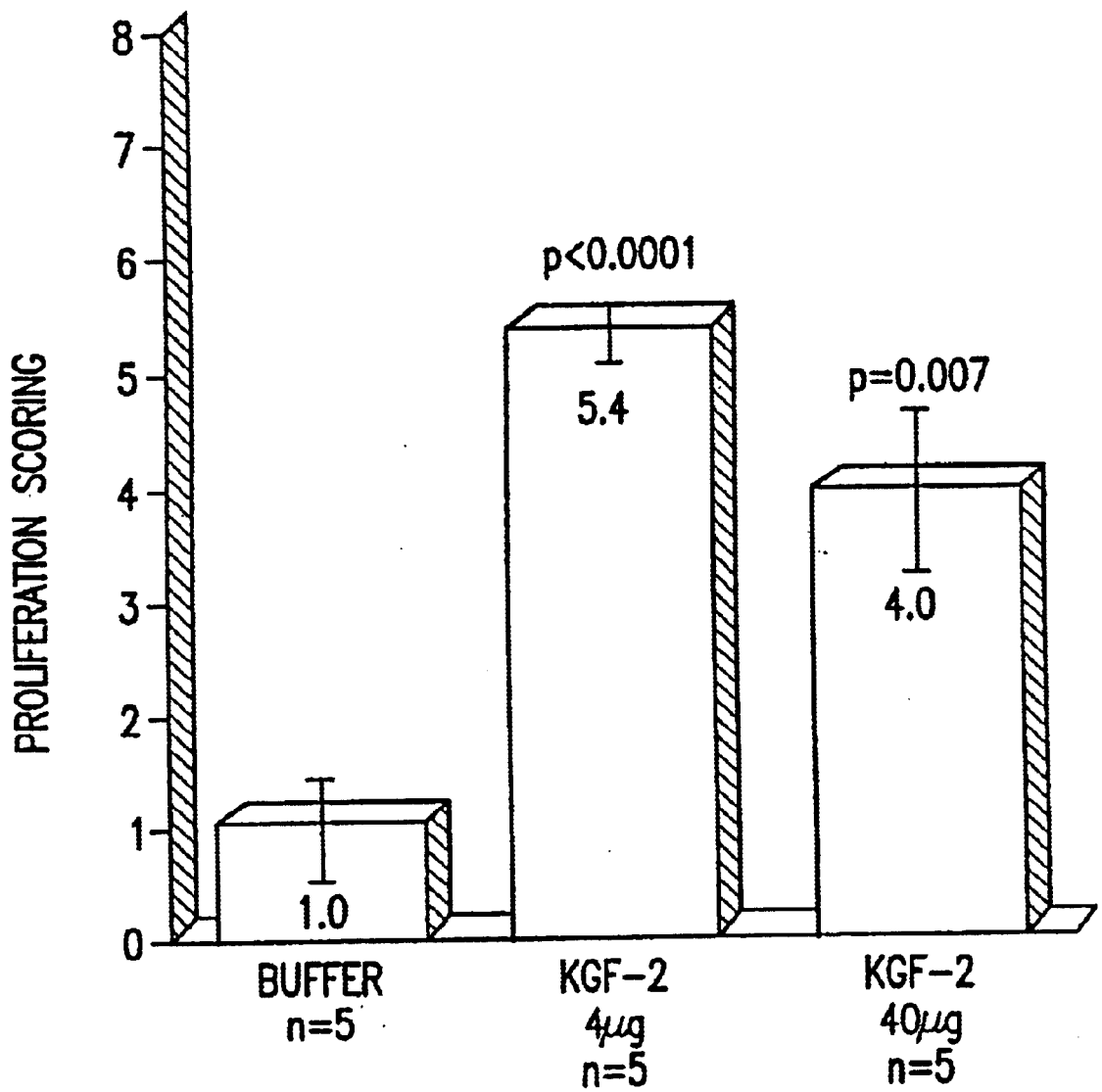
FIG. 13 shows the effect of skin proliferation in the diabetic mice. Scores were given by a blind observer. Statisical analysis performed using an unpaired t test (mean+/–SEM, n=5).
Figure 14:
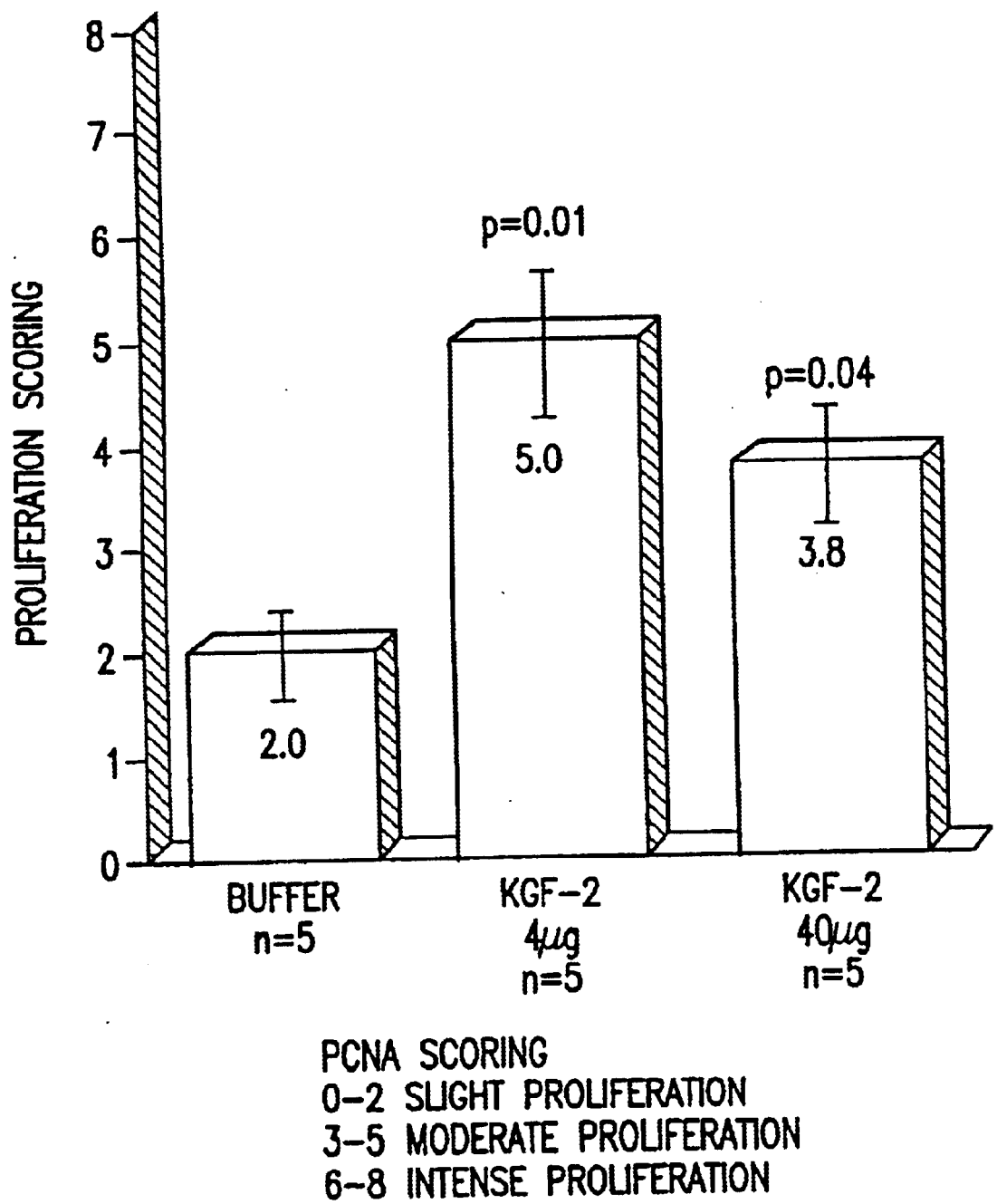
FIG. 14 shows the effect of skin proliferation in the non-diabetic mice. Scores were given by a blind observer. Statisical analysis performed using an unpaired t test (mean+/–SEM, n=5).

Proliferating cell nuclear antigen immunostaining demonstrated significant proliferation in both the 4 $\mu$g and 40 $\mu$g groups (FIG. 13). The non-diabetic group displayed similar results as both groups receiving both doses of KGF-2 showed higher significant scoring compared to the buffer control group (FIG. 14). Epidermal proliferation was observed especially on the basal layer of the epidermis. In addition, high density PCNA-labeled cells were observed in the dermis, especially in the hair follicles.

Conclusion

The results demonstrate that KGF-2 specifically stimulates growth of primary epidermal keratinocytes. In addition, these experiments demonstrate that topically applied recombinant human KGF-2 markedly accelerates the rate of healing of full-thickness excisional dermal wounds in diabetic mice. Histologic assessment shows KGF-2 to induce keratinocyte proliferation with epidermal thickening. This proliferation is localized in the basal layer of the epidermis as demonstrated by proliferating cell nuclear antigen (PCNA). At the level of the dermis, collagen deposition, fibroblast proliferation, and neo-vascularization re-established the normal architecture of the skin.

The high density of PCNA-labeled cells on KGF-2 treated animals in contrast with the buffer group, which had fewer PCNA-labeled cells, indicates the stimulation of keratinocytes at the dermal-epidermal level, fibroblasts and hair follicles. The enhancement of the healing process by KGF-2 was consistently observed in this experiment. This effect was statistically significant in the parameters evaluated (percent re-epithelialization and wound closure). Importantly, PCNA-labeled keratinocytes were mainly observed at the lower-basal layer of the epidermis. The dermis showed normalized tissue with fibroblasts, collagen, and granulation tissue.

The activity observed in the non-diabetic animals indicates that KGF-2 had significant pharmacologic response in the percentage of wound closure at day 8, as well as during the course of the experiment, based on daily measurements. Although the histopathologic evaluation was not significantly different when compared with the buffer control, keratinocyte growth and PCNA scores demonstrated significant effects.

In summary, these results demonstrated that KGF-2 shows significant activity in both impaired and normal excisional wound models using the db+/+ mouse model and therefore may be useful in the treatment of wounds including surgical wounds, diabetic ulcers, venous stasis ulcers, burns, and other skin conditions.

EXAMPLE 8

KGF-2 Mediated Wound Healing in the Steroid-Impaired Rat Model

The inhibition of wound healing by steroids has been well documented in various in vitro and in vivo systems (Wahl, S. M. Glucocorticoids and Wound healing. In Anti-Inflammatory Steroid Action: Basic and Clinical Aspects. 280–302 (1989); Wahl, S. M. et al., *J. Immunol.* 115: 476–481 (1975); Werb, Z. et al., *J. Exp. Med.* 147:1684–1694 (1978)). Glucocorticoids retard wound healing by inhibiting angiogenesis, decreasing vascular permeability (Ebert, R. H., et al., *An. Intern. Med.* 37:701–705 (1952)), fibroblast proliferation, and collagen synthesis (Beck, L. S. et al., *Growth Factors.* 5: 295–304 (1991);

Haynes, B. F., et al., *J. Clin. Invest.* 61: 703–797 (1978)) and producing a transient reduction of circulating monocytes (Haynes, B. F., et al., *J. Clin. Invest.* 61: 703–797 (1978); Wahl, S. M. Glucocorticoids and wound healing. In Antiinflammatory Steroid Action: Basic and Clinical Aspects. Academic Press. New York. pp. 280–302 (1989)). The systemic administration of steroids to impaired wound healing is a well establish phenomenon in rats (Beck, L. S. et al., *Growth Factors.* 5: 295–304 (1991); Haynes, B. F., et al., *J. Clin. Invest.* 61: 703–797 (1978); Wahl, S. M. Glucocorticoids and wound healing. In Antiinflammatory Steroid Action: Basic and Clinical Aspects. Academic Press. New York. pp. 280–302 (1989); Pierce, G. F., et al., *Proc. Natl. Acad. Sci. USA*. 86: 2229–2233 (1989)).

To demonstrate that KGF-2 would accelerate the healing process, the effects of multiple topical applications of KGF-2 on full thickness excisional skin wounds in rats in which healing has been impaired by the systemic administration of methylprednisolone was assesed. In vitro studies have demonstrated that KGF-2 specifically stimulates growth of primary human epidermal keratinocytes. This example demonstrates that topically applied recombinant human KGF-2 accelerates the rate of healing of full-thickness excisional skin wounds in rats by measuring the wound gap with a calibrated Jameson caliper and by histo-morphometry and immunohistochemistry. Histologic assessment demonstrates that KGF-2 accelerates re-epithelialization and subsequently, wound repair.

Animals

Young adult male Sprague Dawley rats weighing 250–300 g (Charles River Laboratories) were used in this example. The animals were purchased at 8 weeks of age and were 9 weeks old at the beginning of the study. The healing response of rats was impaired by the systemic administration of methylprednisolone (17 mg/kg/rat intramuscularly) at the time of wounding. Animals were individually housed and received food and water ad libitum. All manipulations were performed using aseptic techniques. This study was conducted according to the rules and guidelines of Human Genome Sciences, Inc. Institutional Animal Care and Use Committee and the Guidelines for the Care and Use of Laboratory Animals.

KGF-2

Recombinant human KGF-2 was over-expressed and purified from pQE60–Cys37, an *E. coli* expression vector system (pQE-9, Qiagen). The protein expressed from this construct is the KGF-2 from Cysteine at position 37 to Serine at position 208 with a 6X(His) tag attached to the N-terminus of the protein (FIG. 15) (SEQ ID NOS: 29–30). Fractions containing greater than 95% pure recombinant materials were used for the experiment. KGF-2 was formulated in a vehicle containing 1×PBS. The final concentrations were 20 µg/mL and 80 µg/mL of stock solution. Dilutions were made from stock solution using the same vehicle.

KGF-2Δ28 was over-expressed and purified from an *E. coli* expression vector system. Fractions containing greater than 95% pure recombinant materials were used for the experiment. KGF-2 was formulated in a vehicle containing 1×PBS. The final concentrations were 20 µg/mL and 80 µg/mL of stock solution. Dilutions were made from stock solution using the same vehicle.

Surgical Wounding

The wounding protocol was followed according to Example 7, above. On the day of wounding, animals were anesthetized with an intramuscular injection of ketamine (50 mg/kg) and xylazine (5 mg/kg). The dorsal region of the animal was shaved and the skin washed with 70% ethanol and iodine solutions. The surgical area was dried with sterile gauze prior to wounding. An 8 mm full-thickness wound was created using a Keyes tissue punch. The wounds were left open for the duration of the experiment. Applications of the testing materials were given topically once a day for 7 consecutive days commencing on the day of wounding and subsequent to methylprednisolone administration. Prior to treatment, wounds were gently cleansed with sterile saline and gauze sponges.

Wounds were visually examined and photographed at a fixed distance at the day of wounding and at the end of treatment. Wound closure Was determined by daily measurement on days 1–5 and on day 8 for Figure. Wounds were measured horizontally and vertically using a calibrated Jameson caliper. Wounds were considered healed if granulation tissue was no longer visible and the wound was covered by a continuous epithelium.

A dose response was performed using two different doses of KGF-2, one at 1 µg per wound per day and the second at 4 µg per wound per day for 5 days in 50 µL of vehicle. Vehicle control groups received 50 µL of 1×PB.

Animals were euthanized on day 8 with an intraperitoneal injection of sodium pentobarbital (300 mg/kg). The wounds and surrounding skin were then harvested for histology. Tissue specimens were placed in 10% neutral buffered formalin in tissue cassettes between biopsy sponges for further processing.

Experimental Design

Four groups of 10 animals each (5 with methylprednisolone and 5 without glucocorticoid) were evaluated: 1) Untreated group 2) Vehicle placebo control 3) KGF-2 µg/day and 4) KGF-2 4 µg/day. This study was designed as follows:

| n | Group | Treatment |
|---|-------|-----------|
| Glucocorticoid-Treated | | |
| N = 5 | Untreated | — |
| N = 5 | Vehicle | 50 µL |
| N = 5 | KGF-2 (1 µg) | 50 µL |
| N = 5 | KGF-2 (4 µg) | 50 µL |
| Without Glucocorticoid | | |
| N = 5 | Untreated | — |
| N = 5 | Vehicle | 50 µL |
| N = 5 | KGF-2 (1 µg) | 50 µL |
| N = 5 | KGF-2 (4 µg) | 50 µL |

Measurement of Wound Area and Closure

Wound closure was analyzed by measuring the area in the vertical and horizontal axis and obtaining the total area of the wound. Closure was then estimated by establishing the differences between the initial wound area (day 0) and that of post treatment (day 8). The wound area on day 1 was 64 mm$^2$, the corresponding size of the dermal punch. Calculations were made using the following formula:

[Open area on day 8]–[Open area on day 1]/[Open area on day 1]

Histology

Specimens were fixed in 10% buffered formalin and paraffin embedded blocks were sectioned perpendicular to the wound surface (5 µm) and cut using an Olympus microtome. Routine hematoxylin-eosin (H&E) staining was performed on cross-sections of bisected wounds. Histologic examination of the wounds allowed us to assess whether the healing process and the morphologic appearance of the repaired skin was improved by treatment with KGF-2. A calibrated lens micrometer was used by a blinded observer to determine the distance of the wound gap.

Statistical Analysis

Experimental data were analyzed using an unpaired t test. A p value of <0.05 was considered significant. The data was expressed as the mean±SEM.

Results

Figure 16:
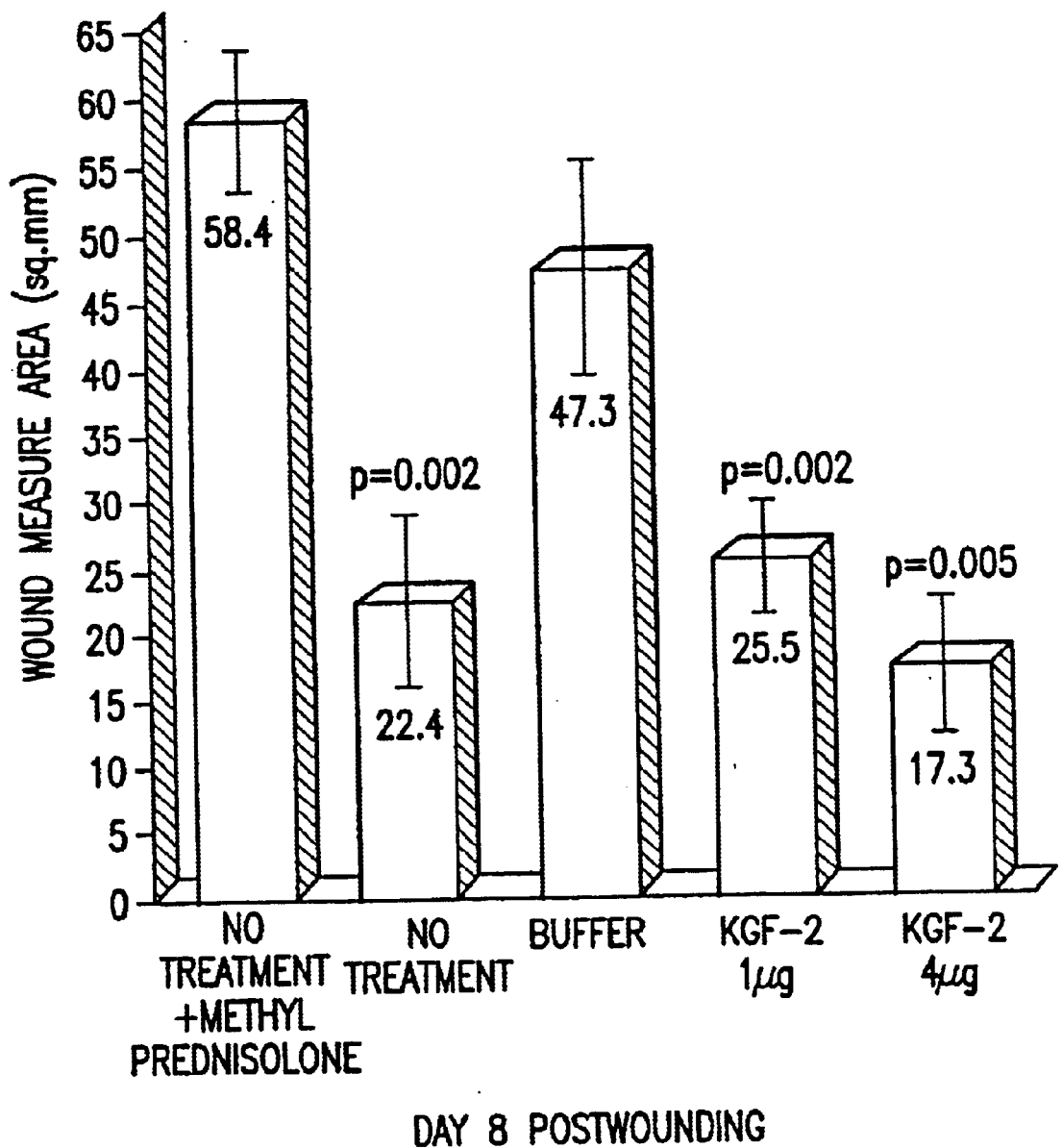
FIG. 16 shows the effect of methyl prednisolone on wound healing in rats. Male SD adult rats (n=5) were injected on day of wounding with 5 mg of methyl prednisolone. Animals received dermal punch wounds (8 mm) and were treated daily with buffer solution or KGF-2 solution in 50 $\mu$L buffer solution for 5 consecutive days. Wounds were measured daily on days 1–5 and on day 8 with a calibrated Jameson caliper. Values represent measurements taken on day 8. (Mean+/–SEM)

A comparison of the wound closure of the untreated control groups with and without methylprednisolone demonstrates that methylprednisiolone-treated rats have significant impairment of wound healing at 8 days post-wounding compared with normal rats. The total wound area measured 58.4 mm$^2$ in the methylprednisolone injected group and 22.4 mm$^2$ in the group not receiving glucocorticoid (FIG. 16).

Effect of KGF-2 on Wound Closure

Figure 17:
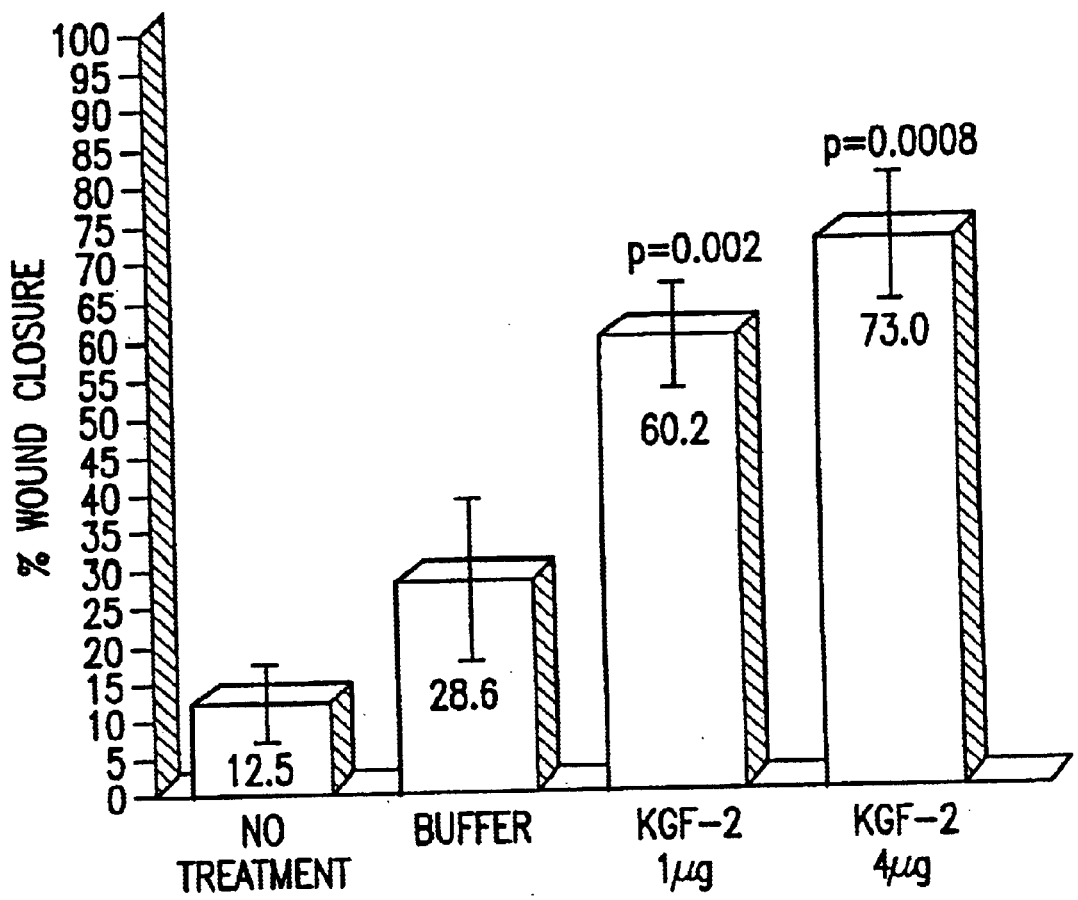
FIG. 17 shows the effect of KGF-2 on wound closure. Male SD adult rats (n=5) received dermal punch wounds (8 mm) and 5 mg of methyl-prednisolone on day of wounding. Animals were treated daily with a buffer solution or KGF-2 in 50 $\mu$L of buffer solution for 5 consecutive days commencing on the day of wounding. Measurements were made daily for 5 consecutive days and on day 8. Wound closure was calculated by the following formula: [Area on Day 8]–[Area on Day 1]/[Area on Day 1]. Area on day 1 was determined to be 64 sq. mm, the area made by the dermal punch. Statistical analysis was done using an unpaired t test. (Mean+/–SEM)

Systemic administration of methylprednisolone in rats at the time of wounding delayed wound closure (p=0.002) of normal rats. Wound closure measurements of the methlyprednisolone-impaired groups at the end of the experiment on day 8 demonstrated that wound closure with KGF-2 was significantly greater statistically (1 μg p=0.002 & 4 μg p=0.005) when compared with the untreated group (FIG. 16). Percentage wound closure was 60.2% in the group receiving 1 μg KGF-2 (p=0.002) and 73% in the group receiving 4 μg KGF-2 (p=0.0008). In contrast, the wound closure of untreated group was 12.5% and the vehicle placebo group was 28.6% (FIG. 17).

Figure 18:
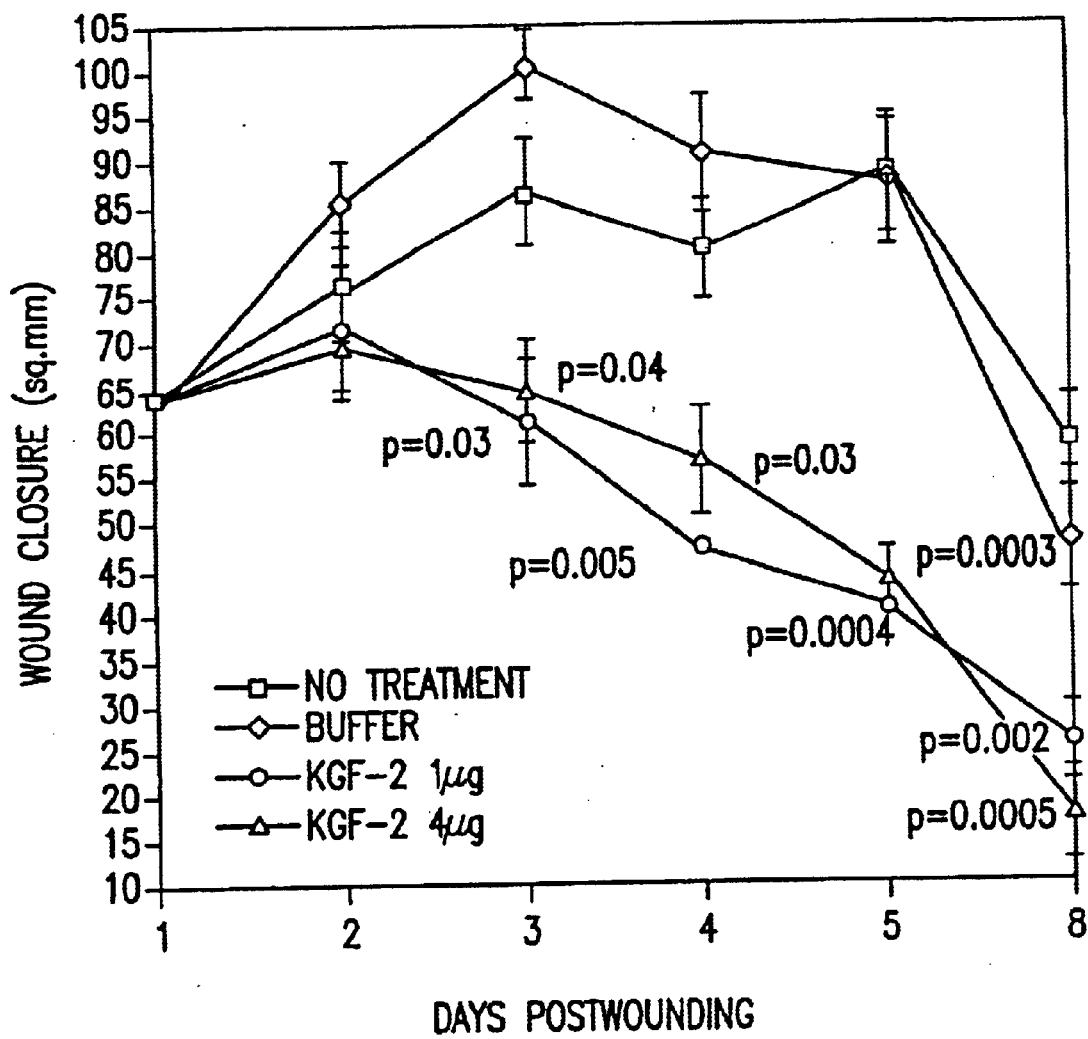
FIG. 18 shows the time course of wound healing in the glucocorticoid-impaired model of wound healing. Male SD adult rats (n=5) received dermal punch wounds (8 mm) on day 1 and were treated daily for 5 consecutive days with a buffer solution or a KGF-2 solution in 50 $\mu$L. Animals received 5 mg of methyl-prednisolone on day of wounding. Wounds were measured daily for five consecutive days commencing on day of wounding and on day 8 with a calibrated Jameson caliper. Statistical analysis was done using an unpaired t test. (Mean +/– SEM)

Longitudinal analysis of wound closure in the glucocorticoid groups from day 1 to 8 shows a significant reduction of wound size from day 3 to 8 postwounding in both doses of KGF-2 in the treated groups (FIG. 18).

Figure 19A:
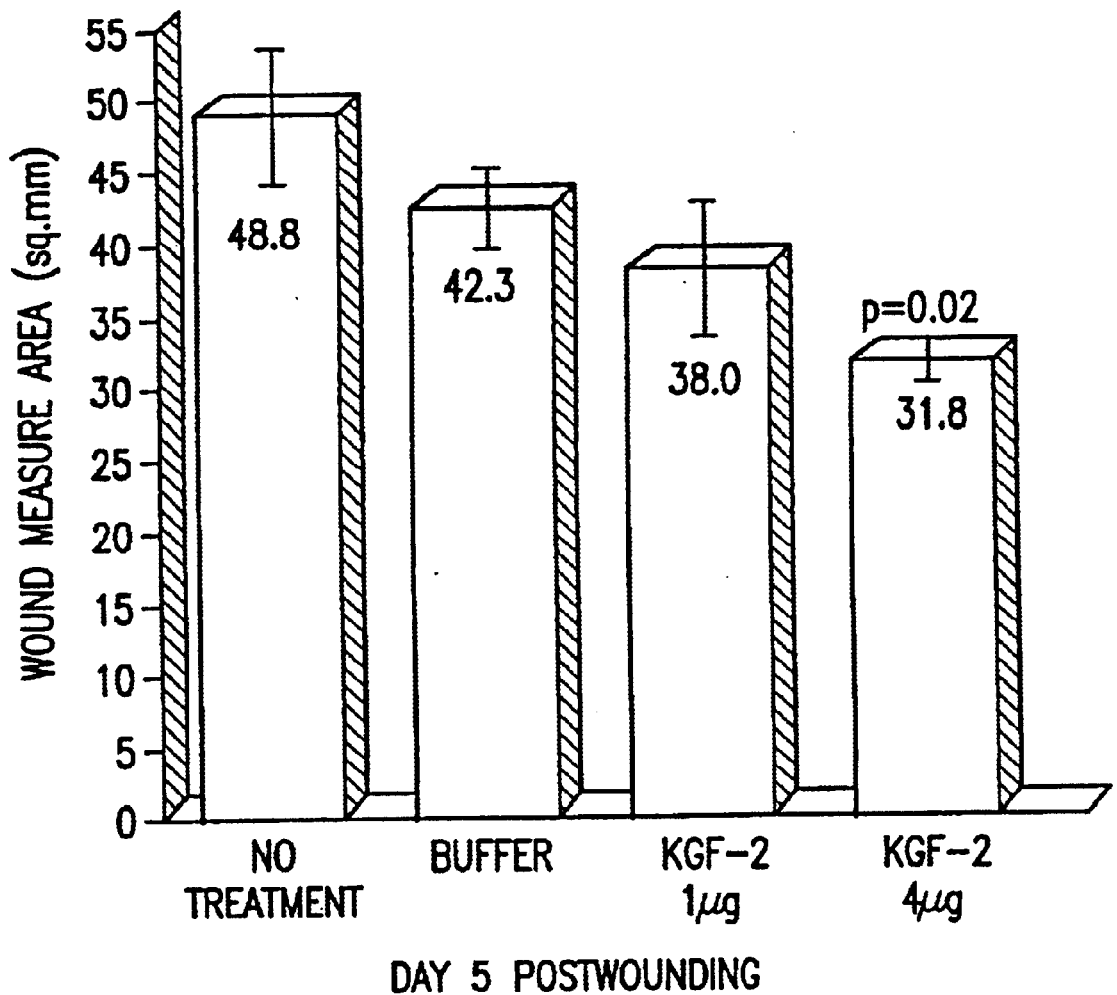
FIG. 19 (A) shows the effect of KGF-2 on wound area in rat model of wound healing without methylprednisolone at day 5 postwounding. Male SD rats (n=5) received dermal punch wounds (8 mm) on day 1 and were treated daily with either a buffer solution or KGF-2 in a 50 $\mu$L solution on day of wounding and thereafter for 5 consecutive days. Wounds were measured daily using a calibrated Jameson caliper. Statistical analysis was done using an unpaired t test. (Mean+/–SEM). (B) Evaluation of PDGF-BB and KGF-2 in Male SD Rats (n=6). All rats received 8 mm dorsal wounds and methylprednisolone (MP) (17 mg/kg) to impair wound healing. Wounds were treated daily with buffer or various concentrations of PDGF-BB and KGF-2. Wounds were measured on Days 2, 4, 6, 8, and 10 using a calibrated Jameson caliper. Statistical analysis was performed using an unpaired t-test. (Mean+/–SE) *Compared with buffer. **PDGF-BB 1 $\mu$g vs KGF-2/E3 $\mu$g.

The results demonstrate that the group treated with the 4 μg KGF-2 had statistically significant (p=0.05) accelerated wound closure compared with the untreated group (FIG. 19A). Although it is difficult to assess the ability of a protein or other compounds to accelerate wound healing in normal animal (due to rapid recovery), nonetheless, KGF-2 was shown to accelerate wound healing in this model.

Histopathologic Evaluation of KGF-2 Treated Wounds

Figure 20:
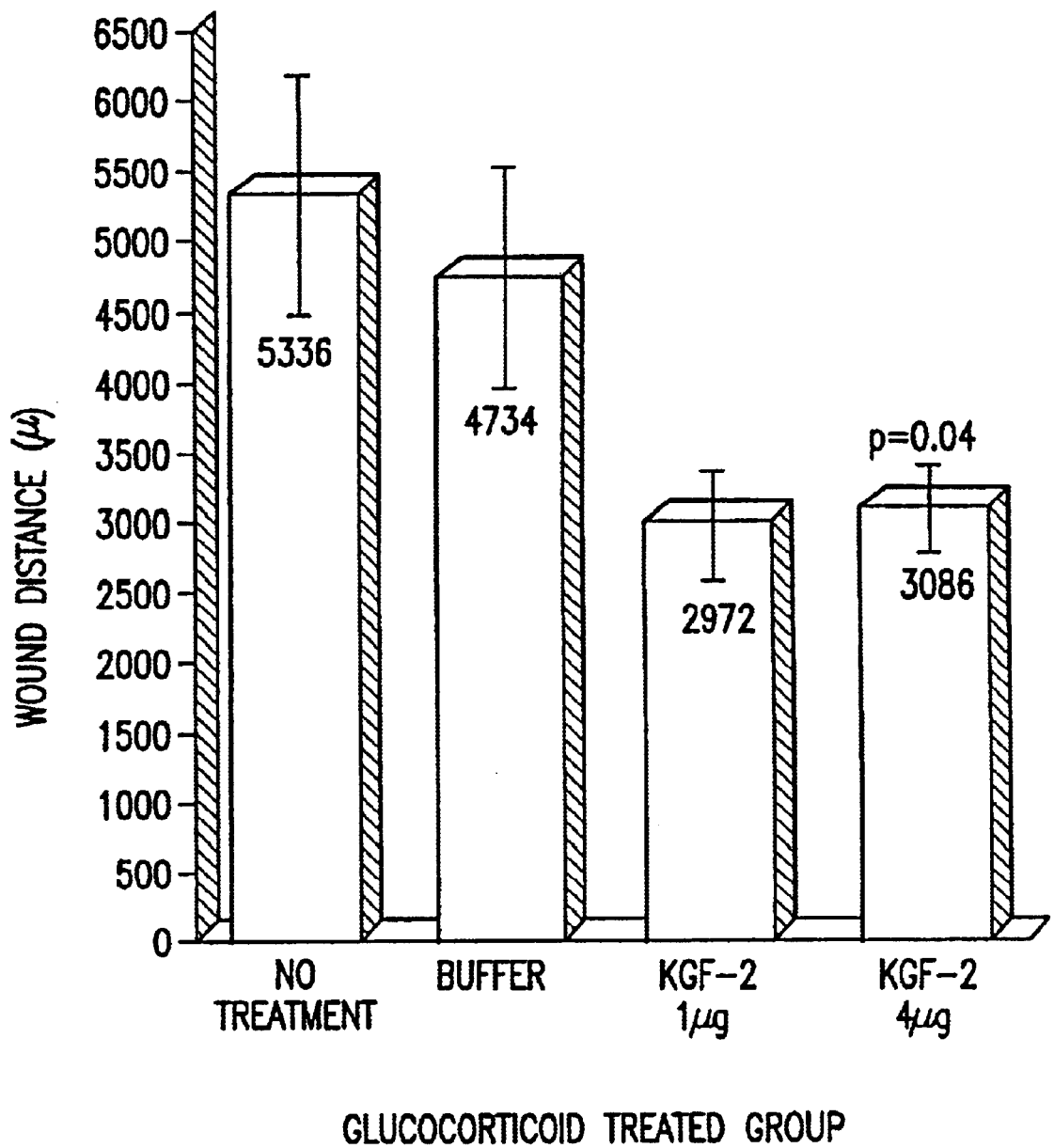
FIG. 20 shows the effect of KGF-2 on wound distance in the glucocorticoid-impaired model of wound healing. Male SD adult rats (n=5) received dermal punch wounds (8 mm) and of 17 mg/kg methyl-prednisolone on the day of wounding. Animals were treated daily with a buffer solution or KGF-2 in 50 µL of buffer solution for 5 consecutive days and on day 8. Wound distance was measured under light microscopy with a calibrated micrometer. Statistical analysis was done using an unpaired t test. (Mean+/−SEM)

Histomorphometry of the wound gap indicated a reduction in the wound distance of the KGF-2 treated group. The wound gap observed for the untreated group was 5336μ while the group treated with 1 μg KGF-2 had a wound gap reduction to 2972μ; and the group treated with 4 μg KGF-2 (p=0.04) had a wound gap reduction to 3086μ. (FIG. 20)

Effects of KGF-2Δ28 in Wound Healing

Evaluation of KGF-2Δ28 and PDGF-BB in wound healing in the methylprednisolone impared rat model was also examined. The experiment was carried out the same as for the KGF-2 protein above, except that the KGF-2Δ28 protein is not His tagged and wound healing was measured on days 2, 4, 6, 8, and 10. The buffer vehicle for the proteins was 40 mM NaOAc and 150 mM NaCl, pH6.5 for all but the "E2" preparation of the full length KGF-2. The buffer vehicle for the "E2" KGF-2 preparation was 20 mM NaOAc and 4 mM NaCl, pH6.4.

Figure 19B:
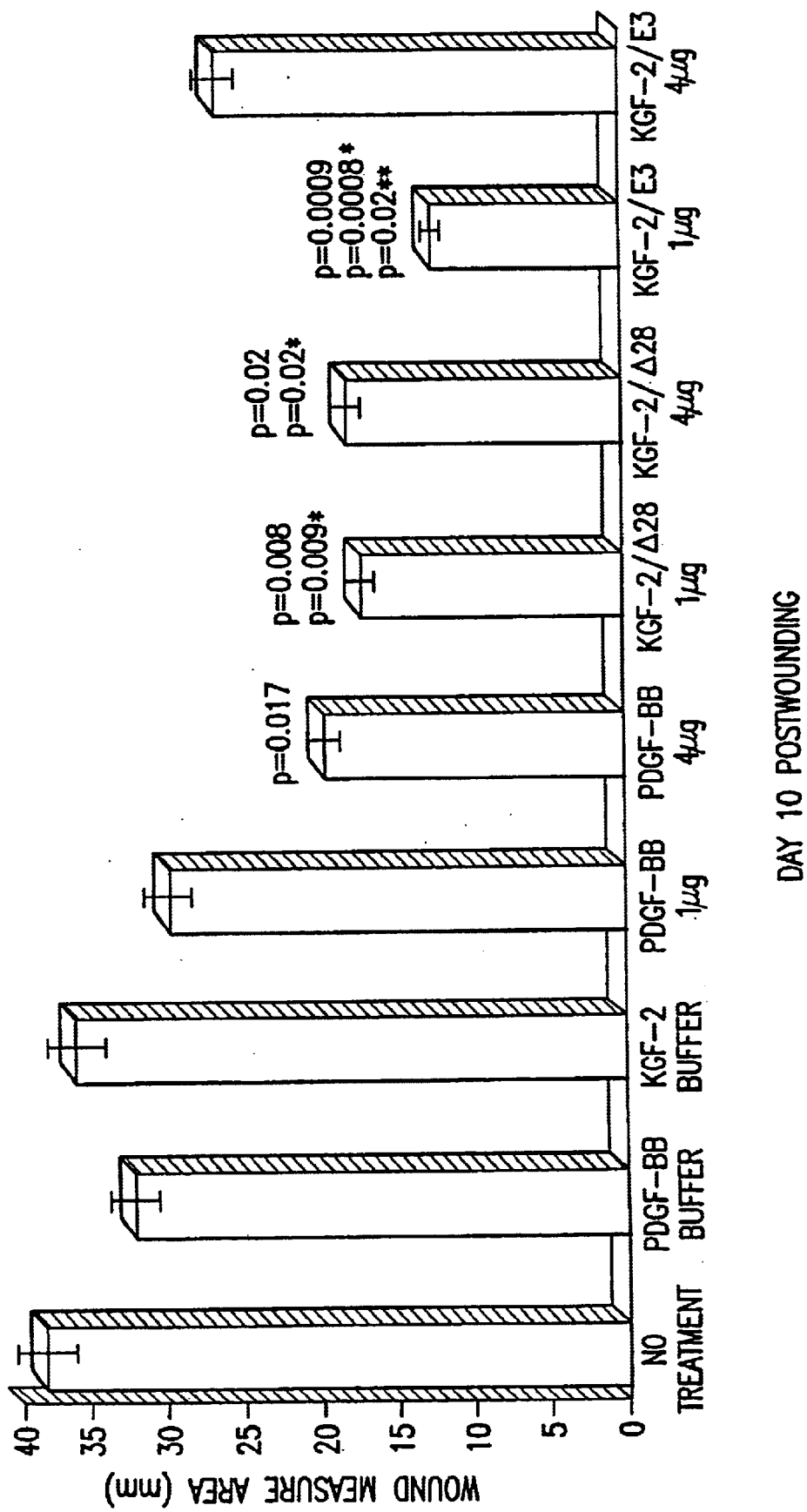

The results shown in FIG. 19B demonstrate that KGF-2Δ28 has statistically significant accelerated wound closure compared with the untreated group and has reversed the effects of methylprednisolone on wound healing.

Conclusions

This example demonstrates that KGF-2 reversed the effects of methylprednisolone on wound healing. The exogenous application of growth factors may accelerate granulation tissue formation by drawing inflammatory cells into the wound. Similar activity was also observed in animals not receiving methylprednisolone indicating that KGF-2 had significant pharmacologic response in the percentage of wound closure at day 5 based on daily measurements. The glucocorticoid-impaired wound healing model in rats was shown to be a suitable and reproducible model for measuring efficacy of KGF-2 and other compounds in the wound healing area.

In summary, the results demonstrate that KGF-2 shows significant activity in both glucocorticoid impaired and in normal excisional wound models. Therefore, KGF-2 may be clinically useful in stimulating wound healing including surgical wounds, diabetic ulcers, venous stasis ulcers, burns, and other abnormal wound healing conditions such as uremia, malnutrition, vitamin deficiencies and systemic treatment with steroids and antineoplastic drugs.

EXAMPLE 9

Tissue Distribution of KGF-2 mRNA Expression

Northern blot analysis is carried out to examine the levels of expression of the gene encoding the KGF-2 protein in human tissues, using methods described by, among others, Sambrook et al., cited above, A probe corresponding to the entire open reading frame of KGF-2 of the present invention (SEQ ID NO:1) was obtained by PCR and was labeled with $^{32}$P using the rediprime™ DNA labeling system (Amersham Life Science), according to manufacturer's instructions. After labelling, the probe was purified using a CHROMA SPIN-100™ column (Clontech Laboratories, Inc.), according to manufacturer's protocol number PT1200–1. The purified labelled probe was then used to examine various human tissues for the expression of the gene encoding KGF-2.

Multiple Tissue Northern (MTN) blots containing poly A RNA from various human tissues (H) or human immune system tissues (IM) were obtained from Clontech and were examined with labelled probe using ExpressHyb™ Hybridization Solution (Clontech) according to manufacturer's protocol number PT1190-1. Following hybridization and washing, the blots are mounted and exposed to film at −70° C. overnight, and films developed according to standard procedures.

A major mRNA species of apporximately 4.2 kb was observed in most human tissues. The KGF-2 mRNA was relatively abundant in heart, pancreas, placenta and ovary. A minor mRNA species of about 5.2 kb was also observed ubiquitously. The identity of this 5.2 kb mRNA species was not clear. It is possible that the 5.2 kb transcript encodes an alternatively spliced form of KGF-2 or a third member of the KGF family. The KGF-2 cDNA was 4.1 kb, consistent with the size of the mRNA of 4.2 kb.

EXAMPLE 10

Keratinocyte Proliferation Assays

Dermal keratinocytes are cells in the epidermis of the skin. The growth and spreading of keratinocytes in the skin is an important process in wound healing. A proliferation assay of keratinocyte is therefore a valuable indicator of protein activities in stimulating keratinocyte growth and consequently, wound healing.

Keratinocytes are, however, difficult to grow in vitro. Few keratinocyte cell lines exist. These cell lines have different cellular and genetic defects. In order to avoid complications of this assay by cellular defects such as loss of key growth factor receptors or dependence of key growth factors for growth, primary dermal keratinocytes are chosen for this assay. These primary keratinocytes are obtained from Clonetics, Inc. (San Diego, Calif.).

Keratinocyte proliferation assay with alamarBlue alamarBlue is a viable blue dye that is metabolized by the mitochondria when added to the culture media. The dye then turns red in tissue culture supernatants. The amounts of the red dye may be directly quantitated by reading difference in optical densities between 570 nm and 600 nm. This reading reflects cellular activities and cell number.

Normal primary dermal keratinocytes (CC-0255, NHEK-Neo pooled) are purchased from Clonetics, Inc. These cells are passage 2. Keratinocytes are grown in complete keratinocyte growth media (CC-3001, KGM; Clonetics, Inc.) until they reach 80% confluency. The cells are trypsinized according to the manufacturer's specification. Briefly, cells were washed twice with Hank's balanced salt solution. 2–3 ml of trypsin was added to cells for about 3–5 min at room temperature. Trypsin neutralization solution was added and cells were collected. Cells are spun at 600×g for 5 min at room temperature and plated into new flasks at 3,000 cells per square centimeter using pre-warmed media.

For the proliferation assay, plate 1,000–2,000 keratinocytes per well of the Corning flat bottom 96-well plates in complete media except for the outermost rows. Fill the outer wells with 200 µl of sterile water. This helps to keep temperature and moisture fluctuations of the wells to the minimum. Grow cells overnight at 37° C. with 5% $CO_2$. Wash cells twice with keratinocyte basal media (CC-3101, KBM, Clonetics, Inc.) and add 100 µl of KBM into each well. Incubate for 24 hours. Dilute growth factors in KBM in serial dilution and add 100 µl to each well. Use KGM as a positive control and KBM as a negative control. Six wells are used for each concentration point. Incubate for two to three days. At the end of incubation, wash cells once with KBM and add 100 µl of KBM with 10% v/v alamarBlue pre-mixed in the media. Incubate for 6 to 16 hours until media color starts to turn red in the KGM positive control. Measure O.D. 570 nm minus O.D. 600 nm by directly placing plates in the plate reader.

Results

Stimulation of Keratinocyte proliferation by KGF-2

Figure 21A:
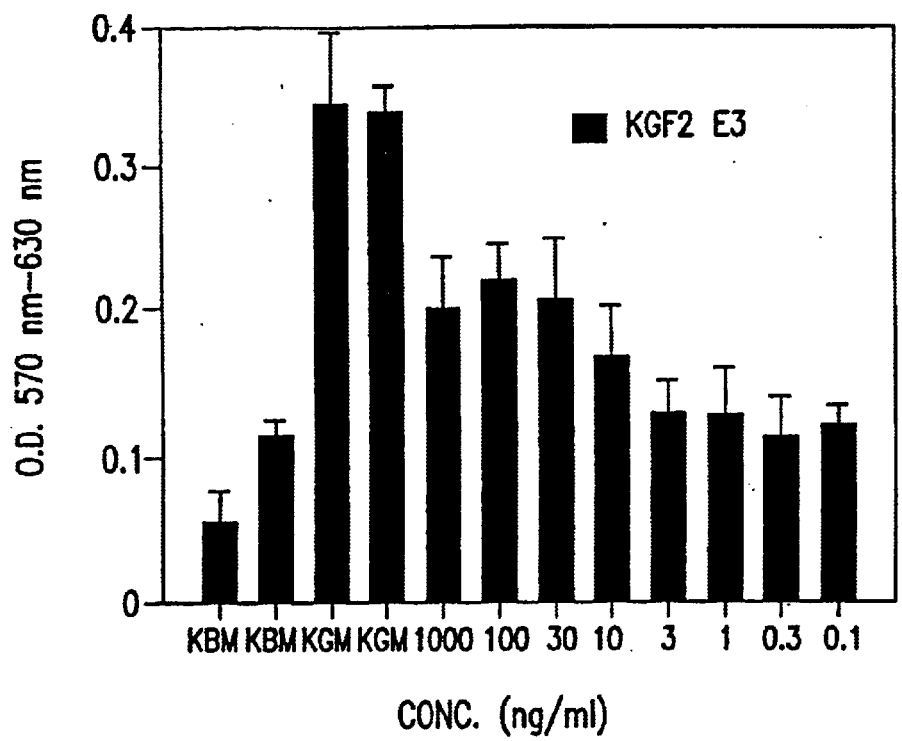
FIG. 21 (A) shows the stimulation of normal primary epidermal keratinocyte proliferation by KGF-2. (B) shows the stimulation of normal primary epidermal keratinocyte proliferation by KGF-2Δ33. (C) shows the stimulation of normal primary epidermal keratinocyte proliferation by KGF-2 Δ28. Human normal primary epidermal keratinocytes were incubated with various concentrations of KGF-2, KGF-2Δ33 or KGF-2Δ28 for thee days. For all three experiments alamarBlue was then added for 16 hr and the intensity of the red color converted from alamarBlue by the cells was measured by the difference between O.D. 570 nm and O.D. 600 nm. For each of the KGF-2 proteins a positive control with complete keratinocyte growth media (KGM), and a negative control with keratinocyte basal media (KBM) were included in the same assay plate.
Figure 21B:
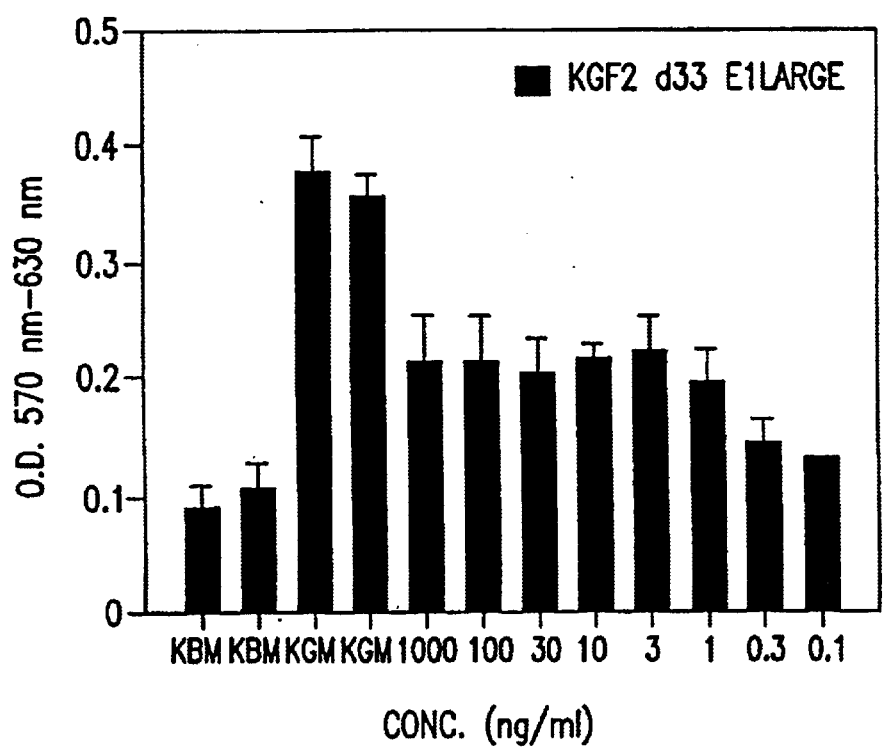
Figure 21C:
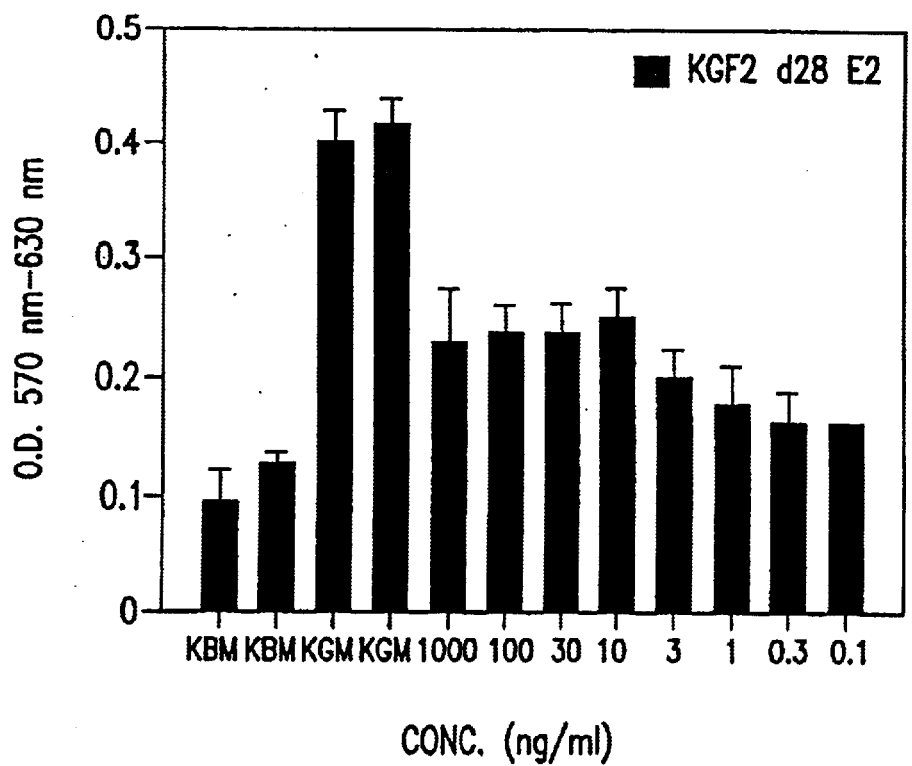

To demonstrate that KGF-2 (i.e., starting at amino acid Cys37 as described in Examples 7 and 8 above) and N-terminal deletion mutants KGF-2Δ33 and KGF-2Δ28 were active in stimulating epidermal keratinocyte growth, normal primary human epidermal keratinocytes were incubated with the E. coli-expressed and purfied KGF-2 protein (batch number E3)(SEQ ID NO:2), KGF-2Δ33 (batch number E1) and KGF-2Δ28 (batch number E2). The KGF-2 protein stimulated the growth of epidermal keratinocytes with an EC50 of approximately 5 ng/ml, equivalent to that of FGF7/KGF-1 (FIG. 21A). In contrast, other FGF's such as FGF-1 and FGF-2 did not stimulate the growth of primary keratinocytes. The EC50 for KGF-2Δ33 was 0.2 ng/ml and that for KGF-2Δ28 2 ng/ml (See FIGS. 21B and C). Thus, KGF-2 appeared to be as potent as FGF7/KGF in stimulating the proliferation of primary epidermal keratinocytes. However, KGF-2Δ33 is more potent in stimulating keratinocyte proliferation than the "Cys (37)" KGF-2 described in Examples 7 and 8 above and the KGF-2Δ28.

Scarring of wound tissues involves hyperproliferation of dermal fibroblasts. To determine whether the stimulatory effects of KGF-2 was specific for keratinocytes but not for fibroblasts, mouse Balb.c.3T3 fibroblsts and human lung fibroblasts were tested. Niether types of fibroblasts responded to KGF-2 in proliferation assays. Therefore, KGF-2 appeared to be a mitogen specific for epidermal keratinocytes but not mesenchymal cells such as fibroblasts. This suggested that the likelyhood of KGF-2 causing scarring of the wound tissues was low.

EXAMPLE 11

A. Mitogenic Effects of KGF-2 on Cells Transfected with Specific FGF Receptors

To determine which FGF receptor isoform(s) mediate the proliferative effects of KGF-2, the effects of KGF-2 on cells expressing specific PGF receptor isoforms were tested according to the method described by Santos-Ocampo et al. J. Biol. Chem. 271:1726–1731 (1996). FGF7/KGF was known to induce mitogenesis of epithelial cells by binding to and specifically activating the FGFR2iiib form (Miki et al. Science 251:72–75 (1991)). Therefore, the proliferative effects of KGF-2 in mitogensis assays were tested using cells expressing one of the following FGF receptor isoforms: FGFR1iiib, FGFR2iiib, FGFR3iiib, and FGFR4.

Mitogensis assay of cells expressing FGF receptors

Thymidine incorporation of BaF3 cells expressing specific FGF receptors were performed as described by Santos-Ocampo et al. J. Biol. Che. 271:1726–1731 (1996). Briefly, BaF3 cells expressing specific FGF receptors were washed and resuspended in Dubeco's modified Eagle's medium, 10% neonatal bovine serum, L-glutanime. Approximately 22,500 cells were plated per well in a 96-well assay plate in media containing 2 µg/ml Heparin. Test reagents were added to each well for a total volume of 200 µl per well. The cells were incubated for 2 days at 37° C. To each wll, 1 µCi of $^3$H-thymidine was then added in a volume of 50 µl. Cells were harvested after 4–5 hours by filteration through glass fiber paper. Incorporated $^3$H-thyridine was counted on a Wallac beta plate scintillaion counter.

Results

The results revealed that KGF-2 protein (Thr (36)-Ser (208) of FIG. 1 (SEQ ID NO:2) with a N-terminal Met added thereto) strongly stimulated the proliferation of Baf3 cells expressing the KGF receptor, FGFR2iiib isoform, as indicated by $^3$H-thymidine incorporation (FIG. 22A). Interestingly, a slight stimulatory effect of KGF-2 on the proliferation of Baf3 cells expressing the FGFR1iiib isoform was observed. KGF-2 did not have any effects on cells expressing the FGFR3iiib or the FGFR4 forms of the receptor.

FGF7/KGF stimulated the proliferation of cells expressing the KGF receptor, FGFR2iiib but not FGFR1iiib isoform. The difference between KGF-2 and FGF7/KGF was intriguing. In the control experiments, aFGF stimulated its receptors, FGFR1iiib and iiic and bFGF stimulated its receptor FGFR2iiic. Thus, these results suggested that KGF-2 binds to FGFR2iiib isoform and stimulates mitogenesis. In contrast to FGF7/KGF, KGF-2 also binds FGFR1iiib isoform and stimulates mitogenesis.

B. Mitogenic Effects of KGF-2Δ33 on Cells Transfected with Specific FGF Receptors As demonstrated above FGFs or KGF-1 and -2 both bind to and activate the FGF 2iiib receptor (FGFR 2iiib). The proliferative effects of KGF-2Δ33 in mitogensis assays were tested using cells expressing one of the following FGF receptor isoforms: FGFR2iiib or FGFR2iiic (the 2iiic receptor-transfected cells are included as a negative control).

The experiments were performed as above in part A of this example. Briefly, BaF3 cells were grown in RPMI containing 10% bovine calf serum (BCS—not fetal serum), 10% conditioned medium from cultures of WEHI3 cells (grown in RPMI containing 5% BCS), 50 nM β-mercaptoethanol, L-Glu (2% of a 100×stock) and pen/strep (1% of a 100× stock).

For the assay, BaF3 cells were rinsed twice in RPMI medium containing 10% BCS and 1 µg/ml heparin. BaF3 cells (22,000/well) were plated in a 96-well plate in 150 µl of RPMI medium containing 10% BCS and 1 μg/ml heparin. Acidic FGF, basic FGF, KGF-1 (HG15400) or KGF-2 proteins (HG03400, 03401, 03410 or 03411) were added at concentrations from approximately 0 to 10 nM. The cells were incubated in a final volume of 200 μl for 48 hours at 37° C. All assays were done in triplicate. Tritiated thymidine (0.5 μCi) was added to each well for 4 hours at 37° C. and the cells were then harvested by filtration through a glass fiber filter. The total amount of radioactivity incorporated was then determined by liquid scintillation counting. The following positive controls were used: basic FGF and acidic FGF for FGFR2iiic cells; acidic FGF and KGF-1 for FGFR2iiib cells. The following negative controls were used: Basal medium (RPMI medium containing 10% BCS and 1 μg/ml heparin).

Results

Figure 22B:
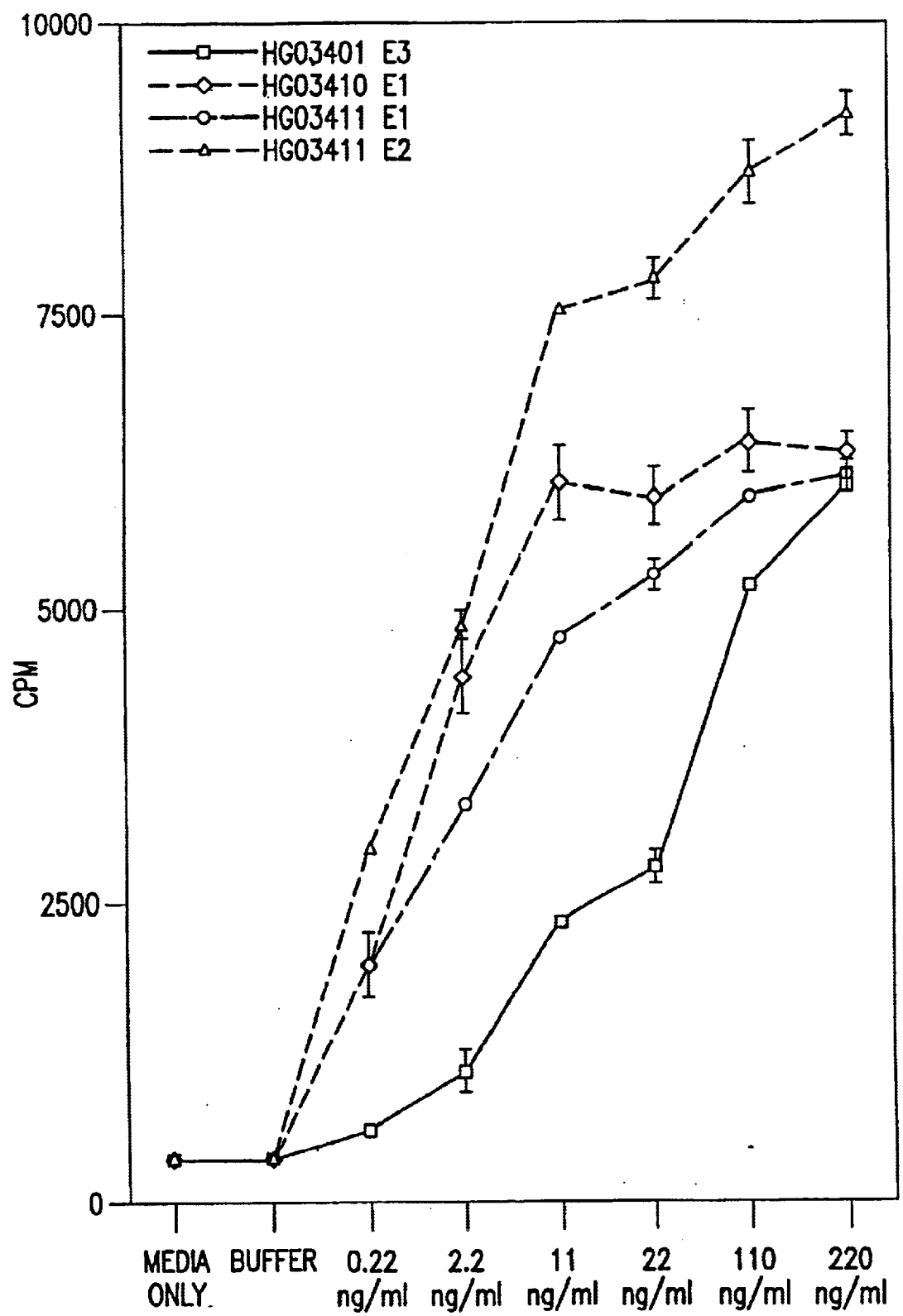
Figure 22C:
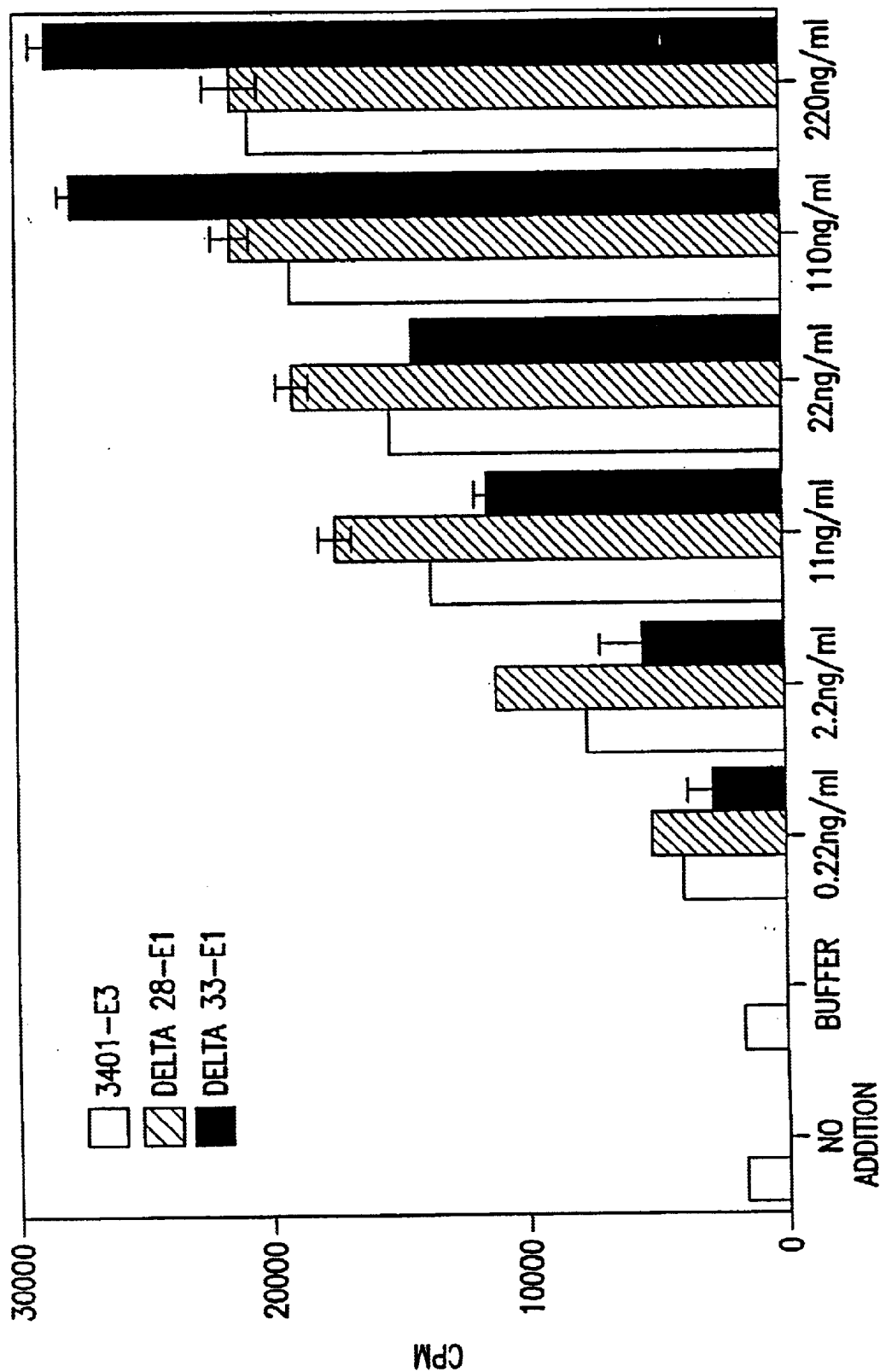

The results revealed that KGF-2 (Thr (36)-Ser (208) with N-terminal Met added), KGF-2Δ33 and KGF-2Δ28 proteins strongly stimulated the proliferation of BaF3 cells expressing the KGF receptor, FGFR2iiib isoform, as indicated by $^3$H-thymidine incorporation (FIGS. 22A-C). The KGF-2 proteins did not have any effects on cells expressing the FGFR2iiic forms of the receptor. These results suggested that KGF-2 proteins bind to FGFR2iiib isoform and stimulates mitogenesis. In addition, it appears that KGF-2Δ33 was able to stimulate the proliferation of the BaF3 cells better than the KGF-2 (Thr(36)-Ser (208)).

EXAMPLE 12

A. Construction of *E. coli* Optimized Full Length KGF-2

In order to increase expression levels of full length KGF-2 in an *E. coli* expression system, the codons of the amino terminal portion of the gene were optimized to highly used *E. coli* codons. For the synthesis of the optimized region of KGF-2, a series of six oligonucleotides were synthesized: numbers 1–6 (sequences set forth below). These overlapping oligos were used in a PCR reaction for seven rounds at the following conditions:

| Denaturation | 95 degrees | 20 seconds |
| Annealing | 58 degrees | 20 seconds |
| Extension | 72 degrees | 60 seconds |

A second PCR reaction was set up using 1 μl of the first PCR reaction with KFG-2 sythetic primer 6 as the 3' primer and KGF-2 synthetic 5' BamHI as the 5' primer using the same conditions as described above for 25 cycles. The product produced by this final reaction was restricted with AvaII and BamHI. The KGF-2 construct of Example 1 was restricted with AvaII and HindIII and the fragment was isolated. These two fragments were cloned into pQE-9 restricted with BamHI and HindIII in a three fragment ligation.

Primers used for constructing the optimized synthetic KGF-2 1/208:

```
KGF-2 Synthetic Primer 1:
ATGTGGAAATGGATACTGACCCACTGCGCTTCTGCT (SEQ ID NO:31)
TTCCCGCACCTGCCGGGTTGCTGCTGCTGCTGCTGC
TGCTGCTGTTC KGF-2 Synthetic Primer 2:
CCGGAGAAACCATGTCCTGACCCAGAGCCTGGCAGG (SEQ ID NO:32)
TAACCGGAACAGAAGAAACCAGGAACAGCAGCAGGA
AGCAGCAGCA KGF-2 Synthetic Primer 3:
GGGTCAGGACATGGTTTCTCCGGAAGCTACCAACTC (SEQ ID NO:33)
TTCTTCTTCTTCTTTCTCTTCTCCGTCTTCTGCTGG
TCGTCACG KGF-2 Synthetic Primer 4:
GGTGAAAGAGAACAGTTTACGCCAACGAACGTCACC (SEQ ID NO:34)
CTGCAGGTGGTTGTAAGAACGAACGTGACGACCAGC
AGAAGACGG KGF-2 Synthetic Primer 5:
CGTTGGCGTAAACTGTTCTCTTTCACCAAATACTTC (SEQ ID NO:35)
CTGAAAATCGAAAAAAACGGTAAAGTTTCTGGGACC
AAA KGF-2 Synthetic Primer 6:
TTTGGTCCCAGAAACTTTACCGTTTTTTTCGATTTT (SEQ ID NO:36)
CAG KGF-2 Synthetic 5' BamHI
AAAGGATCCATGTGGAAATGGATACTGACCCACTGC (SEQ ID NO:37)
```

The resulting clone is shown in FIG. 23 (SEQ ID NOS: 38 and 39).

B. Construction of *E. coli* Optimized Mature KGF-2

In order to further increase expression levels of the mature form of KGF-2 in an *E. coli* expression system, the codons of the amino terminal portion of the gene were optimized to highly used *E. coli* codons. To correspond with the mature form of KGF-1, a truncated form of KGF-2 was constructed starting at threonine 36. *E. coli* synthetic KGF-2 from Example 12 A was used as a template in a PCR reaction using BspHI 5' KGF-2 as the 5' primer (sequence given below) and HindIII 3' KGF-2 as the 3' primer (sequence given below). Amplification was performed using standard conditions as given above in Example 12 A for 25 cycles. The resulting product was restricted with BspHI and HindII and cloned into the *E. coli* expression vector pQE60 digested with NcoI and HindIII.

```
BspHI 5'KGF-2 Primer:
TTTCATGACTTGTCAAGCTCTGGGTCAAGATATGGT (SEQ ID NO:40)
TC HindIII 3' KGF-2 Primer:
GCCCAAGCTTCCACAAACGTTGCCTTCC           (SEQ ID NO:41)
```

The resulting clone is shown in FIG. 24A (SEQ ID NO:42 and 43).

C. Construction of an Alternate *E. coli* Optimized Mature KGF 2

In order to further increase expression levels of the mature form of KGF-2 in an *E. coli* expression system, the codons of 53 amino acids at the amino terminal portion of the *E. coli* optimized gene were changed to alternate highly used *E. coli* codons. For the synthesis of the optimized region of KGF-2, a series of six oligonucleotides were synthesized: numbers 18062, 18061, 18058, 18064, 18059, and 18063 (sequences set forth below). These overlapping oligos were used in a PCR reaction for seven rounds at the following conditions:

| Denaturation | 95 degrees | 20 seconds |
| Annealing | 58 degrees | 20 seconds |
| Extension | 72 degrees | 60 seconds |

Following the seven rounds of synthesis, a 5' primer to this region, 18169 and a 3' primer to this entire region, 18060, were added to a PCR reaction, containing 1 microliter from the initial reaction of the six oligonucleotides. This product was amplified for 30 rounds using the following conditions:

| Denaturation | 95 degrees | 20 seconds |
| Annealing | 55 degrees | 20 seconds |
| Extension | 72 degrees | 60 seconds |

A second PCR reaction was set up to amplify the 3' region of the gene using primers 18066 and 18065 under the same conditions as described above for 25 rounds. The resulting products were separated on an agarose gel. Gel slices containing the product were diluted in 10 mM Tris, 1mM EDTA, pH 7.5 One microliter each from each of diluted gel slices were used in an additional PCR reaction using primer 18169 as the 5' primer, and primer 18065 as the 3' primer. The product was amplified for 25 cycles using the same conditions as above. The product produced by this final reaction was and restricted with Eco R1 and HindIII, and cloned into pQE60, which was also cut with Eco R1 and HindIII (pQE6 now).

Sequences of the 5' Synthetic Primers

```
18169 KGF2 5'EcoRI/RBS:
TCAGTGAATTCATTAAAGAGGAGAAATTAATCATGA [SEQ ID NO:44]
CTTGCCAGG

18062 KGF2 synth new R1 sense:
TCATGACTTGCCAGGCACTGGGTCAAGACATGGTTT [SEQ ID NO:45]
CCCCGCAAGCTA 18061 KGF2 synth R2 sense:
GCTTCAGCAGCCCATCTAGCGCGCAGGTCGTCACGT [SEQ ID NO:46]
TCGCTCTTACAACC 18058 KGF2 Synth R3 sense:
GTTCGTTGGCGCAAACTGTTCAGCTTTACCAAGTAC [SEQ ID NO:47]
TTCCTGAAAATC 18066 KGF 2 20 bp Ava II sense:
TCGAAAAAAACGGTAAAGTTTCTGGGAC         [SEQ ID NO:48]

18064 KGF2 synth F1 antisense:
GATGGGCTGCTGAAGCTAGAGCTGGAGCTGTTGGTA [SEQ ID NO:49]
GCTTCCGGGAA 18059 KGF2 Synth F2 antisense:
AACAGTTTGCGCCAACGAACATCACCCTGTAAGTGG [SEQ ID NO:50]
TTGTAAGAG 18063 KGF2 Synth F3 antisense:
TTCTTGGTCCCAGAAACTTTACCGTTTTTTTCGATT [SEQ ID NO:51]
TTCAGGAAGTA 18060 KGF 2 Ava II antisense:
TTCTTGGTCCCAGAAACTTTACCG             [SEQ ID NO:52]

18065 KGF2 HindIII 3' Stop:
AGATCAGGCTTCTATTATTATGAGTGTACCACCATT [SEQ ID NO:53]
GGAAGAAAG
```

The sequence of the synthetic KGF-2 gene and it corresponding amino acid is shown in FIG. 24B (SEQ ID NO: 54 and 55)

EXAMPLE 13
Construction of KGF-2 Deletion Mutants

Deletion mutants were constructed from the 5' terminus and 3' terminus of KGF-2 gene using the optimized KGF-2 construct from Example 12 A as a template. The deletions were selected based on regions of the gene that might negatively affect expression in E. coli. For the 5' deletion the primers listed below were used as the 5' primer. These primers contain the indicated restriction site and an ATG to code for the initiator methionine. The KGF-2 (FGF-12) 208 amino acid 3' HindIII primer was used for the 3' primer. PCR amplification for 25 rounds was performed using standard conditions as set forth in Example 12. The products for the KGF-2 36aa/208aa deletion mutant were restricted BspHI for the 5' site and HindIII for the 3' site and cloned into the pQE60 which has bee digested with BspHI and HindIII. All other products were restricted with NcoI for the 5' restriction enzyme and HindIII for the 3' site, and cloned into the pQE60 which had been digested with NcoI and HindIII. For KGF.2 (FGF-12), 36aa/153aa and 128aa 3' HindIII was used as the 3' primer with FGF-12 36aa/208aa as the 5' primer. For FGF-12 62aa/153aa, 128aa 3' HindIII was used as the 3' primer with FGF-12 62aa/208aa as the 5' primer. The nomenclature of the resulting clones indicates the first and last amino acid of the polypeptide that results from the deletion. For example, KGF-2 36aa/153aa indicates that the first amino acid of the deletion mutant is amino acid 36 and the last amino acid is amino acid 153 of KGF-2. Further, as indicated in FIGS. 25-33, each mutant has N-terminal Met added thereto.

Sequences of the Deletion Primers

```
FGF12 36aa/208aa:
5'BsphI GGACCCTCATGACCTGCCAGGCTCTGGG [SEQ ID NO:56]
TCAGGAC FGF12 63aa/208aa:
5'NcoI GGACAGCCATGGCTGGTCGTCACGTTCG [SEQ ID NO:57]

FGF12 77aa/208aa:
5'NcoI GGACAGCCATGGTTCGTTGGCGTAAACTG [SEQ ID NO:58]

FGF12 93aa/208aa:
5'NcoI GGACCCCCATGGAGAACTGCCCGTAGAGC [SEQ ID NO:59]

FGF12 104aa/208aa:
5'NcoI GGACCCCCATGGAGAACTGCCCGTAGAGC [SEQ ID NO:60]

FGF12 123aa/208aa:
5'NcoI GGACCCCCATGGTCAAAGCCATTAACAGC [SEQ ID NO:61]
AAC

FGF12 138aa/208aa:
5'NcoI GGACCCCCATGGGGAAACTCTATGGCTCA [SEQ ID NO:62]
AAAG

FGF12 3'HindIII: (Used for all above
deletion clones)
CTGCCCAAGCTTATTATGAGTGTACCACCATTGGA [SEQ ID NO:63]
AG FGF12 36aa/153aa:
5'BspbI (as above)
3'HindIII CTGCCCAAGCTTATTACTTCAGCTTA [SEQ ID NO:64]
CAGTCATTGT FGFl2 63aa/153aa:
5'NcoI and 3'HindIII, as above
```

The sequences for the resulting deletion mutations are set forth in FIGS. 25–33. [SEQ ID NOS:65–82]

EXAMPLE 14
Construction of Cysteine Mutants of KGF-2

Construction of C-37 mutation primers 5457 5' BsphI and 5258 173aa 3' HindIII were used to amplify the KGF-2 (FGF-12) template from Example 12 A. Primer 5457 5' BsphI changes cysteine 37 to a serine. Amplification was done using the standard conditions outlined above in Example 12 A for 25 cycles. The resulting product was restricted with BsphI and HindIII and cloned into E. coli expression vector pQE60, digested with BsphI and HindIII. (FIG. 34) [SEQ ID NO:83]

For mutation of Cysteine 106 to serine, two PCR reactions were set up for oligonucleotide site directed mutagenesis of this cysteine. In one reaction, 5453 BsphI was used as the 5' primer, and 5455 was used as the 3' primer in the reaction. In a second reaction, 5456 was used as the 5' primer, and 5258 HindIII was used as the 3' primer. The reactions were amplified for 25 rounds under standard conditions as set forth in Example 12. One microliter from each of these PCR reactions was used as template in a subsequent reaction using, as a 5' primer, 5453 BspHI, and as a 3' primer, 5258 HindIII. Amplification for 25 rounds was performed using standard conditions as set forth in Example 12. The resulting product was restricted with BspHI and HindIII and cloned into the E. coli expression vector pQE60, which was restricted with NcoI and HindIII.

Two PCR reactions were required to make the C-37/C-106 mutant. Primers 5457 Bsph1 and 5455 were used to create the 5' region of the mutant containing cysteine 37 to serine substitution, and primer 5456 and 5258 HindIII were used to create the 3' region of the mutant containing cysteine 106 to serine substitution. In the second reaction, the 5457 BsphI primer was used as the 5' primer and the 5258 HindIII primer was used as the 3' primer to create the C-37/C-106 mutant using 1 µl from each of the initial reactions together as the template. This PCR product was restricted with BsphI and HindIII, and cloned into pQE60 that had been restricted with NcoI and HindIII. The resulting clone is shown in FIG. 35 (SEQ ID NO:84)

Sequences of the Cysteine Mutant Primers:

```
5457 BspHI:
GGACCCTCATGACCTCTCAGGCTCTGGGT          (SEQ ID NO:85)

5456:
AAGGAGAACTCTCCGTACAGC                  (SEQ ID NO:86)

5455:
GCTGTACGGTCTGTTCTCCTT                  (SEQ ID NO:87)

5453 BspHI:
GGACCCTCATGACCTGCCAGGCTCTGGGTCAGGAC    (SEQ ID NO:88)

5258 HindIII:
CTGCCCAAGCTTATTATGAGTGTACCACCATTGGA    (SEQ ID NO:89)
AG
```

EXAMPLE 15

Production and Purification of KGF-2 (FGF-12)

The DNA sequence encoding the optimized mature protein described in Example 12 B (i.e., amino acids T36 through S208 of KGF-2) was cloned into plasmid pQE-9 (Qiagen). E. coli (M15/rep4; Qiagen) were grown to stationary phase overnight at 37° C. in LB containing 100 µg/ml Ampicillin and 25 µg/ml Kanamycin. This culture was used to innoculate fresh LB media containing containing 100 µg/ml Ampicillin and 25 µg/ml Kanamycin at a dilution of 1:50. The cells were grown at 37° C. to an O.D.$_{595}$ of 0.7, induced by the addition of isopropyl 1-thio-b-D-galactopyranoside (IPTG) to a final concentration of 1 mM. After 3–4 hours, the cells were harvested by centrifugation, and resuspended in a buffer containing 60 mM NaPO$_4$ and 360 mM NaCl at a ratio of 5 volumes of buffer: 1 volume of cell paste. After disruption in a Mautin Gaulin, the extract was adjusted to pH to 8.0 by the addition of NaOH and clarified by centrifugation. The clarified soluble extract was applied to a Poros HS-50 column (2.0×10.0 cm; PerSeptive Biosystems, Inc.) and bound proteins step-eluted with 50 mM NaPO$_4$ pH 8.0 containing 0.5 M, 1.0 M and 1.5 M NaCl. The KGF-2 eluted in the 1.5 M salt fraction which was then diluted five-fold with 50 mM NaPO$_4$ pH 6.5 to a final salt concentration of 300 mM. This KGF-2 containing fraction was then passed sequentially over a Poros HQ-20 column (2.0×7.0 cm; PerSeptive Biosystems, Inc.) and then bound to a Poros CM-20 column (2.0×9.0 cm; PerSeptive Biosystems, Inc.). KGF-2 (FGF-12)-containing fractions that eluted at about 500 mM to about 750 mM NaCl were pooled, diluted and re-applied to an CM-20 column to concentrate. Finally, the protein was seperated on a gel filtration column (S-75; Pharmacia) in 40 mM NaOAC pH6.5; 150 mM NaCl (Batch E-5) Alternatively, the gel filtration column was run in Phosphate Buffered Saline (PBS, Batch E-4). KGF-2 containing fractions were pooled and protein concentration determined by Bio-Rad Protein Assay. Proteins were judged to be >90% pure by SDS-PAGE. Finally, endotoxin levels determined by Limulus Amebocyte Lysate Assay (Cape Cod Associates) were found to be ≦1 Eu/mg. Proteins prepared in this way were able to bind heparin which is a hallmark of FGF family members.

EXAMPLE 16

A. Construction of N-terminal Deletion Mutant KGF-2Δ33

To increase the level of expression of KGF2 in E. coli, and to enhance the solubilty and stability properties of E. coli expressed KGF2, a deletion variant KGF-2Δ33 (KGF-2 aa 69–208) (SEQ ID NO:96) which removes the first 68 amino acids of the pre-processed KGF2 was generated. The rationale for creating this deletion variant was based on the following observations. Firstly, mature KGF2 (KGF-2 aa 36–208) contains an uneven number (three) of cysteine residues which can lead to aggregation due to intra-molecular disulphide bridge formation. The KGFΔ33 deletion variant contains only two cysteine residues, which reduces the potential for intra-molecular disulphide bridge formation and subsequent aggregation. A decrease in aggregation should lead to an increase in the yield of active KGF2 protein. Secondly, the KGFΔ33 deletion variant removes a poly-serine stretch which is not present in KGF-1 and does not appear to be important for activity, but may hinder expression of the protein in E. coli. Thus, removal of the poly-serine stretch may increase expression levels of active KGF-2 protein. Thirdly, expression of KGFΔ33 in E. coli, results in natural cleavage of KGF-2 between residues 68 and 69. Thus, it is anticipated that KGF2 Δ33 will be processed efficiently and will be stable in E. coli.

Construction of KGF2Δ33 in pQE6

To permit Polymerase Chain Reaction directed amplification and sub-cloning of KGF2Δ33 into the E. coli protein expression vector, pQE6, two oligonucleotide primers (5952 and 19138) complementary to the desired region of KGF2 were synthesized with the following base sequence.

```
Primer 5952:
5' GCGGCACATGTCTTACAACCACCTGCAGGGTG 3'     (SEQ ID
                                            NO:91)

Primer 19138:
5' GGGCCCAAGCTTATGAGTGTACCACCAT 3'          (SEQ ID
                                            NO:92)
```

In the case of the N-terminal primer (5952), an AflIII restriction site was incorporated, while in the case of the C-terminal primer (19138) a HindIII restriction site was incorporated. Primer 5952 also contains an ATG sequence adjacent and in frame with the KGF2 coding region to allow translation of the cloned fragment in E. coli, while primer 19138 contains two stop codons (preferentially utilized in E. coli) adjacent and in frame with the KGF2 coding region which ensures correct translational termination in E. coli.

The Polymerase Chain Reaction was performed using standard conditions well known to those skilled in the art and the nucleotide sequence for the mature KGF-2 (aa 36–208) (constructed in Example 12C) as template. The resulting amplicon was restriction digested with AflIII and HindIII and subcloned into NcoI/HindIII digested pQE6 protein expression vector.

Construction of KGF2Δ33 in pHE1

To permit Polymerase Chain Reaction directed amplification and subcloning of KGF2Δ33 into the *E. coli* expression vector, pHE1, two oligonucleotide primers (6153 and 6150) corresponding to the desired region of KGF2 were synthesized with the following base sequence.

```
Primer 6153:
5' CCGGCGGATCCCATATGTCTTACAACCACCTGCAGG 3'  (SEQ ID
                                             NO:93)

Primer 6150:
5' CCGGCGGTACCTTATTATGAGTGTACCACCTTGG 3'    (SEQ ID
                                             NO:94)
```

In the case of the N-terminal primer (6153), an NdeI restriction site was incorporated, while in the case of the C-terminal primer (6150) an Asp718 restriction site was incorporated. Primer 6153 also contains an ATG sequence adjacent and in frame with the KGF2 coding region to allow translation of the cloned fragment in *E. coli*, while primer 6150 contains two stop codons (preferentially utilized in *E. coli*) adjacent and in frame with the KGF2 coding region which ensures correct translational termination in *E. coli*.

The Polymerase Chain Reaction was performed using standard conditions well known to those skilled in the art and the nucleotide sequence for the mature KGF-2 (aa 36–208) (constructed in Example 12C) as template. The resulting amplicon was restriction digested with NdeI and Asp718 and subcloned into NdeI/Asp718 digested pHE1 protein expression vector.

```
Nucleotide sequence of KGF2 Δ33:
ATGTCTTACAACCACCTGCAGGGTGACGTTCGTTGG (SEQ ID NO:95)
CGTAAACTGTTCTCTTTCACCAAATACTTCCTGAAA
ATCGAAAA
AAACGGTAAAGTTTCTGGGACCAAGAAGGAGAACTG
CCCGTACAGCATCCTGGAGATAACATCAGTAGAAAT
CGGAGTTG
TTGCCGTCAAAGCCATTAACAGCAACTATTACTTAG
CCATGAACAAGAAGGGGAAACTCTATGGCTCAAAAG
AATTTAAC
AATGACTGTAAGCTGAAGGAGAGGATAGAGGAAAAT
GGATACAATACCTATGCATCATTTAACTGGCAGCAT
AATGGGAG
GCAAATGTATGTGGCATTGAATGGAAAAGGAGCTCC
AAGGAGAGGACAGAAAACACGAAGGAAAAACACCTC
TGCTCACTTTCTTCCAATGGTGGTACACTCATAA Amino Acid sequence of KGF Δ33:
MSYNHLQGDVRWRKLFSFTKYFLKIEKNGKVSGTKK (SEQ ID NO:96)
ENCPYSILEITSVEIGVVAVKAINSNYYLAMNKKGK
LYGSKEFNNDCKLKERIEENGYNTYASFNWQHNGRQ
MYVALNGKGAPRRGQKTRRKNTSAHFLPMVVHS
```

B. Construction of an Optimized KGF-2Δ33

In order to increase the expression levels of KGF2Δ33 in *E. coli*, the codons of the complete gene were optimized to match those most highly used in *E. coli*. As the template utilised to generate the KGF2Δ33 was codon optimized within the N-terminal region, the C-terminal amino acids (84–208) required optimization.

Firstly, amino acids 172–208 were codon optimized to generate KGF2Δ33(s172–208). This was achieved by an overlapping PCR strategy. Oligonucleotides PM07 and PM08 (corresponding to amino acids 172–208) were combined and annealed together by heating them to 70° C. and allowing them to cool to 37° C. The annealed oligonucleotides were then utilized as template for a standard PCR reaction which was directed by primers PM09 and PM10. In a separate PCR reaction following standard conditions well known to those skilled in the art and using KGF2Δ33 as template, oligonucleotides PM05 (which overlaps with the Pst1 site within coding region of KGF2) and PM11 were used to amplify the region of KGF2 corresponding to amino acids 84–172. In a third PCR reaction, the product of the first PCR reaction (corresponding to codon optimized amino acids 172–208) and the product of the second PCR reaction (corresponding to codon non-optimized amino acids 84–172) were combined and used as template for a standard PCR reaction directed by oligonucleotides PM05 and PM10. The resulting amplicon was digested with Pst1/HindIII and sub-cloned into Pst1/HindIII digested pQE6KGF2Δ33, effectively substituting the corresponding non codon optimized region, and creating pQE6KGF2Δ33(s172–208).

To complete the codon optimization of KGF2, a synthetic gene codon optimized for the region of KGF2 corresponding to amino acids 84–172 was generated utilising overlapping oligonucleotides. Firstly, four oligonucleotides (PM31, PM32, PM33 and PM 34) were combined and seven cycles of the following PCR was performed: 94° C., 30 secs; 46.5° C., 30 secs; and 72° C., 30 secs.

A second PCR reaction directed by primers PM35 and PM36 was then performed following standard procedures, utilizing 1 μl of the first PCR reaction as template. The resulting codon optimized gene fragment was then digested with Pst1/Sal1 and subcloned into Pst1/Sal1 digested pQE6KGF2Δ33(s172–208) to create a fully optimized KGF2 encoding gene, pQE6KGF2Δ33s.

To create an alternative *E. coli* protein expression vector, KGF2Δ33s was PCR amplified utilising primers PM102 and PM130 on pQE6KGF2Δ33s. The resulting amplicon was digested with NdeI and EcoRV and subcloned into the pHE1 expression vector which had been digested with NdeI and Asp718 (blunt ended) to create pHE1Δ33s.

Oligonucleotide Sequences used in construction of codon optimized KGF2Δ33s:

```
PM05:
CAACCACCTGCAGGGTGACG               (SEQ ID NO:97)

PM07:
AACGGTCGACAAATGTATGTGGCACTGAACGGTA (SEQ ID NO:98)
AAGGTGCTCCACGTCGTGGTCAGAAAACCCGTCG
TAAAAACACC

PM08:
GGGCCCAAGCTTAAGAGTGTACCACCATTGGCAG (SEQ ID NO:99)
AAAGTGAGCAGAGGTGTTTTTACGACGGGTTTTC
TGACCACG

PM09:
GCCACATACATTTGTCGACCGTT            (SEQ ID NO:100)

PM10:
GGGCCCAAGCTTAAGAGTG                (SEQ ID NO:101)

PM11:
GCCACATACATTTGTCGACCGTT            (SEQ ID NO:102)

PM31:
CTGCAGGGTGACGTTCGTTGGCGTAAACTGTTCT (SEQ ID NO:103)
CCTTCACCAAATACTTCCTGAAAATCGAAAAAAC
GGTAAAGTTTCTGGTACCAAG
```

-continued

PM32:
AGCTTTAACAGCAACAACACCGATTTCAACGGAG (SEQ ID NO:104)
GTGATTTCCAGGATGGAGTACGGGCAGTTTTCTT
TCTTGGTACCAGAAACTTTACC

PM33:
GGTGTTGTTGCTGTTAAAGCTATCAACTCCAACT (SEQ ID NO:105)
ACTACCTGGCTATGAACAAGAAAGGTAAACTGTA
CGGTTCCAAAGAATTTAACAAC

PM34:
GTCGACCGTTGTGCTGCCAGTTGAAGGAAGCGTA (SEQ ID NO:106)
GGTGTTGTAACCGTTTTCTTCGATACGTTCTTTC
AGTTTACAGTCGTTGTTAAATTCTTTGGAACC

PM35:
GCGGCGTCGACCGTTGTGCTGCCAG (SEQ ID NO:107)

PM36:
GCGGCCTGCAGGGTGACGTTCGTTGG (SEQ ID NO:108)

PM102:
CCGGCGGATCCCATATGTCTTACAACCACCTGCA (SEQ ID NO:109)
GG

PM130:
CGCGCGATATCTTATTAAGAGTGTACCACCATTG (SEQ ID NO:110)

Nucleotide sequence of KGF2 Δ33(s172-208):
ATGTCTTACAACCACCTGCAGGGTGACGTTCGTT (SEQ ID NO:111)
GGCGTAAACTGTTCTCCTTCACCAAATACTTCCT
GAAAATCGAAAAAACGGTAAAGTTTCTGGTACC
AAGAAAGAAAACTGCCCGTACTCCATCCTGGAAA
TCACCTCCGTTGAAATCGGTGTTGTTGCTGTTAA
AGCTATCAACTCCAACTACTACCTGGCTATGAAC
AAGAAAGGTAAACTGTACGGTTCCAAAGAATTTA
ACAACGACTGTAAACTGAAAGAACGTATCGAAGA
AAACGGTTACAACACCTACGCTTCCTTCAACTGG
CAGCACAACGGTCGACAAATGTATGTGGCACTGA
ACGGTAAAGGTGCTCCACGTCGTGGTCAGAAAAC
CCGTCGTAAAAACACCTCTGCTCACTTTCTCGCC
AATGGTGGTACACTCTTAA Amino Acid Sequence of KGF2 Δ33(s172-208):
MSYNHLQGDVRWRKLFSFTKYFLKJEKNGKVSGT (SEQ ID NO:112)
KKENCPYSILEITSVEIGVVAVKAINSNYYLAMN
KKGKLYGSKEFNNDCKLKERIEENGYNTYASFNW
QHGRQMYVALNGKGAPRGQKTRRKNTSAHFLPMV
VHS C. Construction of N-terminal Deletion Mutant KGF-24

To increase the level of expression of KGF2 in E. coli and to enhance the stability and solubility properties of E. coli expressed KGF2, a deletion variant KGF2Δ4 (amino acids 39–208) which removes the first 38 amino acids of pre-processed KGF2 was constructed, including the cysteine at position 37. As the resulting KGF2 deletion molecule contains an even number of cysteines, problems due to aggregation caused by intra-molecular disulphide bridge formation should be reduced, resulting in an enhanced level of expresssion of active protein.

To permit Polymerase Chain Reaction directed amplification and sub-cloning of KGF2Δ4 into the E. coli protein expression vector, pQE6, two oligonucleotide primers (PM61 and 19138) were synthesized with the following base sequence.

PM61:
CGCGGCCATGGCTCTGGGTCAGGACATG (SEQ ID NO:113)

19138:
GGGCCCAAGCTTATGAGTGTACCACCAT (SEQ ID NO:114)

In the case of the N-terminal primer (PM61), an NcoI restriction site was incorporated, while in the case of the C-terminal primer (19138) a HindIII restriction site was incorporated. PM61 also contains an ATG sequence adjacent and in frame with the KGF2 coding region to allow translation of the cloned fragment in E. coli, while 19138 contains a stop codon (preferentially utilized in E. coli) adjacent to and in frame with the KGF2 coding region which ensures correct translational termination in E. coli.

The Polymerase Chain Reaction was performed using standard conditions well known to those skilled in the art and the full length KGF2 (aa 36–208) as template (constructed in Example 12C). The resulting amplicon was restriction digested with NcoI and HindIII and subcloned into NcoI/HindIII digested pQE6 protein expression vector.

Nucleotide Sequence of KGF2 Δ4:
ATGGCTCTGGGTCAAGATATGGTTTCTCCGGAAG (SEQ ID NO:115)
CTACCAACTCTTCCTCTTCCTCTTTCTCTTCCCC
GTCTTCCGCTGG
TCGTCACGTTCGTTCTTACAACCACCTGCAGGGT
GACGTTCGTTGGCGTAAACTGTTCTCTTTCACCA
AATACTTCCTGA
AAATCGAAAAAACGGTAAAGTTTCTGGGACCAA
GAAGGAGAACTGCCCGTACAGCATCCTGGAGATA
ACATCAGTAGAA
ATCGGAGTTGTTGCCGTCAAAGCCATTAACAGCA
ACTATTACTTAGCCATGAACAAGAAGGGGAAACT
CTATGGCTCAAA
AGAATTTAACAATGACTGTAAGCTGAAGGAGAGG
ATAGAGGAAAATGGATACAATACCTATGCATCAT
TTAACTGGCAGC
ATAATGGGAGGCAAATGTATGTGGCATTGAATGG
AAAAGGAGCTCCAAGGAGAGGACAGAAAACACGA
AGGAAAAACACCTCTGCTCACTTTCTTCCAATGG
TGGTACACTCATAA Amino Acid Sequence of KGF2Δ4:
MALGQDMVSPEATNSSSSSFSSPSSAGRHVRSYN (SEQ ID NO:116)
HLQGDVRWRKLFSFTKYFLKIEKNGKVSGTKKEN
CPYSILEITSVEIGVVAVKAINSNYYLAMNKKGK
LYGSKEFNNDCKLKERIEENGYNTYASFNWQHNG
RQMYVALNGKGAPRRGQKTRRKNTSAHFLPMVVH
S

EXAMPLE 17

KGF-2Δ33 Stimulated Wound Healing in Normal Rat

To demonstrate that KGF-2Δ33 would accelerate the healing process, wound healing of excisional wounds were examined using the following model.

A dorsal 6 mm excisional wound is created on Sprague Dawley rats (n=5) with a Keyes skin punch. The wounds are left open and treated topically with various concentrations of KGF-2Δ33 (in 40 mM NaOAc and 150 mM NaCl, pH 6.5 buffer) and buffer (40 mM NaOAc and 150 mM NaCl, pH 6.5) for 4 days commencing on the day of wounding. Wounds are measured daily using a calibrated Jameson caliper. Wound size is expressed in square millimeters. On the final day wounds were measured and harvested for further analysis. Statistical analysis was done using an unpaired t test (mean±SE). Evaluation parameters include percent wound closure, histological score (1–3 minimal cell accumulation, no granulation; 4–6 immature granulation, inflammatory cells, capillaries; 7–9 granulation tissue, cells, fibroblasts, new epithelium 10–12 mature dermis with fibroblasts, collagen, epithelium), re-epithelialization and immunohistochemistry.

Figure 36:
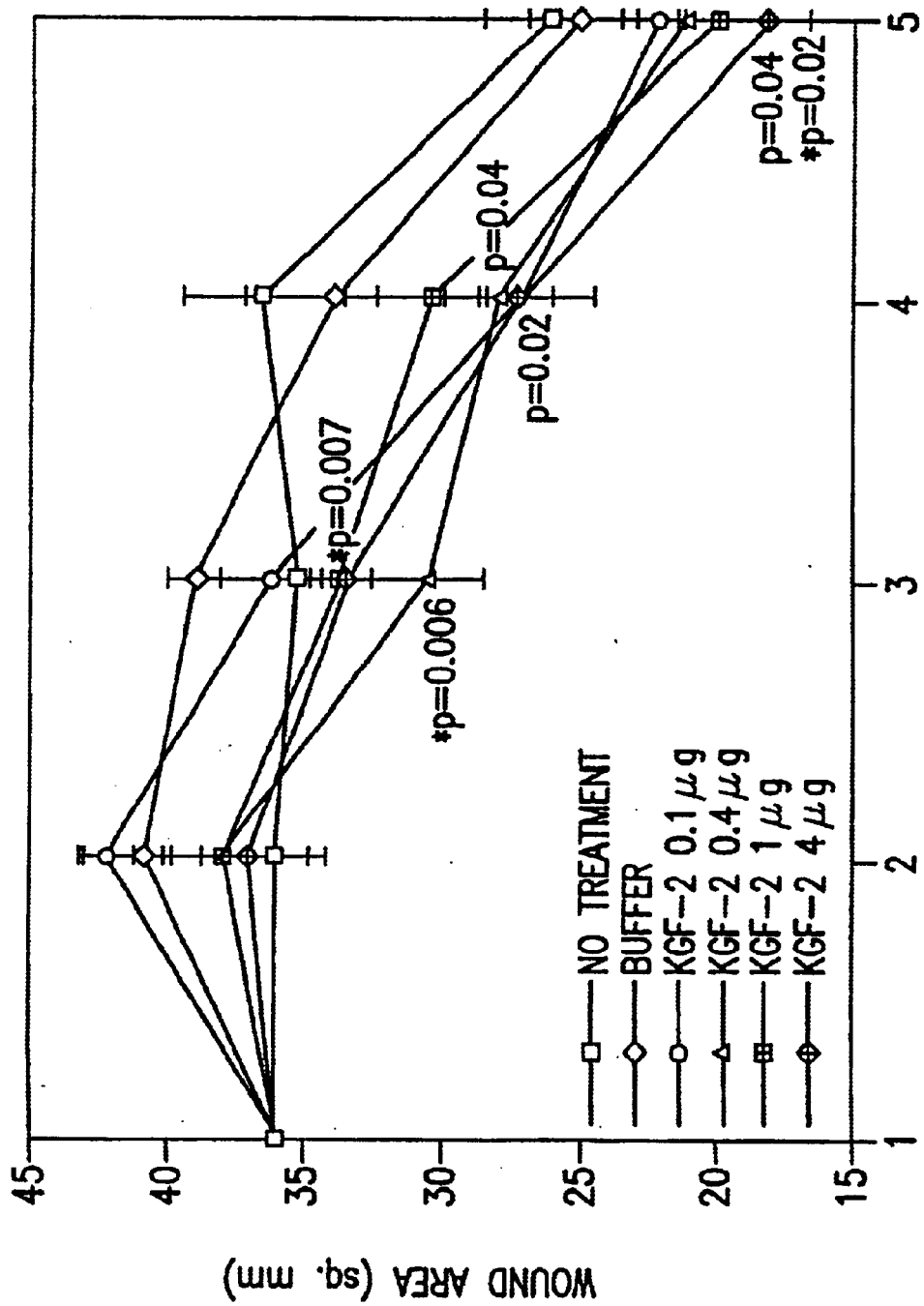
FIG. 36 shows the evaluation of KGF-2Δ33 effects on wound healing in male SD rats (n=5). Animals received 6 mm dorsal wounds and were treated with various concentrations buffer, or KGF-2Δ33 for 4 consecutive days. Wounds were measured daily using a calibrated Jameson caliper. Statistical analysis was done using an unpaired t-test.(Mean+/−SE) *Compared with buffer.

At three days postwounding, treatment with KGF-2Δ33 displayed a decrease in wound size (30.4 mm$^2$ at 4 μg, p=0.006, 33.6 mm$^2$ at 1 μg, p=0.0007) when compared to the buffer control of 38.9 mm$^2$. At day four postwounding, treatment with KGF-2Δ33 displayed a decrease in wound size (27.2 mm$^2$ at 0.1 μg p=0.02, 27.9 mm$^2$ at 0.4 μg p=0.04) when compared to buffer control of 33.8 mm$^2$. At day five postwounding, treatment with KGF-2Δ33 displayed a decrease in wound size (18.1) mm² at 4 μg p=0.02 when compared to buffer control of 25.1 mm². See FIG. 36.

Following wound harvest on day 5, additional parameters were evaluated. KGF-2Δ33 displayed an increase in the percentage of wound closure at 4 μg (71.2%, p=0.02) when compared to buffer control 60.2%. Administration of KGF-2Δ33 also results in an improvement in histological score at 1 and 4 μg (8.4 at 1 μg p=0.005, 8.5 at 4 μg p=0.04) relative to buffer control of 6.4. Re-epithelialization was also improved at 1 and 4 μg KGF-2Δ33 (1389 μm at 1 μg p=0.007, 1220 μm at 4 μg p=0.02) relative to the buffer control of 923 μm. See FIG. 37.

This study demonstrates that daily treatment with KGF-2Δ33 accelerates the rate of wound healing in normal animals as shown by a decrease in the gross wound area. In addition, the histological evaluation of wound samples and assessment of re-epithelialization also show that KGF-2Δ33 improves the rate of healing in this normal rat model.

EXAMPLE 18
KGF-2Δ33 Effect on Tensile Strength and Epidermal Thickness in Normal Rat To demonstrate that KGF-2Δ33 would increase tensile strength and epidermal thickness of wounds the following experiment was performed.

A 2.5 cm full thickness midline incisional wound is created on the back of male Sprague Dawley rats (n=8 or 9). Skin incision is closed using 3 equidistant metal skin staples. Buffer (40 mM NaOAc and 150 mM NaCl, pH 6.5) or KGF-2Δ33 (in 40 mM NaOAc and 150 mM NaCl, pH 6.5 buffer) were topically applied at the time of wounding. Four wound strips measuring 0.5 cm in width are excised at day 5. Specimens are used for the study of breaking strength using an Instron™ skin tensiometer, hydroxyproline determination and histopathological assessment. Breaking strength was defined as the greatest force withheld by each wound prior to rupture. Statistical analysis was clone using an unpaired t test (mean±SE).

Figure 38:
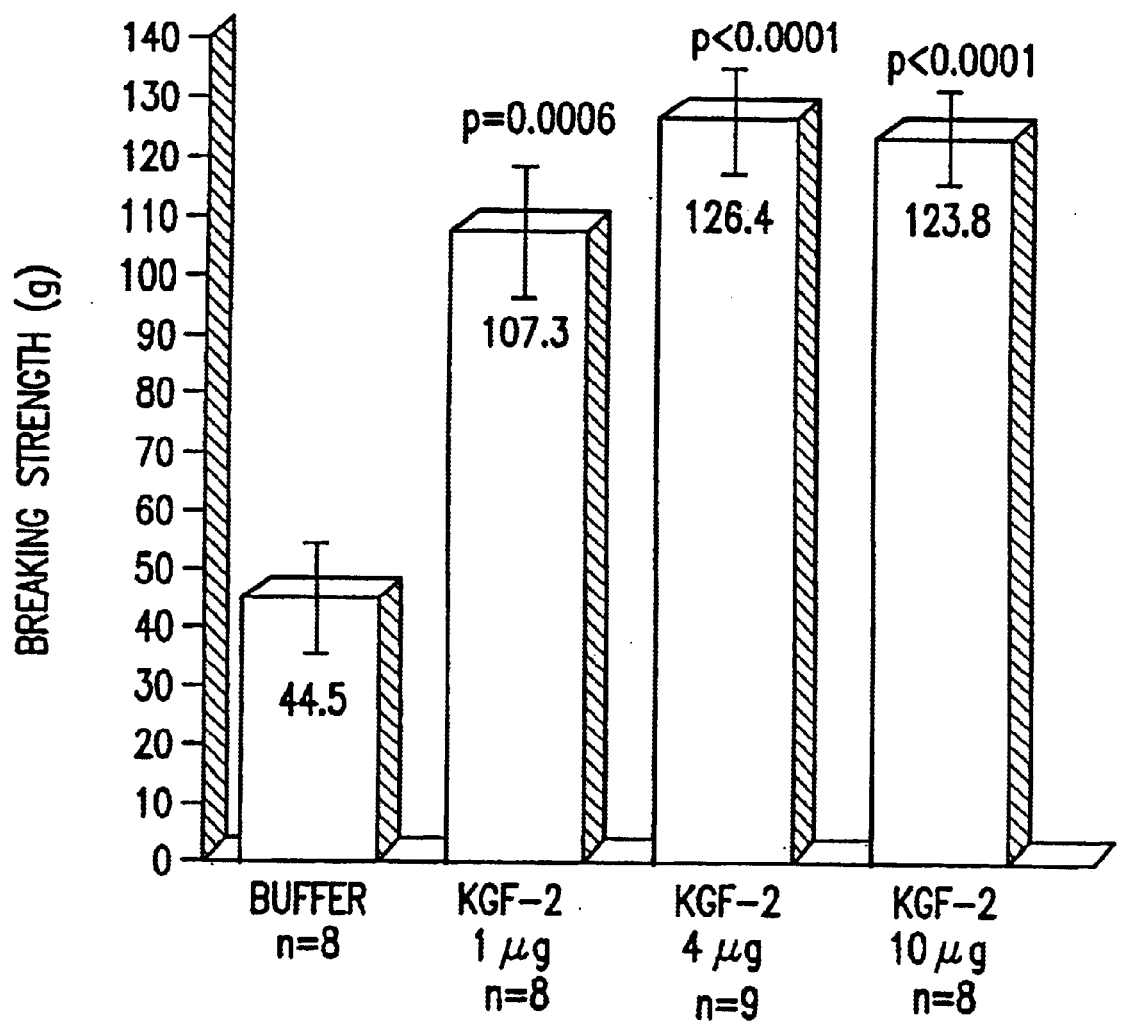
FIG. 38 shows the effect of KGF-2Δ33 on breaking strength in incisional wounds. Male adult SD rats (n=10) received 2.5 cm full thickness incisional wounds on day 1 and were intraincisionally treated post wounding with one application of either buffer or KGF-2 (Delta 33) (1,4, and 10 µg). Animals were sacrificed on day 5 and 0.5 cm wound specimens were excised for routine histology, and breaking strength analysis. Biomechanical testing was accomplished using an Instron skin tensiometer with a force applied across the wound. Breaking strength was defined as the greatest force withheld by each wound prior to rupture. Statistical analysis was done using an unpaired t-test. (Mean+/−SE).

In an incisional skin rat model, topically applied KGF-2Δ33 exhibited a statistically significant increase in breaking strength, tensile strength and epidermal thickness as a result of a single intraincisional application subsequent to wounding. In one study, the breaking strength of KGF-2 treated wounds at 1, 4, and 10 μg was significantly higher when compared to the buffer controls (107.3 g at 1 μg p=0.0006, 126.4 g at 4 μg p<0.0001, 123.8 g at 10, μg p<0.0001). See FIG. 38.

Figure 39:
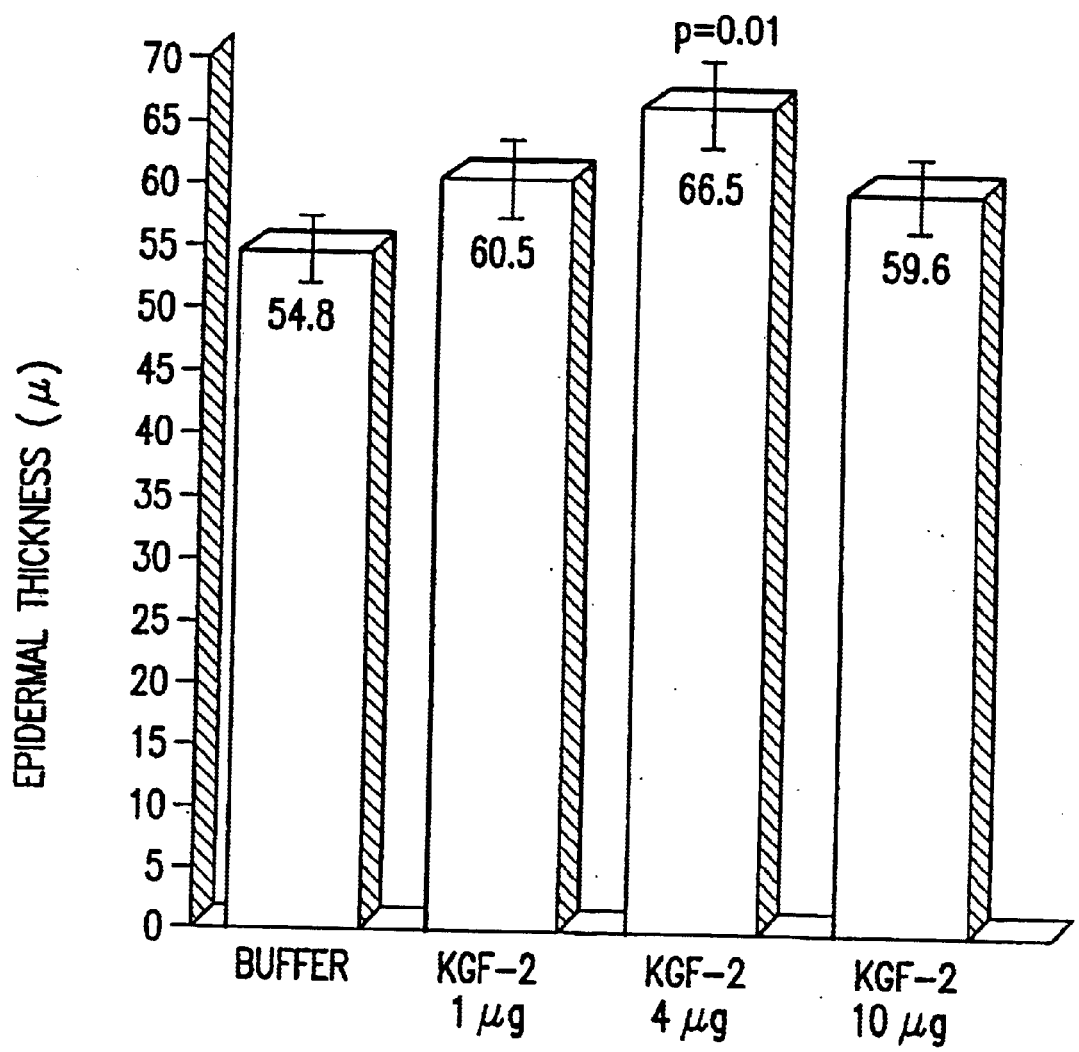
FIG. 39 shows the effect of KGF-2 (Delta 33) on epidermal thickness in incisional wounds. Male adult SD rats (n=10) received 2.5 cm full thickness incisional wounds on day 1 and were intracisionally treated postwounding with one application of either buffer or KGF-2 (Delta 33) (1,4, and 10 µg). Animals were sacrificed on day 5 and 0.5 cm wound specimens were excised for routine histology and breaking strength analysis. Epidermal thickness was determined by taking the mean of 6 measurements taken around the wound site. Measurements were taken by a blind observer on Masson Trichrome stained sections under light microscopy using a calibrated lens micrometer. Statistical analysis was done using an unpaired t-test. (Mean+/−SE).

Epidermal thickness was assessed under light microscopy on Masson Trichrome sections. KGF-2Δ33 treated wounds displayed increased epidermal thickening (60.5μ at 1 μg, 66.51μ at 4 μg p=0.01, 59.6μ at 10 μg) in contrast with the buffer control of 54.8μ. See FIG. 39.

These studies demonstrate that a single intraincisional application of KGF-2 augments and accelerates the wound healing process characterized by an increase in breaking strength and epidermal thickness of incisional wounds.

EXAMPLE 19
KGF-2Δ33 Effect on Normal Rat Skin

In order to determine the effect of KGF-2Δ33 on normal rat skin following intradermal injection the following experiment was performed.

Male adult SD rats (n=3) received six intradermal injections of either placebo or KGF-2Δ33 (in 40 mM NaOAc and 150 mM NaCl, pH 6.5 buffer) in a concentration of 1 and 4 μg in 50 μl on day 0. Animals were injected with 5-2'-bromo-deoxyrudine (BrdU)(100 mg/kg i.p.) two hours prior to sacrifice at 24 and 48 hours. Epidermal thickness was measured from the granular layer to the bottom of the basal layer. Approximately, 20 measurements were mode along the injection site and the mean thickness quantitated. Measurements were determined using a calibrated micrometer on Masson Trichrome stained sections under light microscopy. BrdU scoring was done by two blinded observers under light microscopy using the following scoring system: 0–3 none to minimal BrdU labeled cells; 4–6 moderate labeling; 7–10 intense labeled cells. Animals were sacrificed 24 and 48 hours post injection. Statistical analysis was done using an unpaired t test. (mean±SE).

Figure 40:
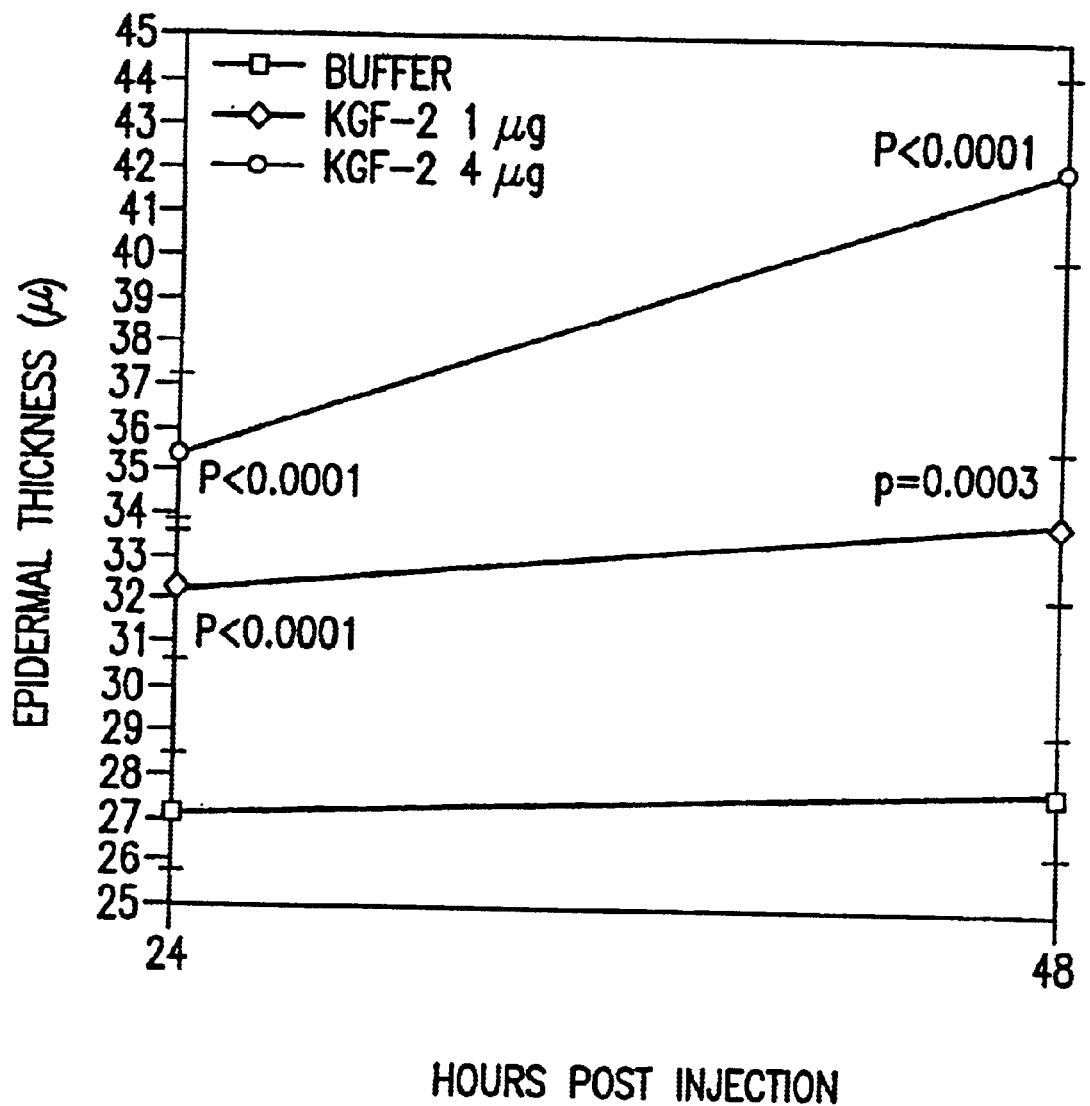
FIG. 40 shows the effect of KGF-2 (Delta 33) on epidermal thickness after a single intradermal injection. Male adult SD rats (n=18) received 6 intradermal injections of either buffer or KGF-2 in a concentration of 1 and 4 µg in 50 µL on day 0. Animals were sacrificed 24 and 48 hours post injection. Epidermal thickness was measured from the granular layer to the bottom of the basal layer. Approximately 20 measurements were made along the injection site and the mean thickness quantitated. Measurements were determined using a calibrated micrometer on Masson Trichrome stained sections under light microscopy. Statistical analysis was done using an unpaired t-test. (Mean +/−SE).
Figure 41:
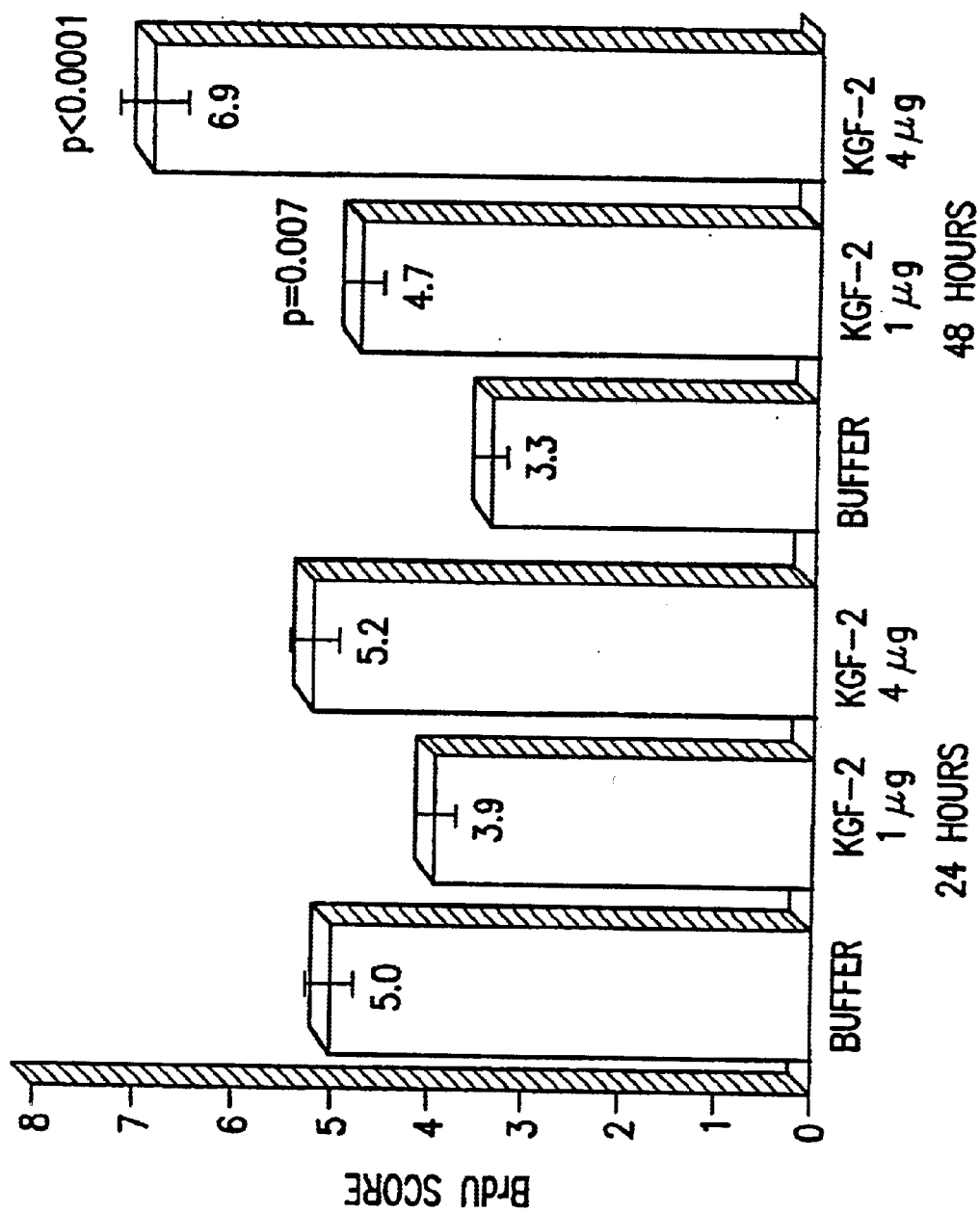
FIG. 41 shows the effect of KGF-2 (Delta 33) on BrdU scoring. Male adult SD rats (n=18) received 6 intradermal injections of either placebo or KGF-2 in a concentration of 1 and 4 µg in 50 µL on day 0. Animals were sacrificed 24 and 48 hours post injection. Animals were injected with 5–2'-Bromo-deoxyrudine (100 mg/kg ip) two hours prior to sacrifice. Scoring was done by a blinded observer under light microscopy using the following scoring system: 0–3 none to minimal BrdU labeled cells; 4–6 moderate labeling; 7–10 intense labeled cells. Statistical analysis was done using an unpaired t-test. (Mean+/−SE).

KGF-2Δ33 treated skin displayed increased epidermal thickening at 24 hours (32.2μ at 1 μg p<0.001, 35.4μ at 4 μg p<0.0001) in contrast with the buffer control of 27.1μ. At 48 hours KGF-2Δ33 treated skin displayed increased epidermal thickening (34.0μ at 1 μg p=0.0003, 42.4μ at 4 μg p<0.0001) compared to buffer control of 27.8μ. See FIG. 40. KGF-2Δ33 treated skin also displayed increased BrdU immunostaining at 48 hours (4.73 at 1 μg p=0.07, 6.85 at 4 μg p<0.0001) compared to buffer control of 3.33. See FIG. 41.

These studies demonstrate that a intradermal injection of KGF-2 augments and accelerates epidermal thickening. Thus, KGF-2 would have applications to prevent or alleviate wrinkles, improve aging skin and reduce scaring or improve healing from cosmetic surgery. In addition, KGF-2 can be used prophylactically to prevent or reduce oral mucosistis (mouth ulcers), intestinal inflammation in response to chemotherapy or other agents.

EXAMPLE 20
Anti-inflammatory Effect of KGF-2 on PAF-induced Paw Edema

To demonstrate an anti-inflammatory effect of KGF-2 the following experiment was performed using PAF-induced paw edema inflammation model.

Groups of four lewis rats (190–210 gm) were injected subcutaneously in the foot pad of the right hind paw with 120 μl solution containing 2.5 nMol of PAF, together with the following reagents: 125 μg of Ckb-10(B5), 24 μg of LPS, 73 μg of KGF-2 (Thr (36)–Ser (208) of FIG. 1 (SEQ ID NO:2) with a N-terminal Met) or no protein. The left hind paws were given the same amount of buffer to use as parallel control. Paw volume was quantified immediately before, or 30 and 90 minutes after PAF injection using a plethysmograph system. Percent (%) change of paw volume were calculated.

| | Testing reagents in experiment No. 1 and No. 2 | | | | |
|---|---|---|---|---|---|
| Groups (N = 4) | PAF(R.) 2.5 nMol | Ckβ-10(R.) 1.04 mg/ml | LPS(R.) 200 μg/ml | KGF-2(R.) 0.73 mg/ml | Buffer |
| 1 | 20 μl | — | — | — | 100 μl |
| 2 | 20 μl | 100 μl | — | — | — |
| 3 | 20 μl | — | 100 μl | — | — |
| 4 | 20 μl | — | — | 100 μl | — |

Figure 42A:
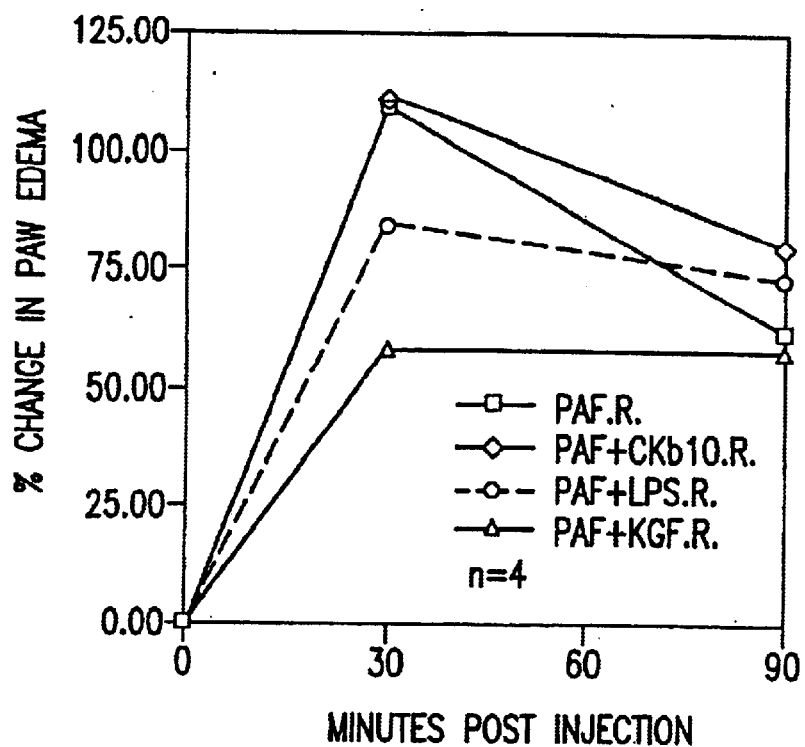
FIGS. 42A and 42B shows the anti-inflammatory effect of KGF-2 on PAF-induced paw edema.
Figure 42B:
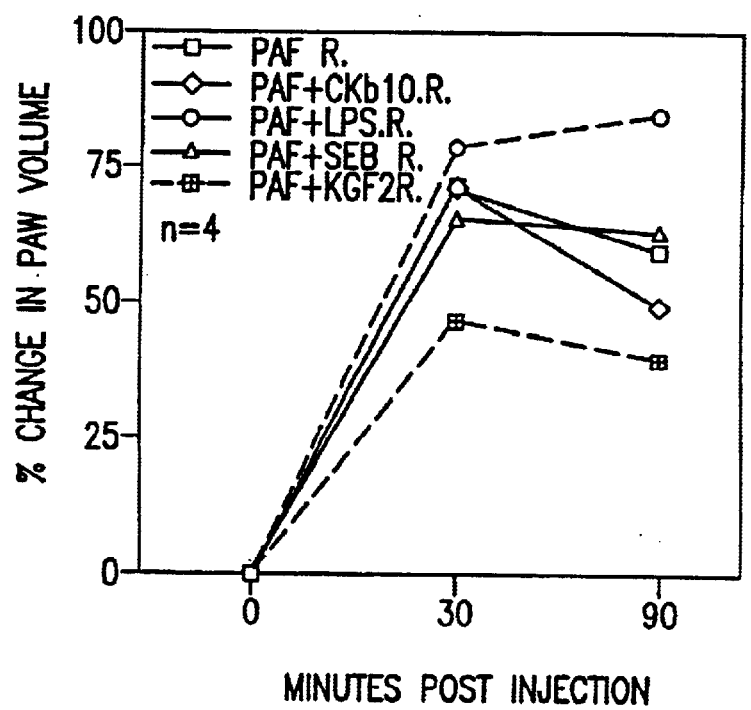

As shown in FIG. 42, right hind paws injected with PAF alone resulted in a significant increase in paw volume (75 or 100% for experiment No. 1 or No. 2, respectively) at 0.5 hour post injection as expected; while left hind paws receiving buffer or right hind paws receiving LPS or SEB alone show little sign of edema (data not shown). However, when KGF-2 was given together with PAF locally, there is a substantial reduction (25 or 50% for experiment No. 1 or No. 2, respectively) in paw volume compared with PAF alonechallenged paws. The reduction of paw edema was not observed in animal receiving PAF together with Ckb-10 (a different protein), LPS or SEB (two inflammatory mediators). These results suggest that the anti-inflammatory effect of KGF-2 is specific and not due to some non-specific nature of the protein.

Effect of KGF-2Δ33 on PAF-induced Paw Edema in Rats

Following the experiments described above with KGF-2Δ33 to confirm its in vitro biological activities for stimulating keratinocyte proliferation and its in vivo effect on wound healing, KGF-2Δ33 was further evaluated in the PAF-induced paw edema model in rats. Groups of four Lewis rats (190~210 gm) were injected subcutaneously in the foot pad of the right hind paw with 12 $\mu$l solution containing 2.5 nMol of PAF, together with 210 $\mu$g of KGF-2Δ33 or albumin. The left hind paws were given the same amount of buffer, albumin or KGF-2Δ33 alone to use as parallel control. Paw volume was quantified at different intervals after PAF injection using a plethysmograph system. Percent (%) change of paw volume was calculated.

Figure 43:
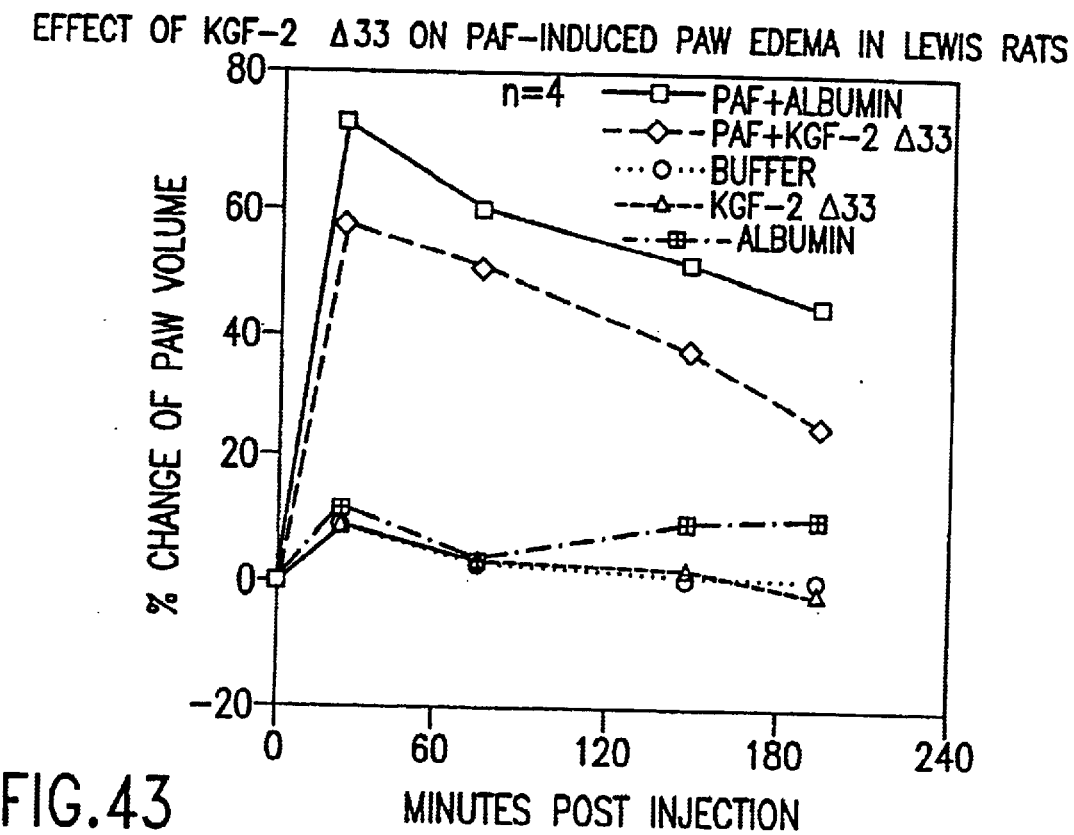
FIG. 43 shows the anti-inflammatory effect of KGF-2Δ33 on PAF-induced paw edema in Lewis rats.

As shown in FIG. 43, right hind paws injected with PAF and albumin resulted in a significant increase (75%) in paw volume at 0.5 hour post injection as expected; while left hind paws receiving buffer, albumin or KGF-2Δ33 alone showed little sign of edema. However, when KGF-2Δ33 was given together with PAF locally, there was a substantial reduction (average 20%) in paw volume, when compared with PAF plus albumin-challenged paws, throughout the entire experiment which was ended in 4 hours. These results confirm the anti-inflammatory property of KGF-2Δ33.

| | | Testing Reagents | | |
|---|---|---|---|---|
| Groups (N = 4) | PAF 2.5 nMol | Albumin 2.1 mg/ml | KGF-2 Δ33 2.1 mg/ml | Buffer |
| 1 | 20 $\mu$l | 100 $\mu$l | — | — |
| 2 | 20 $\mu$l | — | 100 $\mu$l | — |
| 3 | — | 120 $\mu$l | — | — |
| 4 | — | — | 120 $\mu$l | — |
| 5 | — | — | — | 120 $\mu$l |

Thus, KGF-2 is useful for treating acute and chronic conditions in which inflammation is a key pathogenesis of the diseases including but not limiting to psoriasis, eczema, dermatitis and/or arthritis.

EXAMPLE 21

Effect of KGF-2Δ33 on End-to-End Colonic Anastomosis Rat Model

This example demonstrates that KGF-2Δ33 will increase the rate of intestinal repair in a model of intestinal or colonic anastomosis in Wistar or Sprague Dawley rats.

The use of the rat in experimental anastomosis is a well characterized, relevant and reproducible model of surgical wound healing. This model can also be extended to study the effects of chronic steriod treatment or the effects of various chemotherapeutic regimens on the quality and rate of surgical wound healing in the colon and small intestine (Mastboom W. J. B. et al. Br, J. Surg. 78: 54–56 (1991), Salm R. et al. J Surg. Oncol. 47: 5–11, (1991), Weiber S. et al. Eur. Surg. Res. 26: 173–178 (1994)). Healing of anastomosis is similar to that of wound healing elsewhere in the body. The early phases of healing are characterized by acute inflammation followed by fibroblast proliferation and synthesis of collagen. Collagen is gradually modeled and the wound is strengthened as new collagen is synthesized. (Koruda M. J., and Rolandelli, R. H. J. Surg. Res. 48: 504–515 (1990). Most postoperative complications such as anastomotic leakage occur during the first few days following surgery—a period during which strength of the colon is mainly secured by the ability of the wound margin to hold sutures. The suture holding capacity of the GI tract has been reported to decrease by as much as 80% during the first postoperative days (Hogstrom H and Haglund U. Acta Chir Scand 151: 533–535 (1985), Jonsson K, et al. Am J. Surg. 145: 800–803 (1983)).

Male adult SD rats (n=5) were anesthetized with a combination of ketamine (50 mg/kg) and xylazine (5 mg/kg) intramuscularly. The abdominal cavity was opened with a 4 cm long midline incision. A 1 cm wide segment of the left colon was resected 3 cm proximal to the peritoneal reflection while preserving the marginal vessels. A single layer end-to-end anatomosis was performed with 8–10 interrupted 5-0 Vicryl inverted sutures to restore intestinal continuity. The anastomosis was then topically treated via syringe with either buffer or KGF-2Δ33 at concentrations of 1 and 4 $\mu$g. The incisional wound was closed with 3-0 running silk suture for the muscle layer and surgical staples for the skin. Treatments were then administered daily thereafter and consisted of buffer or KGF-2Δ33 and 1 and 5 mg/kg sc. Weights were taken on the day of surgery and daily thereafter. Animals were euthanized 24 hours following the last treatment (day 5). Animals were anesthetized and received barium enemas and were x-rayed at a fixed distance. Radiologic analysis following intracolonic administration by 2 blinded observers revealed that KGF-2Δ33 treated groups had 1) a decreased rate of barium leakage at the surgical site, 2) lesser degree of constriction at the surgical site, and 3) an increase in the presence of fecal pellets distal to the surgical site.

| | Colonic Anastomosis Radiologic Analysis | | | |
|---|---|---|---|---|
| Groups | Feces Present | Anastomotic Constriction | Proximal Distension | Peritoneal Leakage |
| No Treatment (N = 5) | 20% | 80% | 80% | 60% |
| Buffer (N = 5) | 40% | 60% | 80% | 75% |
| KGF-2 Δ33 [1 mg/kg] (N = 5) | 60% | 20% | 100% | 20% |
| KGF-2 Δ33 [5 mg/kg] (N = 4) | 100% | 0% | 75% | 25% |

EXAMPLE 22

Construction of Carboxy Terminal Mutations in KGF-2

The carboxyl terminus of KGF-2 is highly charged. The density of these charged residues may affect the stability and consequently he solubility of the protein. To produce muteins that might stabilize the protein in solution a series of mutations were created in this region of the gene.

To create point mutants 194 R/E, 194 R/Q, 191 K/E, 191 K/Q, 188R/E, 188R/Q, the 5952 KGFΔ33 5' Afl III 5' primer was used with the indicated 3' primers, which contain the appropriate point mutations for KGF-2, in PCR reactions using standard conditions well known to those skilled in the art with KGF-2Δ33 as template. The resulting products were restricted with AflIII and Hind III and cloned into the E. coli expression vector, pQE60 restricted with NcoI and Hind III.

KGF2Δ33, 194R/E Construction
The following primers were used:

5952KGFΔ33 5' Afl III:
5'GCGGCACATGTCTTACAACCACCTGCAGGG (SEQ ID NO:117)
TG 3'

KGF2 3'HindIII 194aa R to E:
5'CTGCCC<u>AAGCTT</u>TTATGAGTGTACCACCATTG (SEQ ID NO:118)
GAAGAAAGTGAGCAGAGGTGTTTTT<u>TTC</u>TCGTGT
TTTCTGTCC 3'

KGF2Δ33,194 R/E Nucleotide
sequence:
ATGTCTTACAACCACCTGCAGGGTGACGTTCGTT (SEQ ID NO:119)
GGCGTAAACTGTTCTCTTTCACCAAATACTFCCT
GAAAATCGAAAA
AAACGGTAAAGTTTCTGGGACCAAGAAGGAGAAC
TGCCCGTACAGCATCCTGGAGATAACATCAGTAG
AAATCGGAGAGTTG
TTGCCGTCAAAGCCATTAACAGCAACTATTACTT
AGCCATGAACAAGAAGGGGAAACTCTATGGCTCA
AAAGAATTTAAC
AATGACTGTAAGCTGAAGGAGAGGATAGAGGAAA
ATGGATACAATACCTATGCATCATTTAACTGGCA
GCATAATGGGAG
GCAAATGTATGTGGCATTGAATGGAAAAGGAGCT
CCAAGGAGAGGACAGAAAACACGA<u>GAA</u>AAAAACA
CCTCTGCTCACTTTCTTCCAATGGTGGTACACTC
ATAG KGF2Δ33,194 R/E Amino acid
sequence:
MSYNHLQGDVRWRKLFSFTKYFLKIEKNGKVSGT (SEQ ID NO:120)
KKENCPYSILEITSVEIGVVAVKAINSNYYLAMN
KKGKLYGSKEFNNDCKLKERIEENGYNTYASFNW
QHNGRQMYVALNGKGAPRRGQKTR<u>E</u>KNTSAHFLP
MVVHS

KGF2Δ33, 194R/Q Construction
The following primers were used:

5952 KGF Δ33 5' Afl III:
5'GCGGCACATGTCTTACAACCACCTGCAGGGTG (SEQ ID NO:121)
3'

KGF2 3' HindIII 194 aa R to Q:
5'CTGCCC<u>AAGCTT</u>TTATGAGTGTACCACCATTG (SEQ ID NO:122)
GAAGAAAGTGAGCAGAGGTGTTTTT<u>CTG</u>TCGTGT
TTTCTGTCC 3'

KGF2 Δ33,194 R/Q Nucleotide
Sequence:
ATGTCTTACAACCACCTGCAGGGTGACGTTCGTT (SEQ ID NO:123)
GGCGTAAACTGTTCTCTTTCACCAAATACTTCCT
GAAAATCGAAAAAACGGTAAAGTTTCTGGGACC
AAGAAGGAGAACTGCCCGTACAGCATCCTGGAGA
TAACATCAGTAGAAATCGGAGTTGTTGCCGTCAA
AGCCATTAACAGCAACTATTACTTAGCCATGAAC
AAGAAGGGGAAACTCTATGGCTCAAAAGAATTTA
ACAATGACTGTAAGCTGAAGGAGAGGATAGAGGA
AAATGGATACAATACCTATGCATCATTTAACTGG
CAGCATAATGGGAGGCAAATGTATGTGGCATTGA
ATGGAAAAGGAGCTCCAAGGAGAGGA<u>CAG</u>AAAAC
ACGACAGAAAAACACCTCTGCTCACTTTCTTCCA
ATGGTGGTACACTCATAG KGF2 Δ33,194 R/Q Amino Acid
Sequence:
MSYNHLQGDVRWRKLFSFTKYFLKIEKNGKVSGT (SEQ ID NO:124)
KKENCPYSILEITSVEIGVVAVKAINSNYYLAMN
KKGKLYGSKEFNNDCKLKERIEENGYNTYASFNW
QHNGRQMYVALNGKGAPRRGQKTR<u>Q</u>KNTSAHFLP
MVVHS

KGF2Δ33, 191K/E Construction
The following primers were used:

5952 KGF Δ33 5' Afl III:
5'GCGGCACATGTCTTACAACCACCTGCAGGG (SEQ ID NO:125)
TG 3'

KGF2 3'HindIII 191aa K to E
5'CTGCCC<u>AAGCTT</u>TTATGAGTGTACCACCATTG (SEQ ID NO:126)
GAAGAAAGTGAGCAGAGGTGTTTTTCCTTTCGTG
TTT<u>C</u>CTGTCCTCTCCTTGG 3'

KGF2Δ33,191 K/E Nucleotide
Sequence:
ATGTCTTACAACCACCTGCAGGGTGACGTTCGTT (SEQ ID NO:127)
GGCGTAAACTGTTCTCTTTCACCAAATACTTCCT
GAAAATCGAAAAAACGGTAAAGTTTCTGGGACC
AAGAAGGAGAACTGCCCGTACAGCATCCTGGAGA
TAACATCAGTAGAAATCGGAGTTGTTGCCGTCAA
AGCCATTAACAGCAACTATTACTTAGCCATGAAC
AAGAAGGGGAAACTCTATGGCTCAAAAGAATTTA
ACAATGACTGTAAGCTGAAGGAGAGGATAGAGGA
AAATGGATACAATACCTATGCATCATTTAACTGG
CAGCATAATGGGAGGCAAATGTATGTGGCATTGA
ATGGAAAAGGAGCTCCAAGGAGAGGACAG<u>GAA</u>AC
ACGAAGGAAAAACACCTCTGCTCACTTTCTTCCA
ATGGTGGTACACTCATAG KGF2Δ33,191 K/E Amino Acid
Sequence:
MSYNHLQGDVRWRKLFSFTKYFLKIEKNGKVSGT (SEQ ID NO:128)
KKENCPYSILEITSVEIGVVAVKAINSNYYLAMN
KKGKLYGSKEFNNDCKLKERIEENGYNTYASFNW
QHNGRQMYVALNGKGAPRRGQ<u>E</u>TRRKNTSAHFLP
MVVHS

KGF2Δ33, 191K/Q Construction
The following primers were used:

5952 KGFΔ33 5' Afl III:
5'GCGGCACATGTCTTACAACCACCTGCAGGG (SEQ ID NO:129)
TG 3'

KGF2 3' HindIII 191aa K to Q
5'CTGCCC<u>AAGCTT</u>TTATGAGTGTACCACCATTG (SEQ ID NO:130)
GAAGAAAGTGAGCAGAGGTGTTTTTCCTTCGTGT
<u>CTG</u>CTGTCCTCTCCTTGG 3'

KGF2 Δ33,191 K/Q Nucleotide
Sequence:
ATGTCTTACAACCACCTGCAGGGTGACGTTCGTT (SEQ ID NO:131)
GGCGTAAACTGTTCTCTTTCACCAAATACTTCCT
GAAAATCGAAAAAACGGTAAAGTTTCTGGGACC
AAGAAGGAGAACTGCCCGTACAGCATCCTGGAGA
TAACATCAGTAGAAATCGGAGTTGTTGCCGTCAA
AGCCATTAACAGCAACTATTACTTAGCCATGAAC
AAGAAGGGGAAACTCTATGGCTCAAAAGAATTTA
ACAATGACTGTAAGCTGAAGGAGAGGATAGAGGA
AAATGGATACAATACCTATGCATCATTTAACTGG
CAGCATAATGGGAGGCAAATGTATGTGGCATTGA
ATGGAAAAGGAGCTCCAAGGAGAGGACAG<u>CAG</u>AC
ACGAGGAAAAACACCTCTGCTCACTTTCTTCCAA
TGGTGGTACACTCATAG KGF2 Δ33,191 k/Q Amino Acid
Sequence:
MSYNHLQGDVRWRKLFSFTKYFLKIEKNGKVSGT (SEQ ID NO:132)
KKENCPYSILEITSVEIGVVAVKAINSNYYLAMN
KKGKLYGSKEFNNDCKLKERIEENGYNTYASFNW
QHNGRQMYVALNGKGAPRRGQ<u>Q</u>TRRKNTSAHFLP
MVVHS KGF2Δ33, 188R/E Construction
The following primers were used:

5952 KGFΔ33 5' Afl III:
5'GCGGCACATGTCTTACAACCACCTGCAGGG  (SEQ ID NO:133)
TG 3'

KGF2 3' HindIII 188aa R to E:
5'CTGCCC<u>AAGCTT</u>TTATGAGTGTACCACCATTG  (SEQ ID NO:134)
GAAGAAAGTGAGCAGAGGTGTTTTTCCTTCGTGT
TTTCTGTCC<u>TTC</u>CCTTGGAGCTCCTTT 3'

KGF2Δ33, 188R/E Nucleotide
Sequence:
ATGTCTTACAACCACCTGCAGGGTGACGTTCGTT  (SEQ ID NO:135)
GGCGTAAACTGTTCTCTTTCACCAAATACTTCCT
GAAAATCGAAAAAAACGGTAAAGTTTCTGGGACC
AAGAAGGAGAACTGCCCGTACAGCATCCTGGAGA
TAACATCAGTAGAAATCGGAGTTGTTGCCGTCAA
AGCCATTAACAGCAACTATTACTTAGCCATGAAC
AAGAAGGGGAAACTCTATGGCTCAAAAGAATTTA
ACAATGACTGTAAGCTGAAGGAGAGGATAGAGGA
AAATGGATACAATACCTATGCATCATTTAACTGG
CAGCATAATGGGAGGCAAATGTATGTGGCATTGA
ATGGAAAAGGAGCTCCAAGGG<u>AA</u>GGACAGAAAAC
ACGAAGGAAAAACACCTCTGCTCACTTTCTTCCA
ATGGTGGTACACTCATAG KGF2Δ33, 188R/E Amino Acid
Sequence:
MYNHLQGDVRWRKLFSFTKYFLKIEKNGKVSGTK  (SEQ ID NO:136)
KENCPYSILEITSVEIGVVAVKAINSNYYLAMNK
KGKLYGSKEFNNDCKLKERIEENGYNTYASFNWQ
HNGRQMYVALNGKGAPR<u>E</u>GQKTRRKNTSAHFLPM
VVHS KGF2Δ33, 188R/Q Construction
The following primers were used:

5952 KGF Δ33 5' Afl III:
5'GCGGCACATGTCTTACAACCACCTGCAGGG  (SEQ ID NO:137)
TG 3'

KGF2 3' HindIII 188aa R to Q:
5'CTGCCC<u>AAGCTT</u>TTATGAGTGTACCACCATTG  (SEQ ID NO:138)
GAAGAAAGTGAGCAGAGGTGTTTTTCCTTCGTGT
TTTCTGTCC<u>CTG</u>CCTTGGAGCTCCTTT 3'

KGF2Δ33, 188 R/Q Nucleotide
Sequence:
ATGTCTTACAACCACCTGCAGGGTGACGTTCGTT  (SEQ ID NO:139)
GGCGTAAACTGTTCTCTTTCACCAAATACTTCCT
GAAAATCGAAAAAAACGGTAAAGTTTCTGGGACC
AAGAAGGAGAACTGCCCGTACAGCATCCTGGAGA
TAACATCAGTAGAAATCGGAGTTGTTGCCGTCAA
AGCCATTAACAGCAACTATTACTTAGCCATGAAC
AAGAAGGGGAAAGTCTATGGCTCAAAAGAATTTA
ACAATGACTGTAAGCTGAAGGAGAGGATAGAGGA
AAATGGATACAATACCTATGCATCATTTAACTGG
CAGCATAATGGGAGGCAAATGTATGTGGCATTGA
ATGGAAAAGGAGCTCCAAGGC<u>AG</u>GGACAGAAAAC
ACGAAGGAAAAACACCTCTGCTCACTTTCTTCCA
ATGGTGGTACACTCATAG KGF2Δ33, 188 R/Q Amino Acid
Sequence:
MSYNHLQGDVRWRKLFSFTKYFLKIEKNGKVSGT  (SEQ ID NO:140)
KKENCPYSILEITSVEIGVVAVKAINSNYYLAMN
KKGKLYGSKEFNNDCKLKERIEENGYNTYASFNW
QHNGRQMYVALNGKGAPR<u>Q</u>GQKTRRKNTSAHFLP
MVVHS KGF2Δ33, 183K/E Construction
For mutation 183K/E, two PCR reactions were set up for oligonucleotide site directed mutagenesis of this lysine. In one reaction, 5952 KGFΔ33 5' AflIII was used as the 5' primer, and KGF2 183aa K to E antisense was used as the 3' primer in the reaction. In a second reaction, KGF2 5' 183aa K to E sense was used as the 5' primer, and KGF2 3' HindIII TAA stop was used as the 3' primer. KGF-2Δ33 was used as template for these reactions. The reactions were amplified under standard conditions well known to those skilled in the art. One microliter from each of these PCR reactions was used as template in a subsequent reaction using, as a 5' primer, 5453 BsphI, and as a 3' primer, 5258 HindIII. Amplification was performed using standard conditions well known to those skilled in the art. The resulting product was restricted with Afl III and HindIII and cloned into the *E. coli* expression vector pQE60, which was restricted with NcoI and HindIII.

The following primers were used:

5952 KGF Δ33 5' Afl III:
5'GCGGCACATGTCTTACAACCACCTGCAGGG  (SEQ ID NO:141)
TG 3'

KGF2 5' 183aa K to E sense:
5'TTGAATGGAGAA<u>GG</u>AGCTCCA 3'  (SEQ ID NO:142)

KGF2 183aa K to E antisense:
5'TGGAGCTCC<u>TTC</u>TCCATTCAA 3'  (SEQ ID NO:143)

KGF2 3' HindIII TAA stop:
5'CTGCCC<u>AAGCTTTT</u>ATGAGTGTACCACCATT  (SEQ ID NO:144)
GG 3'

KGF2 Δ33, 183K/E Nucleotide
Sequence:
ATGTCTTACAACCACCTGCAGGGTGACGTTCGTT  (SEQ ID NO:145)
GGCGTAAACTGTTCTCTTTCACCAAATACTTCCT
GAAAATCGAAAA
AAACGGTAAAGTTTCTGGGACCAAGAAGGAGAAC
TGCCCGTACAGCATCCTGGAGATAACATCAGTAG
AAATCGGAGTTG
TTGCCGTCAAAGCCATTAACAGCAACTATTACTT
AGCCATGAACAAGAAGGGGAAACTCTATGGCTCA
AAAGAATTTAAC
AATGACTGTAAGCTGAAGGAGAGGATAGAGGAA
ATGGATACAATACCTATGCATCATTTAACTGGCA
GCATAATGGGAG
GCAAATGTATGTGGCATTGAATGGA<u>GA</u>AGGAGCT
CCAAGGAGAGGACAGAAAACACGAAGGAAAAACA
CCTCTGCTCACTTTCTTCCAATGGTGGTACACTC
ATAG KGF2 Δ33, 183K/E Amino Acid
Sequence:
MSYNHLQGDVRWRKLFSFTKYFLKIEKNGKVSGT  (SEQ ID NO:146)
KKENCPYSILEITSVEIGVVAVKAINSNYYLAMN
KKGKLYGSKEFNNDCKLKERIEENGYNTYASFNW
QHNGRQMYVALNG<u>E</u>GAPRRGQKTRRKNTSAHFLP
MVVHS

EXAMPLE 23

Effect of KGF-2 on Survival after Total Body Irradiation in Balb/c Mice

Ionizing radiation is commonly used to treat many malignancies, including lung and breast cancer, lymphomas and pelvic tumors (Ward, W. F. et al., *CRC Handbook of Animal Models of Pulmonary Disease*, CRC Press, pp. 165–195 (1989)). However, radiation-induced injury (lung, intestine, etc.) limits the intensity and the success of radiation therapy (Morgan, G. W. et al., *Int. J Radiat. Oncol. Biol. Phys.* 31:361 (1995)). The gastrointestinal mucosa has a rapid cell cycle and is particularly sensitive to cytotoxic agents (Potten, C. S., et al., *In: Cytotoxic Insult to Tissue*, Churchill Livingstone, pp. 105–152 (1983)). Some of the manifestations of intestinal radiation damage include acute proctitis, intestinal fibrosis, stricture or fistula formation (Anseline, D. F. et al. *Ann. Surg.* 194:716–724 (1981)). A treatment which protects normal structures from radiation without altering the radiosensisitivity of the tumor would be beneficial in the management of these disorders. Regardless of the irradiated area, the dose of radiation is limited by the radiosensitivity of normal tissue. Complications following total or partial body irradiation include pneumonitis, fibrosis, gastro-intestinal injury and bone marrow disorders.

Several cytokines including IL-1, TNF, IL-6, IL-12 have demonstrated radioprotective effects following TBI (Neta, R. et al., *J. Exp. Med.* 173:1177 (1991)). IL-11 has been shown to protect small intestinal mucosal cells after combined irradiation and chemotherapy (Du, X. X. et al., *Blood* 83:33 (1994)) and radiation-induced thoracic injury (Redlich, C. A. et al. *The Journal of Immunology* 157:1705–1710 (1996)).

Animals

All experiments were performed using BALB/c mice. Animals were purchased at 6 weeks of age and were 7 weeks old at the beginning of the study. All manipulations were performed using aseptic techniques. This study was conducted according to the guidelines set forth by the Human Genome Sciences, Inc., Institutional Animal Care and Use Committee which reviewed and approved the experimental protocol.

KGF-2

The protein consists of a 141 amino acid human protein termed KGF-2 Δ33. This protein is a truncated isoform of KGF-2 that lacks the first 33 amino-terminal residues of the mature protein. The gene encoding this protein has been cloned into an *E. coli* expression vector. Fractions containing greater that 95% pure recombinant materials were used for the experiment. KGF-2 was formulated in a vehicle containing 40 mM Na Acetate+150 mM NaCl, pH 6.5. Dilutions were made from the stock solution using the same vehicle.

Total Body Irradiation and Experimental Design

Mice were irradiated with 519 RADS (5.19 Gy) using a 68 Mark I Shepherd Cesium Irradiator. The KGF-2Δ33 was administered daily subcutaneously, starting 2 days before irradiation and continuing for 7 days after irradiation. Daily weights were obtained in all mice. Groups of mice were randomized to receive one of three treatments: Total body irradiation (TBI) plus buffer, TBI plus KGF-2Δ33 (1 mg/kg sq), TBI plus KGF-2Δ33 (5 mg/kg sq). Two independent experiments were performed.

Results

Figure 44:
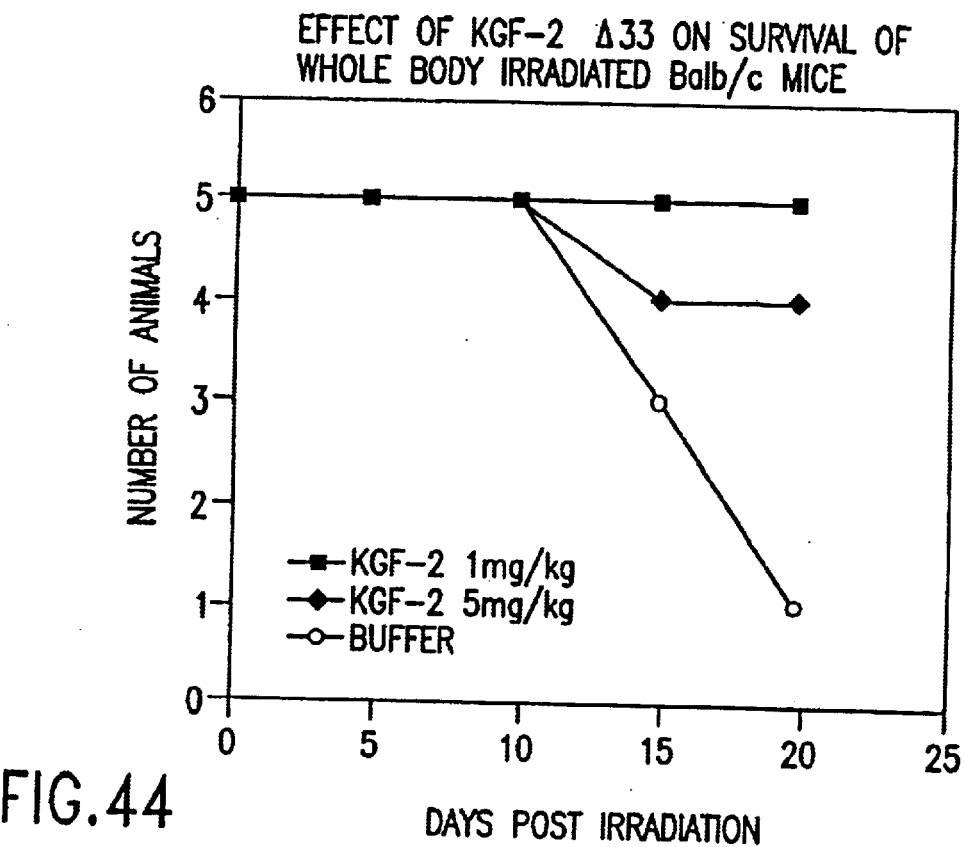
FIG. 44 shows the effect of KGF-2Δ33 on the survival of whole body irradiated Balb/c mice. Balb/c male mice (n=5), 22.1 g were irradiated with 519 RADS. Animals were treated with buffer or KGF-2 (1 & 5 mg/kg, s.q.) 2 days prior to irradiation and daily thereafter for 7 days.

Two studies were performed using irradiated animals. In the first study, animals were irradiated with 519 RADS (5.19 Gy). Animals were treated with buffer or KGF-2Δ33 at 1 & 5 mg/kg, s.q. two days prior to irradiation and daily thereafter for 7 days. At day 25 after total body irradiation 1/5 animals survived in the buffer group. In contrast, KGF-2 treated groups had 5/5 animals @ 1 mg/kg and 4/5 @ 5 mg/kg (FIG. 44).

Figure 45:
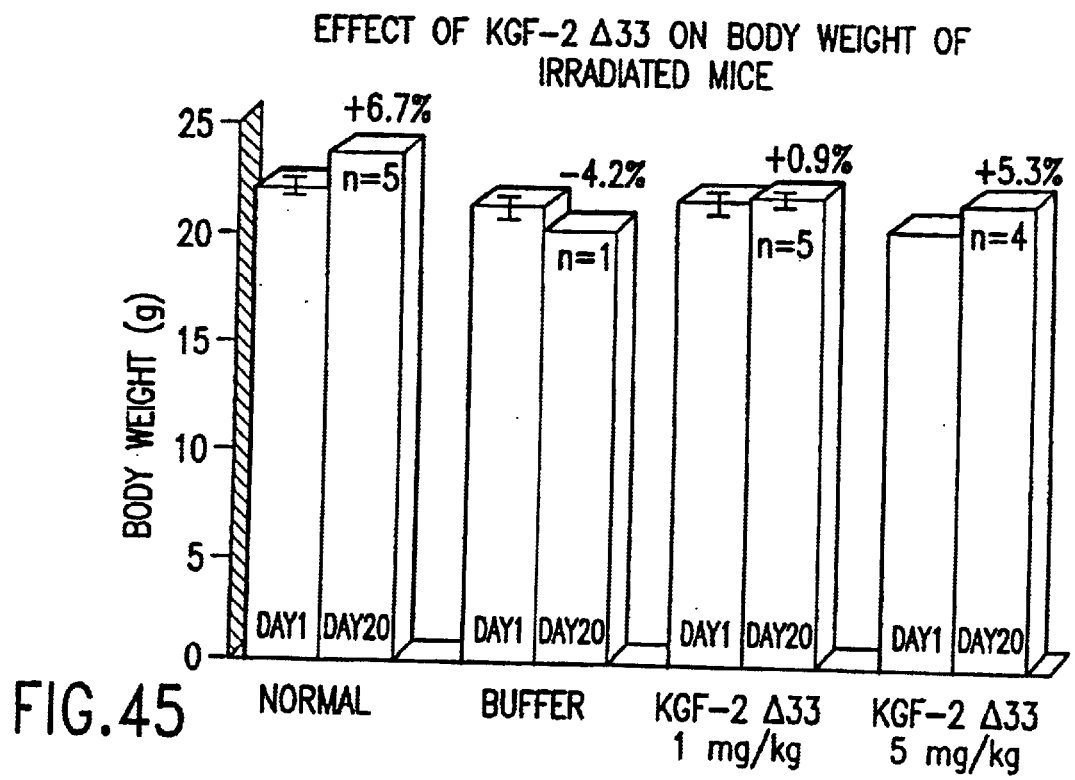
FIG. 45 shows the effect of KGF-2Δ33 on body weight of irradiated mice. Balb/c male mice (n=5) weighing 22.1 g were injected with either Buffer or KGF-2Δ33 (1, 5 mg/kg) for 2 days prior to irradiation with 519 Rad/min. The animals were weighed daily and injected for 7 days following irradiation.

In addition, KGF-2 treated animals displayed 0.9% and 5.3%, weight gain at day 20 post-TBI. In contrast, the buffer treated group had 4.2% weight loss at day 20. Normal non-irradiated age matched control animals showed 6.7% weight gain in the same time period (FIG. 45).

Animals in the second study were also irradiated with 519 RADS (5.19 Gy). These animals were treated with buffer or KGF-2Δ33 at 1 & 5 mg/kg, s.q. two days prior to irradiation and daily thereafter for 7 days. At day 15 after total body irradiation all the animals in the buffer group were dead.

Figure 46:
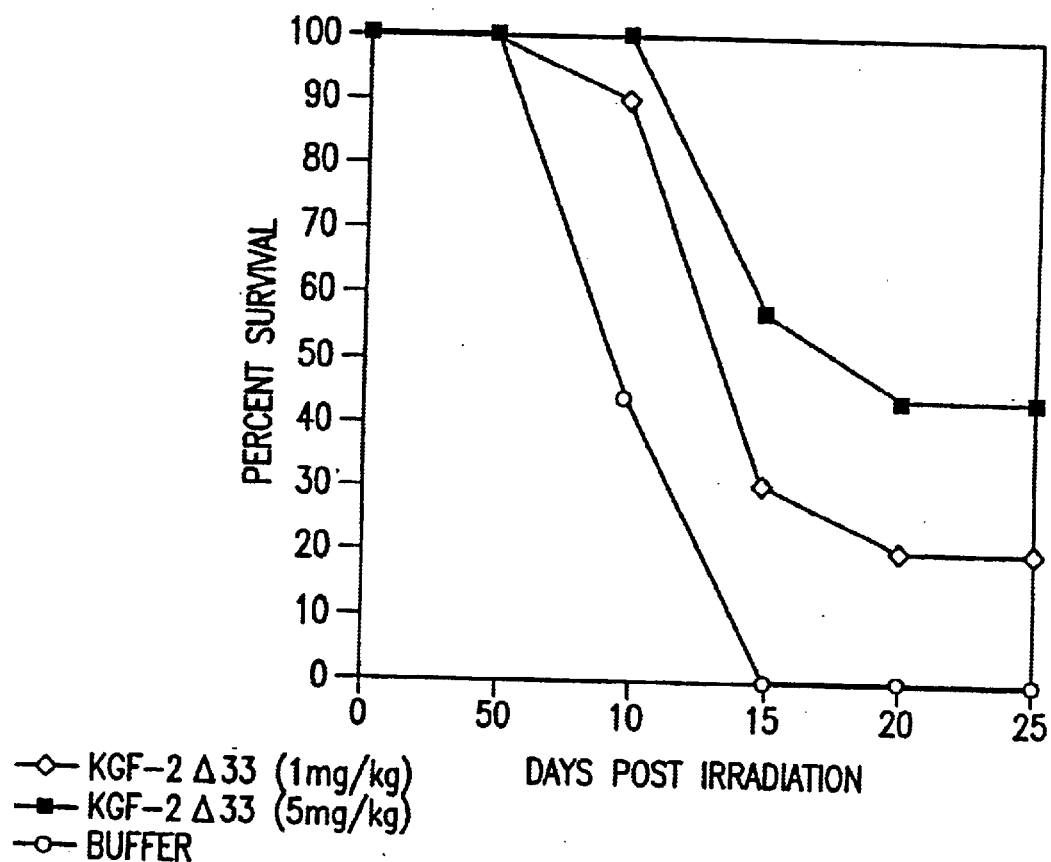
FIG. 46 shows the effect of KGF-2Δ33 on the survival rate of whole body irradiated Balb/c mice. Balb/c male mice (n=7), 22.1 g were irradiated with 519 RADS. Animals were treated with buffer or KGF-2 (1 and 5 mg/kg, s.q.) 2 days prior to irradiation and daily thereafter for 7 days.

KGF-2 at 1 mg/kg had 30% survival and 60% survival at 5 mg/kg. At day 25 after TBI the 1 mg/kg group showed 20% survival and the 5 mg/kg 50% survival (FIG. 46).

Conclusions

In summary, these results demonstrate that KGF-2 has protective effect after TBI. The ability of KGF-2 to increase survival rate of animals subjected to TBI suggests that it would also be useful in radiation-induced injuries and to increase the therapeutic ratio of irradiation in the treatment of malignancies.

EXAMPLE 24

Evaluation of KGF-2 in the TPA Model of Cutaneous Inflammation in Mice

To demonstrate that KGF-2 would attenuate the progression of contact dermatitis, a tetradecanoylphorbol acetate (TPA)-induced cutaneous inflammation model in mice is used. The use of the female BALB/c and male Swiss Webster mice in experimental cutaneous inflammation are well-characterized, relevant and reproducible models of contact dermatitis. These strains of mice have been shown to develop a long-lasting inflammatory response, following topical application of TPA, which is comprised of local hemodynamics, vascular permeability and local migration of leukocytes, and these pathological changes are similar to those of human dermatitis (Rao et al. 1993, Inflammation 17(6):723; Rao et al. 1994, J. Kipid Mediators Cell Signalling 10:213).

Groups of mice receive either vehicle or KGF-2 intraperitoneally, sub-cutaneously, or intravenously 60 min after the topical application of TPA (4 μg/ear) applied as a solution in acetone (200 μg/ml), 10 μl each to the inner and outer surface of ear. The control group receives 20 μl of acetone as a topical application. Four hours following the application of TPA, increase in ear thickness is measured and ears are excised for histology. To determine vascular permeability in response to TPA, mice are intravenously injected through tail veins with Evans blue (300 mg/kg) at selected times after topical application of TPA and mice are sacrificed 15 min thereafter. Ears are excised and removed, then extracted into dimethylformamide and centrifuged. Absorbance readings are spectrophotometrically measured at 590 nm.

EXAMPLE 25

Effect of KGF-2Δ33 in Wound Healing

The biological effects of KGF-2Δ33 in the skin were examined based on the initial in vitro data demonstrating KGF-2's capacity to stimulate primary human epidermal keratinocytes as well as murine pro-B BaF3 cells transfected with the FGFR isoform 2iiib. Initial experiments were performed to determine the biological effects of KGF-2Δ33 following intradermal administration. Following the intradermal studies, KGF-2Δ33 was explored in a variety of wound healing models (including full thickness punch biopsy wounds and incisional wounds) to determine its potential as a wound healing agent.

Effect of KGF-2Δ33 in a Glucocorticoid-Impaired Rat Model of Wound Healing

Impaired wound healing is an important clinical problem associated with a variety of pathologic conditions such as diabetes and is a complication of the systemic administration of steroids or antimetabolites. Treatment with systemic glucocorticoids is known to impair wound healing in humans and in animal models of tissue repair. A decrease in circulating monocyte levels and an inhibition of procollagen synthesis have been observed subsequent to glucocorticoid administration. The inflammatory phase of healing and matrix synthesis are therefore important factors involved in the complex process of tissue repair. In the present study the effects of multiple topical applications of KGF-2 were assessed on full thickness excisional skin wounds in rats in which healing has been impaired by the systemic administration of methylprednisolone.

Figure 47:
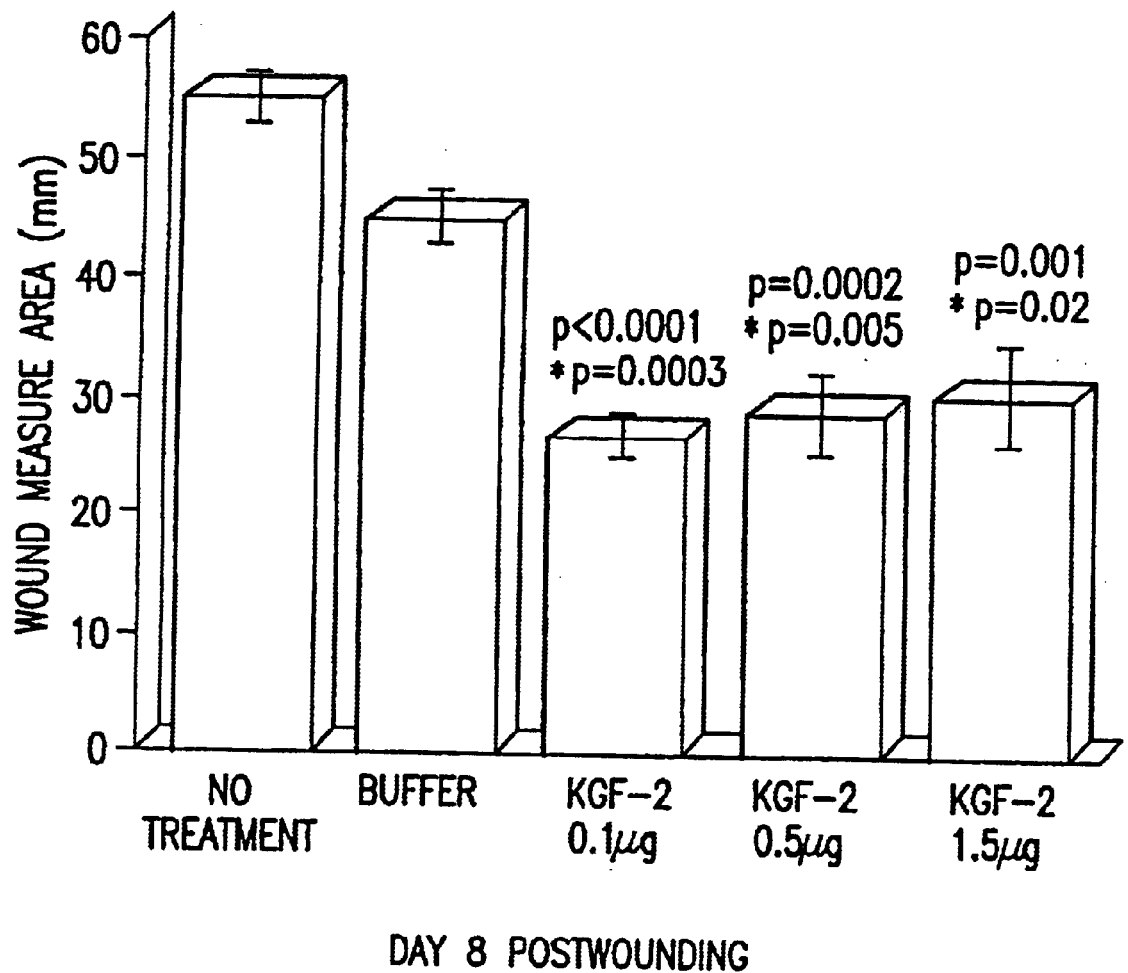
FIG. 47 shows the effect of KGF-2Δ33 on wound healing in a glucocorticoid-impaired rat model.

Sprague Dawley rats (n=5/treatment group) received 8 mm dorsal wounds and methylprednisolone (17 mg/kg, i.m.) to impair healing. Wounds were treated topically each day with buffer or KGF-2 at doses of 0.1, 0.5 and 1.5 μg in a volume of 50 μl. Wounds were measured on days 2,4,6, and 8 using a calibrated Jameson caliper. On day 6 (data not shown), and day 8 (FIG. 47) KGF-2 treated groups showed a statistically significant reduction in wound closure when compared to the buffer control.

Effect of KGF-2Δ33 on Wound Healing in a Diabetic Mouse Model

Genetically diabetic homozygous female (db+/db+) mice, 6 weeks of age (n=6), weighing 30–35 g were given a dorsal full thickness wound with a 6 mm biopsy punch. The wounds were left open and treated daily with placebo or KGF-2 at 0.1, 0.5 and 1.5 μg. Wound closure was determined using a Jameson caliper. Animals were euthanized at day 10 and the wounds were harvested for histology.

KGF-2 displayed a significantly improvement in percent wound closure at 0.1 μg (p0.02) when compared to placebo or with the untreated group. Administration of KGF-2 also resulted in an improvement in histological score at 0.1 μg (p=0.03) when compared to placebo or with the untreated group (p=0.01) and 1.5 μg (p=0.05) compared to the untreated group.

Conclusions

Based on the results presented above, KGF-2 shows significant activity in impaired conditions such as glucocorticoid administration and diabetes. Therefore, KGF-2 may be clinically useful in stimulating healing of wounds after surgery, chronic ulcers in patients with diabetes or poor circulation (e.g., venous insufficiency and venous ulcers), burns and other abnormal wound healing conditions such as uremia, malnutrition, vitamin deficiencies and systemic treatment with steroids and antineoplastic drugs.

EXAMPLE 26

Effects of KGF-2Δ33 on Oral Mucosa

Cytotoxic agents used clinically have the unfortunate effect of inhibiting the proliferation of the normal epithelia in some locations, such as the oral mucosa, leading to life-threatening disturbances in the mucosal barrier. We have conducted studies to examine the efficacy of KGF-2 in this clinical area. The data supports a therapeutic effect of KGF-2 in models of mucositis.

Effects of KGF-2Δ33 on Hamster Oral Mucosa

Figure 48:
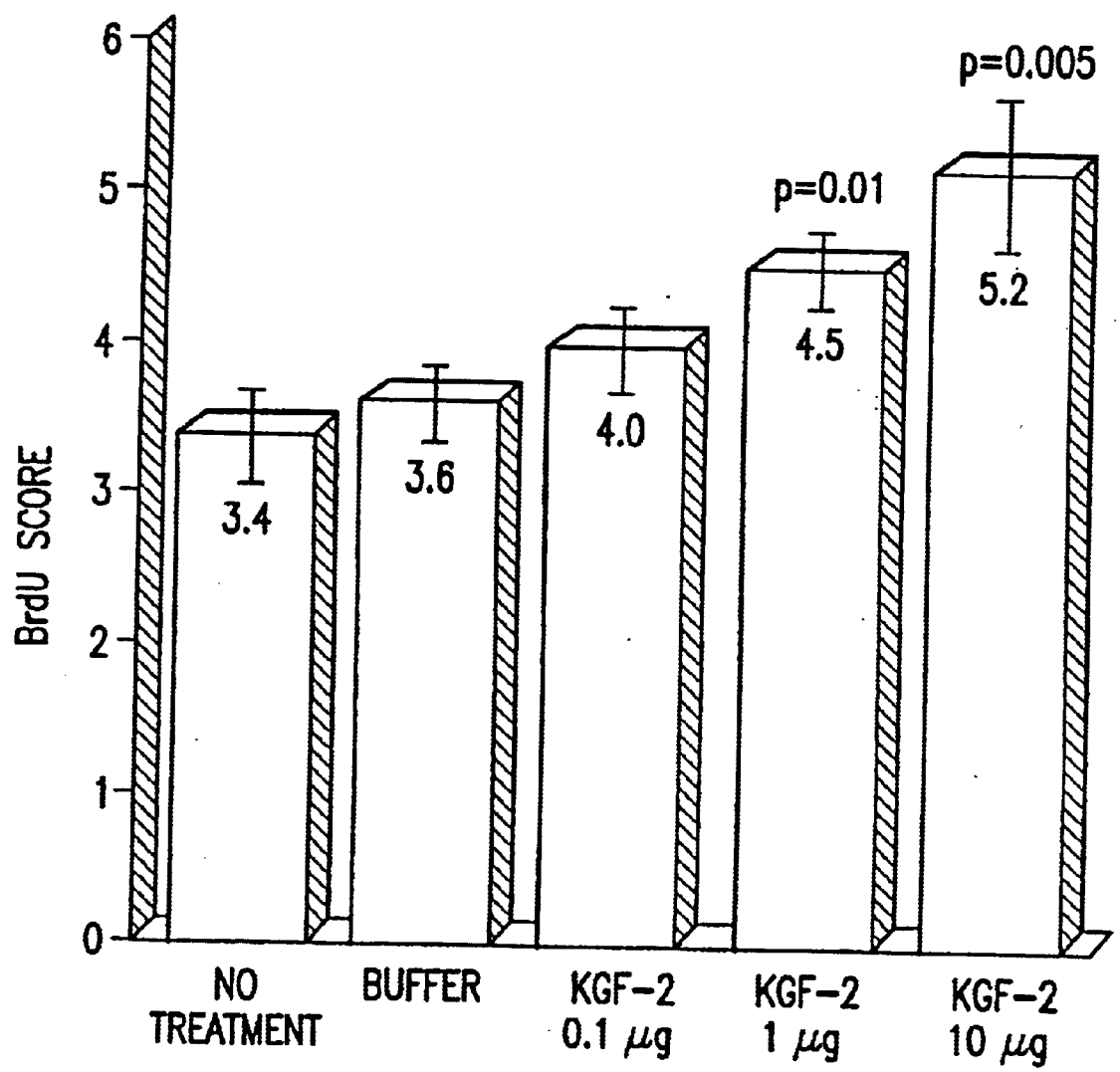
FIG. 48 shows the effect of KGF-2Δ33 on cell proliferation as determined using BrdU labeling.

We sought to determine if KGF-2 might induce proliferation of normal oral mucosal epithelium. The effect of KGF-2 in the oral mucosa was assessed in male Golden Syrian hamsters. The cheek pouch of the hamster was treated daily with buffer or KGF-2Δ3 3 (at 0.1, 1 and 10 μg/cheek) which were applied topically to anesthetized hamster cheeks in a volume of 100 μl per cheek. The compound was in contact with the cheek for a minimum of 60 seconds and subsequently swallowed. After 7 days of treatment, animals were injected with BrdU and sacrificed as described above. Proliferating cells were labeled using anti-BrdU antibody. FIG. 48 shows that there was a significant increase in BrdU labeling (cell proliferation) when animals were treated with 1 μg and 10 μg of KGF-2Δ33 (when compared to buffer treatment).

Topical treatment with KGF-2 induced the proliferation of normal mucosal epithelial cells. Based upon these results, KGF-2 may be clinically useful in the prevention of oral mucositis caused by any chemotherapeutic agents (or other toxic drug regimens), radiation therapy, or any combined chemotherapeutic-radiation therapy regimen. In addition, KGF-2 may be useful as a therapeutic agent by decreasing the severity of damage to the oral mucosa as a result of toxic agents (chemotherapy) or radiotherapy.

EXAMPLE 27

The Effect of KGF-2Δ33 on Ischemic Wound Healing in Rats

The aim of the experiments presented in this example was to determine the efficacy of KGF-2 in wound healing using an ischemic wound healing model.

The blood supply of local skin was partially interrupted by raising of a single pedicle full-thickness random myocutaneous flap (3×4 cm). A full-thickness wound was made into the local skin, which is composed of the myocutaneous flap. Sixty, adult Sprague-Dawley rats were used and randomly divided into treatments of KGF-2Δ33 and placebo groups for this study (5 animals/group/time-point). The wounds were harvested respectively at day 1, 3, 5, 7, 10 and 15 post-wounding.

The wound breaking strength did not show a significant difference between KGF-2 and buffer treated groups at early time points until day 10 and 15 post-wounding.

The results indicated that KGF-2 improved significantly the wound breaking strength in ischemic wound repair after 10 days post-wounding. These results also suggest that ischemia delays the healing process in both groups compared to the data previously obtained in studies of normal wound healing.

This myocutaneous flap model supplies data and information in an ischemic situation which results from venous return. These results suggest that KGF-2 could be used in the treatment of chronic venous leg ulcers caused by an impairment of venous return and/or insufficiency.

EXAMPLE 28

Evaluation of KGF-2 in the Healing of Colonic Anastomosis in Rats

The results of the present experiment demonstrate that KGF-2Δ33 increases the rate of intestinal repair in a model of intestinal or colonic anastomosis in Wistar or Sprague Dawley rats. In addition, this model can be used to demonstrate that KGF-2 and its isoforms increase the capability of the gastrointestinal or colon wall to bind sutures.

The use of the rat in experimental anastomosis is a well characterized, relevant and reproducible model of surgical wound healing. This model can also be extended to study the effects of chronic steroid treatment or the effects of various chemotherapeutic regimens on the quality and rate of surgical wound healing in the colon and small intestine (Mastboom, W. J. B. et al., Br. *J. Surg.* 78:54–56 (1991); Salm, R. et al., *J. Surg. Oncol.* 47:5–11 (1991); Weiber, S. et al., *Eur. Surg. Res.* 26:173–178 (1994)). Healing of anastomosis is similar to that of wound healing elsewhere in the body. The early phases of healing are characterized by acute inflammation followed by fibroblast proliferation and synthesis of collagen. Collagen is gradually modeled and the wound is strengthened as new collagen is synthesized (Koruda, M. J., and Rolandelli, R. H., *J. Surg. Res.* 48:504–515 (1990)). Most postoperative complications such as anastomotic leakage occur during the first few days following surgery—a period during which strength of the colon is mainly secured by the ability of the wound margin to hold sutures. The suture holding capacity of the GI tract has been reported to decrease by as much as 80% during the first postoperative days (Hogstrom, H. and Haglund, U., *Acta Chir. Scand.* 151:533–535 (1985); Jonsson, K. et al., *Am J. Surg.* 145:800–803 (1983)).

Rats were anesthetized with a combination of ketamine (50 mg/kg) and xylazine (5 mg/kg) intramuscularly. Animals were kept on a heating pad during skin disinfection, surgery, and post-surgery. The abdominal cavity was opened with a 4 cm long midline incision. A 1 cm wide segment of the left colon was resected 3 cm proximal to the peritoneal reflection while preserving the marginal blood vessels. A single layer end-to-end anastomosis was performed with 8-10 interrupted 8-0 propylene inverted sutures which were used to restore intestinal continuity. The incisional wound was closed with 3-O running silk suture for the muscle layer and surgical staples for the skin. Daily clinical evaluations were conducted on each animal consisting of individual body weight, body temperature, and food consumption patterns.

KGF-2Δ33 and placebo treatment were daily administered sc, topically, ip, im, intragastrically, or intracolonically immediately following surgery and were continued thereafter until the day of sacrifice, day 7. There was an untreated control, a placebo group, and KGF-2Δ33 groups. Two hours prior to euthanasia, animals were injected with 100 mg/kg BrdU i.p. Animals were euthanized 24 hours following the last treatment (day 5). A midline incision was made on the anterior abdominal wall and a 1 cm long colon segment, including the anastomosis, was removed. A third segment at the surgical site was taken for total collagen analysis.

Figure 49:
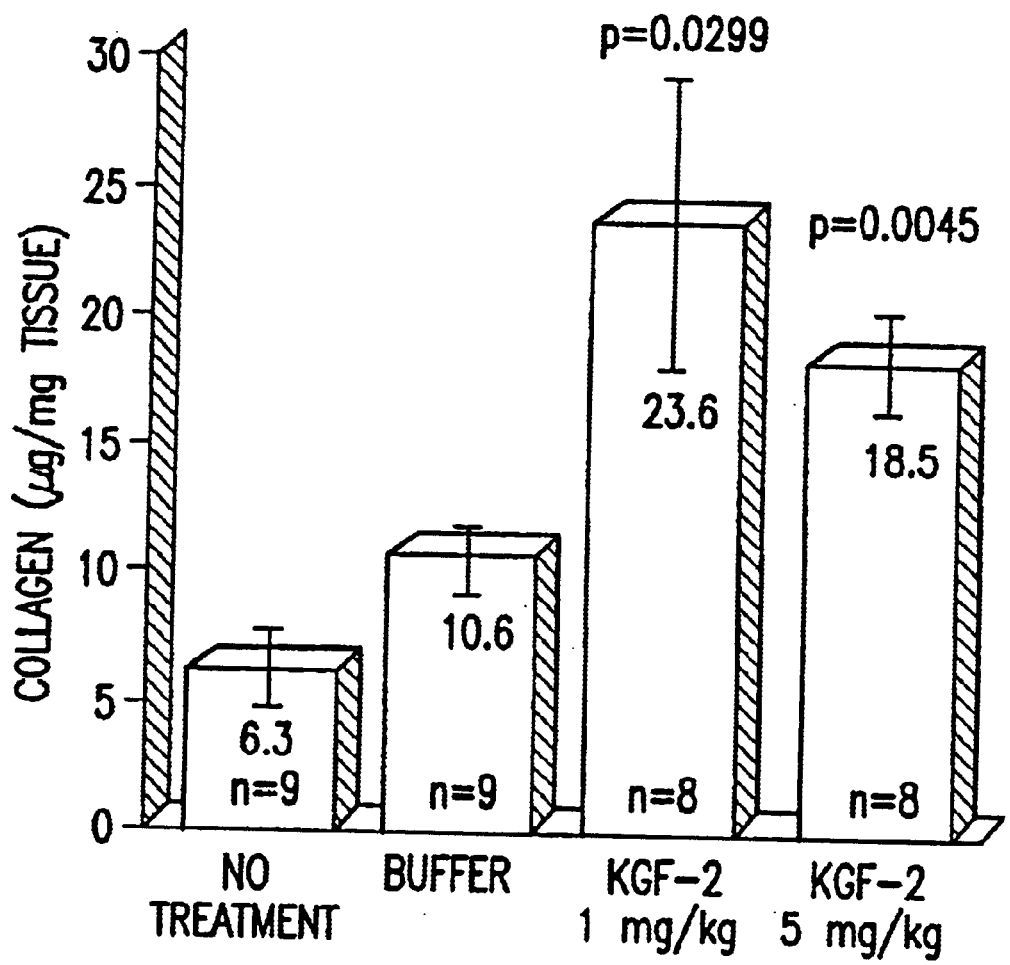
FIG. 49 shows the effect of KGF-2Δ33 on the collagen content localized at anastomotic surgical sites in the colons of rats.

In a series of two experiments, male adult SD rats (n=5) were anaesthetized and received a single layer end-to-end anastomosis of the distal colon with 8-10 interrupted 6-0 prolene inverted sutures. The anastomotic site was then topically treated via syringe with either buffer or KGF-2Δ33 at concentrations of 1 and 4 μg. Animals were then treated daily thereafter with either buffer or KGF-2Δ33 at concentrations of 1 mg/kg or 5 mg/kg ip. Animals were euthanized on day 5 and the colon excised and snap frozen in liquid nitrogen, lyophilized and subjected to collagen determinations. Collagen concentration is expressed as μg collagen/ mg dry weight tissue. Statistical analysis was done using an unpaired t test. Mean±SE. On day 5 rats were anesthetized and subjected to barium enemas followed by radiographic analysis. Barium enema radiologic assessment of end-to-end left colonic anastomosis from two experiments showed a consistent reduction in peritoneal leakage with KGF-2 treated animals at 1 and 5 mg/kg. This data is shown in the Table below. In addition, breaking strength at the site of surgery was also examined using a tensiometer. No significant differences were observed between the KGF-2Δ33 and buffer groups. As shown in FIG. 49, significant increases in collagen content at the surgical site were demonstrated at both 1 mg/kg KGF-2Δ33 (p=0.02) and 5 mg/kg (p=0.004) relative to buffer controls.

TABLE

| Groups | Colonic Anastomosis Radiologic Analysis | | |
|---|---|---|---|
| | Feces Present | Anastomotic Constriction* | Peritoneal Leakage |
| No Treatment (N = 8) | 50% | 2.0 | 75% |
| Buffer (N = 7) | 57% | 1.0 | 50% |
| KGF-2Δ33 [1 mg/kg] (N = 8) | 50% | 1.3 | 37% |
| KGF-2Δ33 [5 mg/kg] (N = 9) | 77% | 1.6 | 11% |

*Anastomotic Constriction Scoring: 0 -no constriction; 1–5 -minimal to severe constriction Male adult SD rats (n = 5) were anesthetized with a combination of ketamine (50 mg/kg) and xylazine (5 mg/kg) intramuscularly. The abdominal cavity was opened with a 4 cm long midline incision. A 1 cm wide segment of the left colon was resected 3 cm proximal to the peritoneal reflection while preserving the marginal vessels. A single layer end-to-end anastomosis was performed with 8–10 interrupted 6–0 prolene inverted sutures to restore intestinal, continuity. The anastomosis was then topically treated via syringe with either buffer or KGF-2 at concentrations of 1 and 4 μg. The incisional wound was closed with 3-O running silk suture for the muscle layer and surgical staples for the skin. Treatments were then administered daily thereafter and consisted of buffer or KGF-2 Δ33 at 1 and 5 mg/kg sc. Weights were taken on the day of surgery and daily thereafter. Animals were euthanized 24 hours following the last treatment (day 5). Animals were anesthetized and received barium enemas and were x-rayed at a fixed distance. The anastomosis was then excised for histopathological and biomechanical analysis.

EXAMPLE 29

Evaluation of KGF-2 in a Model of Inflammatory Bowel Disease

KGF-2 is a protein that induces keratinocyte proliferation in vitro and is active in a variety of wound healing models in vivo. The purpose of this study was to determine whether KGF-2 was efficacious in a model of murine colitis induced by ad libitum exposure to dextran sodium sulfate in the drinking water.

Six to eight week old female Swiss Webster mice (20–25 g, Charles River, Raleigh, N.C.)) were used in a model of inflammatory bowel disease induced with a 4% solution of sodium sulfate (DSS, 36,000–44,000 MW, American International Chemistry, Natick, Mass.)) administered ad libitum for one week. KGF-2 was given by daily parenteral administration (n=10). Three parameters were used to determine efficacy: 1) clinical score, based on evaluation of the stool; 2) histological score, based on evaluation of the colon; and 3) weight change. The clinical score was comprised of two parts totaling a maximum of score of four. Stool consistency was graded as: 0=firm; 1=loose; 2 diarrhea. Blood in the stool was also evaluated on a 0 to 2 scale with 0=no blood; 1=occult blood; and 2=gross rectal bleeding. A mean group score above 3 indicated probable lethality, and disease which had progressed beyond its treatable stage. Clinical scores were taken on Day 0, 4, 5, 6, and 7. To arrive at a histological score, slides of the ascending, transverse and descending colon were evaluated in a blinded fashion based on inflammation score (0–3) and crypt score (0–4). Body weight was measured daily. Data was expressed as mean+SEM. An unpaired Student's t test was used to determine significant differences compared to the disease control (* $p<0.05$;  $p<0.01$; * $p<0.001$).

When DSS-treated mice were given a daily, intraperitoneal (IP) injection of KGF-2Δ33 at a dose of 1, 5 or 10 mg/kg for 7 days, KGF-2 significantly reduced clinical score, 28, 38 and 50 percent, respectively. Histological evaluation closely paralleled the dose dependent inhibition of the clinical score, with the 1, 5 and 10 mg/kg dose reducing histological score a significant 26, 48 and 51 percent. KGF-2 also significantly reduced weight loss associated with DSS-induced colitis.

In a second study, a comparison was made of the relative efficacy of KGF-2Δ33 (10 mg/kg) when given IP or subcutaneous (SC) daily. By the end of the experiment on Day 7, animals injected IP with KGF-2 had a significant, 34 percent reduction in clinical score while KGF-2 injected SC resulted in a significant 46 percent reduction. The SC dose also significantly reduced weight loss over DSS controls. Based on measurement of clinical score and body weight, SC administration of KGF-2 is at least as efficacious as IP administration.

EXAMPLE 30

Effects of KGF-2Δ33 on Normal Urinary Bladder and Prostate and in Cyclophosphamide-Induced Hemorrhagic Cystitis in Rats The purpose of this example is to show that KGF-2Δ33 is capable of stimulating urinary bladder proliferation in normal rats and that there is a therapeutic effect of KGF-2Δ33 in a rat model of Cyclophosphamide-induced hemorrhagic cystitis.

Some cytotoxic agents used clinically have side effects resulting in the inhibition of the proliferation of the normal epithelium in the bladder, leading to potentially life-threatening ulceration and breakdown in the epithelial lining of the bladder. For example, cyclophosphamide causes hemorrhagic cystitis in some patients, a complication which can be severe and in some cases fatal. Fibrosis of the urinary bladder may also develop with or without cystitis. This injury is thought to be caused by cyclophosphamide metabolites excreted in the urine. Hematuria caused by cyclophosphamide usually is present for several days, but may persist. In severe cases medical or surgical treatment is required. Instances of severe hemorrhagic cystitis result in discontinued cyclophosphamide therapy. In addition, urinary bladder malignancies generally occur within two years of cyclophosphamide treatment and occurs in patients who previously had hemorrhagic cystitis (CYTOXAN (cyclophosphamide) package insert). Cyclophosphamide has toxic effects on the prostate and male reproductive systems. Cyclophosphamide treatment can result in the development of sterility, and result in some degree of testicular atrophy.

Effects of KGF-2 d33 on Normal Bladder, Testes and Prostate Experimental Design

Male Sprague-Dawley rats (160–220 g), (n=4 to 6/treatment group) were used in these studies. KGF-2Δ33 was administered at a dose of 5 mg/kg/day. Daily ip or sc injections of recombinant KGF-2Δ33 or buffer (40 mM sodium acetate+150 mM NaCl at pH 6.5) were administered for a period of 1–7 days and the rats were sacrificed the following day. To examine the reversibility of effects induced with KGF-2Δ33, additional animals were injected ip daily for 7 days with KGF-2Δ33 or buffer and sacrificed after a 7 day treatment-free period.

On the day of sacrifice, rats were injected ip with 100 mg/kg of BrdU. Two hours later the rats were overdosed with ether and selected organs removed. Samples of tissues were fixed in 10% neutral buffered formalin for 24 hours and paraffin embedded. To detect BrdU incorporation into replicating cells, five micron sections were subjected to immunohistochemical procedures using a mouse anti-BrdU monoclonal antibody and the ABC Elite detection system. The sections were lightly counterstained with hematoxylin.

Sections were read by blinded observers. The number of proliferating cells was counted in 10 random fields per animal at a 1×magnification for the prostate. To assess the effects of KGF-2Δ33 in the bladder, cross-sections of these tissues were prepared and the number of proliferating and non-proliferating cells were counted in ten random fields at 20×magnification. The results are expressed as the percentage of labeled to unlabeled cells. Data are presented as mean+SEM. Statistical analyses (two-tailed unpaired t-test) were performed with the StatView Software Package and statistical significance is defined as p<0.05.

Results

Bladder

Intraperitoneal injection of KGF-2Δ33 induced proliferation of bladder epithelial cells over the 7 day study period (solid squares, FIG. 52) but this did not influence the weight of the organ. Subcutaneous administration elicited a small increase in proliferation but this failed to achieve statistical significance (solid circles, FIG. 52).

Prostate and Testes

Both sc and ip administration of KGF-2Δ33 induced significant proliferation of the prostate (FIG. 53) but this normalized after two injections. Prolonged ip treatment with KGF-2Δ33 did not increase the weight of the prostate or testes.

Effects of KGF-2Δ33 on Cyclophosphamide-Induced Hemorrhagic Cystitis Experimental Design Male Sprague Dawley rats (300–400 g) (n=5/group) were injected i.v. via the tail vein with buffer placebo or KGF-2Δ33 at concentrations of 1 or 5 mg/kg 24 hours prior to a 200 mg/kg i.p. injection of cyclophosphamide. On the final day, 48 hours after cyclophosphamide injection, rats were injected ip with 100 mg/kg of BrdU. Two hours later the rats were killed by $CO_2$ administration. Fixation of the bladder was done by direct injection of 10% formalin into the lumen of the bladder and rinsing of the exterior of the bladder with formalin. After 5 minutes, the bladder and prostate were removed. The urinary bladder and prostate gland were paraffin embedded, cross-sectioned and stained with H&E and a mouse anti-BrdU monoclonal antibody. The extent of urothelial damage was assessed using the following scoring system: Bladders were graded by two independent observers to describe the extent of the loss of urothelium. (Urothelial damage was scored as 0, 25%, 50%, 75% and 100% loss of the urothelium). In addition, the thickness of the bladder wall was measured at 10 random sites per section and expressed in $\mu$m.

Results

Macroscopic Observations

In rats treated with placebo and cyclophosphamide, bladders were thick and rigid. Upon injection of 10% formalin, very little expansion of the bladders was noted. However, in the groups pretreated with KGF-2Δ33, a greater elasticity of the bladder was noted upon direct injection with formalin suggesting a lesser degree of fibrosis.

Microscopic Observations

Figure 54:
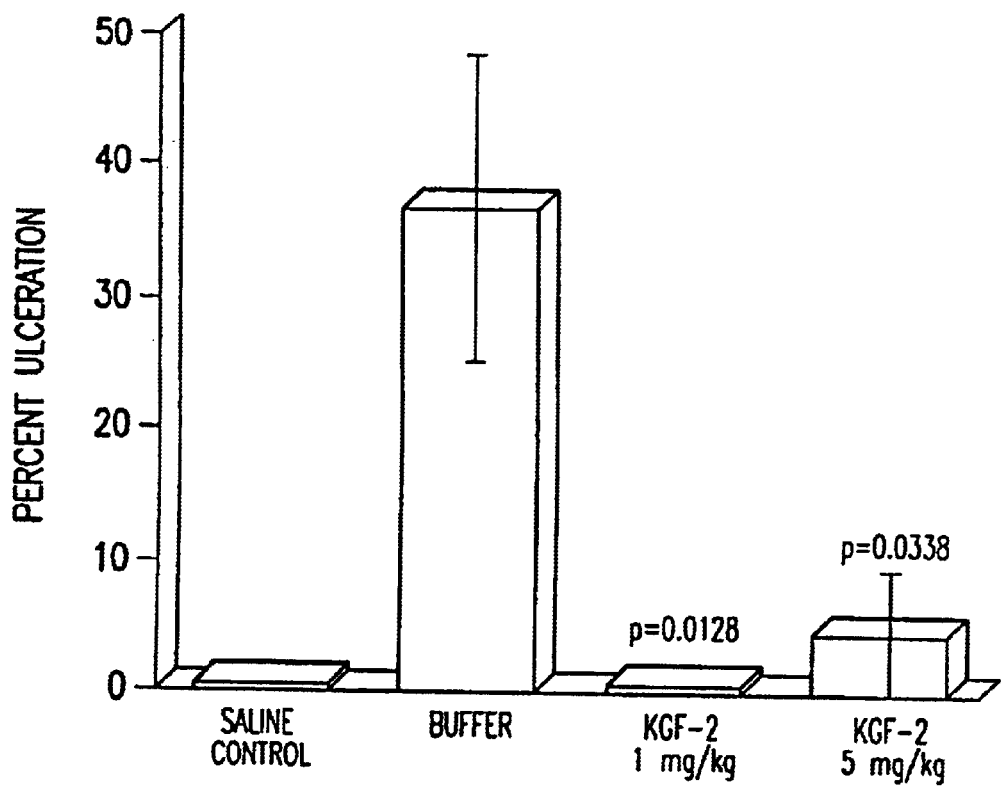
FIG. 54 shows the effect of KGF-2Δ33 on bladder wall ulceration in a cyclophosphamide-induced hemorrhagic cystitis model in the rat.

FIG. 54 shows the results of KGF-2Δ33 pretreatment on the extent of ulceration in the bladder. In normal rats treated with i.p. saline (saline control), the bladders appeared normal histologically and no ulceration of the urothelium was observed. Administration of 200 mg/kg i.p. of cyclophosphamide resulted in ulceration of the bladder epithelium that was between 25 and 50% of the total epithelial area (with a mean of 37%). Administration of KGF-2Δ33 24 hours prior to cyclophosphamide resulted in a significant reduction in the extent of ulceration (1 mg/kg 0.4% p=0.0128, and 5 mg/kg 5%, p=0.0338%) when compared to placebo treated animals receiving cyclophosphamide.

Figure 55:
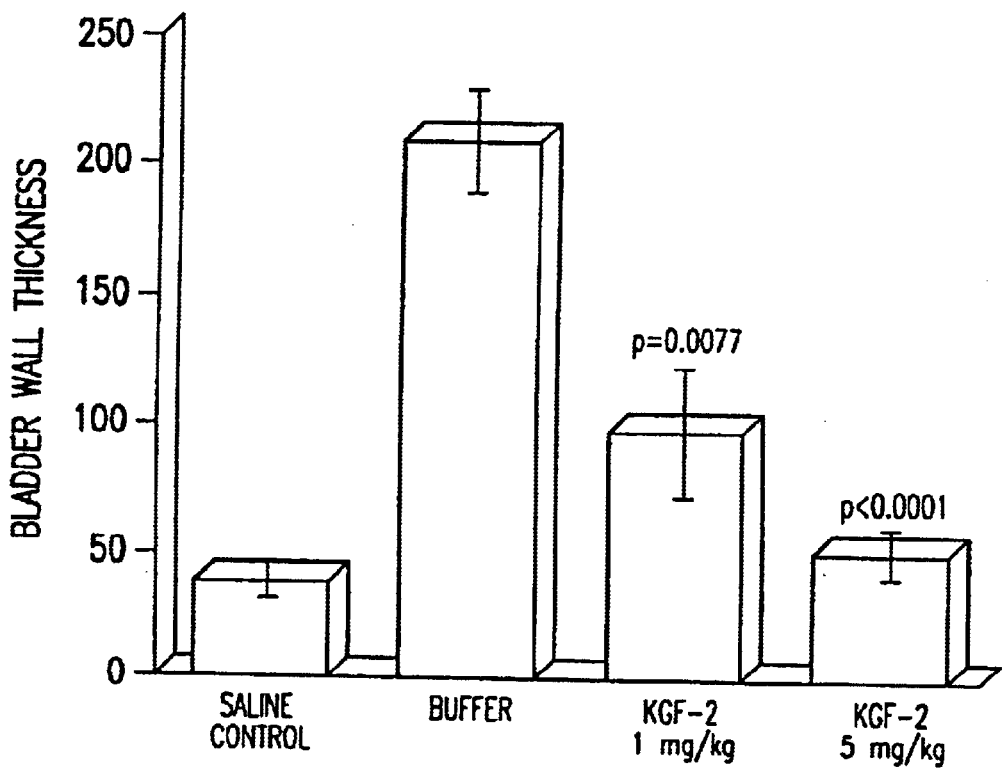
FIG. 55 shows the effect of KGF-2Δ33 on bladder wall thickness in a cyclophosphamide-induced cystitis rat model.

FIG. 55 shows the effects of KGF-2Δ33 on the thickness of the urinary bladder wall which includes epithelium, smooth muscle layers and the serosal surface. In groups treated with buffer alone, the thickness of the bladder wall is approximately 40 $\mu$m. Treatment with cyclophosphamide results in a 5 fold increase in bladder wall thickness to 210 $\mu$m. KGF-2Δ33 pretreatment of cyclophosphamide treated animals resulted in a significant inhibition of cyclophosphamide enlargement of the bladder wall (1 mg/kg 98.6 μm (p=0.007) and at 5 mg/kg 52.3 μm (p<0.0001)) when compared to the cyclophosphamide treatment alone.

Microscopic Observations

Prostate Gland: In rats receiving buffer and cyclophosphamide, marked atrophy of the prostatic glands (acini) was observed accompanied by enlargement of interstitial spaces with remarkable edema when compared to normals. In addition, epithelial cells lining the prostatic glands were observed to be much shorter and less dense than in corresponding normal prostatic tissue. KGF-2Δ33 pretreatment at both 1 mg/kg and 5 mg/kg displayed a normal histological appearance of the prostatic gland. No increase in the interstitial spaces or edema was observed, and the epithelial cells lining the prostatic glands were similar in size and density to normal prostatic tissue.

Conclusion

The results demonstrate that KGF-2 specifically induces proliferation of bladder epithelial cells and the epithelial cells lining the prostatic glands. The results also demostrate that KGF-2 specifically results in a significant reduction in the extent of ulceration in cyclophosphamide-induced hemorrhagic cystitis.

EXAMPLE 31

Effect of KGF-2 on the Proliferation of Cells in Normal Rats

Introduction

KGF-2, a member of the FGF family, induces proliferation of normal human and rat keratinocytes. It has approximately 57% homology to KGF-1 (a member of the FGF family). KGF-1 has been reported to induce proliferation of epithelia of many organs (Housley et al., Keratinocyte growth factor induces proliferation of hepatocytes and epithelial cells throughout the rat gastrointestinal tract. *J Clin Invest* 94: 1764–1777 (1994); Ulich et al., Keratinocyte growth factor is a growth factor for type II pneumocytes in vivo. *J Clin Invest* 9.3: 1298–1306 (1994); Ulich et al., Keratinocyte growth factor is a growth factor for mammary epithelium in vivo. The mammary epithelium of lactating rats is resistant to the proliferative action of keratinocyte growth factor. *Am J Pathol* 144:862–868 (1994); Nguyen et al., Expression of keratinocyte growth factor in embryonic liver of transgenic mice causes changes in epithelial growth and differentiation resulting in polycystic kidneys and other organ malformations. *Oncogene* 12:2109–2119 (1996); Yi et al., Keratinocyte growth factor induces pancreatic ductal epithelial proliferation. *Am J Pathol* 145:80–85 (1994); and Yi et al., Keratinocyte growth factor causes proliferation of urothelium in vitro. *J Urology* 154:1566–1570 (1995)). We performed similar experiments with KGF-2 to determine if it induces proliferation of normal epithelia in rats when administered systemically using sc and ip routes.

Methods

Male Sprague-Dawley rats, weighing 160–220 g, were obtained from Harlan Sprague Dawley for these studies. KGF-2Δ33 (HG03411-E2) was administered at a dose of 5 mg/kg/day. Daily ip or sc injections of KGF-2Δ33 or recombinant buffer (40 mM sodium acetate +150 mM NaCl at pH 6.5) were administered for a period of 1–7 days and the rats were sacrificed the following day (see below). To examine the reversibility of effects induced with KGF-2 Δ33, additional animals were injected ip daily for 7 days with KGF-2Δ33 or buffer and sacrificed after a 7 day treatment-free period.

On the day of sacrifice, rats were injected ip with 100 mg/kg of BrdU. Two hours later the rats were overdosed with ether and selected organs removed. Samples of tissues were fixed in 10% neutral buffered formalin for 24 hours and paraffin embedded. To detect BrdU incorporation into replicating cells, five micron sections were subjected to immunohistochemical procedures using a mouse anti-BrdU monoclonal antibody (Boehringer Mannheim) and the ABC Elite detection system (Vector Laboratories). The sections were lightly counterstained with hematoxylin.

Sections were read by blinded observers. The number of proliferating cells was counted in 10 random fields per animal at a 1×magnification for the following tissues: liver, pancreas, prostate, and heart. Ten random fields were used also for the lung analysis except the proliferation was quantitated at 20×magnification. Since the kidney has many functionally discrete areas, the proliferation was assessed in a coronal cross-section taken through the center of one kidney per animal. To assess the effects of KGF-2Δ33 in the esophagus and bladder, cross-sections of these tissues were prepared and the number of proliferating and non-proliferating cells were counted in ten random fields at a 10× and 20×magnification, respectively. The results are expressed as the percentage of labeled to unlabeled cells.

Data are presented as mean±SEM. Statistical analyses (two-tailed unpaired t-test) were performed with the StatView Software Package (Abacus Concepts, Inc., Berkeley, Calif.) and statistical significance is defined as p<0.05.

Results

Figure 56:
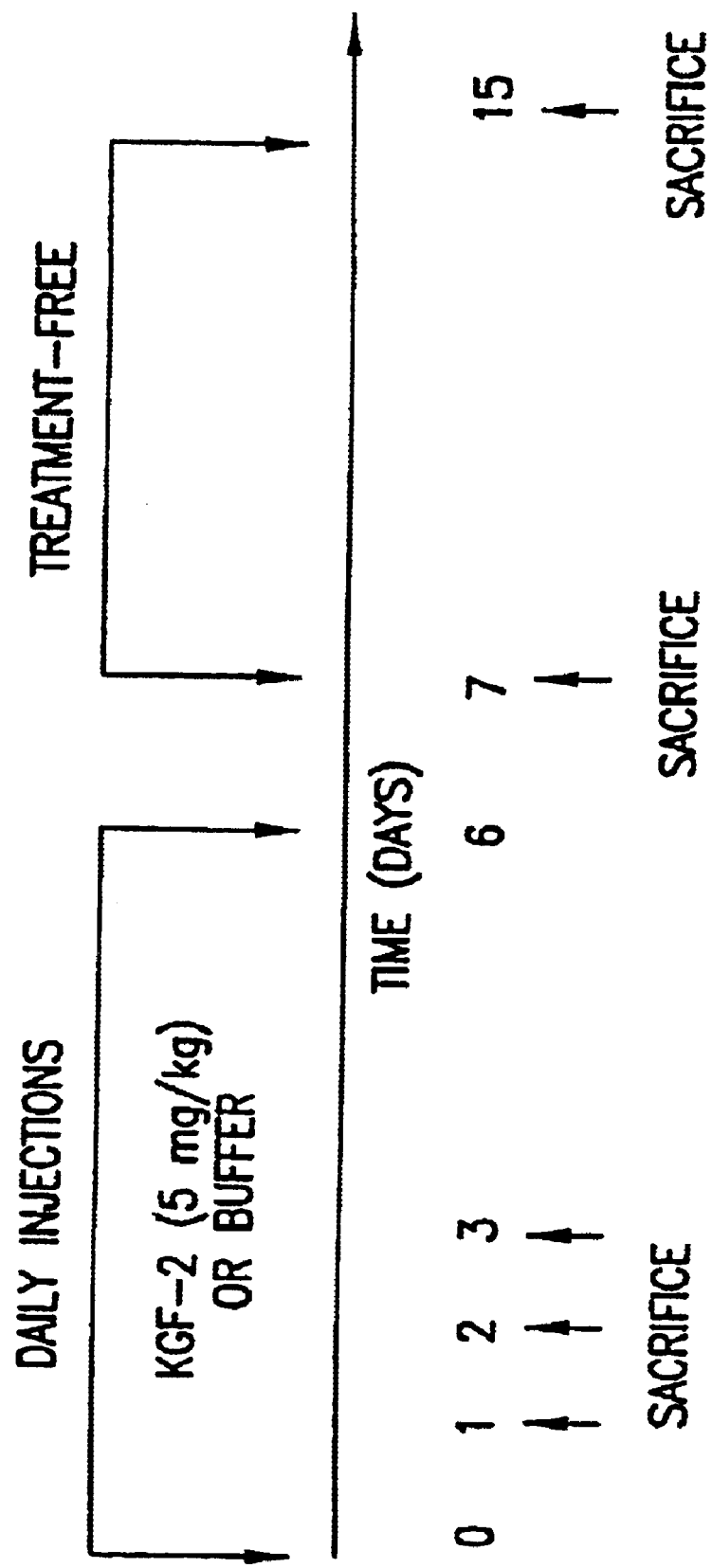
FIG. 56 provides an overview of the study design to determine whether KGF-2Δ33 induces proliferation of normal epithelia in rats when administered administered systemically using SC and IP routes.

FIG. 56 shows an overview of the experimental protocol. Six animals were used per group. However, during the analysis by the blinded observers it became clear that occasionally the BrdU injection was unsuccessful. Before the results were uncoded, the data from 8 rats out of 116 rats (or 7% of the animals) were excluded from the study and the resultant group sizes are shown in the Table below.

| Group sizes used in these studies | | | |
|---|---|---|---|
| | | n = | |
| Treatment | Time | ip | sc |
| KGF-2 Δ33 | 1 day | 6 | 5 |
| buffer | 1 day | 6 | 6 |
| KGF-2 Δ33 | 2 days | 6 | 4 |
| buffer | 2 days | 6 | 6 |
| KGF-2 Δ33 | 3 days | 5 | 5 |
| buffer | 3 days | 5 | 5 |
| KGF-2 Δ33 | 7 days | 6 | 6 |
| buffer | 7 days | 6 | 5 |
| KGF-2 Δ33 | 7 days + 7 days treatment-free | 6 | ND |
| buffer | 7 days + 7 days treatment-free | 6 | ND |

Figure 57:
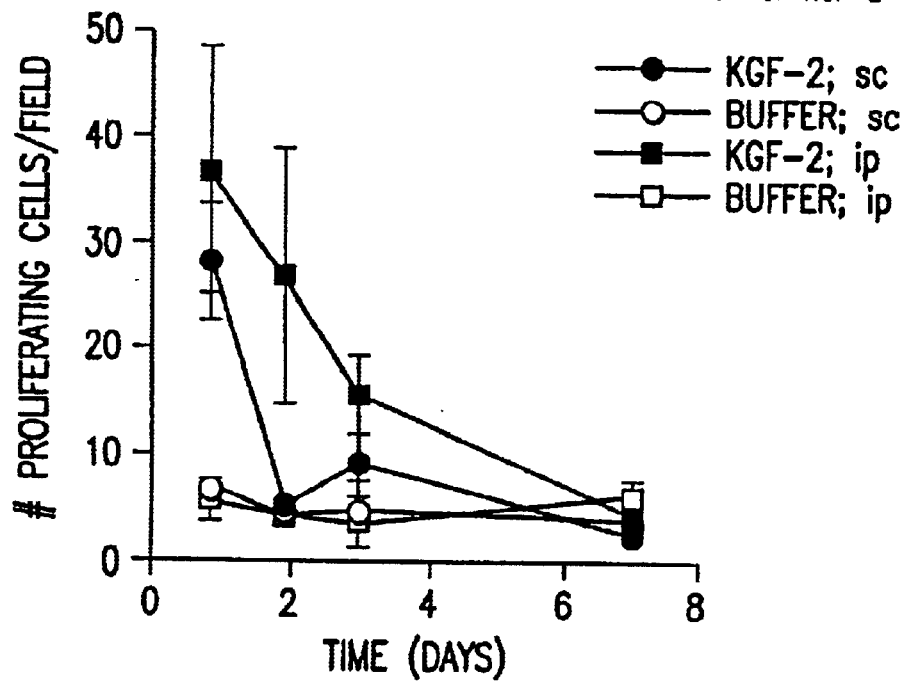
FIG. 57. Normal Sprague Dawley rats were injected daily with KGF-2 Δ33 (5 mg/kg; HG03411-E2) or buffer and sacrificed one day after the final injection. A blinded observer counted the proliferating cells in ten randomly chosen fields per animals at a 10× magnification. SC administration of KGF-2 Δ33 elicited a significant proliferation after one day which then returned to normal by 2 days. KGF-2Δ33 given ip stimulated proliferation from 1–3 days but only the results from days 1 and 3 were statistically significant.

Liver. When administered ip, KGF-2Δ33 induced a rapid proliferation of hepatocytes (solid squares) (FIG. 57) after 1 injection and this augmented mitotic activity persisted for three days, returning to normal after 7 days of daily injections. In contrast to the dramatic effect ip administration of KGF-2 exerted on the liver, when given sc (solid circle, FIG. 57) this growth factor demonstrated minor effects. Proliferation was elevated after one day of treatment but returned to normal values after two daily injections.

Figure 58:
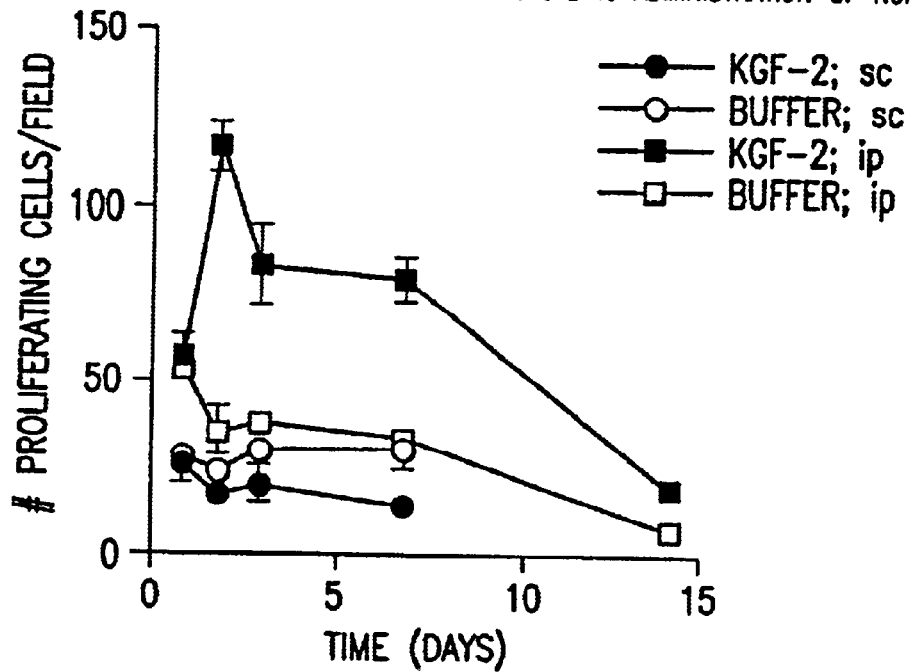
FIG. 58. Normal Sprague Dawley rats were injected daily with KGF-2 Δ33 (5 mg/kg; HG03411-E2) or buffer and sacrificed one day after the final injection. A blinded observer counted the proliferating cells in ten randomly chosen fields per animal at a 10× magnification. KGF-2Δ33 given ip stimulated proliferation over the entire study period while sc administration of KGF-2Δ33 did not increase the proliferation at any time point.

Pancreas. In contrast to the quickly reversible effects of ip administered KGF-2Δ33 on the liver, such injections induced proliferation of the pancreas which continued over the 14 day study period (solid squares, FIG. 58). Surprisingly, subcutaneous administration of KGF-2Δ33 (solid circles) failed to induce proliferation at any time point.

Figure 59:
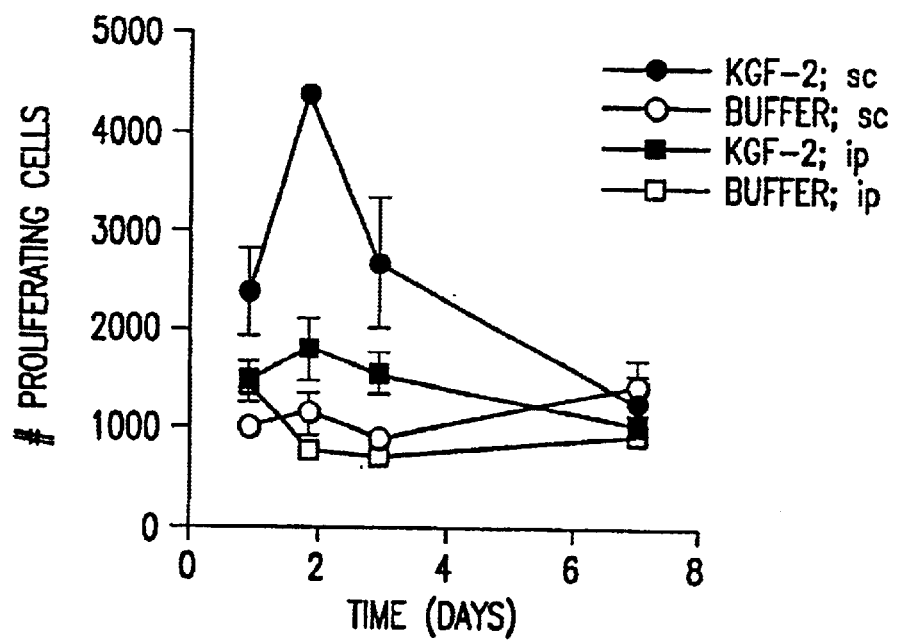
FIG. 59. Normal Sprague Dawley rats were injected daily with KGF-2 Δ33 (5 mg/kg; HG03411-E2) or buffer and sacrificed one day after the final injection. A blinded observer counted the proliferating cells in one cross-section per animal at a 10×magnification. KGF-2Δ33 given sc elicited a significant increase in proliferation after 1, 2, and 3 days of daily administration. When KGF-2Δ33 was given ip, proliferation was seen after 2 and 3 days only.

Kidney and Bladder. KGF-2Δ33 induced proliferation of renal epithelia when given either by the sc or ip route but the former induced a greater effect. SC administration induced a rapid increase in proliferation (solid circles) that peaked after 2 days which then returned to normal after 7 daily treatments (FIG. 59). When KGF-2Δ33 was given ip (solid squares), there was a modest, but significant increase in proliferation seen at days 2 and 3 only. Intraperitoneal injection of KGF-2Δ33 also induced proliferation of bladder epithelial cells over the 7 day study period (solid squares, FIG. 52). Subcutaneous administration elicited a small increase in proliferation but this failed to achieve statistical significance (solid circles, FIG. 52).

Prostate. Both sc and ip administration of KGF-2Δ33 induced significant proliferation of the prostate (FIG. 53) but this normalized after two injections.

Esophagus. KGF-2Δ33 given sc or ip elicited an early, short-lived increase in the proliferation of the esophageal cells (1 and 2 days, respectively) that rapidly returned to normal (results not shown).

Other organs. Systemic administration of KGF-2Δ33 by the ip and sc routes failed to elicit proliferation of the lung epithelia over a 7 day dosing period (results not shown).

Discussion

When administered in a sc route, we observed stimulation of normal epithelial proliferation in some organs (liver, kidney, esophagus. and prostate) but these effects, for the most part, were short-lived and all were reversible. The proliferation in these organs reversed even during daily sc administration of KGF-2.

The route of administration had dramatic effects on the observed proliferation. While daily ip administration increased the rate of liver proliferation over a 3 day period, animals given KGF-2 sc daily exhibited elevated rates after one day of treatment only. Even more surprising was the response of the pancreas. When animals were given KGF-2 ip, the pancreas exhibited a significantly elevated level of proliferation over the 14 day study period. However, sc administration of KGF-2 induced no increased mitotic activity in the pancreas. Likewise, ip, but not sc, treatment with K.GF-2 elicited proliferation of the bladder mucosa.

IP administration of KGF-2 elicited a short-lived, small burst of proliferation in the kidney that was centered in the region containing collecting ducts. Daily sc treatment induced a prolonged, exaggerated proliferation in this area.

EXAMPLE 32
Effects of KGF-2Δ33 on Lung Cellular Proliferation Following Intratracheal Administration The purpose of this example is to show that KGF-2Δ33 is capable of stimulating lung proliferation in normal rats following intratracheal administration (administration of KGF-2Δ33 directly to the lung).

Methods

Male Lewis rats (220–270 g), (n=5/treatment group) were used in these studies. KGF-2Δ33 or placebo (40 mM sodium acetate +150 mM NaCl at pH 6.5) was administered intratracheally at doses of 1 and 5 mg/kg in a volume of 0.6 mls followed by 3 mls of air. Treatments were administered on stay 1 and day 2 of the experimental protocol.

On day 3, the day of sacrifice, rats were injected ip with 100 mg/kg of BrdU. Two hours later the rats were killed by C02 asphyxiation. Lungs were inflated with 10% buffered formalin via intratracheal catheter, and saggital sections of lung were paraffin embedded. To detect BrdU incorporation into replicating cells, five micron sections were subjected to immunohistochemical procedures using a mouse anti-BrdU monoclonal antibody and the ABC Elite detection system. The sections were lightly counterstained with hematoxylin.

Sections were read by two blinded observers. The number of proliferating cells was counted in 10 random fields per section at a 20×magnification. The results are expressed as the number of BrdU positive cells per field. Data are presented as mean +SEM. Statistical analyses (unpaired t-test) were performed with the Instat v2.0.1 and statistical significance is defined as $p<0.05$.

Results

Figure 60:
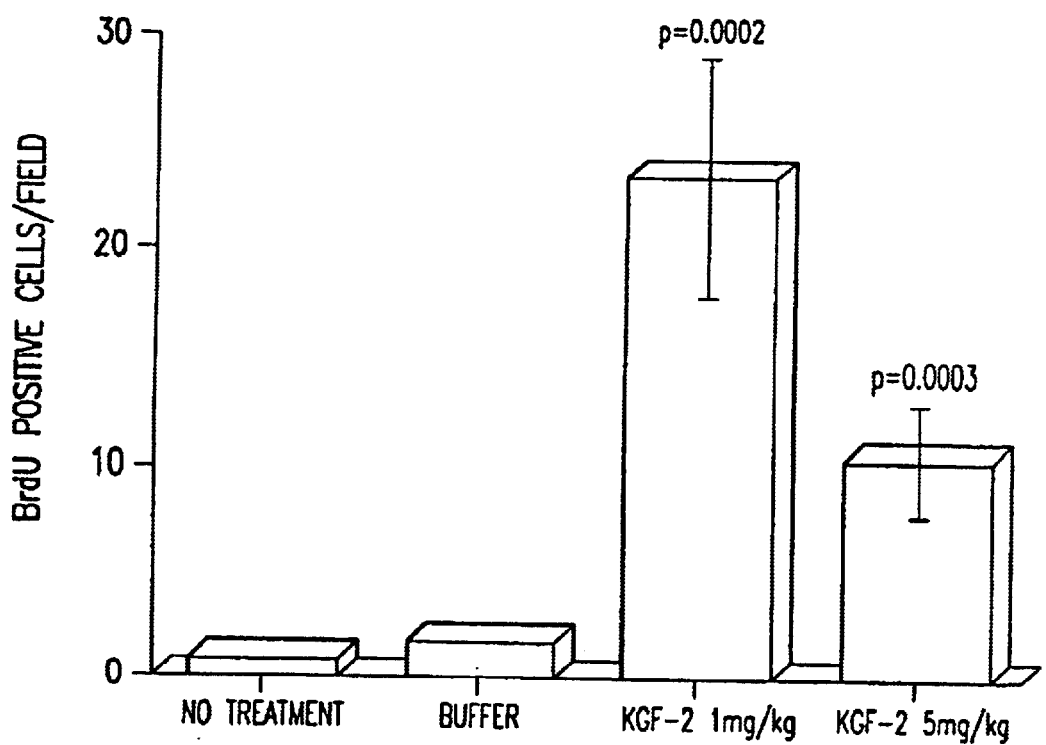
FIG. 60 demonstrates KGF-2Δ33 induced proliferation in normal rat lung.

Intratracheal injection of KGF-2Δ33 at 1 and 5 mg/kg resulted in an increase in proliferation of lung epithelial cells as shown in FIG. 60. KGF-2 Δ33 treatment resulted in statistically significant increases in the number of BrdU positive cells/field at 1 mg/kg 23.4 cells/field (p=0.0002) and at 5 mg/kg 10.3 cells/field (p0.0003) relative to buffer controls of 1.58 cells per field.

It will be clear that the invention may be practiced otherwise than as particularly described in the foregoing description and examples.

Numerous modifications and variations of the present invention are possible in light of the above teachings and, therefore, within the scope of the appended claims, the invention may be practiced otherwise than as particularly described.

The entire disclosure of all publications (including patents, patent applications, journal articles, laboratory manuals, books, or other documents) cited herein are hereby incorporated by reference.

SEQUENCE LISTING (1) GENERAL INFORMATION:

(iii) NUMBER OF SEQUENCES: 148

(2) INFORMATION FOR SEQ ID NO:1:

(i) SEQUENCE CHARACTERISTICS:
      (A) LENGTH: 627 base pairs
      (B) TYPE: nucleic acid
      (C) STRANDEDNESS: double
      (D) TOPOLOGY: both (ii) MOLECULE TYPE: DNA (genomic)

(ix) FEATURE:

(A) NAME/KEY: CDS
        (B) LOCATION: 1..624

(xi) SEQUENCE DESCRIPTION: SEQ ID NO:1:

ATG TGG AAA TGG ATA CTG ACA CAT TGT GCC TCA GCC TTT CCC CAC CTG    48
Met Trp Lys Trp Ile Leu Thr His Cys Ala Ser Ala Phe Pro His Leu
 1               5                  10                  15

CCC GGC TGC TGC TGC TGC TGC TTT TTG TTG CTG TTC TTG GTG TCT TCC    96
Pro Gly Cys Cys Cys Cys Cys Phe Leu Leu Leu Phe Leu Val Ser Ser
                20                  25                  30

GTC CCT GTC ACC TGC CAA GCC CTT GGT CAG GAC ATG GTG TCA CCA GAG   144
Val Pro Val Thr Cys Gln Ala Leu Gly Gln Asp Met Val Ser Pro Glu
            35                  40                  45

GCC ACC AAC TCT TCT TCC TCC TCC TTC TCC TCT CCT TCC AGC GCG GGA   192
Ala Thr Asn Ser Ser Ser Ser Ser Phe Ser Ser Pro Ser Ser Ala Gly
        50                  55                  60

AGG CAT GTG CGG AGC TAC AAT CAC CTT CAA GGA GAT GTC CGC TGG AGA   240
Arg His Val Arg Ser Tyr Asn His Leu Gln Gly Asp Val Arg Trp Arg
 65                  70                  75                  80

AAG CTA TTC TCT TTC ACC AAG TAC TTT CTC AAG ATT GAG AAG AAC GGG   288
Lys Leu Phe Ser Phe Thr Lys Tyr Phe Leu Lys Ile Glu Lys Asn Gly
                85                  90                  95

AAG GTC AGC GGG ACC AAG AAG GAG AAC TGC CCG TAC AGC ATC CTG GAG   336
Lys Val Ser Gly Thr Lys Lys Glu Asn Cys Pro Tyr Ser Ile Leu Glu
            100                 105                 110

ATA ACA TCA GTA GAA ATC GGA GTT GTT GCC GTC AAA GCC ATT AAC AGC   384
Ile Thr Ser Val Glu Ile Gly Val Val Ala Val Lys Ala Ile Asn Ser
        115                 120                 125

AAC TAT TAC TTA GCC ATG AAC AAG AAG GGG AAA CTC TAT GGC TCA AAA   432
Asn Tyr Tyr Leu Ala Met Asn Lys Lys Gly Lys Leu Tyr Gly Ser Lys
    130                 135                 140

GAA TTT AAC AAT GAC TGT AAG CTG AAG GAG AGG ATA GAG GAA AAT GGA   480
Glu Phe Asn Asn Asp Cys Lys Leu Lys Glu Arg Ile Glu Glu Asn Gly
145                 150                 155                 160

TAC AAT ACC TAT GCA TCA TTT AAC TGG CAG CAT AAT GGG AGG CAA ATG   528
Tyr Asn Thr Tyr Ala Ser Phe Asn Trp Gln His Asn Gly Arg Gln Met
                165                 170                 175

TAT GTG GCA TTG AAT GGA AAA GGA GCT CCA AGG AGA GGA CAG AAA ACA   576
Tyr Val Ala Leu Asn Gly Lys Gly Ala Pro Arg Arg Gly Gln Lys Thr
            180                 185                 190

CGA AGG AAA AAC ACC TCT GCT CAC TTT CTT CCA ATG GTG GTA CAC TCA   624
Arg Arg Lys Asn Thr Ser Ala His Phe Leu Pro Met Val Val His Ser
        195                 200                 205

TAG                                                               627

(2) INFORMATION FOR SEQ ID NO:2:

(i) SEQUENCE CHARACTERISTICS:
        (A) LENGTH: 208 amino acids
        (B) TYPE: amino acid
        (D) TOPOLOGY: linear (ii) MOLECULE TYPE: protein (xi) SEQUENCE DESCRIPTION: SEQ ID NO:2:

Met Trp Lys Trp Ile Leu Thr His Cys Ala Ser Ala Phe Pro His Leu
 1               5                  10                  15

Pro Gly Cys Cys Cys Cys Cys Phe Leu Leu Leu Phe Leu Val Ser Ser
                20                  25                  30

Val Pro Val Thr Cys Gln Ala Leu Gly Gln Asp Met Val Ser Pro Glu
            35                  40                  45

```
Ala Thr Asn Ser Ser Ser Ser Phe Ser Ser Pro Ser Ser Ala Gly
     50              55                  60

Arg His Val Arg Ser Tyr Asn His Leu Gln Gly Asp Val Arg Trp Arg
 65              70                  75                      80

Lys Leu Phe Ser Phe Thr Lys Tyr Phe Leu Lys Ile Glu Lys Asn Gly
                 85                  90                  95

Lys Val Ser Gly Thr Lys Lys Glu Asn Cys Pro Tyr Ser Ile Leu Glu
             100                 105                 110

Ile Thr Ser Val Glu Ile Gly Val Val Ala Val Lys Ala Ile Asn Ser
             115                 120                 125

Asn Tyr Tyr Leu Ala Met Asn Lys Lys Gly Lys Leu Tyr Gly Ser Lys
             130                 135             140

Glu Phe Asn Asn Asp Cys Lys Leu Lys Glu Arg Ile Glu Glu Asn Gly
145             150                 155                     160

Tyr Asn Thr Tyr Ala Ser Phe Asn Trp Gln His Asn Gly Arg Gln Met
             165                 170                 175

Tyr Val Ala Leu Asn Gly Lys Gly Ala Pro Arg Arg Gly Gln Lys Thr
             180                 185                 190

Arg Arg Lys Asn Thr Ser Ala His Phe Leu Pro Met Val Val His Ser
             195                 200                 205
```

(2) INFORMATION FOR SEQ ID NO:3:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

CCCCACATGT GGAAATGGAT ACTGACACAT TGTGCC                            36

(2) INFORMATION FOR SEQ ID NO:4:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

CCCAAGCTTC CACAAACGTT GCCTTCCTCT ATGAG                             35

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CATGCCATGG CGTGCCAAGC CCTTGGTCAG GACATG                            36

(2) INFORMATION FOR SEQ ID NO:6:

(i) SEQUENCE CHARACTERISTICS:
    (A) LENGTH: 35 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:6:

CCCAAGCTTC CACAAACGTT GCCTTCCTCT ATGAG                         35

(2) INFORMATION FOR SEQ ID NO:7:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

GCGGGATCCG CCATCATGTG GAAATGGATA CTCAC                         35

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GCGCGGTACC ACAAACGTTG CCTTCCT                                  27

(2) INFORMATION FOR SEQ ID NO:9:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

TAACGAGGAT CCGCCATCAT GTGGAAATGG ATACTGACAC                    40

(2) INFORMATION FOR SEQ ID NO:10:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

TAAGCACTCG AGTGAGTGTA CCACCATTGG AAGAAATG                      38

(2) INFORMATION FOR SEQ ID NO:11:

(i) SEQUENCE CHARACTERISTICS:
        (A) LENGTH: 54 base pairs
        (B) TYPE: nucleic acid
        (C) STRANDEDNESS: single -continued (D) TOPOLOGY: linear (ii) MOLECULE TYPE: cDNA (xi) SEQUENCE DESCRIPTION: SEQ ID NO:11:

ATTAACCCTC ACTAAAGGGA GGCCATGTGG AAATGGATAC TGACACATTG TGCC          54

(2) INFORMATION FOR SEQ ID NO:12:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

CCCAAGCTTC CACAAACGTT GCCTTCCTCT ATGAG                               35

(2) INFORMATION FOR SEQ ID NO:13:

(i) SEQUENCE CHARACTERISTICS:
        (A) LENGTH: 206 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:13:

Met Ser Gly Pro Gly Thr Ala Ala Val Ala Leu Leu Pro Ala Val Leu
 1               5                  10                  15

Leu Ala Leu Leu Ala Pro Trp Ala Gly Arg Gly Gly Ala Ala Ala Pro
                20                  25                  30

Thr Ala Pro Asn Gly Thr Leu Glu Ala Glu Leu Glu Arg Arg Trp Glu
            35                  40                  45

Ser Leu Val Ala Leu Ser Leu Ala Arg Leu Pro Val Ala Ala Gln Pro
    50                  55                  60

Lys Glu Ala Ala Val Gln Ser Gly Ala Gly Asp Tyr Leu Leu Gly Ile
65                  70                  75                  80

Lys Arg Leu Arg Arg Leu Tyr Cys Asn Val Gly Ile Gly Phe His Leu
                85                  90                  95

Gln Ala Leu Pro Asp Gly Arg Ile Gly Gly Ala His Ala Asp Thr Arg
            100                 105                 110

Asp Ser Leu Leu Glu Leu Ser Pro Val Glu Arg Gly Val Val Ser Ile
        115                 120                 125

Phe Gly Val Ala Ser Arg Phe Phe Val Ala Met Ser Ser Lys Gly Lys
    130                 135                 140

Leu Tyr Gly Ser Pro Phe Phe Thr Asp Glu Cys Thr Phe Lys Glu Ile
145                 150                 155                 160

Leu Leu Pro Asn Asn Tyr Asn Ala Tyr Glu Ser Tyr Lys Tyr Pro Gly
                165                 170                 175

Met Phe Ile Ala Leu Ser Lys Asn Gly Lys Thr Lys Lys Gly Asn Arg
            180                 185                 190

Val Ser Pro Thr Met Lys Val Thr His Phe Leu Pro Arg Leu
        195                 200                 205

(2) INFORMATION FOR SEQ ID NO:14:

(i) SEQUENCE CHARACTERISTICS:

```
      (A) LENGTH: 198 amino acids
      (B) TYPE: amino acid
      (C) STRANDEDNESS: Not Relevant
      (D) TOPOLOGY: Not Relevant (ii) MOLECULE TYPE: protein (xi) SEQUENCE DESCRIPTION: SEQ ID NO:14:

Met Ser Arg Gly Ala Gly Arg Leu Gln Gly Thr Leu Trp Ala Leu Val
1               5                  10                  15

Phe Leu Gly Ile Leu Val Gly Met Val Val Pro Ser Pro Ala Gly Thr
            20                  25                  30

Arg Ala Asn Asn Thr Leu Leu Asp Ser Arg Gly Trp Gly Thr Leu Leu
        35                  40                  45

Ser Arg Ser Arg Ala Gly Leu Ala Gly Glu Ile Ala Gly Val Asn Trp
    50                  55                  60

Glu Ser Gly Tyr Leu Val Gly Ile Lys Arg Gln Arg Leu Tyr Cys
65                  70                  75                  80

Asn Val Gly Ile Gly Phe His Leu Gln Val Leu Pro Asp Gly Arg Ile
                85                  90                  95

Ser Gly Thr His Glu Glu Asn Pro Tyr Ser Leu Leu Glu Ile Ser Thr
            100                 105                 110

Val Glu Arg Gly Val Val Ser Leu Phe Gly Val Arg Ser Ala Leu Phe
        115                 120                 125

Val Ala Met Asn Ser Lys Gly Arg Leu Tyr Ala Thr Pro Ser Phe Gln
130                 135                 140

Glu Glu Cys Lys Phe Arg Glu Thr Leu Leu Pro Asn Asn Tyr Asn Ala
145                 150                 155                 160

Tyr Glu Ser Asp Leu Tyr Gln Gly Thr Tyr Ile Ala Leu Ser Lys Tyr
                165                 170                 175

Gly Arg Val Lys Arg Gly Ser Lys Val Ser Pro Ile Met Thr Val Thr
            180                 185                 190

His Phe Leu Pro Arg Ile
            195

(2) INFORMATION FOR SEQ ID NO:15:

(i) SEQUENCE CHARACTERISTICS:
        (A) LENGTH: 268 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:15:

Met Ser Leu Ser Phe Leu Leu Leu Phe Ser His Leu Ile Leu
1               5                  10                  15

Ser Ala Trp Ala His Gly Glu Lys Arg Leu Ala Pro Lys Gly Gln Pro
            20                  25                  30

Gly Pro Ala Ala Thr Asp Arg Asn Pro Arg Gly Ser Ser Ser Arg Gln
        35                  40                  45

Ser Ser Ser Ser Ala Met Ser Ser Ser Ala Ser Ser Ser Pro Ala
    50                  55                  60

Ala Ser Leu Gly Ser Gln Gly Ser Gly Leu Glu Gln Ser Ser Phe Gln
65                  70                  75                  80

Trp Ser Pro Ser Gly Arg Arg Thr Gly Ser Leu Tyr Cys Arg Val Gly
                85                  90                  95
```

-continued

```
Ile Gly Phe His Leu Gln Ile Tyr Pro Asp Gly Lys Val Asn Gly Ser
            100                 105                 110

His Glu Ala Asn Met Leu Ser Val Leu Glu Ile Phe Ala Val Ser Gln
        115                 120                 125

Gly Ile Val Gly Ile Arg Gly Val Phe Ser Asn Lys Phe Leu Ala Met
    130                 135                 140

Ser Lys Lys Gly Lys Leu His Ala Ser Ala Lys Phe Thr Asp Asp Cys
145                 150                 155                 160

Lys Phe Arg Glu Arg Phe Gln Glu Asn Ser Tyr Asn Thr Tyr Ala Ser
                165                 170                 175

Ala Ile His Arg Thr Glu Lys Thr Gly Arg Glu Trp Tyr Val Ala Leu
            180                 185                 190

Asn Lys Arg Gly Lys Ala Lys Arg Gly Cys Ser Pro Arg Val Lys Pro
        195                 200                 205

Gln His Ile Ser Thr His Phe Leu Pro Arg Phe Lys Gln Ser Glu Gln
    210                 215                 220

Pro Glu Leu Ser Phe Thr Val Thr Val Pro Glu Lys Lys Asn Pro Pro
225                 230                 235                 240

Ser Pro Ile Lys Ser Lys Ile Pro Leu Ser Ala Pro Arg Lys Asn Thr
                245                 250                 255

Asn Ser Val Lys Tyr Arg Leu Lys Phe Arg Phe Gly
            260                 265
```

(2) INFORMATION FOR SEQ ID NO:16:

(i) SEQUENCE CHARACTERISTICS:
    (A) LENGTH: 155 amino acids
    (B) TYPE: amino acid
    (C) STRANDEDNESS: Not Relevant
    (D) TOPOLOGY: Not Relevant (ii) MOLECULE TYPE: protein (xi) SEQUENCE DESCRIPTION: SEQ ID NO:16:

```
Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

(2) INFORMATION FOR SEQ ID NO:17:

```
    (i) SEQUENCE CHARACTERISTICS:
        (A) LENGTH: 155 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:17:

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
50                  55                  60

Gln Ala Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
130                 135                 140

Ala Ile Leu Phe Leu Pro Met Ser Ala Lys Ser
145                 150                 155

(2) INFORMATION FOR SEQ ID NO:18:

(i) SEQUENCE CHARACTERISTICS:
        (A) LENGTH: 208 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:18:

Met Ala Pro Leu Gly Glu Val Gly Asn Tyr Phe Gly Val Gln Asp Ala
1               5                   10                  15

Val Pro Phe Gly Asn Val Pro Val Leu Pro Val Asp Ser Pro Val Leu
            20                  25                  30

Leu Ser Asp His Leu Gly Gln Ser Glu Ala Gly Gly Leu Pro Arg Gly
        35                  40                  45

Pro Ala Val Thr Asp Leu Asp His Leu Lys Gly Ile Leu Arg Arg Arg
50                  55                  60

Gln Leu Tyr Cys Arg Thr Gly Phe His Leu Glu Ile Phe Pro Asn Gly
65                  70                  75                  80

Thr Ile Gln Gly Thr Arg Lys Asp His Ser Arg Phe Gly Ile Leu Glu
            85                  90                  95

Phe Ile Ser Ile Ala Val Gly Leu Val Ser Ile Arg Gly Val Asp Ser
        100                 105                 110

Gly Leu Tyr Leu Gly Met Asn Glu Lys Gly Glu Leu Tyr Gly Ser Glu
        115                 120                 125

Lys Leu Thr Gln Glu Cys Val Phe Arg Glu Gln Phe Glu Glu Asn Trp
130                 135                 140
```

```
Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu Ser Gln Ser
            195                 200                 205
```

(2) INFORMATION FOR SEQ ID NO:19:

(i) SEQUENCE CHARACTERISTICS:
        (A) LENGTH: 194 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:19:

```
Met His Lys Trp Ile Leu Thr Trp Ile Leu Pro Thr Leu Leu Tyr Arg
1               5                   10                  15

Ser Cys Phe His Ile Ile Cys Leu Val Gly Thr Ile Ser Leu Ala Cys
                20                  25                  30

Asn Asp Met Thr Pro Glu Gln Met Ala Thr Asn Val Asn Cys Ser Ser
            35                  40                  45

Pro Glu Arg His Thr Arg Ser Tyr Asp Tyr Met Glu Gly Gly Asp Ile
    50                  55                  60

Arg Val Arg Arg Leu Phe Cys Arg Thr Gln Trp Tyr Leu Arg Ile Asp
65                  70                  75                  80

Lys Arg Gly Lys Val Lys Gly Thr Gln Glu Met Lys Asn Asn Tyr Asn
                85                  90                  95

Ile Met Glu Ile Arg Thr Val Ala Val Gly Ile Val Ala Ile Lys Gly
                100                 105                 110

Val Glu Ser Glu Phe Tyr Leu Ala Met Asn Lys Glu Gly Lys Leu Tyr
                115                 120                 125

Ala Lys Lys Glu Cys Asn Glu Asp Cys Asn Phe Lys Glu Leu Ile Leu
            130                 135                 140

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
                165                 170                 175

Lys Lys Thr Lys Lys Glu Gln Lys Thr Ala His Phe Leu Pro Met Ala
            180                 185                 190

Ile Thr
```

(2) INFORMATION FOR SEQ ID NO:20:

(i) SEQUENCE CHARACTERISTICS:
        (A) LENGTH: 208 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:20:

```
Met Trp Lys Trp Ile Leu Thr His Cys Ala Ser Ala Phe Pro His Leu
1               5                   10                  15
```

```
Pro Gly Cys Cys Cys Cys Phe Leu Leu Leu Phe Leu Val Ser Ser
            20                  25                  30

Val Pro Val Thr Cys Gln Ala Leu Gly Gln Asp Met Val Ser Pro Glu
            35                  40                  45

Ala Thr Asn Ser Ser Ser Ser Phe Ser Ser Pro Ser Ser Ala Gly
    50                  55                  60

Arg His Val Arg Ser Tyr Asn His Leu Gln Gly Asp Val Arg Trp Arg
65                  70                  75                  80

Lys Leu Phe Ser Phe Thr Lys Tyr Phe Leu Lys Ile Glu Lys Asn Gly
                85                  90                  95

Lys Val Ser Gly Thr Lys Lys Glu Asn Cys Pro Tyr Ser Ile Leu Glu
                100                 105                 110

Ile Thr Ser Val Glu Ile Gly Val Val Ala Val Lys Ala Ile Asn Ser
            115                 120                 125

Asn Tyr Tyr Leu Ala Met Asn Lys Lys Gly Lys Leu Tyr Gly Ser Lys
    130                 135                 140

Glu Phe Asn Asn Asp Cys Lys Leu Lys Glu Arg Ile Glu Glu Asn Gly
145                 150                 155                 160

Tyr Asn Thr Tyr Ala Ser Phe Asn Trp Gln His Asn Gly Arg Gln Met
                165                 170                 175

Tyr Val Ala Leu Asn Gly Lys Gly Ala Pro Arg Arg Gly Gln Lys Thr
                180                 185                 190

Arg Arg Lys Asn Thr Ser Ala His Phe Leu Pro Met Val Val His Ser
                195                 200                 205
```

(2) INFORMATION FOR SEQ ID NO:21:

(i) SEQUENCE CHARACTERISTICS:
        (A) LENGTH: 239 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:21:

```
Met Gly Leu Ile Trp Leu Leu Leu Ser Leu Leu Glu Pro Gly Trp
1               5                   10                  15

Pro Ala Ala Gly Pro Gly Ala Arg Leu Arg Arg Asp Ala Gly Gly Arg
                20                  25                  30

Gly Gly Val Tyr Glu His Leu Gly Gly Ala Pro Arg Arg Arg Lys Leu
            35                  40                  45

Tyr Cys Ala Thr Lys Tyr His Leu Gln Leu His Pro Ser Gly Arg Val
    50                  55                  60

Asn Gly Ser Leu Glu Asn Ser Ala Tyr Ser Ile Leu Glu Ile Thr Ala
65                  70                  75                  80

Val Glu Val Gly Ile Val Ala Ile Arg Gly Leu Phe Ser Gly Arg Tyr
                85                  90                  95

Leu Ala Met Asn Lys Arg Gly Arg Leu Tyr Ala Ser Glu His Tyr Ser
                100                 105                 110

Ala Glu Cys Glu Phe Val Glu Arg Ile His Glu Leu Gly Tyr Asn Thr
            115                 120                 125

Tyr Ala Ser Arg Leu Tyr Arg Thr Val Ser Ser Thr Pro Gly Ala Arg
    130                 135                 140

Arg Gln Pro Ser Ala Glu Arg Leu Trp Tyr Val Ser Val Asn Gly Lys
145                 150                 155                 160
```

```
Gly Arg Pro Arg Arg Gly Phe Lys Thr Arg Thr Gln Lys Ser Ser
                165                 170                 175

Leu Phe Leu Pro Arg Val Leu Asp His Arg Asp His Glu Met Val Arg
                180                 185                 190

Gln Leu Gln Ser Gly Leu Pro Arg Pro Gly Lys Gly Val Gln Pro
            195                 200                 205

Arg Arg Arg Arg Gln Lys Gln Ser Pro Asp Asn Leu Glu Pro Ser His
        210                 215                 220

Val Gln Ala Ser Arg Leu Gly Ser Gln Leu Glu Ala Ser Ala His
225                 230                 235
```

(2) INFORMATION FOR SEQ ID NO:22:

(i) SEQUENCE CHARACTERISTICS:
        (A) LENGTH: 268 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:22:

```
Met Gly Ser Pro Arg Ser Ala Leu Ser Cys Leu Leu Leu His Leu Leu
1               5                   10                  15

Val Leu Cys Leu Gln Ala Gln Val Arg Ser Ala Ala Gln Lys Arg Gly
                20                  25                  30

Pro Gly Ala Gly Asn Pro Ala Asp Thr Leu Gly Gln Gly His Glu Asp
            35                  40                  45

Arg Pro Phe Gly Gln Arg Ser Arg Ala Gly Lys Asn Phe Thr Asn Pro
50                  55                  60

Ala Pro Asn Tyr Pro Glu Glu Gly Ser Lys Glu Gln Arg Asp Ser Val
65                  70                  75                  80

Leu Pro Lys Val Thr Gln Arg His Val Arg Glu Gln Ser Leu Val Thr
                85                  90                  95

Asp Gln Leu Ser Arg Arg Leu Ile Arg Thr Tyr Gln Leu Tyr Ser Arg
                100                 105                 110

Thr Ser Gly Lys His Val Gln Val Leu Ala Asn Lys Arg Ile Asn Ala
            115                 120                 125

Met Ala Glu Asp Gly Asp Pro Phe Ala Lys Leu Ile Val Glu Thr Asp
130                 135                 140

Thr Phe Gly Ser Arg Val Arg Val Arg Gly Ala Glu Thr Gly Leu Tyr
145                 150                 155                 160

Ile Cys Met Asn Lys Lys Gly Lys Leu Ile Ala Lys Ser Asn Gly Lys
                165                 170                 175

Gly Lys Asp Cys Val Phe Thr Glu Ile Val Leu Glu Asn Asn Tyr Thr
            180                 185                 190

Ala Leu Gln Asn Ala Lys Tyr Glu Gly Trp Tyr Met Ala Phe Thr Arg
        195                 200                 205

Lys Gly Arg Pro Arg Lys Gly Ser Lys Thr Arg Gln His Gln Arg Glu
210                 215                 220

Val His Phe Met Lys Arg Leu Pro Arg Gly His His Thr Thr Glu Gln
225                 230                 235                 240

Ser Leu Arg Phe Glu Phe Leu Asn Tyr Pro Pro Phe Thr Arg Ser Leu
                245                 250                 255

Arg Gly Ser Gln Arg Thr Trp Ala Pro Glu Pro Arg
            260                 265
```

-continued (2) INFORMATION FOR SEQ ID NO:23:

(i) SEQUENCE CHARACTERISTICS:
        (A) LENGTH: 4177 base pairs
        (B) TYPE: nucleic acid
        (C) STRANDEDNESS: double
        (D) TOPOLOGY: both (ii) MOLECULE TYPE: DNA (genomic)

(ix) FEATURE:
        (A) NAME/KEY: CDS
        (B) LOCATION: 593..1216

(xi) SEQUENCE DESCRIPTION: SEQ ID NO:23:

```
GGAATTCCGG GAAGAGAGGG AAGAAAACAA CGGCGACTGG GCAGCTGCCT CCACTTCTGA    60

CAACTCCAAA GGGATATACT TGTAGAAGTG GCTCGCAGGC TGGGGCTCCG CAGAGAGAGA   120

CCAGAAGGTG CCAACCGCAG AGGGGTGCAG ATATCTCCCC CTATTCCCCA CCCCACCTCC   180

CTTGGGTTTT GTTCACCGTG CTGTCATCTG TTTTTCAGAC CTTTTTGGCA TCTAACATGG   240

TGAAGAAAGG AGTAAAGAAG AGAACAAAGT AACTCCTGGG GGAGCGAAGA GCGCTGGTGA   300

CCAACACCAC CAACGCCACC ACCAGCTCCT GCTGCTGCGG CCACCCACGT CCACCATTTA   360

CCGGGAGGCT CCAGAGGCGT AGGCAGCGGA TCCGAGAAAG GAGCGAGGGG AGTCAGCCGG   420

CTTTTCCGAG GAGTTATGGA TGTTGGTGCA TTCACTTCTG GCCAGATCCG CGCCCAGAGG   480

GAGCTAACCA GCAGCCACCA CCTCGAGCTC TCTCCTTGCC TTGCATCGGG TCTTACCCTT   540

CCAGTATGTT CCTTCTGATG AGACAATTTC CAGTGCCGAG AGTTTCAGTA CA ATG       595
                                                          Met
                                                            1
```

```
TGG AAA TGG ATA CTG ACA CAT TGT GCC TCA GCC TTT CCC CAC CTG CCC     643
Trp Lys Trp Ile Leu Thr His Cys Ala Ser Ala Phe Pro His Leu Pro
          5                  10                  15

GGC TGC TGC TGC TGC TGC TTT TTG TTG CTG TTC TTG GTG TCT TCC GTC     691
Gly Cys Cys Cys Cys Cys Phe Leu Leu Leu Phe Leu Val Ser Ser Val
         20                  25                  30

CCT GTC ACC TGC CAA GCC CTT GGT CAG GAC ATG GTG TCA CCA GAG GCC     739
Pro Val Thr Cys Gln Ala Leu Gly Gln Asp Met Val Ser Pro Glu Ala
     35                  40                  45

ACC AAC TCT TCT TCC TCC TCC TTC TCC TCT CCT TCC AGC GCG GGA AGG     787
Thr Asn Ser Ser Ser Ser Ser Phe Ser Ser Pro Ser Ser Ala Gly Arg
 50                  55                  60                  65

CAT GTG CGG AGC TAC AAT CAC CTT CAA GGA GAT GTC CGC TGG AGA AAG     835
His Val Arg Ser Tyr Asn His Leu Gln Gly Asp Val Arg Trp Arg Lys
                 70                  75                  80

CTA TTC TCT TTC ACC AAG TAC TTT CTC AAG ATT GAG AAG AAC GGG AAG     883
Leu Phe Ser Phe Thr Lys Tyr Phe Leu Lys Ile Glu Lys Asn Gly Lys
             85                  90                  95

GTC AGC GGG ACC AAG AAG GAG AAC TGC CCG TAC AGC ATC CTG GAG ATA     931
Val Ser Gly Thr Lys Lys Glu Asn Cys Pro Tyr Ser Ile Leu Glu Ile
         100                 105                 110

ACA TCA GTA GAA ATC GGA GTT GTT GCC GTC AAA GCC ATT AAC AGC AAC     979
Thr Ser Val Glu Ile Gly Val Val Ala Val Lys Ala Ile Asn Ser Asn
     115                 120                 125

TAT TAC TTA GCC ATG AAC AAG AAG GGG AAA CTC TAT GGC TCA AAA GAA    1027
Tyr Tyr Leu Ala Met Asn Lys Lys Gly Lys Leu Tyr Gly Ser Lys Glu
130                 135                 140                 145

TTT AAC AAT GAC TGT AAG CTG AAG GAG AGG ATA GAG GAA AAT GGA TAC    1075
```

```
              Phe Asn Asn Asp Cys Lys Leu Lys Glu Arg Ile Glu Glu Asn Gly Tyr
                              150                 155                 160

AAT ACC TAT GCA TCA TTT AAC TGG CAG CAT AAT GGG AGG CAA ATG TAT           1123
Asn Thr Tyr Ala Ser Phe Asn Trp Gln His Asn Gly Arg Gln Met Tyr
            165                 170                 175

GTG GCA TTG AAT GGA AAA GGA GCT CCA AGG AGA GGA CAG AAA ACA CGA           1171
Val Ala Leu Asn Gly Lys Gly Ala Pro Arg Arg Gly Gln Lys Thr Arg
        180                 185                 190

AGG AAA AAC ACC TCT GCT CAC TTT CTT CCA ATG GTG GTA CAC TCA               1216
Arg Lys Asn Thr Ser Ala His Phe Leu Pro Met Val Val His Ser
    195                 200                 205

TAGAGGAAGG CAACGTTTGT GGATGCAGTA AAACCAATGG CTCTTTTGCC AAGAATAGTG         1276

GATATTCTTC ATGAAGACAG TAGATTGAAA GGCAAAGACA CGTTGCAGAT GTCTGCTTGC         1336

TTAAAAGAAA GCCAGCCTTT GAAGGTTTTT GTATTCACTG CTGACATATG ATGTTCTTTT         1396

AATTAGTTCT GTGTCATGTC TTATAATCAA GATATAGGCA GATCGAATGG GATAGAAGTT         1456

ATTCCCAAGT GAAAACATT GTGGCTGGGT TTTTTGTTGT TGTTGTCAAG TTTTTGTTTT          1516

TAAACCTCTG AGATAGAACT TAAAGGACAT AGAACAATCT GTTGAAAGAA CGATCTTCGG         1576

GAAAGTTATT TATGGAATAC GAACTCATAT CAAAGACTTC ATTGCTCATT CAAGCCTAAT        1636

GAATCAATGA ACAGTAATAC GTGCAAGCAT TTACTGGAAA GCACTTGGGT CATATCATAT        1696

GCACAACCAA AGGAGTTCTG GATGTGGTCT CATGGAATAA TTGAATAGAA TTTAAAAATA        1756

TAAACATGTT AGTGTGAAAC TGTTCTAACA ATACAAATAG TATGGTATGC TTGTGCATTC        1816

TGCCTTCATC CCTTTCTATT TCTTTCTAAG TTATTTATTT AATAGGATGT AAATATCTT         1876

TTGGGGTTTT AAAGAGTATC TCAGCAGCTG TCTTCTGATT TATCTTTTCT TTTTATTCAG        1936

CACACCACAT GCATGTTCAC GACAAAGTGT TTTTAAAACT TGGCGAACAC TTCAAAAATA        1996

GGAGTTGGGA TTAGGGAAGC AGTATGAGTG CCCGTGTGCT ATCAGTTGAC TTAATTTGCA        2056

CTTCTGCAGT AATAACCATC AACAATAAAT ATGGCAATGC TGTGCCATGG CTTGAGTGAG       2116

AGATGTCTGC TATCATTTGA AAACATATAT TACTCTCGAG GCTTCCTGTC TCAAGAAATA        2176

GACCAGAAGG CCAAATTCTT CTCTTTCAAT ACATCAGTTT GCCTCCAAGA ATATACTAAA        2236

AAAAGGAAAA TTAATTGCTA AATACATTTA AATAGCCTAG CCTCATTATT TACTCATGAT        2296

TTCTTGCCAA ATGTCATGGC GGTAAAGAGG CTGTCCACAT CTCTAAAAAC CCTCTGTAAA       2356

TTCCACATAA TGCATCTTTC CCAAAGGAAC TATAAAGAAT TTGGTATGAA GCGCAACTCT        2416

CCCAGGGGCT TAAACTGAGC AAATCAAATA TATACTGGTA TATGTGTAAC CATATACAAA        2476

AACCTGTTCT AGCTGTATGA TCTAGTCTTT ACAAAACCAA ATAAAACTTG TTTTCTGTAA       2536

ATTTAAAGAG CTTTACAAGG TTCCATAATG TAACCATATC AAAATTCATT TTGTTAGAGC       2596

ACGTATAGAA AAGAGTACAT AAGAGTTTAC CAATCATCAT CACATTGTAT TCCACTAAAT       2656

AAATACATAA GCCTTATTTG CAGTGTCTGT AGTGATTTTA AAAATGTAGA AAATACTAT         2716

TTGTTCTAAA TACTTTTAAG CAATAACTAT AATAGTATAT TGATGCTGCA GTTTTATCTT       2776

CATATTTCTT GTTTTGAAAA AGCATTTTAT TGTTTGGACA CAGTATTTTG GTACAAAAAA      2836

AAAGACTCAC TAAATGTGTC TTACTAAAGT TTAACCTTTG GAAATGCTGG CGTTCTGTGA      2896

TTCTCCAACA AACTTATTTG TGTCAATACT TAACCAGCAC TTCCAGTTAA TCTGTTATTT     2956

TTAAAAATTG CTTTATTAAG AAATTTTTTG TATAATCCCA TAAAAGGTCA TATTTTTCCC      3016

ATTCTTCAAA AAAACTGTAT TTCAGAAGAA ACACATTTGA GGCACTGTCT TTTGGCTTAT      3076

AGTTTAAATT GCATTTCATC ATACTTTGCT TCCAACTTGC TTTTTGGCAA ATGAGATTAT      3136
```

| | | | | |
|---|---|---|---|---|
| AAAAATGTTT | AATTTTTGTG | GTTGGAATCT | GGATGTTAAA | ATTTAATTGG TAACTCAGTC | 3196 |
| TGTGAGCTAT | AATGTAATGC | ATTCCTATCC | AAACTAGGTA | TCTTTTTTTC CTTTATGTTG | 3256 |
| AAATAATAAT | GGCACCTGAC | ACATAGACAT | AGACCACCCA | CAACCTAAAT TAAATGTTTG | 3316 |
| GTAAGACAAA | TACACATTGG | ATGACCACAG | TAACAGCAAA | CAGGGCACAA ACTGGATTCT | 3376 |
| TATTTCACAT | AGACATTTAG | ATTACTAAAG | AGGGCTATGT | GTAAACAGTC ATCATTATAG | 3436 |
| TACTCAAGAC | ACTAAAACAG | CTTCTAGCCA | AATATATTAA | AGCTTGCAGA GGCCAAAAAT | 3496 |
| AGAAAACATC | TCCCCTGTCT | CTCCCACATT | TCCCTCACAG | AAAGACAAAA AACCTGCCTG | 3556 |
| GTGCAGTAGC | TCACACCTGT | AATCCCAGCA | GTTTGGGAGA | CTGTGGGAAG ATGGCTTGAG | 3616 |
| TCCAGGAGTT | CTAGACAGGC | CTGAGAAACC | TAGTGAGACA | TCCTTCTCTT AAACAAAACA | 3676 |
| AAACAAAACA | AATGTAGCCA | TGCGTGGTGG | CATATACCTG | TGGTCCCAAC TACTCAGGAG | 3736 |
| GCTGAAACGG | AAGGATCTCT | TGGGCCCCAG | GAGTTTGAGG | CTGCAGTGAG CTATAATCTT | 3796 |
| GCCATTGCAC | TCCAGCCTGG | GTGAAAAAGA | GCCAGAAAGA | AAGGAAAGAG AGAAAAGAGA | 3856 |
| AAAGAAAGAG | AGAAAAGACA | GAAAGACAGG | AAGGAAGGAA | GGAAGGAAGG AAGGAAGGAA | 3916 |
| GGAAGCAAGG | AAAGAAGGAA | GGAAGGAAAG | AAGGGAGGGA | AGGAAGGAGA GAGAAAGAAA | 3976 |
| GATTGTTTGG | TAAGGAGTAA | TGACATTCTC | TTGCATTTAA | AAGTGGCATA TTTGCTTGAA | 4036 |
| ATGGAAATAG | AATTCTGGTC | CCTTTTGCAA | CTACTGAAGA | AAAAAAAAAG CAGTTTCAGC | 4096 |
| CCTGAATGTT | GTAGATTTGA | AAAAAAAAAA | AAAAAAACTC | GAGGGGGGGC CCGTACCCAA | 4156 |
| TTCGCCCTAT | AGTGAGTCGT | A | | | 4177 |

(2) INFORMATION FOR SEQ ID NO:24:

(i) SEQUENCE CHARACTERISTICS:
        (A) LENGTH: 208 amino acids
        (B) TYPE: amino acid
        (D) TOPOLOGY: linear (ii) MOLECULE TYPE: protein (xi) SEQUENCE DESCRIPTION: SEQ ID NO:24:

```
Met Trp Lys Trp Ile Leu Thr His Cys Ala Ser Ala Phe Pro His Leu
  1               5                  10                  15

Pro Gly Cys Cys Cys Cys Cys Phe Leu Leu Leu Phe Leu Val Ser Ser
             20                  25                  30

Val Pro Val Thr Cys Gln Ala Leu Gly Gln Asp Met Val Ser Pro Glu
         35                  40                  45

Ala Thr Asn Ser Ser Ser Ser Phe Ser Ser Pro Ser Ser Ala Gly
     50                  55                  60

Arg His Val Arg Ser Tyr Asn His Leu Gln Gly Asp Val Arg Trp Arg
 65                  70                  75                  80

Lys Leu Phe Ser Phe Thr Lys Tyr Phe Leu Lys Ile Glu Lys Asn Gly
                 85                  90                  95

Lys Val Ser Gly Thr Lys Lys Glu Asn Cys Pro Tyr Ser Ile Leu Glu
            100                 105                 110

Ile Thr Ser Val Glu Ile Gly Val Val Ala Val Lys Ala Ile Asn Ser
            115                 120                 125

Asn Tyr Tyr Leu Ala Met Asn Lys Lys Gly Lys Leu Tyr Gly Ser Lys
        130                 135                 140

Glu Phe Asn Asn Asp Cys Lys Leu Lys Glu Arg Ile Glu Glu Asn Gly
145                 150                 155                 160

Tyr Asn Thr Tyr Ala Ser Phe Asn Trp Gln His Asn Gly Arg Gln Met
```

```
                        165                 170                 175
Tyr Val Ala Leu Asn Gly Lys Gly Ala Pro Arg Arg Gly Gln Lys Thr
            180                 185                 190
Arg Arg Lys Asn Thr Ser Ala His Phe Leu Pro Met Val Val His Ser
            195                 200                 205
```

(2) INFORMATION FOR SEQ ID NO:25:

(i) SEQUENCE CHARACTERISTICS:
        (A) LENGTH: 31 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:25:

```
Gly Gln Asp Met Val Ser Pro Glu Ala Thr Asn Ser Ser Ser Ser
1               5                   10                  15
Phe Ser Ser Pro Ser Ser Ala Gly Arg His Val Arg Ser Tyr Asn
            20                  25                  30
```

(2) INFORMATION FOR SEQ ID NO:26:

(i) SEQUENCE CHARACTERISTICS:
        (A) LENGTH: 19 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:26:

```
Lys Ile Glu Lys Asn Gly Lys Val Ser Gly Thr Lys Lys Glu Asn Cys
1               5                   10                  15
Pro Tyr Ser
```

(2) INFORMATION FOR SEQ ID NO:27:

(i) SEQUENCE CHARACTERISTICS:
        (A) LENGTH: 30 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:27:

```
Asn Lys Lys Gly Lys Leu Tyr Gly Ser Lys Glu Phe Asn Asn Asp Cys
1               5                   10                  15
Lys Leu Lys Glu Arg Ile Glu Glu Asn Gly Tyr Asn Thr Tyr
            20                  25                  30
```

(2) INFORMATION FOR SEQ ID NO:28:

(i) SEQUENCE CHARACTERISTICS:
        (A) LENGTH: 19 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:28:

```
Asn Gly Lys Gly Ala Pro Arg Arg Gly Gln Lys Thr Arg Arg Lys Asn
1               5                   10                  15
```

Thr Ser Ala (2) INFORMATION FOR SEQ ID NO:29:

(i) SEQUENCE CHARACTERISTICS:
        (A) LENGTH: 555 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..553

(xi) SEQUENCE DESCRIPTION: SEQ ID NO:29:

```
ATG AGA GGA TCG CAT CAC CAT CAC CAT CAC GGA TCC TGC CAG GCT CTG       48
Met Arg Gly Ser His His His His His His Gly Ser Cys Gln Ala Leu
  1               5                  10                  15

GGT CAG GAC ATG GTT TCT CCG GAA GCT ACC AAC TCT TCC TCT TCC TCT       96
Gly Gln Asp Met Val Ser Pro Glu Ala Thr Asn Ser Ser Ser Ser Ser
             20                  25                  30

TTC TCT TCC CCG TCT TCC GCT GGT CGT CAC GTT CGT TCT TAC AAC CAC      144
Phe Ser Ser Pro Ser Ser Ala Gly Arg His Val Arg Ser Tyr Asn His
         35                  40                  45

CTG CAG GGT GAC GTT CGT TGG CGT AAA CTG TTC TCT TTC ACC AAA TAC      192
Leu Gln Gly Asp Val Arg Trp Arg Lys Leu Phe Ser Phe Thr Lys Tyr
 50                  55                  60

TTC CTG AAA ATC GAA AAA AAC GGT AAA GTT TCT GGG ACC AAG AAG GAG      240
Phe Leu Lys Ile Glu Lys Asn Gly Lys Val Ser Gly Thr Lys Lys Glu
 65                  70                  75                  80

AAC TGC CCG TAC AGC ATC CTG GAG ATA ACA TCA GTA GAA ATC GGA GTT      288
Asn Cys Pro Tyr Ser Ile Leu Glu Ile Thr Ser Val Glu Ile Gly Val
                 85                  90                  95

GTT GCC GTC AAA GCC ATT AAC AGC AAC TAT TAC TTA GCC ATG AAC AAG      336
Val Ala Val Lys Ala Ile Asn Ser Asn Tyr Tyr Leu Ala Met Asn Lys
            100                 105                 110

AAG GGG AAA CTC TAT GGC TCA AAA GAA TTT AAC AAT GAC TGT AAG CTG      384
Lys Gly Lys Leu Tyr Gly Ser Lys Glu Phe Asn Asn Asp Cys Lys Leu
        115                 120                 125

AAG GAG AGG ATA GAG GAA AAT GGA TAC AAT ACC TAT GCA TCA TTT AAC      432
Lys Glu Arg Ile Glu Glu Asn Gly Tyr Asn Thr Tyr Ala Ser Phe Asn
    130                 135                 140

TGG CAG CAT AAT GGG AGG CAA ATG TAT GTG GCA TTG AAT GGA AAA GGA      480
Trp Gln His Asn Gly Arg Gln Met Tyr Val Ala Leu Asn Gly Lys Gly
145                 150                 155                 160

GCT CCA AGG AGA GGA CAG AAA ACA CGA AGG AAA AAC ACC TCT GCT CAC      528
Ala Pro Arg Arg Gly Gln Lys Thr Arg Arg Lys Asn Thr Ser Ala His
                165                 170                 175

TTT CTT CCA ATG GTG GTA CAC TCA TAG                                  555
Phe Leu Pro Met Val Val His Ser
            180
```

(2) INFORMATION FOR SEQ ID NO:30:

(i) SEQUENCE CHARACTERISTICS:
        (A) LENGTH: 184 amino acids
        (B) TYPE: amino acid
        (D) TOPOLOGY: linear (ii) MOLECULE TYPE: protein (xi) SEQUENCE DESCRIPTION: SEQ ID NO:30:

```
Met Arg Gly Ser His His His His His Gly Ser Cys Gln Ala Leu
 1               5                  10                  15

Gly Gln Asp Met Val Ser Pro Glu Ala Thr Asn Ser Ser Ser Ser Ser
            20                  25                  30

Phe Ser Ser Pro Ser Ser Ala Gly Arg His Val Arg Ser Tyr Asn His
        35                  40                  45

Leu Gln Gly Asp Val Arg Trp Arg Lys Leu Phe Ser Phe Thr Lys Tyr
    50                  55                  60

Phe Leu Lys Ile Glu Lys Asn Gly Lys Val Ser Gly Thr Lys Lys Glu
65                  70                  75                  80

Asn Cys Pro Tyr Ser Ile Leu Glu Ile Thr Ser Val Glu Ile Gly Val
                85                  90                  95

Val Ala Val Lys Ala Ile Asn Ser Asn Tyr Tyr Leu Ala Met Asn Lys
            100                 105                 110

Lys Gly Lys Leu Tyr Gly Ser Lys Glu Phe Asn Asn Asp Cys Lys Leu
            115                 120                 125

Lys Glu Arg Ile Glu Glu Asn Gly Tyr Asn Thr Tyr Ala Ser Phe Asn
    130                 135                 140

Trp Gln His Asn Gly Arg Gln Met Tyr Val Ala Leu Asn Gly Lys Gly
145                 150                 155                 160

Ala Pro Arg Arg Gly Gln Lys Thr Arg Arg Lys Asn Thr Ser Ala His
                165                 170                 175

Phe Leu Pro Met Val Val His Ser
            180
```

(2) INFORMATION FOR SEQ ID NO:31:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

```
ATGTGGAAAT GGATACTGAC CCACTGCGCT TCTGCTTTCC CGCACCTGCC GGGTTGCTGC    60

TGCTGCTGCT TCCTGCTGCT GTTC                                          84
```

(2) INFORMATION FOR SEQ ID NO:32:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

```
CCGGAGAAAC CATGTCCTGA CCCAGAGCCT GGCAGGTAAC CGGAACAGAA GAAACCAGGA    60

ACAGCAGCAG GAAGCAGCAG CA                                            82
```

(2) INFORMATION FOR SEQ ID NO:33:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

GGGTCAGGAC ATGGTTTCTC CGGAAGCTAC CAACTCTTCT TCTTCTTCTT TCTCTTCTCC    60

GTCTTCTGCT GGTCGTCACG                                                80

(2) INFORMATION FOR SEQ ID NO:34:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

GGTGAAAGAG AACAGTTTAC GCCAACGAAC GTCACCCTGC AGGTGGTTGT AAGAACGAAC    60

GTGACGACCA GCAGAAGACG G                                              81

(2) INFORMATION FOR SEQ ID NO:35:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

CGTTGGCGTA AACTGTTCTC TTTCACCAAA TACTTCCTGA AAATCGAAAA AAACGGTAAA    60

GTTTCTGGGA CCAAA                                                     75

(2) INFORMATION FOR SEQ ID NO:36:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

TTTGGTCCCA GAAACTTTAC CGTTTTTTTC GATTTTCAG                            39

(2) INFORMATION FOR SEQ ID NO:37:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

AAAGGATCCA TGTGGAAATG GATACTGACC CACTGC                               36

(2) INFORMATION FOR SEQ ID NO:38:

(i) SEQUENCE CHARACTERISTICS:
        (A) LENGTH: 627 base pairs
        (B) TYPE: nucleic acid (C) STRANDEDNESS: double
        (D) TOPOLOGY: both (ii) MOLECULE TYPE: DNA (genomic)

(ix) FEATURE:
        (A) NAME/KEY: CDS
        (B) LOCATION: 1..624

(xi) SEQUENCE DESCRIPTION: SEQ ID NO:38:

```
ATG TGG AAA TGG ATA CTG ACC CAC TGC GCT TCT GCT TTC CCG CAC CTG     48
Met Trp Lys Trp Ile Leu Thr His Cys Ala Ser Ala Phe Pro His Leu
 1               5                  10                  15

CCG GGT TGC TGC TGC TGC TTC CTG CTG CTG TTC CTG GTT TCT TCT         96
Pro Gly Cys Cys Cys Cys Phe Leu Leu Leu Phe Leu Val Ser Ser
             20                  25                  30

GTT CCG GTT ACC TGC CAG GCT CTG GGT CAG GAC ATG GTT TCT CCG GAA    144
Val Pro Val Thr Cys Gln Ala Leu Gly Gln Asp Met Val Ser Pro Glu
         35                  40                  45

GCT ACC AAC TCT TCC TCT TCC TCT TTC TCT TCC CCG ACT TCC GCT GGT    192
Ala Thr Asn Ser Ser Ser Ser Ser Phe Ser Ser Pro Thr Ser Ala Gly
 50                  55                  60

CGT CAC GTT CGT TCT TAC AAC CAC CTG CAG GGT GAC GTT CGT TGG CGT    240
Arg His Val Arg Ser Tyr Asn His Leu Gln Gly Asp Val Arg Trp Arg
 65                  70                  75                  80

AAA CTG TTC TCT TTC ACC AAA TAC TTC CTG AAA ATC GAA AAA AAC GGT    288
Lys Leu Phe Ser Phe Thr Lys Tyr Phe Leu Lys Ile Glu Lys Asn Gly
                 85                  90                  95

AAA GTT TCT GGG ACC AAG AAG GAG AAC TGC CCG TAC AGC ATC CTG GAG    336
Lys Val Ser Gly Thr Lys Lys Glu Asn Cys Pro Tyr Ser Ile Leu Glu
             100                 105                 110

ATA ACA TCA GTA GAA ATC GGA GTT GTT GCC GTC AAA GCC ATT AAC AGC    384
Ile Thr Ser Val Glu Ile Gly Val Val Ala Val Lys Ala Ile Asn Ser
         115                 120                 125

AAC TAT TAC TTA GCC ATG AAC AAG AAG GGG AAA CTC TAT GGC TCA AAA    432
Asn Tyr Tyr Leu Ala Met Asn Lys Lys Gly Lys Leu Tyr Gly Ser Lys
130                 135                 140

GAA TTT AAC AAT GAC TGT AAG CTG AAG GAG AGG ATA GAG GAA AAT GGA    480
Glu Phe Asn Asn Asp Cys Lys Leu Lys Glu Arg Ile Glu Glu Asn Gly
145                 150                 155                 160

TAC AAT ACC TAT GCA TCA TTT AAC TGG CAG CAT AAT GGG AGG CAA ATG    528
Tyr Asn Thr Tyr Ala Ser Phe Asn Trp Gln His Asn Gly Arg Gln Met
                165                 170                 175

TAT GTG GCA TTG AAT GGA AAA GGA GCT CCA AGG AGA GGA CAG AAA ACA    576
Tyr Val Ala Leu Asn Gly Lys Gly Ala Pro Arg Arg Gly Gln Lys Thr
            180                 185                 190

CGA AGG AAA AAC ACC TCT GCT CAC TTT CTT CCA ATG GTG GTA CAC TCA    624
Arg Arg Lys Asn Thr Ser Ala His Phe Leu Pro Met Val Val His Ser
        195                 200                 205

TAG                                                                627
```

(2) INFORMATION FOR SEQ ID NO:39:

(i) SEQUENCE CHARACTERISTICS:
        (A) LENGTH: 208 amino acids
        (B) TYPE: amino acid
        (D) TOPOLOGY: linear (ii) MOLECULE TYPE: protein (xi) SEQUENCE DESCRIPTION: SEQ ID NO:39:

```
Met Trp Lys Trp Ile Leu Thr His Cys Ala Ser Ala Phe Pro His Leu
 1               5                  10                  15
```

```
Pro Gly Cys Cys Cys Cys Phe Leu Leu Leu Phe Leu Val Ser Ser
            20                  25                  30

Val Pro Val Thr Cys Gln Ala Leu Gly Gln Asp Met Val Ser Pro Glu
        35                  40                  45

Ala Thr Asn Ser Ser Ser Ser Phe Ser Ser Pro Thr Ser Ala Gly
    50                  55                  60

Arg His Val Arg Ser Tyr Asn His Leu Gln Gly Asp Val Arg Trp Arg
65                  70                  75                  80

Lys Leu Phe Ser Phe Thr Lys Tyr Phe Leu Lys Ile Glu Lys Asn Gly
                85                  90                  95

Lys Val Ser Gly Thr Lys Lys Glu Asn Cys Pro Tyr Ser Ile Leu Glu
                100                 105                 110

Ile Thr Ser Val Glu Ile Gly Val Val Ala Val Lys Ala Ile Asn Ser
            115                 120                 125

Asn Tyr Tyr Leu Ala Met Asn Lys Lys Gly Lys Leu Tyr Gly Ser Lys
    130                 135                 140

Glu Phe Asn Asn Asp Cys Lys Leu Lys Glu Arg Ile Glu Glu Asn Gly
145                 150                 155                 160

Tyr Asn Thr Tyr Ala Ser Phe Asn Trp Gln His Asn Gly Arg Gln Met
                165                 170                 175

Tyr Val Ala Leu Asn Gly Lys Gly Ala Pro Arg Arg Gly Gln Lys Thr
            180                 185                 190

Arg Arg Lys Asn Thr Ser Ala His Phe Leu Pro Met Val Val His Ser
            195                 200                 205

(2) INFORMATION FOR SEQ ID NO:40:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

TTTCATGACT TGTCAAGCTC TGGGTCAAGA TATGGTTC                          38

(2) INFORMATION FOR SEQ ID NO:41:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:41:

GCCCAAGCTT CCACAAACGT TGCCTTCC                                    28

(2) INFORMATION FOR SEQ ID NO:42:

(i) SEQUENCE CHARACTERISTICS:
        (A) LENGTH: 525 base pairs
        (B) TYPE: nucleic acid
        (C) STRANDEDNESS: double
        (D) TOPOLOGY: both (ii) MOLECULE TYPE: DNA (genomic)

(ix) FEATURE:
```

(A) NAME/KEY: CDS
         (B) LOCATION: 1..522

(xi) SEQUENCE DESCRIPTION: SEQ ID NO:42:

| | |
|---|---:|
| ATG ACC TGC CAG GCT CTG GGT CAG GAC ATG GTT TCT CCG GAA GCT ACC<br>Met Thr Cys Gln Ala Leu Gly Gln Asp Met Val Ser Pro Glu Ala Thr<br>1               5                      10                   15 | 48 |
| AAC TCT TCC TCT TCC TCT TTC TCT TCC CCG TCT TCC GCT GGT CGT CAC<br>Asn Ser Ser Ser Ser Ser Phe Ser Ser Pro Ser Ser Ala Gly Arg His<br>                   20                      25                   30 | 96 |
| GTT CGT TCT TAC AAC CAC CTG CAG GGT GAC GTT CGT TGG CGT AAA CTG<br>Val Arg Ser Tyr Asn His Leu Gln Gly Asp Val Arg Trp Arg Lys Leu<br>        35                      40                   45 | 144 |
| TTC TCT TTC ACC AAA TAC TTC CTG AAA ATC GAA AAA AAC GGT AAA GTT<br>Phe Ser Phe Thr Lys Tyr Phe Leu Lys Ile Glu Lys Asn Gly Lys Val<br>50                      55                      60 | 192 |
| TCT GGG ACC AAG AAG GAG AAC TGC CCG TAC AGC ATC CTG GAG ATA ACA<br>Ser Gly Thr Lys Lys Glu Asn Cys Pro Tyr Ser Ile Leu Glu Ile Thr<br>65                      70                      75                   80 | 240 |
| TCA GTA GAA ATC GGA GTT GTT GCC GTC AAA GCC ATT AAC AGC AAC TAT<br>Ser Val Glu Ile Gly Val Val Ala Val Lys Ala Ile Asn Ser Asn Tyr<br>                   85                      90                   95 | 288 |
| TAC TTA GCC ATG AAC AAG AAG GGG AAA CTC TAT GGC TCA AAA GAA TTT<br>Tyr Leu Ala Met Asn Lys Lys Gly Lys Leu Tyr Gly Ser Lys Glu Phe<br>                 100                  105                110 | 336 |
| AAC AAT GAC TGT AAG CTG AAG GAG AGG ATA GAG GAA AAT GGA TAC AAT<br>Asn Asn Asp Cys Lys Leu Lys Glu Arg Ile Glu Glu Asn Gly Tyr Asn<br>               115                  120                125 | 384 |
| ACC TAT GCA TCA TTT AAC TGG CAG CAT AAT GGG AGG CAA ATG TAT GTG<br>Thr Tyr Ala Ser Phe Asn Trp Gln His Asn Gly Arg Gln Met Tyr Val<br>130                     135                  140 | 432 |
| GCA TTG AAT GGA AAA GGA GCT CCA AGG AGA GGA CAG AAA ACA CGA AGG<br>Ala Leu Asn Gly Lys Gly Ala Pro Arg Arg Gly Gln Lys Thr Arg Arg<br>145                     150                  155                160 | 480 |
| AAA AAC ACC TCT GCT CAC TTT CTT CCA ATG GTG GTA CAC TCA<br>Lys Asn Thr Ser Ala His Phe Leu Pro Met Val Val His Ser<br>               165                  170 | 522 |
| TAG | 525 |

(2) INFORMATION FOR SEQ ID NO:43:

(i) SEQUENCE CHARACTERISTICS:
        (A) LENGTH: 174 amino acids
        (B) TYPE: amino acid
        (D) TOPOLOGY: linear (ii) MOLECULE TYPE: protein (xi) SEQUENCE DESCRIPTION: SEQ ID NO:43:

Met Thr Cys Gln Ala Leu Gly Gln Asp Met Val Ser Pro Glu Ala Thr
1               5                      10                   15

Asn Ser Ser Ser Ser Ser Phe Ser Ser Pro Ser Ser Ala Gly Arg His
                   20                      25                   30

Val Arg Ser Tyr Asn His Leu Gln Gly Asp Val Arg Trp Arg Lys Leu
        35                      40                   45

Phe Ser Phe Thr Lys Tyr Phe Leu Lys Ile Glu Lys Asn Gly Lys Val
50                      55                      60

Ser Gly Thr Lys Lys Glu Asn Cys Pro Tyr Ser Ile Leu Glu Ile Thr
65                      70                      75                   80

Ser Val Glu Ile Gly Val Val Ala Val Lys Ala Ile Asn Ser Asn Tyr

```
                        85                  90                  95
Tyr Leu Ala Met Asn Lys Lys Gly Lys Leu Tyr Gly Ser Lys Glu Phe
                100                 105                 110
Asn Asn Asp Cys Lys Leu Lys Glu Arg Ile Glu Glu Asn Gly Tyr Asn
                115                 120                 125
Thr Tyr Ala Ser Phe Asn Trp Gln His Asn Gly Arg Gln Met Tyr Val
            130                 135                 140
Ala Leu Asn Gly Lys Gly Ala Pro Arg Arg Gly Gln Lys Thr Arg Arg
145                 150                 155                 160
Lys Asn Thr Ser Ala His Phe Leu Pro Met Val Val His Ser
                165                 170
```

(2) INFORMATION FOR SEQ ID NO:44:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:44:

TCAGTGAATT CATTAAAGAG GAGAAATTAA TCATGACTTG CCAGG          45

(2) INFORMATION FOR SEQ ID NO:45:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:45:

TCATGACTTG CCAGGCACTG GGTCAAGACA TGGTTTCCCC GGAAGCTA       48

(2) INFORMATION FOR SEQ ID NO:46:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:46:

GCTTCAGCAG CCCATCTAGC GCAGGTCGTC ACGTTCGCTC TTACAACC       48

(2) INFORMATION FOR SEQ ID NO:47:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:47:

GTTCGTTGGC GCAAACTGTT CAGCTTTACC AAGTACTTCC TGAAAATC       48

(2) INFORMATION FOR SEQ ID NO:48:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:48:

TCGAAAAAAA CGGTAAAGTT TCTGGGAC                                              28

(2) INFORMATION FOR SEQ ID NO:49:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:49:

GATGGGCTGC TGAAGCTAGA GCTGGAGCTG TTGGTAGCTT CCGGGGAA                        48

(2) INFORMATION FOR SEQ ID NO:50:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:50:

AACAGTTTGC GCCAACGAAC ATCACCCTGT AAGTGGTTGT AAGAG                           45

(2) INFORMATION FOR SEQ ID NO:51:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:51:

TTCTTGGTCC CAGAAACTTT ACCGTTTTTT TCGATTTTCA GGAAGTA                         47

(2) INFORMATION FOR SEQ ID NO:52:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:52:

TTCTTGGTCC CAGAAACTTT ACCG                                                  24

(2) INFORMATION FOR SEQ ID NO:53:

(i) SEQUENCE CHARACTERISTICS:
            (A) LENGTH: 45 base pairs
            (B) TYPE: nucleic acid

```
        (C) STRANDEDNESS: single
        (D) TOPOLOGY: linear (ii) MOLECULE TYPE: cDNA (xi) SEQUENCE DESCRIPTION: SEQ ID NO:53:

AGATCAGGCT TCTATTATTA TGAGTGTACC ACCATTGGAA GAAAG                  45

(2) INFORMATION FOR SEQ ID NO:54:

(i) SEQUENCE CHARACTERISTICS:
        (A) LENGTH: 525 base pairs
        (B) TYPE: nucleic acid
        (C) STRANDEDNESS: double
        (D) TOPOLOGY: both (ii) MOLECULE TYPE: DNA (genomic)

(ix) FEATURE:
        (A) NAME/KEY: CDS
        (B) LOCATION: 1..522

(xi) SEQUENCE DESCRIPTION: SEQ ID NO:54:

ATG ACT TGC CAG GCA CTG GGT CAA GAC ATG GTT TCC CCG GAA GCT ACC    48
Met Thr Cys Gln Ala Leu Gly Gln Asp Met Val Ser Pro Glu Ala Thr
 1               5                  10                  15

AAC AGC TCC AGC TCT AGC TTC AGC AGC CCA TCT AGC GCA GGT CGT CAC    96
Asn Ser Ser Ser Ser Ser Phe Ser Ser Pro Ser Ser Ala Gly Arg His
            20                  25                  30

GTT CGC TCT TAC AAC CAC TTA CAG GGT GAT GTT CGT TGG CGC AAA CTG   144
Val Arg Ser Tyr Asn His Leu Gln Gly Asp Val Arg Trp Arg Lys Leu
        35                  40                  45

TTC AGC TTT ACC AAG TAC TTC CTG AAA ATC GAA AAA AAC GGT AAA GTT   192
Phe Ser Phe Thr Lys Tyr Phe Leu Lys Ile Glu Lys Asn Gly Lys Val
 50                  55                  60

TCT GGG ACC AAG AAG GAG AAC TGC CCG TAC AGC ATC CTG GAG ATA ACA   240
Ser Gly Thr Lys Lys Glu Asn Cys Pro Tyr Ser Ile Leu Glu Ile Thr
 65                  70                  75                  80

TCA GTA GAA ATC GGA GTT GTT GCC GTC AAA GCC ATT AAC AGC AAC TAT   288
Ser Val Glu Ile Gly Val Val Ala Val Lys Ala Ile Asn Ser Asn Tyr
                 85                  90                  95

TAC TTA GCC ATG AAC AAG AAG GGG AAA CTC TAT GGC TCA AAA GAA TTT   336
Tyr Leu Ala Met Asn Lys Lys Gly Lys Leu Tyr Gly Ser Lys Glu Phe
            100                 105                 110

AAC AAT GAC TGT AAG CTG AAG GAG AGG ATA GAG GAA AAT GGA TAC AAT   384
Asn Asn Asp Cys Lys Leu Lys Glu Arg Ile Glu Glu Asn Gly Tyr Asn
        115                 120                 125

ACC TAT GCA TCA TTT AAC TGG CAG CAT AAT GGG AGG CAA ATG TAT GTG   432
Thr Tyr Ala Ser Phe Asn Trp Gln His Asn Gly Arg Gln Met Tyr Val
    130                 135                 140

GCA TTG AAT GGA AAA GGA GCT CCA AGG AGA GGA CAG AAA ACA CGA AGG   480
Ala Leu Asn Gly Lys Gly Ala Pro Arg Arg Gly Gln Lys Thr Arg Arg
145                 150                 155                 160

AAA AAC ACC TCT GCT CAC TTT CTT CCA ATG GTG GTA CAC TCA             522
Lys Asn Thr Ser Ala His Phe Leu Pro Met Val Val His Ser
                165                 170

TAG                                                                525

(2) INFORMATION FOR SEQ ID NO:55:

(i) SEQUENCE CHARACTERISTICS:
        (A) LENGTH: 174 amino acids
        (B) TYPE: amino acid
        (D) TOPOLOGY: linear
```

(ii) MOLECULE TYPE: protein (xi) SEQUENCE DESCRIPTION: SEQ ID NO:55:

Met Thr Cys Gln Ala Leu Gly Gln Asp Met Val Ser Pro Glu Ala Thr
 1               5                  10                  15

Asn Ser Ser Ser Ser Phe Ser Ser Pro Ser Ser Ala Gly Arg His
            20                  25                  30

Val Arg Ser Tyr Asn His Leu Gln Gly Asp Val Arg Trp Arg Lys Leu
            35                  40                  45

Phe Ser Phe Thr Lys Tyr Phe Leu Lys Ile Glu Lys Asn Gly Lys Val
     50                  55                  60

Ser Gly Thr Lys Lys Glu Asn Cys Pro Tyr Ser Ile Leu Glu Ile Thr
 65              70                  75                  80

Ser Val Glu Ile Gly Val Val Ala Val Lys Ala Ile Asn Ser Asn Tyr
                85                  90                  95

Tyr Leu Ala Met Asn Lys Lys Gly Lys Leu Tyr Gly Ser Lys Glu Phe
                100                 105                 110

Asn Asn Asp Cys Lys Leu Lys Glu Arg Ile Glu Glu Asn Gly Tyr Asn
            115                 120                 125

Thr Tyr Ala Ser Phe Asn Trp Gln His Asn Gly Arg Gln Met Tyr Val
    130                 135                 140

Ala Leu Asn Gly Lys Gly Ala Pro Arg Arg Gly Gln Lys Thr Arg Arg
145                 150                 155                 160

Lys Asn Thr Ser Ala His Phe Leu Pro Met Val Val His Ser
                165                 170

(2) INFORMATION FOR SEQ ID NO:56:

(i) SEQUENCE CHARACTERISTICS:
          (A) LENGTH: 35 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:56:

GGACCCTCAT GACCTGCCAG GCTCTGGGTC AGGAC                              35

(2) INFORMATION FOR SEQ ID NO:57:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:57:

GGACAGCCAT GGCTGGTCGT CACGTTCG                                      28

(2) INFORMATION FOR SEQ ID NO:58:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: cDNA -continued (xi) SEQUENCE DESCRIPTION: SEQ ID NO:58:

GGACAGCCAT GGTTCGTTGG CGTAAACTG                                29

(2) INFORMATION FOR SEQ ID NO:59:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:59:

GGACAGCCAT GGAAAAAAAC GGTAAAGTTT C                              31

(2) INFORMATION FOR SEQ ID NO:60:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:60:

GGACCCCCAT GGAGAACTGC CCGTAGAGC                                29

(2) INFORMATION FOR SEQ ID NO:61:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:61:

GGACCCCCAT GGTCAAAGCC ATTAACAGCA AC                            32

(2) INFORMATION FOR SEQ ID NO:62:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:62:

GGACCCCCAT GGGGAAACTC TATGGCTCAA AAG                           33

(2) INFORMATION FOR SEQ ID NO:63:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:63:

CTGCCCAAGC TTATTATGAG TGTACCACCA TTGGAAG                       37

(2) INFORMATION FOR SEQ ID NO:64:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:64:

```
CTGCCCAAGC TTATTACTTC AGCTTACAGT CATTGT                              36
```

(2) INFORMATION FOR SEQ ID NO:65:

(i) SEQUENCE CHARACTERISTICS:
        (A) LENGTH: 525 base pairs
        (B) TYPE: nucleic acid
        (C) STRANDEDNESS: double
        (D) TOPOLOGY: both (ii) MOLECULE TYPE: DNA (genomic)

(ix) FEATURE:
        (A) NAME/KEY: CDS
        (B) LOCATION: 1..522

(xi) SEQUENCE DESCRIPTION: SEQ ID NO:65:

```
ATG ACC TGC CAG GCT CTG GGT CAG GAC ATG GTT TCT CCG GAA GCT ACC      48
Met Thr Cys Gln Ala Leu Gly Gln Asp Met Val Ser Pro Glu Ala Thr
 1               5                  10                  15

AAC TCT TCC TCT TCC TCT TTC TCT TCC CCG TCT TCC GCT GGT CGT CAC      96
Asn Ser Ser Ser Ser Ser Phe Ser Ser Pro Ser Ser Ala Gly Arg His
             20                  25                  30

GTT CGT TCT TAC AAC CAC CTG CAG GGT GAC GTT CGT TGG CGT AAA CTG     144
Val Arg Ser Tyr Asn His Leu Gln Gly Asp Val Arg Trp Arg Lys Leu
         35                  40                  45

TTC TCT TTC ACC AAA TAC TTC CTG AAA ATC GAA AAA AAC GGT AAA GTT     192
Phe Ser Phe Thr Lys Tyr Phe Leu Lys Ile Glu Lys Asn Gly Lys Val
     50                  55                  60

TCT GGG ACC AAG AAG GAG AAC TGC CCG TAC AGC ATC CTG GAG ATA ACA     240
Ser Gly Thr Lys Lys Glu Asn Cys Pro Tyr Ser Ile Leu Glu Ile Thr
 65                  70                  75                  80

TCA GTA GAA ATC GGA GTT GTT GCC GTC AAA GCC ATT AAC AGC AAC TAT     288
Ser Val Glu Ile Gly Val Val Ala Val Lys Ala Ile Asn Ser Asn Tyr
                 85                  90                  95

TAC TTA GCC ATG AAC AAG AAG GGG AAA CTC TAT GGC TCA AAA GAA TTT     336
Tyr Leu Ala Met Asn Lys Lys Gly Lys Leu Tyr Gly Ser Lys Glu Phe
            100                 105                 110

AAC AAT GAC TGT AAG CTG AAG GAG AGG ATA GAG GAA AAT GGA TAC AAT     384
Asn Asn Asp Cys Lys Leu Lys Glu Arg Ile Glu Glu Asn Gly Tyr Asn
        115                 120                 125

ACC TAT GCA TCA TTT AAC TGG CAG CAT AAT GGG AGG CAA ATG TAT GTG     432
Thr Tyr Ala Ser Phe Asn Trp Gln His Asn Gly Arg Gln Met Tyr Val
    130                 135                 140

GCA TTG AAT GGA AAA GGA GCT CCA AGG AGA GGA CAG AAA ACA CGA AGG     480
Ala Leu Asn Gly Lys Gly Ala Pro Arg Arg Gly Gln Lys Thr Arg Arg
145                 150                 155                 160

AAA AAC ACC TCT GCT CAC TTT CTT CCA ATG GTG GTA CAC TCA             522
Lys Asn Thr Ser Ala His Phe Leu Pro Met Val Val His Ser
                165                 170

TAG                                                                 525
```

-continued (2) INFORMATION FOR SEQ ID NO:66:

(i) SEQUENCE CHARACTERISTICS:
        (A) LENGTH: 174 amino acids
        (B) TYPE: amino acid
        (D) TOPOLOGY: linear (ii) MOLECULE TYPE: protein (xi) SEQUENCE DESCRIPTION: SEQ ID NO:66:

```
Met Thr Cys Gln Ala Leu Gly Gln Asp Met Val Ser Pro Glu Ala Thr
 1               5                  10                  15

Asn Ser Ser Ser Ser Ser Phe Ser Ser Pro Ser Ser Ala Gly Arg His
            20                  25                  30

Val Arg Ser Tyr Asn His Leu Gln Gly Asp Val Arg Trp Arg Lys Leu
        35                  40                  45

Phe Ser Phe Thr Lys Tyr Phe Leu Lys Ile Glu Lys Asn Gly Lys Val
    50                  55                  60

Ser Gly Thr Lys Lys Glu Asn Cys Pro Tyr Ser Ile Leu Glu Ile Thr
65                  70                  75                  80

Ser Val Glu Ile Gly Val Val Ala Val Lys Ala Ile Asn Ser Asn Tyr
                85                  90                  95

Tyr Leu Ala Met Asn Lys Lys Gly Lys Leu Tyr Gly Ser Lys Glu Phe
            100                 105                 110

Asn Asn Asp Cys Lys Leu Lys Glu Arg Ile Glu Glu Asn Gly Tyr Asn
        115                 120                 125

Thr Tyr Ala Ser Phe Asn Trp Gln His Asn Gly Arg Gln Met Tyr Val
    130                 135                 140

Ala Leu Asn Gly Lys Gly Ala Pro Arg Arg Gly Gln Lys Thr Arg Arg
145                 150                 155                 160

Lys Asn Thr Ser Ala His Phe Leu Pro Met Val Val His Ser
                165                 170
```

(2) INFORMATION FOR SEQ ID NO:67:

(i) SEQUENCE CHARACTERISTICS:
        (A) LENGTH: 444 base pairs
        (B) TYPE: nucleic acid
        (C) STRANDEDNESS: double
        (D) TOPOLOGY: both (ii) MOLECULE TYPE: DNA (genomic)

(ix) FEATURE:
        (A) NAME/KEY: CDS
        (B) LOCATION: 1..441

(xi) SEQUENCE DESCRIPTION: SEQ ID NO:67:

```
ATG GCT GGT CGT CAC GTT CGT TCT TAC AAC CAC CTG CAG GGT GAC GTT      48
Met Ala Gly Arg His Val Arg Ser Tyr Asn His Leu Gln Gly Asp Val
 1               5                  10                  15

CGT TGG CGT AAA CTG TTC TCT TTC ACC AAA TAC TTC CTG AAA ATC GAA      96
Arg Trp Arg Lys Leu Phe Ser Phe Thr Lys Tyr Phe Leu Lys Ile Glu
            20                  25                  30

AAA AAC GGT AAA GTT TCT GGG ACC AAG AAG GAG AAC TGC CCG TAC AGC     144
Lys Asn Gly Lys Val Ser Gly Thr Lys Lys Glu Asn Cys Pro Tyr Ser
        35                  40                  45

ATC CTG GAG ATA ACA TCA GTA GAA ATC GGA GTT GTT GCC GTC AAA GCC     192
Ile Leu Glu Ile Thr Ser Val Glu Ile Gly Val Val Ala Val Lys Ala
    50                  55                  60

ATT AAC AGC AAC TAT TAC TTA GCC ATG AAC AAG AAG GGG AAA CTC TAT     240
Ile Asn Ser Asn Tyr Tyr Leu Ala Met Asn Lys Lys Gly Lys Leu Tyr
```

```
                    65                  70                  75                  80
GGC TCA AAA GAA TTT AAC AAT GAC TGT AAG CTG AAG GAG AGG ATA GAG       288
Gly Ser Lys Glu Phe Asn Asn Asp Cys Lys Leu Lys Glu Arg Ile Glu
                85                  90                  95

GAA AAT GGA TAC AAT ACC TAT GCA TCA TTT AAC TGG CAG CAT AAT GGG       336
Glu Asn Gly Tyr Asn Thr Tyr Ala Ser Phe Asn Trp Gln His Asn Gly
            100                 105                 110

AGG CAA ATG TAT GTG GCA TTG AAT GGA AAA GGA GCT CCA AGG AGA GGA       384
Arg Gln Met Tyr Val Ala Leu Asn Gly Lys Gly Ala Pro Arg Arg Gly
        115                 120                 125

CAG AAA ACA CGA AGG AAA AAC ACC TCT GCT CAC TTT CTT CCA ATG GTG       432
Gln Lys Thr Arg Arg Lys Asn Thr Ser Ala His Phe Leu Pro Met Val
    130                 135                 140

GTA CAC TCA TAG                                                        444
Val His Ser
145
```

(2) INFORMATION FOR SEQ ID NO:68:

(i) SEQUENCE CHARACTERISTICS:
        (A) LENGTH: 147 amino acids
        (B) TYPE: amino acid
        (D) TOPOLOGY: linear (ii) MOLECULE TYPE: protein (xi) SEQUENCE DESCRIPTION: SEQ ID NO:68:

```
Met Ala Gly Arg His Val Arg Ser Tyr Asn His Leu Gln Gly Asp Val
 1               5                  10                  15

Arg Trp Arg Lys Leu Phe Ser Phe Thr Lys Tyr Phe Leu Lys Ile Glu
                20                  25                  30

Lys Asn Gly Lys Val Ser Gly Thr Lys Lys Glu Asn Cys Pro Tyr Ser
            35                  40                  45

Ile Leu Glu Ile Thr Ser Val Glu Ile Gly Val Val Ala Val Lys Ala
        50                  55                  60

Ile Asn Ser Asn Tyr Tyr Leu Ala Met Asn Lys Lys Gly Lys Leu Tyr
65                  70                  75                  80

Gly Ser Lys Glu Phe Asn Asn Asp Cys Lys Leu Lys Glu Arg Ile Glu
                85                  90                  95

Glu Asn Gly Tyr Asn Thr Tyr Ala Ser Phe Asn Trp Gln His Asn Gly
            100                 105                 110

Arg Gln Met Tyr Val Ala Leu Asn Gly Lys Gly Ala Pro Arg Arg Gly
        115                 120                 125

Gln Lys Thr Arg Arg Lys Asn Thr Ser Ala His Phe Leu Pro Met Val
    130                 135                 140

Val His Ser
145
```

(2) INFORMATION FOR SEQ ID NO:69:

(i) SEQUENCE CHARACTERISTICS:
        (A) LENGTH: 402 base pairs
        (B) TYPE: nucleic acid
        (C) STRANDEDNESS: double
        (D) TOPOLOGY: both (ii) MOLECULE TYPE: DNA (genomic)

(ix) FEATURE:
        (A) NAME/KEY: CDS
        (B) LOCATION: 1..399

-continued (xi) SEQUENCE DESCRIPTION: SEQ ID NO:69:

```
ATG GTT CGT TGG CGT AAA CTG TTC TCT TTC ACC AAA TAC TTC CTG AAA      48
Met Val Arg Trp Arg Lys Leu Phe Ser Phe Thr Lys Tyr Phe Leu Lys
 1               5                  10                  15

ATC GAA AAA AAC GGT AAA GTT TCT GGG ACC AAG AAG GAG AAC TGC CCG      96
Ile Glu Lys Asn Gly Lys Val Ser Gly Thr Lys Lys Glu Asn Cys Pro
             20                  25                  30

TAC AGC ATC CTG GAG ATA ACA TCA GTA GAA ATC GGA GTT GTT GCC GTC     144
Tyr Ser Ile Leu Glu Ile Thr Ser Val Glu Ile Gly Val Val Ala Val
         35                  40                  45

AAA GCC ATT AAC AGC AAC TAT TAC TTA GCC ATG AAC AAG AAG GGG AAA     192
Lys Ala Ile Asn Ser Asn Tyr Tyr Leu Ala Met Asn Lys Lys Gly Lys
     50                  55                  60

CTC TAT GGC TCA AAA GAA TTT AAC AAT GAC TGT AAG CTG AAG GAG AGG     240
Leu Tyr Gly Ser Lys Glu Phe Asn Asn Asp Cys Lys Leu Lys Glu Arg
 65                  70                  75                  80

ATA GAG GAA AAT GGA TAC AAT ACC TAT GCA TCA TTT AAC TGG CAG CAT     288
Ile Glu Glu Asn Gly Tyr Asn Thr Tyr Ala Ser Phe Asn Trp Gln His
                 85                  90                  95

AAT GGG AGG CAA ATG TAT GTG GCA TTG AAT GGA AAA GGA GCT CCA AGG     336
Asn Gly Arg Gln Met Tyr Val Ala Leu Asn Gly Lys Gly Ala Pro Arg
            100                 105                 110

AGA GGA CAG AAA ACA CGA AGG AAA AAC ACC TCT GCT CAC TTT CTT CCA     384
Arg Gly Gln Lys Thr Arg Arg Lys Asn Thr Ser Ala His Phe Leu Pro
        115                 120                 125

ATG GTG GTA CAC TCA TAG                                             402
Met Val Val His Ser
    130
```

(2) INFORMATION FOR SEQ ID NO:70:

(i) SEQUENCE CHARACTERISTICS:
        (A) LENGTH: 133 amino acids
        (B) TYPE: amino acid
        (D) TOPOLOGY: linear (ii) MOLECULE TYPE: protein (xi) SEQUENCE DESCRIPTION: SEQ ID NO:70:

```
Met Val Arg Trp Arg Lys Leu Phe Ser Phe Thr Lys Tyr Phe Leu Lys
 1               5                  10                  15

Ile Glu Lys Asn Gly Lys Val Ser Gly Thr Lys Lys Glu Asn Cys Pro
             20                  25                  30

Tyr Ser Ile Leu Glu Ile Thr Ser Val Glu Ile Gly Val Val Ala Val
         35                  40                  45

Lys Ala Ile Asn Ser Asn Tyr Tyr Leu Ala Met Asn Lys Lys Gly Lys
     50                  55                  60

Leu Tyr Gly Ser Lys Glu Phe Asn Asn Asp Cys Lys Leu Lys Glu Arg
 65                  70                  75                  80

Ile Glu Glu Asn Gly Tyr Asn Thr Tyr Ala Ser Phe Asn Trp Gln His
                 85                  90                  95

Asn Gly Arg Gln Met Tyr Val Ala Leu Asn Gly Lys Gly Ala Pro Arg
            100                 105                 110

Arg Gly Gln Lys Thr Arg Arg Lys Asn Thr Ser Ala His Phe Leu Pro
        115                 120                 125

Met Val Val His Ser
    130
```

(2) INFORMATION FOR SEQ ID NO:71:

(i) SEQUENCE CHARACTERISTICS:
    (A) LENGTH: 354 base pairs
    (B) TYPE: nucleic acid
    (C) STRANDEDNESS: double
    (D) TOPOLOGY: both (ii) MOLECULE TYPE: DNA (genomic)

(ix) FEATURE:
    (A) NAME/KEY: CDS
    (B) LOCATION: 1..351

(xi) SEQUENCE DESCRIPTION: SEQ ID NO:71:

```
ATG GAA AAA AAC GGT AAA GTT TCT GGG ACC AAG AAG GAG AAC TGC CCG      48
Met Glu Lys Asn Gly Lys Val Ser Gly Thr Lys Lys Glu Asn Cys Pro
 1               5                  10                  15

TAC AGC ATC CTG GAG ATA ACA TCA GTA GAA ATC GGA GTT GTT GCC GTC      96
Tyr Ser Ile Leu Glu Ile Thr Ser Val Glu Ile Gly Val Val Ala Val
                20                  25                  30

AAA GCC ATT AAC AGC AAC TAT TAC TTA GCC ATG AAC AAG AAG GGG AAA     144
Lys Ala Ile Asn Ser Asn Tyr Tyr Leu Ala Met Asn Lys Lys Gly Lys
             35                  40                  45

CTC TAT GGC TCA AAA GAA TTT AAC AAT GAC TGT AAG CTG AAG GAG AGG     192
Leu Tyr Gly Ser Lys Glu Phe Asn Asn Asp Cys Lys Leu Lys Glu Arg
 50                  55                  60

ATA GAG GAA AAT GGA TAC AAT ACC TAT GCA TCA TTT AAC TGG CAG CAT     240
Ile Glu Glu Asn Gly Tyr Asn Thr Tyr Ala Ser Phe Asn Trp Gln His
 65                  70                  75                  80

AAT GGG AGG CAA ATG TAT GTG GCA TTG AAT GGA AAA GGA GCT CCA AGG     288
Asn Gly Arg Gln Met Tyr Val Ala Leu Asn Gly Lys Gly Ala Pro Arg
                 85                  90                  95

AGA GGA CAG AAA ACA CGA AGG AAA AAC ACC TCT GCT CAC TTT CTT CCA     336
Arg Gly Gln Lys Thr Arg Arg Lys Asn Thr Ser Ala His Phe Leu Pro
                100                 105                 110

ATG GTG GTA CAC TCA TAG                                              354
Met Val Val His Ser
                115
```

(2) INFORMATION FOR SEQ ID NO:72:

(i) SEQUENCE CHARACTERISTICS:
    (A) LENGTH: 117 amino acids
    (B) TYPE: amino acid
    (D) TOPOLOGY: linear (ii) MOLECULE TYPE: protein (xi) SEQUENCE DESCRIPTION: SEQ ID NO:72:

```
Met Glu Lys Asn Gly Lys Val Ser Gly Thr Lys Lys Glu Asn Cys Pro
 1               5                  10                  15

Tyr Ser Ile Leu Glu Ile Thr Ser Val Glu Ile Gly Val Val Ala Val
                20                  25                  30

Lys Ala Ile Asn Ser Asn Tyr Tyr Leu Ala Met Asn Lys Lys Gly Lys
             35                  40                  45

Leu Tyr Gly Ser Lys Glu Phe Asn Asn Asp Cys Lys Leu Lys Glu Arg
 50                  55                  60

Ile Glu Glu Asn Gly Tyr Asn Thr Tyr Ala Ser Phe Asn Trp Gln His
 65                  70                  75                  80

Asn Gly Arg Gln Met Tyr Val Ala Leu Asn Gly Lys Gly Ala Pro Arg
                 85                  90                  95

Arg Gly Gln Lys Thr Arg Arg Lys Asn Thr Ser Ala His Phe Leu Pro
                100                 105                 110
```

Met Val Val His Ser
       115

(2) INFORMATION FOR SEQ ID NO:73:

(i) SEQUENCE CHARACTERISTICS:
        (A) LENGTH: 321 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..318

(xi) SEQUENCE DESCRIPTION: SEQ ID NO:73:

| | | | | | | | | | | | | | | | |
|---|---|---|---|---|---|---|---|---|---|---|---|---|---|---|---|
| ATG | GAG | AAC | TGC | CCG | TAC | AGC | ATC | CTG | GAG | ATA | ACA | TCA | GTA | GAA | ATC | 48 |
| Met | Glu | Asn | Cys | Pro | Tyr | Ser | Ile | Leu | Glu | Ile | Thr | Ser | Val | Glu | Ile |
| 185 | | | | 190 | | | | 195 | | | | 200 | | | |

```
ATG GAG AAC TGC CCG TAC AGC ATC CTG GAG ATA ACA TCA GTA GAA ATC        48
Met Glu Asn Cys Pro Tyr Ser Ile Leu Glu Ile Thr Ser Val Glu Ile
185             190                 195                 200

GGA GTT GTT GCC GTC AAA GCC ATT AAC AGC AAC TAT TAC TTA GCC ATG        96
Gly Val Val Ala Val Lys Ala Ile Asn Ser Asn Tyr Tyr Leu Ala Met
                205                 210                 215

AAC AAG AAG GGG AAA CTC TAT GGC TCA AAA GAA TTT AAC AAT GAC TGT       144
Asn Lys Lys Gly Lys Leu Tyr Gly Ser Lys Glu Phe Asn Asn Asp Cys
            220                 225                 230

AAG CTG AAG GAG AGG ATA GAG GAA AAT GGA TAC AAT ACC TAT GCA TCA       192
Lys Leu Lys Glu Arg Ile Glu Glu Asn Gly Tyr Asn Thr Tyr Ala Ser
        235                 240                 245

TTT AAC TGG CAG CAT AAT GGG AGG CAA ATG TAT GTG GCA TTG AAT GGA       240
Phe Asn Trp Gln His Asn Gly Arg Gln Met Tyr Val Ala Leu Asn Gly
    250                 255                 260

AAA GGA GCT CCA AGG AGA GGA CAG AAA ACA CGA AGG AAA AAC ACC TCT       288
Lys Gly Ala Pro Arg Arg Gly Gln Lys Thr Arg Arg Lys Asn Thr Ser
265                 270                 275                 280

GCT CAC TTT CTT CCA ATG GTG GTA CAC TCA TAG                           321
Ala His Phe Leu Pro Met Val Val His Ser
                285                 290
```

(2) INFORMATION FOR SEQ ID NO:74:

(i) SEQUENCE CHARACTERISTICS:
        (A) LENGTH: 106 amino acids
        (B) TYPE: amino acid
        (D) TOPOLOGY: linear (ii) MOLECULE TYPE: protein (xi) SEQUENCE DESCRIPTION: SEQ ID NO:74:

```
Met Glu Asn Cys Pro Tyr Ser Ile Leu Glu Ile Thr Ser Val Glu Ile
 1               5                  10                  15

Gly Val Val Ala Val Lys Ala Ile Asn Ser Asn Tyr Tyr Leu Ala Met
                20                  25                  30

Asn Lys Lys Gly Lys Leu Tyr Gly Ser Lys Glu Phe Asn Asn Asp Cys
            35                  40                  45

Lys Leu Lys Glu Arg Ile Glu Glu Asn Gly Tyr Asn Thr Tyr Ala Ser
        50                  55                  60

Phe Asn Trp Gln His Asn Gly Arg Gln Met Tyr Val Ala Leu Asn Gly
 65                  70                  75                  80

Lys Gly Ala Pro Arg Arg Gly Gln Lys Thr Arg Arg Lys Asn Thr Ser
                85                  90                  95
```

```
Ala His Phe Leu Pro Met Val Val His Ser
        100                 105
```

(2) INFORMATION FOR SEQ ID NO:75:

(i) SEQUENCE CHARACTERISTICS:
        (A) LENGTH: 264 base pairs
        (B) TYPE: nucleic acid
        (C) STRANDEDNESS: double
        (D) TOPOLOGY: both (ii) MOLECULE TYPE: DNA (genomic)

(ix) FEATURE:
        (A) NAME/KEY: CDS
        (B) LOCATION: 1..261

(xi) SEQUENCE DESCRIPTION: SEQ ID NO:75:

```
ATG GTC AAA GCC ATT AAC AGC AAC TAT TAC TTA GCC ATG AAC AAG AAG      48
Met Val Lys Ala Ile Asn Ser Asn Tyr Tyr Leu Ala Met Asn Lys Lys
 1               5                  10                  15

GGG AAA CTC TAT GGC TCA AAA GAA TTT AAC AAT GAC TGT AAG CTG AAG      96
Gly Lys Leu Tyr Gly Ser Lys Glu Phe Asn Asn Asp Cys Lys Leu Lys
                20                  25                  30

GAG AGG ATA GAG GAA AAT GGA TAC AAT ACC TAT GCA TCA TTT AAC TGG     144
Glu Arg Ile Glu Glu Asn Gly Tyr Asn Thr Tyr Ala Ser Phe Asn Trp
         35                  40                  45

CAG CAT AAT GGG AGG CAA ATG TAT GTG GCA TTG AAT GGA AAA GGA GCT     192
Gln His Asn Gly Arg Gln Met Tyr Val Ala Leu Asn Gly Lys Gly Ala
     50                  55                  60

CCA AGG AGA GGA CAG AAA ACA CGA AGG AAA AAC ACC TCT GCT CAC TTT     240
Pro Arg Arg Gly Gln Lys Thr Arg Arg Lys Asn Thr Ser Ala His Phe
 65                  70                  75                  80

CTT CCA ATG GTG GTA CAC TCA TAG                                     264
Leu Pro Met Val Val His Ser
                85
```

(2) INFORMATION FOR SEQ ID NO:76:

(i) SEQUENCE CHARACTERISTICS:
        (A) LENGTH: 87 amino acids
        (B) TYPE: amino acid
        (D) TOPOLOGY: linear (ii) MOLECULE TYPE: protein (xi) SEQUENCE DESCRIPTION: SEQ ID NO:76:

```
Met Val Lys Ala Ile Asn Ser Asn Tyr Tyr Leu Ala Met Asn Lys Lys
 1               5                  10                  15

Gly Lys Leu Tyr Gly Ser Lys Glu Phe Asn Asn Asp Cys Lys Leu Lys
                20                  25                  30

Glu Arg Ile Glu Glu Asn Gly Tyr Asn Thr Tyr Ala Ser Phe Asn Trp
         35                  40                  45

Gln His Asn Gly Arg Gln Met Tyr Val Ala Leu Asn Gly Lys Gly Ala
     50                  55                  60

Pro Arg Arg Gly Gln Lys Thr Arg Arg Lys Asn Thr Ser Ala His Phe
 65                  70                  75                  80

Leu Pro Met Val Val His Ser
                85
```

(2) INFORMATION FOR SEQ ID NO:77:

(i) SEQUENCE CHARACTERISTICS:
        (A) LENGTH: 219 base pairs

```
            (B) TYPE: nucleic acid
            (C) STRANDEDNESS: double
            (D) TOPOLOGY: both (ii) MOLECULE TYPE: DNA (genomic)

(ix) FEATURE:
            (A) NAME/KEY: CDS
            (B) LOCATION: 1..216

(xi) SEQUENCE DESCRIPTION: SEQ ID NO:77:

ATG GGG AAA CTC TAT GGC TCA AAA GAA TTT AAC AAT GAC TGT AAG CTG        48
Met Gly Lys Leu Tyr Gly Ser Lys Glu Phe Asn Asn Asp Cys Lys Leu
 1               5                  10                  15

AAG GAG AGG ATA GAG GAA AAT GGA TAC AAT ACC TAT GCA TCA TTT AAC        96
Lys Glu Arg Ile Glu Glu Asn Gly Tyr Asn Thr Tyr Ala Ser Phe Asn
             20                  25                  30

TGG CAG CAT AAT GGG AGG CAA ATG TAT GTG GCA TTG AAT GGA AAA GGA       144
Trp Gln His Asn Gly Arg Gln Met Tyr Val Ala Leu Asn Gly Lys Gly
         35                  40                  45

GCT CCA AGG AGA GGA CAG AAA ACA CGA AGG AAA AAC ACC TCT GCT CAC       192
Ala Pro Arg Arg Gly Gln Lys Thr Arg Arg Lys Asn Thr Ser Ala His
     50                  55                  60

TTT CTT CCA ATG GTG GTA CAC TCA TAG                                   219
Phe Leu Pro Met Val Val His Ser
 65                  70

(2) INFORMATION FOR SEQ ID NO:78:

(i) SEQUENCE CHARACTERISTICS:
            (A) LENGTH: 72 amino acids
            (B) TYPE: amino acid
            (D) TOPOLOGY: linear (ii) MOLECULE TYPE: protein (xi) SEQUENCE DESCRIPTION: SEQ ID NO:78:

Met Gly Lys Leu Tyr Gly Ser Lys Glu Phe Asn Asn Asp Cys Lys Leu
 1               5                  10                  15

Lys Glu Arg Ile Glu Glu Asn Gly Tyr Asn Thr Tyr Ala Ser Phe Asn
             20                  25                  30

Trp Gln His Asn Gly Arg Gln Met Tyr Val Ala Leu Asn Gly Lys Gly
         35                  40                  45

Ala Pro Arg Arg Gly Gln Lys Thr Arg Arg Lys Asn Thr Ser Ala His
     50                  55                  60

Phe Leu Pro Met Val Val His Ser
 65                  70

(2) INFORMATION FOR SEQ ID NO:79:

(i) SEQUENCE CHARACTERISTICS:
            (A) LENGTH: 357 base pairs
            (B) TYPE: nucleic acid
            (C) STRANDEDNESS: double
            (D) TOPOLOGY: both (ii) MOLECULE TYPE: DNA (genomic)

(ix) FEATURE:
            (A) NAME/KEY: CDS
            (B) LOCATION: 1..357

(xi) SEQUENCE DESCRIPTION: SEQ ID NO:79:

ATG ACC TGC CAG GCT CTG GGT CAG GAC ATG GTT TCT CCG GAA GCT ACC        48
Met Thr Cys Gln Ala Leu Gly Gln Asp Met Val Ser Pro Glu Ala Thr
 1               5                  10                  15
```

```
AAC TCT TCC TCT TCC TCT TTC TCT TCC CCG TCT TCC GCT GGT CGT CAC      96
Asn Ser Ser Ser Ser Ser Phe Ser Ser Pro Ser Ser Ala Gly Arg His
            20                  25                  30

GTT CGT TCT TAC AAC CAC CTG CAG GGT GAC GTT CGT TGG CGT AAA CTG     144
Val Arg Ser Tyr Asn His Leu Gln Gly Asp Val Arg Trp Arg Lys Leu
        35                  40                  45

TTC TCT TTC ACC AAA TAC TTC CTG AAA ATC GAA AAA AAC GGT AAA GTT     192
Phe Ser Phe Thr Lys Tyr Phe Leu Lys Ile Glu Lys Asn Gly Lys Val
 50                  55                  60

TCT GGG ACC AAG AAG GAG AAC TGC CCG TAC AGC ATC CTG GAG ATA ACA     240
Ser Gly Thr Lys Lys Glu Asn Cys Pro Tyr Ser Ile Leu Glu Ile Thr
 65                  70                  75                  80

TCA GTA GAA ATC GGA GTT GTT GCC GTC AAA GCC ATT AAC AGC AAC TAT     288
Ser Val Glu Ile Gly Val Val Ala Val Lys Ala Ile Asn Ser Asn Tyr
                 85                  90                  95

TAC TTA GCC ATG AAC AAG AAG GGG AAA CTC TAT GGC TCA AAA GAA TTT     336
Tyr Leu Ala Met Asn Lys Lys Gly Lys Leu Tyr Gly Ser Lys Glu Phe
            100                 105                 110

AAC AAT GAC TGT AAG CTG AAG                                         357
Asn Asn Asp Cys Lys Leu Lys
        115
```

(2) INFORMATION FOR SEQ ID NO:80:

(i) SEQUENCE CHARACTERISTICS:
        (A) LENGTH: 119 amino acids
        (B) TYPE: amino acid
        (D) TOPOLOGY: linear (ii) MOLECULE TYPE: protein (xi) SEQUENCE DESCRIPTION: SEQ ID NO:80:

```
Met Thr Cys Gln Ala Leu Gly Gln Asp Met Val Ser Pro Glu Ala Thr
 1               5                  10                  15

Asn Ser Ser Ser Ser Phe Ser Ser Pro Ser Ser Ala Gly Arg His
            20                  25                  30

Val Arg Ser Tyr Asn His Leu Gln Gly Asp Val Arg Trp Arg Lys Leu
        35                  40                  45

Phe Ser Phe Thr Lys Tyr Phe Leu Lys Ile Glu Lys Asn Gly Lys Val
 50                  55                  60

Ser Gly Thr Lys Lys Glu Asn Cys Pro Tyr Ser Ile Leu Glu Ile Thr
 65                  70                  75                  80

Ser Val Glu Ile Gly Val Val Ala Val Lys Ala Ile Asn Ser Asn Tyr
                 85                  90                  95

Tyr Leu Ala Met Asn Lys Lys Gly Lys Leu Tyr Gly Ser Lys Glu Phe
            100                 105                 110

Asn Asn Asp Cys Lys Leu Lys
        115
```

(2) INFORMATION FOR SEQ ID NO:81:

(i) SEQUENCE CHARACTERISTICS:
        (A) LENGTH: 276 base pairs
        (B) TYPE: nucleic acid
        (C) STRANDEDNESS: double
        (D) TOPOLOGY: both (ii) MOLECULE TYPE: DNA (genomic)

(ix) FEATURE:
        (A) NAME/KEY: CDS
        (B) LOCATION: 1..276

(xi) SEQUENCE DESCRIPTION: SEQ ID NO:81:

```
ATG GCT GGT CGT CAC GTT CGT TCT TAC AAC CAC CTG CAG GGT GAC GTT      48
Met Ala Gly Arg His Val Arg Ser Tyr Asn His Leu Gln Gly Asp Val
 1               5                  10                  15

CGT TGG CGT AAA CTG TTC TCT TTC ACC AAA TAC TTC CTG AAA ATC GAA      96
Arg Trp Arg Lys Leu Phe Ser Phe Thr Lys Tyr Phe Leu Lys Ile Glu
                20                  25                  30

AAA AAC GGT AAA GTT TCT GGG ACC AAG AAG GAG AAC TGC CCG TAC AGC     144
Lys Asn Gly Lys Val Ser Gly Thr Lys Lys Glu Asn Cys Pro Tyr Ser
            35                  40                  45

ATC CTG GAG ATA ACA TCA GTA GAA ATC GGA GTT GTT GCC GTC AAA GCC     192
Ile Leu Glu Ile Thr Ser Val Glu Ile Gly Val Val Ala Val Lys Ala
 50                  55                  60

ATT AAC AGC AAC TAT TAC TTA GCC ATG AAC AAG AAG GGG AAA CTC TAT     240
Ile Asn Ser Asn Tyr Tyr Leu Ala Met Asn Lys Lys Gly Lys Leu Tyr
 65                  70                  75                  80

GGC TCA AAA GAA TTT AAC AAT GAC TGT AAG CTG AAG                     276
Gly Ser Lys Glu Phe Asn Asn Asp Cys Lys Leu Lys
                85                  90
```

(2) INFORMATION FOR SEQ ID NO:82:

(i) SEQUENCE CHARACTERISTICS:
        (A) LENGTH: 92 amino acids
        (B) TYPE: amino acid
        (D) TOPOLOGY: linear (ii) MOLECULE TYPE: protein (xi) SEQUENCE DESCRIPTION: SEQ ID NO:82:

```
Met Ala Gly Arg His Val Arg Ser Tyr Asn His Leu Gln Gly Asp Val
 1               5                  10                  15

Arg Trp Arg Lys Leu Phe Ser Phe Thr Lys Tyr Phe Leu Lys Ile Glu
                20                  25                  30

Lys Asn Gly Lys Val Ser Gly Thr Lys Lys Glu Asn Cys Pro Tyr Ser
            35                  40                  45

Ile Leu Glu Ile Thr Ser Val Glu Ile Gly Val Val Ala Val Lys Ala
 50                  55                  60

Ile Asn Ser Asn Tyr Tyr Leu Ala Met Asn Lys Lys Gly Lys Leu Tyr
 65                  70                  75                  80

Gly Ser Lys Glu Phe Asn Asn Asp Cys Lys Leu Lys
                85                  90
```

(2) INFORMATION FOR SEQ ID NO:83:

(i) SEQUENCE CHARACTERISTICS:
        (A) LENGTH: 525 base pairs
        (B) TYPE: nucleic acid
        (C) STRANDEDNESS: double
        (D) TOPOLOGY: both (ii) MOLECULE TYPE: DNA (genomic)

(xi) SEQUENCE DESCRIPTION: SEQ ID NO:83:

```
ATGACCTCTC AGGCTCTGGG TCAGGACATG GTTTCTCCGG AAGCTACCAA CTCTTCCTCT      60

TCCTCTTTCT CTTCCCCGTC TTCCGCTGGT CGTCACGTTC GTTCTTACAA CCACCTGCAG     120

GGTGACGTTC GTTGGCGTAA ACTGTTCTCT TTCACCAAAT ACTTCCTGAA AATCGAAAAA     180

AACGGTAAAG TTTCTGGGAC CAAGAAGGAG AACTCTCCGT ACAGCATCCT GGAGATAACA     240

TCAGTAGAAA TCGGAGTTGT TGCCGTCAAA GCCATTAACA GCAACTATTA CTTAGCCATG     300
```

```
AACAAGAAGG GGAAACTCTA TGGCTCAAAA GAATTTAACA ATGACTGTAA GCTGAAGGAG      360

AGGATAGAGG AAAATGGATA CAATACCTAT GCATCATTTA ACTGGCAGCA TAATGGGAGG      420

CAAATGTATG TGGCATTGAA TGGAAAAGGA GCTCCAAGGA GAGGACAGAA AACACGAAGG      480

AAAAACACCT CTGCTCACTT TCTTCCAATG GTGGTACACT CATAG                     525
```

(2) INFORMATION FOR SEQ ID NO:84:

(i) SEQUENCE CHARACTERISTICS:
        (A) LENGTH: 525 base pairs
        (B) TYPE: nucleic acid
        (C) STRANDEDNESS: double
        (D) TOPOLOGY: both (ii) MOLECULE TYPE: DNA (genomic)

(xi) SEQUENCE DESCRIPTION: SEQ ID NO:84:

```
ATGACCTGCC AGGCTCTGGG TCAGGACATG GTTTCTCCGG AAGCTACCAA CTCTTCCTCT       60

TCCTCTTTCT CTTCCCCGTC TTCCGCTGGT CGTCACGTTC GTTCTTACAA CCACCTGCAG      120

GGTGACGTTC GTTGGCGTAA ACTGTTCTCT TTCACCAAAT ACTTCCTGAA AATCGAAAAA      180

AACGGTAAAG TTTCTGGGAC CAAGAAGGAG AACTCTCCGT ACAGCATCCT GGAGATAACA      240

TCAGTAGAAA TCGGAGTTGT TGCCGTCAAA GCCATTAACA GCAACTATTA CTTAGCCATG      300

AACAAGAAGG GGAAACTCTA TGGCTCAAAA GAATTTAACA ATGACTGTAA GCTGAAGGAG      360

AGGATAGAGG AAAATGGATA CAATACCTAT GCATCATTTA ACTGGCAGCA TAATGGGAGG      420

CAAATGTATG TGGCATTGAA TGGAAAAGGA GCTCCAAGGA GAGGACAGAA AACACGAAGG      480

AAAAACACCT CTGCTCACTT TCTTCCAATG GTGGTACACT CATAG                     525
```

(2) INFORMATION FOR SEQ ID NO:85:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:85:

```
GGACCCTCAT GACCTCTCAG GCTCTGGGT                                        29
```

(2) INFORMATION FOR SEQ ID NO:86:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:86:

```
AAGGAGAACT CTCCGTACAG C                                                21
```

(2) INFORMATION FOR SEQ ID NO:87:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:87:

GCTGTACGGT CTGTTCTCCT T                                              21

(2) INFORMATION FOR SEQ ID NO:88:

(i) SEQUENCE CHARACTERISTICS:
         (A) LENGTH: 35 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:88:

GGACCCTCAT GACCTGCCAG GCTCTGGGTC AGGAC                               35

(2) INFORMATION FOR SEQ ID NO:89:

(i) SEQUENCE CHARACTERISTICS:
         (A) LENGTH: 37 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:89:

CTGCCCAAGC TTATTATGAG TGTACCACCA TTGGAAG                             37

(2) INFORMATION FOR SEQ ID NO:90:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:90:

AAAGGATCCT GCCAGGCTCT GGGTCAGGAC ATG                                 33

(2) INFORMATION FOR SEQ ID NO:91:

(i) SEQUENCE CHARACTERISTICS:
         (A) LENGTH: 32 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:91:

GCGGCACATG TCTTACAACC ACCTGCAGGG TG                                  32

(2) INFORMATION FOR SEQ ID NO:92:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:92:

```
GGGCCCAAGC TTATGAGTGT ACCACCAT                                          28

(2) INFORMATION FOR SEQ ID NO:93:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:93:

CCGGCGGATC CCATATGTCT TACAACCACC TGCAGG                                 36

(2) INFORMATION FOR SEQ ID NO:94:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:94:

CCGGCGGTAC CTTATTATGA GTGTACCACC ATTGG                                  35

(2) INFORMATION FOR SEQ ID NO:95:

(i) SEQUENCE CHARACTERISTICS:
        (A) LENGTH: 426 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:95:

ATGTCTTACA ACCACCTGCA GGGTGACGTT CGTTGGCGTA AACTGTTCTC TTTCACCAAA        60

TACTTCCTGA AAATCGAAAA AAACGGTAAA GTTTCTGGGA CCAAGAAGGA GAACTGCCCG       120

TACAGCATCC TGGAGATAAC ATCAGTAGAA ATCGGAGTTG TTGCCGTCAA AGCCATTAAC       180

AGCAACTATT ACTTAGCCAT GAACAAGAAG GGGAAACTCT ATGGCTCAAA AGAATTTAAC       240

AATGACTGTA AGCTGAAGGA GAGGATAGAG GAAAATGGAT ACAATACCTA TGCATCATTT       300

AACTGGCAGC ATAATGGGAG GCAAATGTAT GTGGCATTGA ATGGAAAAGG AGCTCCAAGG       360

AGAGGACAGA AAACACGAAG GAAAAACACC TCTGCTCACT TTCTTCCAAT GGTGGTACAC       420

TCATAA                                                                 426

(2) INFORMATION FOR SEQ ID NO:96:

(i) SEQUENCE CHARACTERISTICS:
        (A) LENGTH: 141 amino acids
        (B) TYPE: amino acid
        (C) STRANDEDNESS: single
        (D) TOPOLOGY: Not Relevant (ii) MOLECULE TYPE: protein (xi) SEQUENCE DESCRIPTION: SEQ ID NO:96:

Met Ser Tyr Asn His Leu Gln Gly Asp Val Arg Trp Arg Lys Leu Phe
1               5                  10                  15

Ser Phe Thr Lys Tyr Phe Leu Lys Ile Glu Lys Asn Gly Lys Val Ser
            20                  25                  30
```

```
Gly Thr Lys Lys Glu Asn Cys Pro Tyr Ser Ile Leu Glu Ile Thr Ser
            35                  40                  45

Val Glu Ile Gly Val Val Ala Val Lys Ala Ile Asn Ser Asn Tyr Tyr
 50                  55                  60

Leu Ala Met Asn Lys Lys Gly Lys Leu Tyr Gly Ser Lys Glu Phe Asn
 65                  70                  75                  80

Asn Asp Cys Lys Leu Lys Glu Arg Ile Glu Asn Gly Tyr Asn Thr
                 85                  90                  95

Tyr Ala Ser Phe Asn Trp Gln His Asn Gly Arg Gln Met Tyr Val Ala
                100                 105                 110

Leu Asn Gly Lys Gly Ala Pro Arg Arg Gly Gln Lys Thr Arg Arg Lys
            115                 120                 125

Asn Thr Ser Ala His Phe Leu Pro Met Val Val His Ser
            130                 135                 140

(2) INFORMATION FOR SEQ ID NO:97:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:97:

CAACCACCTG CAGGGTGACG                                                       20

(2) INFORMATION FOR SEQ ID NO:98:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:98:

AACGGTCGAC AAATGTATGT GGCACTGAAC GGTAAAGGTG CTCCACGTCG TGGTCAGAAA          60

ACCCGTCGTA AAAACACC                                                        78

(2) INFORMATION FOR SEQ ID NO:99:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:99:

GGGCCCAAGC TTAAGAGTGT ACCACCATTG GCAGAAAGTG AGCAGAGGTG TTTTTACGAC          60

GGGTTTTCTG ACCACG                                                          76

(2) INFORMATION FOR SEQ ID NO:100:

(i) SEQUENCE CHARACTERISTICS:
        (A) LENGTH: 23 base pairs
        (B) TYPE: nucleic acid
        (C) STRANDEDNESS: single
        (D) TOPOLOGY: linear
```

(ii) MOLECULE TYPE: cDNA (xi) SEQUENCE DESCRIPTION: SEQ ID NO:100:

GCCACATACA TTTGTCGACC GTT                                                   23

(2) INFORMATION FOR SEQ ID NO:101:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:101:

GGGCCCAAGC TTAAGAGTG                                                        19

(2) INFORMATION FOR SEQ ID NO:102:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:102:

GCCACATACA TTTGTCGACC GTT                                                   23

(2) INFORMATION FOR SEQ ID NO:103:

(i) SEQUENCE CHARACTERISTICS:
            (A) LENGTH: 90 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:103:

CTGCAGGGTG ACGTTCGTTG GCGTAAACTG TTCTCCTTCA CCAAATACTT CCTGAAAATC           60

GAAAAAAACG GTAAAGTTTC TGGTACCAAG                                            90

(2) INFORMATION FOR SEQ ID NO:104:

(i) SEQUENCE CHARACTERISTICS:
            (A) LENGTH: 90 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:104:

AGCTTTAACA GCAACAACAC CGATTTCAAC GGAGGTGATT TCCAGGATGG AGTACGGGCA           60

GTTTTCTTTC TTGGTACCAG AAACTTTACC                                            90

(2) INFORMATION FOR SEQ ID NO:105:

(i) SEQUENCE CHARACTERISTICS:
            (A) LENGTH: 90 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:105:

GGTGTTGTTG CTGTTAAAGC TATCAACTCC AACTACTACC TGGCTATGAA CAAGAAAGGT        60

AAACTGTACG GTTCCAAAGA ATTTAACAAC        90

(2) INFORMATION FOR SEQ ID NO:106:

(i) SEQUENCE CHARACTERISTICS:
            (A) LENGTH: 100 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:106:

GTCGACCGTT GTGCTGCCAG TTGAAGGAAG CGTAGGTGTT GTAACCGTTT TCTTCGATAC        60

GTTCTTTCAG TTTACAGTCG TTGTTAAATT CTTTGGAACC        100

(2) INFORMATION FOR SEQ ID NO:107:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:107:

GCGGCGTCGA CCGTTGTGCT GCCAG        25

(2) INFORMATION FOR SEQ ID NO:108:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:108:

GCGGCCTGCA GGGTGACGTT CGTTGG        26

(2) INFORMATION FOR SEQ ID NO:109:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:109:

CCGGCGGATC CCATATGTCT TACAACCACC TGCAGG        36

(2) INFORMATION FOR SEQ ID NO:110:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:110:

| CGCGCGATAT CTTATTAAGA GTGTACCACC ATTG | 34 |

(2) INFORMATION FOR SEQ ID NO:111:

(i) SEQUENCE CHARACTERISTICS:
        (A) LENGTH: 426 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:111:

| ATGTCTTACA ACCACCTGCA GGGTGACGTT CGTTGGCGTA AACTGTTCTC CTTCACCAAA | 60 |
| TACTTCCTGA AAATCGAAAA AAACGGTAAA GTTTCTGGTA CCAAGAAAGA AAACTGCCCG | 120 |
| TACTCCATCC TGGAAATCAC CTCCGTTGAA ATCGGTGTTG TTGCTGTTAA AGCTATCAAC | 180 |
| TCCAACTACT ACCTGGCTAT GAACAAGAAA GGTAAACTGT ACGGTTCCAA AGAATTTAAC | 240 |
| AACGACTGTA AACTGAAAGA ACGTATCGAA GAAAACGGTT ACAACACCTA CGCTTCCTTC | 300 |
| AACTGGCAGC ACAACGGTCG ACAAATGTAT GTGGCACTGA ACGGTAAAGG TGCTCCACGT | 360 |
| CGTGGTCAGA AACCCGTCG TAAAAACACC TCTGCTCACT TTCTGCCAAT GGTGGTACAC | 420 |
| TCTTAA | 426 |

(2) INFORMATION FOR SEQ ID NO:112:

(i) SEQUENCE CHARACTERISTICS:
        (A) LENGTH: 141 amino acids
        (B) TYPE: amino acid
        (C) STRANDEDNESS: single
        (D) TOPOLOGY: Not Relevant (ii) MOLECULE TYPE: protein (xi) SEQUENCE DESCRIPTION: SEQ ID NO:112:

```
Met Ser Tyr Asn His Leu Gln Gly Asp Val Arg Trp Arg Lys Leu Phe
1               5                  10                  15

Ser Phe Thr Lys Tyr Phe Leu Lys Ile Glu Lys Asn Gly Lys Val Ser
            20                  25                  30

Gly Thr Lys Lys Glu Asn Cys Pro Tyr Ser Ile Leu Glu Ile Thr Ser
        35                  40                  45

Val Glu Ile Gly Val Val Ala Val Lys Ala Ile Asn Ser Asn Tyr Tyr
    50                  55                  60

Leu Ala Met Asn Lys Lys Gly Lys Leu Tyr Gly Ser Lys Glu Phe Asn
65                  70                  75                  80

Asn Asp Cys Lys Leu Lys Glu Arg Ile Glu Glu Asn Gly Tyr Asn Thr
                85                  90                  95

Tyr Ala Ser Phe Asn Trp Gln His Asn Gly Arg Gln Met Tyr Val Ala
            100                 105                 110

Leu Asn Gly Lys Gly Ala Pro Arg Arg Gly Gln Lys Thr Arg Arg Lys
        115                 120                 125

Asn Thr Ser Ala His Phe Leu Pro Met Val Val His Ser
    130                 135                 140
```

(2) INFORMATION FOR SEQ ID NO:113:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:113:

CGCGGCCATG GCTCTGGGTC AGGACATG                                28

(2) INFORMATION FOR SEQ ID NO:114:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:114:

GGGCCCAAGC TTATGAGTGT ACCACCAT                                28

(2) INFORMATION FOR SEQ ID NO:115:

(i) SEQUENCE CHARACTERISTICS:
       (A) LENGTH: 516 base pairs
       (B) TYPE: nucleic acid
       (C) STRANDEDNESS: double
       (D) TOPOLOGY: linear (ii) MOLECULE TYPE: cDNA (xi) SEQUENCE DESCRIPTION: SEQ ID NO:115:

ATGGCTCTGG GTCAAGATAT GGTTTCTCCG GAAGCTACCA ACTCTTCCTC TTCCTCTTTC       60

TCTTCCCCGT CTTCCGCTGG TCGTCACGTT CGTTCTTACA ACCACCTGCA GGGTGACGTT      120

CGTTGGCGTA AACTGTTCTC TTTCACCAAA TACTTCCTGA AAATCGAAAA AAACGGTAAA      180

GTTTCTGGGA CCAAGAAGGA GAACTGCCCG TACAGCATCC TGGAGATAAC ATCAGTAGAA      240

ATCGGAGTTG TTGCCGTCAA AGCCATTAAC AGCAACTATT ACTTAGCCAT GAACAAGAAG      300

GGGAAACTCT ATGGCTCAAA AGAATTTAAC AATGACTGTA AGCTGAAGGA GAGGATAGAG      360

GAAAATGGAT ACAATACCTA TGCATCATTT AACTGGCAGC ATAATGGGAG GCAAATGTAT      420

GTGGCATTGA ATGGAAAAGG AGCTCCAAGG AGAGGACAGA AAACACGAAG GAAAAACACC      480

TCTGCTCACT TCTTCCAAT GGTGGTACAC TCATAA                                 516

(2) INFORMATION FOR SEQ ID NO:116:

(i) SEQUENCE CHARACTERISTICS:
       (A) LENGTH: 171 amino acids
       (B) TYPE: amino acid
       (C) STRANDEDNESS: single
       (D) TOPOLOGY: Not Relevant (ii) MOLECULE TYPE: protein (xi) SEQUENCE DESCRIPTION: SEQ ID NO:116:

Met Ala Leu Gly Gln Asp Met Val Ser Pro Glu Ala Thr Asn Ser Ser
1               5                   10                  15

Ser Ser Ser Phe Ser Ser Pro Ser Ser Ala Gly Arg His Val Arg Ser
                20                  25                  30

Tyr Asn His Leu Gln Gly Asp Val Arg Trp Arg Lys Leu Phe Ser Phe
        35                  40                  45

```
Thr Lys Tyr Phe Leu Lys Ile Glu Lys Asn Gly Lys Val Ser Gly Thr
        50                  55                  60

Lys Lys Glu Asn Cys Pro Tyr Ser Ile Leu Glu Ile Thr Ser Val Glu
 65                  70                  75                  80

Ile Gly Val Val Ala Val Lys Ala Ile Asn Ser Asn Tyr Tyr Leu Ala
                     85                  90                  95

Met Asn Lys Lys Gly Lys Leu Tyr Gly Ser Lys Glu Phe Asn Asn Asp
            100                 105                 110

Cys Lys Leu Lys Glu Arg Ile Glu Glu Asn Gly Tyr Asn Thr Tyr Ala
            115                 120                 125

Ser Phe Asn Trp Gln His Asn Gly Arg Gln Met Tyr Val Ala Leu Asn
        130                 135                 140

Gly Lys Gly Ala Pro Arg Arg Gly Gln Lys Thr Arg Arg Lys Asn Thr
145                 150                 155                 160

Ser Ala His Phe Leu Pro Met Val Val His Ser
                165                 170
```

(2) INFORMATION FOR SEQ ID NO:117:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:117:

```
GCGGCACATG TCTTACAACC ACCTGCAGGG TG                              32
```

(2) INFORMATION FOR SEQ ID NO:118:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:118:

```
CTGCCCAAGC TTTTATGAGT GTACCACCAT TGGAAGAAAG TGAGCAGAGG TGTTTTTTTC  60

TCGTGTTTTC TGTCC                                                  75
```

(2) INFORMATION FOR SEQ ID NO:119:

(i) SEQUENCE CHARACTERISTICS:
        (A) LENGTH: 426 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:119:

```
ATGTCTTACA ACCACCTGCA GGGTGACGTT CGTTGGCGTA AACTGTTCTC TTTCACCAAA   60

TACTTCCTGA AAATCGAAAA AAACGGTAAA GTTTCTGGGA CCAAGAAGGA GAACTGCCCG  120

TACAGCATCC TGGAGATAAC ATCAGTAGAA ATCGGAGTTG TTGCCGTCAA AGCCATTAAC  180

AGCAACTATT ACTTAGCCAT GAACAAGAAG GGGAAACTCT ATGGCTCAAA AGAATTTAAC  240

AATGACTGTA AGCTGAAGGA GAGGATAGAG GAAAATGGAT ACAATACCTA TGCATCATTT  300
```

```
AACTGGCAGC ATAATGGGAG GCAAATGTAT GTGGCATTGA ATGGAAAAGG AGCTCCAAGG      360

AGAGGACAGA AAACACGAGA AAAAACACC TCTGCTCACT TTCTTCCAAT GGTGGTACAC       420

TCATAG                                                                 426
```

(2) INFORMATION FOR SEQ ID NO:120:

(i) SEQUENCE CHARACTERISTICS:
        (A) LENGTH: 141 amino acids
        (B) TYPE: amino acid
        (C) STRANDEDNESS: single
        (D) TOPOLOGY: Not Relevant (ii) MOLECULE TYPE: protein (xi) SEQUENCE DESCRIPTION: SEQ ID NO:120:

```
Met Ser Tyr Asn His Leu Gln Gly Asp Val Arg Trp Arg Lys Leu Phe
1               5                   10                  15

Ser Phe Thr Lys Tyr Phe Leu Lys Ile Glu Lys Asn Gly Lys Val Ser
            20                  25                  30

Gly Thr Lys Lys Glu Asn Cys Pro Tyr Ser Ile Leu Glu Ile Thr Ser
        35                  40                  45

Val Glu Ile Gly Val Val Ala Val Lys Ala Ile Asn Ser Asn Tyr Tyr
50                  55                  60

Leu Ala Met Asn Lys Lys Gly Lys Leu Tyr Gly Ser Lys Glu Phe Asn
65                  70                  75                  80

Asn Asp Cys Lys Leu Lys Glu Arg Ile Glu Glu Asn Gly Tyr Asn Thr
                85                  90                  95

Tyr Ala Ser Phe Asn Trp Gln His Asn Gly Arg Gln Met Tyr Val Ala
                100                 105                 110

Leu Asn Gly Lys Gly Ala Pro Arg Arg Gly Gln Lys Thr Arg Glu Lys
            115                 120                 125

Asn Thr Ser Ala His Phe Leu Pro Met Val Val His Ser
        130                 135                 140
```

(2) INFORMATION FOR SEQ ID NO:121:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:121:

```
GCGGCACATG TCTTACAACC ACCTGCAGGG TG                                    32
```

(2) INFORMATION FOR SEQ ID NO:122:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:122:

```
CTGCCCAAGC TTTTATGAGT GTACCACCAT TGGAAGAAAG TGAGCAGAGG TGTTTTTCTG      60

TCGTGTTTTC TGTCC                                                       75
```

(2) INFORMATION FOR SEQ ID NO:123:

(i) SEQUENCE CHARACTERISTICS:
        (A) LENGTH: 426 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:123:

```
ATGTCTTACA ACCACCTGCA GGGTGACGTT CGTTGGCGTA AACTGTTCTC TTTCACCAAA      60

TACTTCCTGA AAATCGAAAA AAACGGTAAA GTTTCTGGGA CCAAGAAGGA GAACTGCCCG     120

TACAGCATCC TGGAGATAAC ATCAGTAGAA ATCGGAGTTG TTGCCGTCAA AGCCATTAAC     180

AGCAACTATT ACTTAGCCAT GAACAAGAAG GGGAAACTCT ATGGCTCAAA AGAATTTAAC     240

AATGACTGTA AGCTGAAGGA GAGGATAGAG GAAAATGGAT ACAATACCTA TGCATCATTT     300

AACTGGCAGC ATAATGGGAG GCAAATGTAT GTGGCATTGA ATGGAAAAGG AGCTCCAAGG     360

AGAGGACAGA AAACACGACA GAAAAACACC TCTGCTCACT TCTTCCAAT GGTGGTACAC      420

TCATAG                                                                426
```

(2) INFORMATION FOR SEQ ID NO:124:

(i) SEQUENCE CHARACTERISTICS:
        (A) LENGTH: 141 amino acids
        (B) TYPE: amino acid
        (C) STRANDEDNESS: single
        (D) TOPOLOGY: Not Relevant (ii) MOLECULE TYPE: protein (xi) SEQUENCE DESCRIPTION: SEQ ID NO:124:

```
Met Ser Tyr Asn His Leu Gln Gly Asp Val Arg Trp Arg Lys Leu Phe
1               5                   10                  15

Ser Phe Thr Lys Tyr Phe Leu Lys Ile Glu Lys Asn Gly Lys Val Ser
            20                  25                  30

Gly Thr Lys Lys Glu Asn Cys Pro Tyr Ser Ile Leu Glu Ile Thr Ser
        35                  40                  45

Val Glu Ile Gly Val Val Ala Val Lys Ala Ile Asn Ser Asn Tyr Tyr
    50                  55                  60

Leu Ala Met Asn Lys Lys Gly Lys Leu Tyr Gly Ser Lys Glu Phe Asn
65                  70                  75                  80

Asn Asp Cys Lys Leu Lys Glu Arg Ile Glu Glu Asn Gly Tyr Asn Thr
                85                  90                  95

Tyr Ala Ser Phe Asn Trp Gln His Asn Gly Arg Gln Met Tyr Val Ala
            100                 105                 110

Leu Asn Gly Lys Gly Ala Pro Arg Arg Gly Gln Lys Thr Arg Gln Lys
        115                 120                 125

Asn Thr Ser Ala His Phe Leu Pro Met Val Val His Ser
    130                 135                 140
```

(2) INFORMATION FOR SEQ ID NO:125:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:125:

GCGGCACATG TCTTACAACC ACCTGCAGGG TG                                    32

(2) INFORMATION FOR SEQ ID NO:126:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:126:

CTGCCCAAGC TTTTATGAGT GTACCACCAT TGGAAGAAAG TGAGCAGAGG TGTTTTTCCT      60

TCGTGTTTCC TGTCCTCTCC TTGG                                            84

(2) INFORMATION FOR SEQ ID NO:127:

(i) SEQUENCE CHARACTERISTICS:
        (A) LENGTH: 426 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:127:

ATGTCTTACA ACCACCTGCA GGGTGACGTT CGTTGGCGTA AACTGTTCTC TTTCACCAAA      60

TACTTCCTGA AAATCGAAAA AAACGGTAAA GTTTCTGGGA CCAAGAAGGA GAACTGCCCG    120

TACAGCATCC TGGAGATAAC ATCAGTAGAA ATCGGAGTTG TTGCCGTCAA AGCCATTAAC    180

AGCAACTATT ACTTAGCCAT GAACAAGAAG GGGAAACTCT ATGGCTCAAA AGAATTTAAC    240

AATGACTGTA AGCTGAAGGA GAGGATAGAG GAAAATGGAT ACAATACCTA TGCATCATTT    300

AACTGGCAGC ATAATGGGAG GCAAATGTAT GTGGCATTGA ATGGAAAAGG AGCTCCAAGG    360

AGAGGACAGG AAACACGAAG GAAAAACACC TCTGCTCACT TCTTCCAAT GGTGGTACAC     420

TCATAG                                                               426

(2) INFORMATION FOR SEQ ID NO:128:

(i) SEQUENCE CHARACTERISTICS:
        (A) LENGTH: 141 amino acids
        (B) TYPE: amino acid
        (C) STRANDEDNESS: single
        (D) TOPOLOGY: Not Relevant (ii) MOLECULE TYPE: protein (xi) SEQUENCE DESCRIPTION: SEQ ID NO:128:

Met Ser Tyr Asn His Leu Gln Gly Asp Val Arg Trp Arg Lys Leu Phe
1               5                  10                  15

Ser Phe Thr Lys Tyr Phe Leu Lys Ile Glu Lys Asn Gly Lys Val Ser
                20                  25                  30

Gly Thr Lys Lys Glu Asn Cys Pro Tyr Ser Ile Leu Glu Ile Thr Ser
            35                  40                  45

Val Glu Ile Gly Val Val Ala Val Lys Ala Ile Asn Ser Asn Tyr Tyr
        50                  55                  60

Leu Ala Met Asn Lys Lys Gly Lys Leu Tyr Gly Ser Lys Glu Phe Asn
65                  70                  75                  80

Asn Asp Cys Lys Leu Lys Glu Arg Ile Glu Glu Asn Gly Tyr Asn Thr
             85                  90                  95

Tyr Ala Ser Phe Asn Trp Gln His Asn Gly Arg Gln Met Tyr Val Ala
            100                 105                 110

Leu Asn Gly Lys Gly Ala Pro Arg Arg Gly Gln Glu Thr Arg Arg Lys
            115                 120                 125

Asn Thr Ser Ala His Phe Leu Pro Met Val Val His Ser
130                 135                 140

(2) INFORMATION FOR SEQ ID NO:129:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:129:

GCGGCACATG TCTTACAACC ACCTGCAGGG TG                              32

(2) INFORMATION FOR SEQ ID NO:130:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:130:

CTGCCCAAGC TTTTATGAGT GTACCACCAT TGGAAGAAAG TGAGCAGAGG TGTTTTTCCT    60

TCGTGTCTGC TGTCCTCTCC TTGG                                                        84

(2) INFORMATION FOR SEQ ID NO:131:

(i) SEQUENCE CHARACTERISTICS:
        (A) LENGTH: 426 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:131:

ATGTCTTACA ACCACCTGCA GGGTGACGTT CGTTGGCGTA AACTGTTCTC TTTCACCAAA    60

TACTTCCTGA AAATCGAAAA AAACGGTAAA GTTTCTGGGA CCAAGAAGGA GAACTGCCCG   120

TACAGCATCC TGGAGATAAC ATCAGTAGAA ATCGGAGTTG TTGCCGTCAA AGCCATTAAC   180

AGCAACTATT ACTTAGCCAT GAACAAGAAG GGGAAACTCT ATGGCTCAAA AGAATTTAAC   240

AATGACTGTA AGCTGAAGGA GAGGATAGAG GAAAATGGAT ACAATACCTA TGCATCATTT   300

AACTGGCAGC ATAATGGGAG GCAAATGTAT GTGGCATTGA ATGGAAAAGG AGCTCCAAGG   360

AGAGGACAGC AGACACGAAG GAAAAACACC TCTGCTCACT TCTTCCAAT GGTGGTACAC   420

TCATAG                                                                                         426

(2) INFORMATION FOR SEQ ID NO:132:

(i) SEQUENCE CHARACTERISTICS:
        (A) LENGTH: 141 amino acids
        (B) TYPE: amino acid

```
            (C) STRANDEDNESS: single
            (D) TOPOLOGY: Not Relevant (ii) MOLECULE TYPE: protein (xi) SEQUENCE DESCRIPTION: SEQ ID NO:132:

Met Ser Tyr Asn His Leu Gln Gly Asp Val Arg Trp Arg Lys Leu Phe
 1               5                  10                  15

Ser Phe Thr Lys Tyr Phe Leu Lys Ile Glu Lys Asn Gly Lys Val Ser
            20                  25                  30

Gly Thr Lys Lys Glu Asn Cys Pro Tyr Ser Ile Leu Glu Ile Thr Ser
        35                  40                  45

Val Glu Ile Gly Val Val Ala Val Lys Ala Ile Asn Ser Asn Tyr Tyr
    50                  55                  60

Leu Ala Met Asn Lys Lys Gly Lys Leu Tyr Gly Ser Lys Glu Phe Asn
65                  70                  75                  80

Asn Asp Cys Lys Leu Lys Glu Arg Ile Glu Glu Asn Gly Tyr Asn Thr
                85                  90                  95

Tyr Ala Ser Phe Asn Trp Gln His Asn Gly Arg Gln Met Tyr Val Ala
            100                 105                 110

Leu Asn Gly Lys Gly Ala Pro Arg Arg Gly Gln Gln Thr Arg Arg Lys
        115                 120                 125

Asn Thr Ser Ala His Phe Leu Pro Met Val Val His Ser
    130                 135                 140

(2) INFORMATION FOR SEQ ID NO:133:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:133:

GCGGCACATG TCTTACAACC ACCTGCAGGG TG                              32

(2) INFORMATION FOR SEQ ID NO:134:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:134:

CTGCCCAAGC TTTTATGAGT GTACCACCAT TGGAAGAAAG TGAGCAGAGG TGTTTTTCCT    60

TCGTGTTTTC TGTCCTTCCC TTGGAGCTCC TTT                                 93

(2) INFORMATION FOR SEQ ID NO:135:

(i) SEQUENCE CHARACTERISTICS:
        (A) LENGTH: 426 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:135:
```

```
ATGTCTTACA ACCACCTGCA GGGTGACGTT CGTTGGCGTA AACTGTTCTC TTTCACCAAA      60

TACTTCCTGA AAATCGAAAA AAACGGTAAA GTTTCTGGGA CCAAGAAGGA GAACTGCCCG     120

TACAGCATCC TGGAGATAAC ATCAGTAGAA ATCGGAGTTG TTGCCGTCAA AGCCATTAAC     180

AGCAACTATT ACTTAGCCAT GAACAAGAAG GGGAAACTCT ATGGCTCAAA AGAATTTAAC     240

AATGACTGTA AGCTGAAGGA GAGGATAGAG GAAAATGGAT ACAATACCTA TGCATCATTT     300

AACTGGCAGC ATAATGGGAG GCAAATGTAT GTGGCATTGA ATGGAAAAGG AGCTCCAAGG     360

GAAGGACAGA AAACACGAAG GAAAAACACC TCTGCTCACT TTCTTCCAAT GGTGGTACAC     420

TCATAG                                                                426
```

(2) INFORMATION FOR SEQ ID NO:136:

(i) SEQUENCE CHARACTERISTICS:
        (A) LENGTH: 140 amino acids
        (B) TYPE: amino acid
        (C) STRANDEDNESS: single
        (D) TOPOLOGY: Not Relevant (ii) MOLECULE TYPE: protein (xi) SEQUENCE DESCRIPTION: SEQ ID NO:136:

```
Met Tyr Asn His Leu Gln Gly Asp Val Arg Trp Arg Lys Leu Phe Ser
1               5                   10                  15

Phe Thr Lys Tyr Phe Leu Lys Ile Glu Lys Asn Gly Lys Val Ser Gly
            20                  25                  30

Thr Lys Lys Glu Asn Cys Pro Tyr Ser Ile Leu Glu Ile Thr Ser Val
        35                  40                  45

Glu Ile Gly Val Val Ala Val Lys Ala Ile Asn Ser Asn Tyr Tyr Leu
    50                  55                  60

Ala Met Asn Lys Lys Gly Lys Leu Tyr Gly Ser Lys Glu Phe Asn Asn
65                  70                  75                  80

Asp Cys Lys Leu Lys Glu Arg Ile Glu Glu Asn Gly Tyr Asn Thr Tyr
                85                  90                  95

Ala Ser Phe Asn Trp Gln His Asn Gly Arg Gln Met Tyr Val Ala Leu
            100                 105                 110

Asn Gly Lys Gly Ala Pro Arg Glu Gly Gln Lys Thr Arg Arg Lys Asn
        115                 120                 125

Thr Ser Ala His Phe Leu Pro Met Val Val His Ser
    130                 135                 140
```

(2) INFORMATION FOR SEQ ID NO:137:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:137:

```
GCGGCACATG TCTTACAACC ACCTGCAGGG TG                                    32
```

(2) INFORMATION FOR SEQ ID NO:138:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:138:

CTGCCCAAGC TTTTATGAGT GTACCACCAT TGGAAGAAAG TGAGCAGAGG TGTTTTTCCT    60

TCGTGTTTTC TGTCCCTGCC TTGGAGCTCC TTT                                 93

(2) INFORMATION FOR SEQ ID NO:139:

(i) SEQUENCE CHARACTERISTICS:
        (A) LENGTH: 426 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:139:

ATGTCTTACA ACCACCTGCA GGGTGACGTT CGTTGGCGTA AACTGTTCTC TTTCACCAAA    60

TACTTCCTGA AAATCGAAAA AAACGGTAAA GTTTCTGGGA CCAAGAAGGA GAACTGCCCG   120

TACAGCATCC TGGAGATAAC ATCAGTAGAA ATCGGAGTTG TTGCCGTCAA AGCCATTAAC   180

AGCAACTATT ACTTAGCCAT GAACAAGAAG GGGAAACTCT ATGGCTCAAA AGAATTTAAC   240

AATGACTGTA AGCTGAAGGA GAGGATAGAG GAAAATGGAT ACAATACCTA TGCATCATTT   300

AACTGGCAGC ATAATGGGAG GCAAATGTAT GTGGCATTGA ATGGAAAAGG AGCTCCAAGG   360

CAGGGACAGA AAACACGAAG GAAAAACACC TCTGCTCACT TCTTCCAAT GGTGGTACAC    420

TCATAG                                                              426

(2) INFORMATION FOR SEQ ID NO:140:

(i) SEQUENCE CHARACTERISTICS:
        (A) LENGTH: 141 amino acids
        (B) TYPE: amino acid
        (C) STRANDEDNESS: single
        (D) TOPOLOGY: Not Relevant (ii) MOLECULE TYPE: protein (xi) SEQUENCE DESCRIPTION: SEQ ID NO:140:

Met Ser Tyr Asn His Leu Gln Gly Asp Val Arg Trp Arg Lys Leu Phe
1               5                   10                  15

Ser Phe Thr Lys Tyr Phe Leu Lys Ile Glu Lys Asn Gly Lys Val Ser
                20                  25                  30

Gly Thr Lys Lys Glu Asn Cys Pro Tyr Ser Ile Leu Glu Ile Thr Ser
            35                  40                  45

Val Glu Ile Gly Val Val Ala Val Lys Ala Ile Asn Ser Asn Tyr Tyr
        50                  55                  60

Leu Ala Met Asn Lys Lys Gly Lys Leu Tyr Gly Ser Lys Glu Phe Asn
65                  70                  75                  80

Asn Asp Cys Lys Leu Lys Glu Arg Ile Glu Glu Asn Gly Tyr Asn Thr
                85                  90                  95

Tyr Ala Ser Phe Asn Trp Gln His Asn Gly Arg Gln Met Tyr Val Ala
            100                 105                 110

Leu Asn Gly Lys Gly Ala Pro Arg Gln Gly Gln Lys Thr Arg Arg Lys
        115                 120                 125

Asn Thr Ser Ala His Phe Leu Pro Met Val Val His Ser
    130                 135                 140

(2) INFORMATION FOR SEQ ID NO:141:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:141:

```
GCGGCACATG TCTTACAACC ACCTGCAGGG TG                          32
```

(2) INFORMATION FOR SEQ ID NO:142:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:142:

```
TTGAATGGAG AAGGAGCTCC A                                      21
```

(2) INFORMATION FOR SEQ ID NO:143:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:143:

```
TGGAGCTCCT TCTCCATTCA A                                      21
```

(2) INFORMATION FOR SEQ ID NO:144:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:144:

```
CTGCCCAAGC TTTTATGAGT GTACCACCAT TGG                         33
```

(2) INFORMATION FOR SEQ ID NO:145:

(i) SEQUENCE CHARACTERISTICS:
        (A) LENGTH: 426 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:145:

```
ATGTCTTACA ACCACCTGCA GGGTGACGTT CGTTGGCGTA AACTGTTCTC TTTCACCAAA    60
TACTTCCTGA AAATCGAAAA AAACGGTAAA GTTTCTGGGA CCAAGAAGGA GAACTGCCCG   120
TACAGCATCC TGGAGATAAC ATCAGTAGAA ATCGGAGTTG TTGCCGTCAA AGCCATTAAC   180
AGCAACTATT ACTTAGCCAT GAACAAGAAG GGGAAACTCT ATGGCTCAAA AGAATTTAAC   240
```

```
AATGACTGTA AGCTGAAGGA GAGGATAGAG GAAAATGGAT ACAATACCTA TGCATCATTT      300

AACTGGCAGC ATAATGGGAG GCAAATGTAT GTGGCATTGA ATGGAGAAGG AGCTCCAAGG      360

AGAGGACAGA AAACACGAAG GAAAAACACC TCTGCTCACT TTCTTCCAAT GGTGGTACAC      420

TCATAG                                                                426
```

(2) INFORMATION FOR SEQ ID NO:146:

(i) SEQUENCE CHARACTERISTICS:
        (A) LENGTH: 141 amino acids
        (B) TYPE: amino acid
        (C) STRANDEDNESS: single
        (D) TOPOLOGY: Not Relevant (ii) MOLECULE TYPE: protein (xi) SEQUENCE DESCRIPTION: SEQ ID NO:146:

```
Met Ser Tyr Asn His Leu Gln Gly Asp Val Arg Trp Arg Lys Leu Phe
  1               5                  10                  15

Ser Phe Thr Lys Tyr Phe Leu Lys Ile Glu Lys Asn Gly Lys Val Ser
             20                  25                  30

Gly Thr Lys Lys Glu Asn Cys Pro Tyr Ser Ile Leu Glu Ile Thr Ser
         35                  40                  45

Val Glu Ile Gly Val Val Ala Val Lys Ala Ile Asn Ser Asn Tyr Tyr
 50                  55                  60

Leu Ala Met Asn Lys Lys Gly Lys Leu Tyr Gly Ser Lys Glu Phe Asn
 65                  70                  75                  80

Asn Asp Cys Lys Leu Lys Glu Arg Ile Glu Glu Asn Gly Tyr Asn Thr
                 85                  90                  95

Tyr Ala Ser Phe Asn Trp Gln His Asn Gly Arg Gln Met Tyr Val Ala
                100                 105                 110

Leu Asn Gly Glu Gly Ala Pro Arg Arg Gly Gln Lys Thr Arg Arg Lys
            115                 120                 125

Asn Thr Ser Ala His Phe Leu Pro Met Val Val His Ser
130                 135                 140
```

(2) INFORMATION FOR SEQ ID NO:147:

(i) SEQUENCE CHARACTERISTICS:
        (A) LENGTH: 3974 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:147:

```
GGTACCTAAG TGAGTAGGGC GTCCGATCGA CGGACGCCTT TTTTTTGAAT TCGTAATCAT       60

GGTCATAGCT GTTTCCTGTG TGAAATTGTT ATCCGCTCAC AATTCCACAC AACATACGAG      120

CCGGAAGCAT AAAGTGTAAA GCCTGGGGTG CCTAATGAGT GAGCTAACTC ACATTAATTG      180

CGTTGCGCTC ACTGCCCGCT TTCCAGTCGG GAAACCTGTC GTGCCAGCTG CATTAATGAA      240

TCGGCCAACG CGCGGGGAGA GGCGGTTTGC GTATTGGGCG CTCTTCCGCT TCCTCGCTCA      300

CTGACTCGCT GCGCTCGGTC GTTCGGCTGC GGCGAGCGGT ATCAGCTCAC TCAAAGGCGG      360

TAATACGGTT ATCCACAGAA TCAGGGGATA ACGCAGGAAA GAACATGTGA GCAAAAGGCC      420

AGCAAAAGGC CAGGAACCGT AAAAAGGCCG CGTTGCTGGC GTTTTTCCAT AGGCTCCGCC      480

CCCCTGACGA GCATCACAAA AATCGACGCT CAAGTCAGAG GTGGCGAAAC CCGACAGGAC      540
```

```
TATAAAGATA CCAGGCGTTT CCCCCTGGAA GCTCCCTCGT GCGCTCTCCT GTTCCGACCC      600
TGCCGCTTAC CGGATACCTG TCCGCCTTTC TCCCTTCGGG AAGCGTGGCG CTTTCTCATA      660
GCTCACGCTG TAGGTATCTC AGTTCGGTGT AGGTCGTTCG CTCCAAGCTG GGCTGTGTGC      720
ACGAACCCCC CGTTCAGCCC GACCGCTGCG CCTTATCCGG TAACTATCGT CTTGAGTCCA      780
ACCCGGTAAG ACACGACTTA TCGCCACTGG CAGCAGCCAC TGGTAACAGG ATTAGCAGAG      840
CGAGGTATGT AGGCGGTGCT ACAGAGTTCT TGAAGTGGTG GCCTAACTAC GGCTACACTA      900
GAAGAACAGT ATTTGGTATC TGCGCTCTGC TGAAGCCAGT TACCTTCGGA AAAAGAGTTG      960
GTAGCTCTTG ATCCGGCAAA CAAACCACCG CTGGTAGCGG TGGTTTTTTT GTTTGCAAGC     1020
AGCAGATTAC GCGCAGAAAA AAAGGATCTC AAGAAGATCC TTTGATCTTT TCTACGGGGT     1080
CTGACGCTCA GTGGAACGAA AACTCACGTT AAGGGATTTT GGTCATGAGA TTATCGTCGA     1140
CAATTCGCGC GCGAAGGCGA AGCGGCATGC ATTTACGTTG ACACCATCGA ATGGTGCAAA     1200
ACCTTTCGCG GTATGGCATG ATAGCGCCCG GAAGAGAGTC AATTCAGGGT GGTGAATGTG     1260
AAACCAGTAA CGTTATACGA TGTCGCAGAG TATGCCGGTG TCTCTTATCA GACCGTTTCC     1320
CGCGTGGTGA ACCAGGCCAG CCACGTTTCT GCGAAAACGC GGGAAAAAGT GGAAGCGGCG     1380
ATGGCGGAGC TGAATTACAT TCCCAACCGC GTGGCACAAC AACTGGCGGG CAAACAGTCG     1440
TTGCTGATTG GCGTTGCCAC CTCCAGTCTG GCCCTGCACG CGCCGTCGCA AATTGTCGCG     1500
GCGATTAAAT CTCGCGCCGA TCAACTGGGT GCCAGCGTGG TGGTGTCGAT GGTAGAACGA     1560
AGCGGCGTCG AAGCCTGTAA AGCGGCGGTG CACAATCTTC TCGCGCAACG CGTCAGTGGG     1620
CTGATCATTA ACTATCCGCT GGATGACCAG GATGCCATTG CTGTGGAAGC TGCCTGCACT     1680
AATGTTCCGG CGTTATTTCT TGATGTCTCT GACCAGACAC CCATCAACAG TATTATTTTC     1740
TCCCATGAAG ACGGTACGCG ACTGGGCGTG GAGCATCTGG TCGCATTGGG TCACCAGCAA     1800
ATCGCGCTGT TAGCGGGCCC ATTAAGTTCT GTCTCGGCGC GTCTGCGTCT GGCTGGCTGG     1860
CATAAATATC TCACTCGCAA TCAAATTCAG CCGATAGCGG AACGGGAAGG CGACTGGAGT     1920
GCCATGTCCG GTTTTCAACA AACCATGCAA ATGCTGAATG AGGGCATCGT TCCCACTGCG     1980
ATGCTGGTTG CCAACGATCA GATGGCGCTG GGCGCAATGC GCGCCATTAC CGAGTCCGGG     2040
CTGCGCGTTG GTGCGGATAT CTCGGTAGTG GGATACGACG ATACCGAAGA CAGCTCATGT     2100
TATATCCCGC CGTTAACCAC CATCAAACAG GATTTTCGCC TGCTGGGGCA AACCAGCGTG     2160
GACCGCTTGC TGCAACTCTC TCAGGGCCAG GCGGTGAAGG GCAATCAGCT GTTGCCCGTC     2220
TCACTGGTGA AAAGAAAAAC CACCCTGGCG CCCAATACGC AAACCGCCTC TCCCCGCGCG     2280
TTGGCCGATT CATTAATGCA GCTGGCACGA CAGGTTTCCC GACTGGAAAG CGGGCAGTGA     2340
GCGCAACGCA ATTAATGTAA GTTAGCGCGA ATTGTCGACC AAAGCGGCCA TCGTGCCTCC     2400
CCACTCCTGC AGTTCGGGGG CATGGATGCG CGGATAGCCG CTGCTGGTTT CCTGGATGCC     2460
GACGGATTTG CACTGCCGGT AGAACTCCGC GAGGTCGTCC AGCCTCAGGC AGCAGCTGAA     2520
CCAACTCGCG AGGGGATCGA GCCCGGGGTG GGCGAAGAAC TCCAGCATGA GATCCCCGCG     2580
CTGGAGGATC ATCCAGCCGG CGTCCCGGAA AACGATTCCG AAGCCCAACC TTTCATAGAA     2640
GGCGGCGGTG GAATCGAAAT CTCGTGATGG CAGGTTGGGC GTCGCTTGGT CGGTCATTTC     2700
GAACCCCAGA GTCCCGCTCA GAAGAACTCG TCAAGAAGGC GATAGAAGGC GATGCGCTGC     2760
GAATCGGGAG CGGCGATACC GTAAAGCACG AGGAAGCGGT CAGCCCATTC GCCGCCAAGC     2820
TCTTCAGCAA TATCACGGGT AGCCAACGCT ATGTCCTGAT AGCGGTCCGC CACACCCAGC     2880
```

-continued

```
CGGCCACAGT CGATGAATCC AGAAAAGCGG CCATTTTCCA CCATGATATT CGGCAAGCAG      2940

GCATCGCCAT GGGTCACGAC GAGATCCTCG CCGTCGGGCA TGCGCGCCTT GAGCCTGGCG      3000

AACAGTTCGG CTGGCGCGAG CCCCTGATGC TCTTCGTCCA GATCATCCTG ATCGACAAGA      3060

CCGGCTTCCA TCCGAGTACG TGCTCGCTCG ATGCGATGTT TCGCTTGGTG GTCGAATGGG      3120

CAGGTAGCCG GATCAAGCGT ATGCAGCCGC CGCATTGCAT CAGCCATGAT GGATACTTTC      3180

TCGGCAGGAG CAAGGTGAGA TGACAGGAGA TCCTGCCCCG GCACTTCGCC CAATAGCAGC      3240

CAGTCCCTTC CCGCTTCAGT GACAACGTCG AGCACAGCTG CGCAAGGAAC GCCCGTCGTG      3300

GCCAGCCACG ATAGCCGCGC TGCCTCGTCC TGCAGTTCAT TCAGGGCACC GGACAGGTCG      3360

GTCTTGACAA AAAGAACCGG GCGCCCCTGC GCTGACAGCC GGAACACGGC GGCATCAGAG      3420

CAGCCGATTG TCTGTTGTGC CCAGTCATAG CCGAATAGCC TCTCCACCCA AGCGGCCGGA      3480

GAACCTGCGT GCAATCCATC TTGTTCAATC ATGCGAAACG ATCCTCATCC TGTCTCTTGA      3540

TCAGATCTTG ATCCCCTGCG CCATCAGATC CTTGGCGGCA AGAAAGCCAT CCAGTTTACT      3600

TTGCAGGGCT TCCCAACCTT ACCAGAGGGC GCCCCAGCTG GCAATTCCGG TTCGCTTGCT      3660

GTCCATAAAA CCGCCCAGTC TAGCTATCGC CATGTAAGCC CACTGCAAGC TACCTGCTTT      3720

CTCTTTGCGC TTGCGTTTTC CCTTGTCCAG ATAGCCCAGT AGCTGACATT CATCCGGGGT      3780

CAGCACCGTT TCTGCGGACT GGCTTTCTAC GTGTTCCGCT TCCTTTAGCA GCCCTTGCGC      3840

CCTGAGTGCT TGCGGCAGCG TGAAGCTTAA AAAACTGCAA AAAATAGTTT GACTTGTGAG      3900

CGGATAACAA TTAAGATGTA CCCAATTGTG AGCGGATAAC AATTTCACAC ATTAAAGAGG      3960

AGAAATTACA TATG                                                       3974
```

(2) INFORMATION FOR SEQ ID NO:148:

(i) SEQUENCE CHARACTERISTICS:
        (A) LENGTH: 112 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:148:

```
AAGCTTAAAA AACTGCAAAA AATAGTTTGA CTTGTGAGCG GATAACAATT AAGATGTACC         60

CAATTGTGAG CGGATAACAA TTTCACACAT TAAAGAGGAG AAATTACATA TG               112
```

What is claimed is:

1. An isolated polypeptide comprising an amino acid sequence at least 95% identical to Ser (69)-Ser (208) of SEQ ID NO:2, wherein said polypeptide stimulates proliferation of epithelial cells.

2. The isolated polypeptide of claim 1, having a Met residue at the N-terminus of said amino acid sequence.

3. The isolated polypeptide of claim 1, wherein said polypeptide is part of a fusion protein.

4. The isolated polypeptide of claim 1, which is produced in a recombinant cell.

5. The isolated polypeptide of claim 4, wherein said recombinant cell is bacterial.

6. A composition comprising the isolated polypeptide of claim 1 and a pharmaceutically acceptable carrier or excipient.

7. An isolated polypeptide comprising an amino acid sequence at least 97% identical to Ser (69)–Ser (208) of SEQ ID NO:2, wherein said polypeptide stimulates proliferation of epithelial cells.

8. The isolated polypeptide of claim 7, having a Met residue at the N-terminus of said amino acid sequence.

9. The isolated polypeptide of claim 7, wherein said polypeptide is part of a fusion protein.

10. The isolated polypeptide of claim 7, which is produced in a recombinant cell.

11. The isolated polypeptide of claim 10, wherein said recombinant cell is bacterial.

12. A composition comprising the isolated polypeptide of claim 7 and a pharmaceutically acceptable carrier or excipient.

* * * * *

UNITED STATES PATENT AND TRADEMARK OFFICE
CERTIFICATE OF CORRECTION

PATENT NO. : 6,903,072 B2
DATED : June 7, 2005
INVENTOR(S) : Ruben et al.

It is certified that error appears in the above-identified patent and that said Letters Patent is hereby corrected as shown below:

Title page,
Item [30], Related U.S. Application Data, after "application No. 08/461,195", insert -- filed on Jun. 5, 1995, now abandoned, --; and replace provisional application No. "60/639,045" with -- 60/039,045 --.
Item [56], References Cited, OTHER PUBLICATIONS,
"Hartung, H. et al." reference, replace "Assignment'" with -- Assignment[a] --;
"Marra, M. et al." reference, after "Accession No.", please insert -- AA472256 --;
"Marra, M. et al." reference, replace "1997" with -- 1998 --; and
"Lee, N.H. et al." reference, replace "1997" with -- 1998 --.

Signed and Sealed this

Sixth Day of September, 2005

JON W. DUDAS
*Director of the United States Patent and Trademark Office*